US010535995B2

(12) United States Patent
Kawata et al.

(10) Patent No.: US 10,535,995 B2
(45) Date of Patent: Jan. 14, 2020

(54) POWER CONTROL SYSTEM, HEALTHCARE INSTRUMENT, ACTIVITY MEASUREMENT APPARATUS, AND POWER INSTRUCTION APPARATUS

(71) Applicants: MITSUBISHI ELECTRIC CORPORATION, Chiyoda-ku, Tokyo (JP); MITSUBISHI ELECTRIC HOME APPLIANCE CO., LTD., Fukaya-shi, Saitama (JP)

(72) Inventors: Yukio Kawata, Fukaya (JP); Asuka Murano, Fukaya (JP); Hirokazu Kinoshita, Fukaya (JP); Masahiro Kobayashi, Fukaya (JP); Susumu Yamamoto, Fukaya (JP); Yosuke Ogura, Fukaya (JP); Masanobu Ito, Fukaya (JP)

(73) Assignees: MITSUBISHI ELECTRIC CORPORATION, Chiyoda-ku, Tokyo (JP); MITSUBISHI ELECTRIC HOME APPLIANCE CO., LTD., Fukaya-shi, Saitama (JP)

( * ) Notice: Subject to any disclaimer, the term of this patent is extended or adjusted under 35 U.S.C. 154(b) by 712 days.

(21) Appl. No.: 15/114,764

(22) PCT Filed: Feb. 3, 2015

(86) PCT No.: PCT/JP2015/052987
§ 371 (c)(1),
(2) Date: Jul. 27, 2016

(87) PCT Pub. No.: WO2015/115663
PCT Pub. Date: Aug. 6, 2015

(65) Prior Publication Data
US 2016/0359325 A1    Dec. 8, 2016

(30) Foreign Application Priority Data

Feb. 3, 2014    (JP) .................................. 2014-018372

(51) Int. Cl.
*H02J 3/14*    (2006.01)
*H02J 13/00*    (2006.01)

(52) U.S. Cl.
CPC ................ *H02J 3/14* (2013.01); *H02J 13/00* (2013.01)

(58) Field of Classification Search
CPC .......... H02J 3/14; H02J 13/00; H02J 13/0006; G16H 20/30; G16H 40/67; G16H 50/50;
(Continued)

(56) References Cited

U.S. PATENT DOCUMENTS 6,018,690 A       1/2000   Saito et al.
2010/0194572 A1*  8/2010   Chan .................... A61B 5/0002
                                                          340/573.1
(Continued)

FOREIGN PATENT DOCUMENTS

EP    2151188 A1     2/2010
JP    05-049603 A    3/1993
(Continued)

OTHER PUBLICATIONS

Office Action (Notice of Reasons for Rejection) dated Mar. 21, 2017, by the Japanese Patent Office in corresponding Japanese Patent Application No. 2015-560076, and an English Translation of the Office Action. (9 pages).
(Continued)

*Primary Examiner* — Tomi Skibinski
(74) *Attorney, Agent, or Firm* — Buchanan Ingersoll & Rooney PC

(57) ABSTRACT

A power control system includes an activity measurement apparatus configured to measure an amount of activity, a
(Continued)

healthcare instrument configured to measure metabolic data, and a power instruction apparatus including a healthcare processing unit configured to acquire these pieces of measurement data. The power instruction apparatus includes an environment detection unit configured to detect ambient environment of each of the activity measurement apparatus and the healthcare instrument. The power instruction apparatus is configured to store, in its internal memory, the measurement data acquired from each of the healthcare instrument and the activity measurement apparatus, display the measurement data on its display screen, measure, with the environment detection unit, the ambient environment of each of the activity measurement apparatus and the healthcare instrument, determine environment suitability based on the measurement data, and display determination result on a display device to notify an occupant of the result.

22 Claims, 47 Drawing Sheets

(58) Field of Classification Search
CPC .. G16H 50/20; Y02B 70/3225; Y02B 70/325; Y02B 70/3275; Y04S 20/222; Y04S 20/224; Y04S 20/228; Y04S 20/244
USPC .................................. 307/35; 700/291, 295
See application file for complete search history.

(56) References Cited

U.S. PATENT DOCUMENTS

| 2010/0321574 | A1* | 12/2010 | Kerofsky | G06Q 50/06 |
| | | | | 348/563 |
| 2011/0093126 | A1* | 4/2011 | Toba | G05B 15/02 |
| | | | | 700/291 |
| 2012/0116792 | A1* | 5/2012 | Lee | G06Q 90/00 |
| | | | | 705/1.1 |
| 2013/0013123 | A1 | 1/2013 | Ozaki | |
| 2014/0129004 | A1 | 5/2014 | Takayama et al. | |

FOREIGN PATENT DOCUMENTS

| JP | 10-94199 | A | | 4/1998 |
| JP | 2002-259570 | A | | 9/2002 |
| JP | 2004-164442 | A | | 6/2004 |
| JP | 2004164442 | A | * | 6/2004 |
| JP | 2009-240661 | A | | 10/2009 |
| JP | 2010-029004 | A | | 2/2010 |
| JP | 2010029004 | A | * | 2/2010 |
| JP | 2011-000191 | A | | 1/2011 |
| JP | 2012-023872 | A | | 2/2012 |
| WO | 2005110209 | A1 | | 11/2005 |
| WO | WO 2012/008392 | A1 | | 1/2012 |
| WO | WO 2013/128934 | A1 | | 9/2013 |
| WO | 2013/171833 | A1 | | 11/2013 |

OTHER PUBLICATIONS

The Partial Supplementary European Search Report dated Sep. 26, 2017, by the European Patent Office in corresponding European Application No. 15744065.2. (13 pages).
Office Action (Notice of Reasons for Rejection) dated Jul. 25, 2017, by the Japanese Patent Office in corresponding Japanese Patent Application No. 2015-560076 and English translation of the Office Action. (4 pages).
Extended European Search Report dated Jan. 9, 2018, issued by the European Patent Office in corresponding European Application No. 15744065.2. (14 pages).
International Search Report (PCT/ISA/210) dated Mar. 31, 2015, by the Japanese Patent Office as the International Searching Authority for International Application No. PCT/JP2015/052987.
Written Opinion (PCT/ISA/237) dated Mar. 31, 2015, by the Japanese Patent Office as the International Searching Authority for International Application No. PCT/JP2015/052987.

* cited by examiner

FIG. 13

```
┌─────────────────────────────────────────────┐
│  ┌───────────────────────────────────────┐  │
│  │HEALTHCARE │ELECTRIC ENERGY│LIVING ENVIRONMENT│──419
│  │INFORMATION│MANAGEMENT     │INFORMATION      │
│  │     ╲      SUBJECT A  ╲    SUBJECT B        │
│  │    417                418                   │
│  │   2014/1/13      8:22 AM                    │
│  │   BLOOD PRESSURE                            │
│  │   HIGHEST  142   7 OVER TARGET UPPER LIMIT  │
│  │   LOWEST    88                     ╲        │
│  │                            ┌────────────┐ 75D│
│  │                            │BACK TO MENU PAGE│
│  │                            └────────────┘   │
│  │ ┌─────┐                                     │
│  │ │CHECK│                                     │
│  │ └─────┘                       232           │
│  │   ╲                                         │
│  │   EV2                                       │
│  └───────────────────────────────────────┘  │
└─────────────────────────────────────────────┘
```

FIG. 14

| LS1 MEASUREMENT DEVICE CODE | LS2 MEASUREMENT CATEGORY | LS3 SUBJECT | LS4 MEASUREMENT DATE AND TIME | LS5 MEASUREMENT VALUE XA | LS6 MEASUREMENT VALUE XB | LS7 ABNORMALITY |
|---|---|---|---|---|---|---|
| XX01 | BLOOD PRESSURE | B | 2014/1/10 07:20 | 140 | 80 | |
| XX01 | BLOOD PRESSURE | B | 2014/1/10 08:35 | 140 | 85 | |
| XX01 | BLOOD PRESSURE | A | 2014/1/11 08:10 | 150 | 90 | E |
| XX01 | BLOOD PRESSURE | B | 2014/1/12 07:10 | 135 | 81 | |
| XX01 | BLOOD PRESSURE | A | 2014/1/12 08:15 | 148 | 92 | E |
| XX01 | BLOOD PRESSURE | B | 2014/1/13 07:18 | 136 | 83 | |
| XX01 | BLOOD PRESSURE | A | 2014/1/13 08:22 | 142 | 88 | |
| | | | | | | |
| | | | | | | |
| | | | | | | |
| | | | | | | |

FIG. 21

| ELECTRIC APPLIANCE GROUP NAME | POWER REDUCTION BY POWER INSTRUCTION APPARATUS | POWER OFF BY EMERGENCY EARTHQUAKE NEWS |
|---|---|---|
| HOMECARE AND NURSING INSTRUMENT | NO | NO |
| HEALTHCARE INSTRUMENT AND ACTIVITY MEASUREMENT APPARATUS | NO | NO |
| TV RECEIVER (MAIN) | NO | NO |
| TV RECEIVER (SUB) | YES | NO |
| GENERAL ILLUMINATION APPARATUS | YES | NO |
| EMERGENCY ILLUMINATION APPARATUS | NO | NO |
| KITCHEN ELECTRIC APPLIANCE | SOME TEMPORARILY NO | YES EXCEPT RICE COOKER |
| AIR-CONDITIONING APPARATUS | YES | YES |
| ELECTRIC VACUUM CLEANER | YES | YES |

FIG. 22

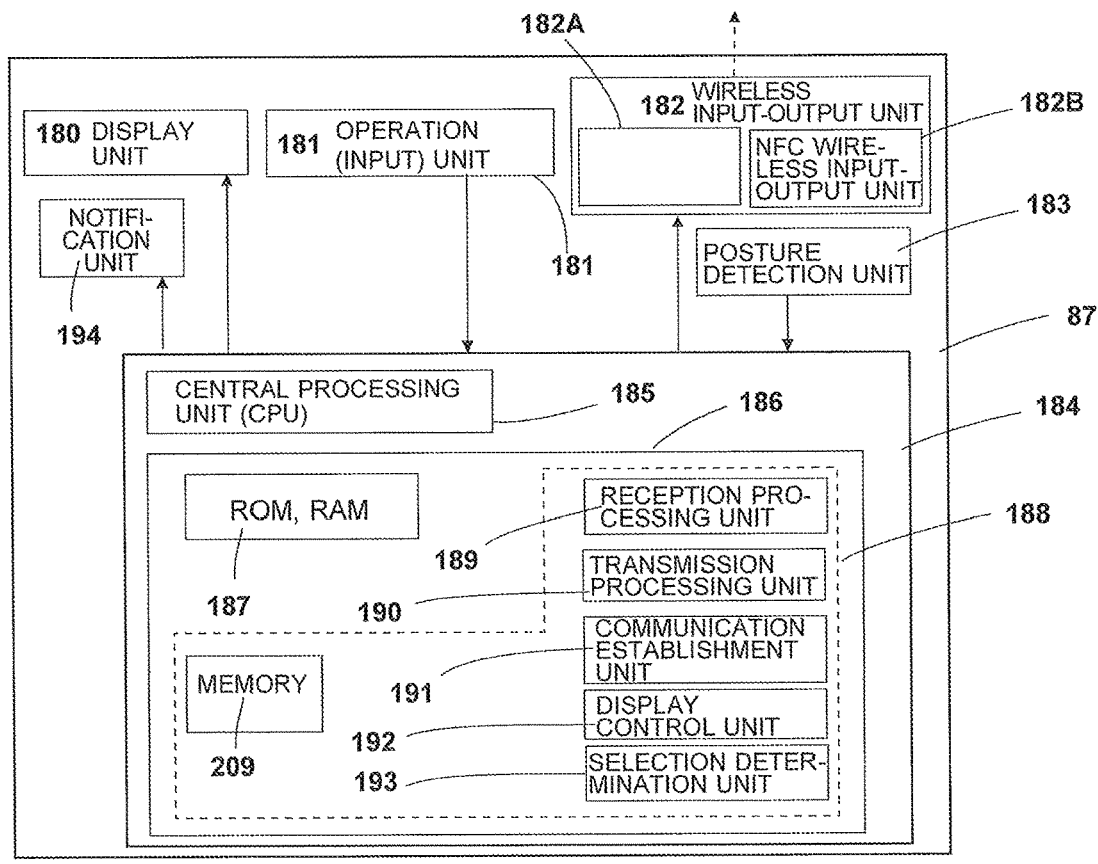

FIG. 58

| | | | | PERMISSION CRITERIA OF ENVIRONMENT DETECTION UNIT | | | |
|---|---|---|---|---|---|---|---|
| JULY 31 | AIR-CONDITIONING APPARATUS | RESERVED OPERATION START TIME | ESTIMATED ROOM TEMPERATURE AT HOME ARRIVAL TIME | ROOM TEMPERATURE TO PERMIT COOLING | HOME ARRIVAL TIME | ROOM TEMPERATURE AT HOME ARRIVAL TIME | RESULT |
| | | 13:00 | 33°C | 29°C OR HIGHER | 18:00 | 27°C | COOLING NOT OPERATED |
| SEPTEMBER 10 | ENTRANCE CEILING ILLUMINATION APPARATUS | RESERVED OPERATION START TIME | ESTIMATED ROOM ILLUMINANCE AT HOME ARRIVAL TIME | ILLUMINANCE TO PERMIT TURNING ON | HOME ARRIVAL TIME | ILLUMINANCE AT HOME ARRIVAL TIME | RESULT |
| | | 20:00 | LOWEST LEVEL | LOWEST LEVEL | 17:45 | MEDIUM LEVEL | NOT TURNED ON |
| SEPTEMBER 11 | SELF-RUNNING CLEANER | RESERVED OPERATION FINISH TIME | ESTIMATED DEGREE OF QUIETNESS AT HOME ARRIVAL TIME (AVERAGE OF LATEST 1 MINUTE) | DEGREE OF QUIETNESS TO PERMIT OPERATION (AVERAGE OF LATEST 1 MINUTE) | HOME ARRIVAL TIME | DEGREE OF QUIETNESS AT HOME ARRIVAL TIME (AVERAGE OF LATEST 1 MINUTE) | RESULT |
| | | 20:00 | MEDIUM LEVEL | MEDIUM LEVEL | 22:30 | HIGHEST LEVEL | NOT OPERATED |
| FEBRUARY 10 | JAR TYPE RICE COOKER | RESERVED OPERATION FINISH TIME | ESTIMATED ROOM TEMPERATURE AT HOME ARRIVAL TIME | ROOM TEMPERATURE AT RICE COOKING (WATER ABSORPTION) START TIME | HOME ARRIVAL TIME | ROOM TEMPERATURE AT HOME ARRIVAL TIME | RESULT |
| | | 20:00 | 8°C | 2°C TO 35°C (2°C TO 23°C TO SKIP KEEP-WARM) | 22:00 | 4°C | OPERATED (PROCEEDED TO KEEP-WARM AFTER RICE COOKING) |

POWER CONTROL SYSTEM, HEALTHCARE INSTRUMENT, ACTIVITY MEASUREMENT APPARATUS, AND POWER INSTRUCTION APPARATUS

TECHNICAL FIELD

The present invention relates to a power control system capable of suppressing power usage of home electric appliances, and to a healthcare instrument, an activity measurement apparatus, and a power instruction apparatus to be used in the power control system.

BACKGROUND ART

In a general household, power is supplied to various electric appliances present in living spaces through a single circuit breaker, and various home electric appliances, such as an induction heating cooker (hereinafter also referred to as "IH cooking heater"), are widely used. The maximum power usage of the induction heating cooker is as high as 4,800 W (or 5,800 W) and occupies a major part of the power usage of the household. Accordingly, various proposals have thus far been made to prevent the circuit breaker from tripping (disconnecting the circuit) when another electric appliance, for example, an air-conditioning apparatus is used at the same time as the induction heating cooker. For example, there has been known a power supply control system configured to output a control signal for supplying power to a plurality of electric appliances, through wired or wireless transmission to the electric appliances. The system includes an information collecting device configured to collect information about power usage of the electric appliance, a determining device configured to determine whether or not power can be supplied to the electric appliance within a predetermined allowable power range based on the information about the power usage collected by the information collecting device, and a device configured to permit power consumption of the electric appliance that the determining device has determined power can be supplied to (see, for example, Patent Literature 1).

Further, along with increasing consciousness of health management, there has been a growing number of cases where an occupant acquires biological data, e.g., blood pressure by the occupant oneself in each household. As a typical example, there has been proposed a system capable of measuring and storing blood pressure, pulse rate, body temperature, weight, or other items and displaying the data on a display, to thereby enable health counseling via telephone by transmitting the data to a predetermined hospital. This system includes a measurement unit configured to detect and measure, for example, blood pressure with a sensor and to output the data, a clock unit configured to output data regarding the date, a memory unit configured to store the data from the measurement unit together with the data of the date, a data processing unit configured to process the data stored in the memory unit to convert the data into graphic data, e.g., graphs, a display unit configured to display the graphic data transmitted from the data processing unit, and a control unit configured to control each of the measurement unit, the clock unit, the memory unit, the data processing unit, and the display unit (see, for example, Patent Literature 2).

Still further, in order to enable access from the household to a doctor present at a distant location via a communication device (network) so that the doctor can provide health suggestion information and medical diagnosis information to a user, there has been proposed a health management system including a television set, a center server configured to transmit or receive data via a network, and an information terminal apparatus including a first communication device to be connected to the television set to communicate with the outside via the network and a second communication device configured to communicate with a health measurement instrument. In the system, health measurement data measured in the health measurement instrument is communicated with the second communication device to be accumulated in an information storage device of the information terminal apparatus. The health measurement data is then transmitted to the center server via the network with the first communication device to be accumulated in the center server. A medical institution or a control center for health control accesses the accumulated health measurement data to create diagnosis service information based on the health measurement data. The diagnosis service information is transmitted to the information terminal apparatus via the network to be displayed on the television set, and thus the information is provided (see, for example, Patent Literature 3).

CITATION LIST

Patent Literature

Patent Literature 1: Japanese Unexamined Patent Application Publication No. 10-94199 (page 1, FIG. 1)
Patent Literature 2: Japanese Unexamined Patent Application Publication No. 5-49603 (page 1, FIG. 1)
Patent Literature 3: Japanese Unexamined Patent Application Publication No. 2002-259570 (page 1, FIG. 1)

SUMMARY OF INVENTION

Technical Problem

As described above, the related-art power control system only has a control function to decrease the total power consumption when the induction heating cooker is used or when the induction heating cooker and another electric appliance are used at the same time. However, general households have recently become more conscious of peak-shift or power saving to prevent unexpected power failure due to tight electricity supply and demand, in particular to avoid power concentration in the daytime in summer, and an increasing number of households are introducing apparatus for a power control system. Meanwhile, there is growing interest in regards to health management and exercise using the measured blood pressure and body fat rate, and it has become more popular for households to utilize various healthcare instruments and activity measurement apparatuses for promoting aerobic exercise, etc. Therefore, a wide variety of electric appliances, healthcare instruments, and activity appliances are utilized in various locations and situations in the household. In the related art listed in Citation List, however, the apparatus are not linked with each other, and therefore useful information and functions of those apparatus are not always effectively and appropriately fully utilized.

It is an object of the present invention to provide a power control system capable of recognizing and using health-related information measured by a healthcare instrument or an activity apparatus, to thereby improve user-friendliness in terms of both power control and health management in a household, and to provide a healthcare instrument, an activity measurement apparatus, and a power instruction apparatus to be used in the power control system.

Solution to Problem

A power control system according to a first aspect of the present invention includes a power instruction apparatus configured to limit total electric power in a household by individually controlling an upper power limit of each of a plurality of home electric appliances in the household, a display device connected to the power instruction apparatus via wired or wireless communication and configured to display operation information of the power instruction apparatus, and an activity measurement apparatus configured to measure an amount of activity of a user in the household, the power instruction apparatus including an environment detection unit configured to measure at least one of temperature and humidity of each of a plurality of living spaces in the household to acquire environment information, and a healthcare processing unit configured to acquire measurement data measured by the activity measurement apparatus, the display device being configured to display the environment information acquired by the environment detection unit of the power instruction apparatus and the measurement data measured by the activity measurement apparatus, in response to an instruction from a user.

An activity measurement apparatus according to a second aspect of the present invention includes a measurement unit configured to measure data of an amount of activity of a user (living body), a memory configured to temporarily store the measurement data acquired by the measurement unit, a transmission unit configured to transmit the measurement data stored in the memory to a power instruction apparatus configured to limit total electric power in a household by individually controlling an upper power limit of each of a plurality of home electric appliances in the household, an operation unit configured to output an instruction of a measurement operation and a transmission operation, an apparatus-side display unit configured to read out and display the measurement data stored in the memory, and a control unit configured to process the measurement data, the transmission unit configured to transmit a usage notice signal to the power instruction apparatus before start of measurement by the measurement unit.

A healthcare instrument according to a third aspect of the present invention includes a measurement unit configured to measure measurement data of a person (living body), a memory configured to temporarily store the measurement data acquired by the measurement unit, a transmission unit configured to transmit the measurement data stored in the memory to a power instruction apparatus configured to limit total electric power in a household by individually controlling an upper power limit of each of a plurality of home electric appliances in the household, an operation unit configured to output an instruction of a measurement operation and a transmission operation, an apparatus-side display unit configured to read out and display the measurement data stored in the memory, and a control unit configured to process the measurement data, the transmission unit configured to transmit a usage notice signal to the power instruction apparatus before start of measurement by the measurement unit.

A power instruction apparatus according to a fourth aspect of the present invention is configured to limit total electric power in a household by individually controlling power usage of each of a plurality of home electric appliances in the household, the power instruction apparatus including an environment detection unit configured to measure at least one of temperature and humidity of each of a plurality of living spaces in the household to generate environment information, a power use limit setting device configured to receive operation information from each of the plurality of home electric appliances to transmit a power control signal to each of the plurality of home electric appliances, a healthcare processing unit configured to receive measurement data from an activity measurement apparatus configured to measure an amount of activity of a user, a control unit configured to control the healthcare processing unit and the power use limit setting device, and a display device configured to display, collectively or individually, information of the power usage, data of the amount of activity received by the healthcare processing unit, and the environment information of a living space in which the activity measurement apparatus is present.

Advantageous Effects of Invention

With the power control system according to the first aspect, the measurement information relating to human health and activity as well as the environment data of the living space can be displayed by utilizing the information transmission system of the power instruction apparatus. Therefore, the environment of the living space can be confirmed, and the user is motivated to become more conscious of energy saving and health management.

With the activity measurement apparatus according to the second aspect, the information of the amount of activity can be displayed by utilizing the power instruction apparatus configured to display the power usage information, and further the usage notice signal can be transmitted to the power instruction apparatus before measurement of the amount of activity.

With the healthcare instrument according to the third aspect, the information relating to health management can be displayed by utilizing the power instruction apparatus configured to display the power usage information, and further the usage notice signal can be transmitted to the power instruction apparatus before measurement of the human body.

With the power instruction apparatus according to the fourth aspect, power usage of the plurality of home electric appliances in the household can be individually controlled to enable centralized control of the total electric power in the household. In addition, the measurement results of the measurement data received from the activity measurement apparatus can be displayed, and therefore the user is motivated to become more conscious of energy saving and health management through activity.

FIG. 13 is a schematic diagram for illustrating an example of the TV receiver screen in the power control system according to Embodiment 1 of the present invention.

FIG. 14 is an explanatory diagram for showing configurations of blood pressure data and incidental data acquired by the healthcare instrument used in the power control system according to Embodiment 1 of the present invention.

FIG. 21 is an explanatory diagram for showing appliances that are objects of power reduction by the power instruction apparatus and appliances that are objects of power cut-off upon reception of an Earthquake Early Warning, in the power control system illustrated in FIG. 1 to FIG. 19.

FIG. 22 is a block diagram for illustrating an internal configuration of a mobile phone terminal used in the power control system according to Embodiment 1 of the present invention.

FIG. 58 is a table for showing examples of various reservation statuses of home electric appliances and examples of correspondence relationships of permission criteria specified by an environment detection unit.

DESCRIPTION OF EMBODIMENTS

Embodiment 1

Figure 1:
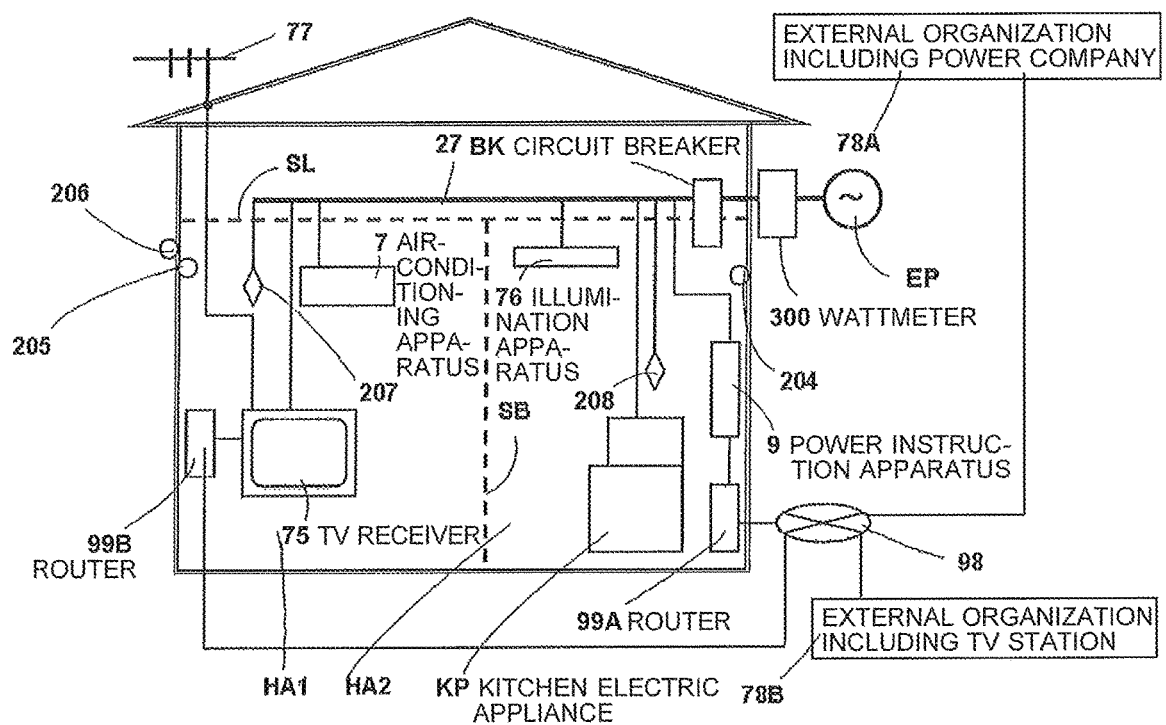
FIG. 1 is a schematic diagram for illustrating a household to which a power control system according to Embodiment 1 of the present invention is applied.
Figure 72:
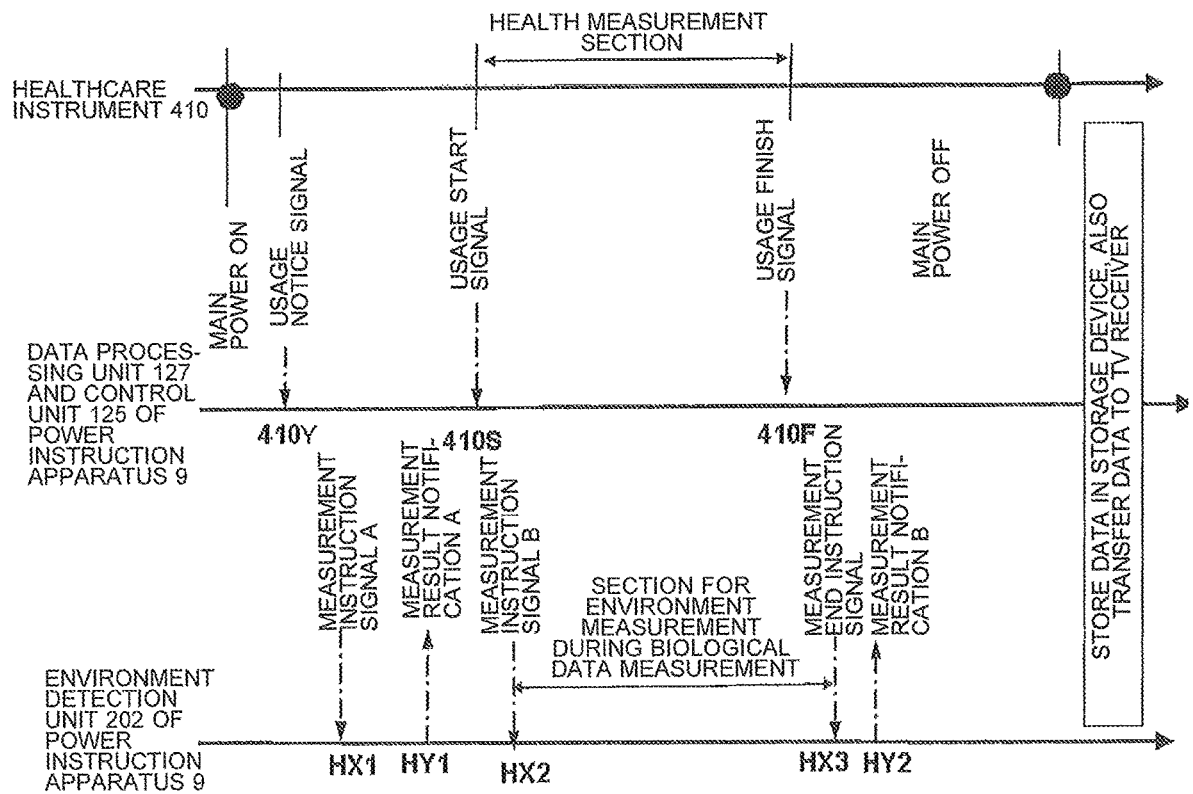
FIG. 72 is an explanatory diagram for illustrating mutual signal transmission between the power instruction apparatus and the healthcare instrument according to Embodiment 1 of the present invention in time series.

FIG. 1 to FIG. 72 relate to Embodiment 1 of the present invention. A power control system, a healthcare instrument, an activity measurement apparatus, and a power instruction apparatus according to Embodiment 1 are described below with reference to FIG. 1 to FIG. 72.

In Embodiment 1, the term "identification information" of a home electric appliance EE refers to information unique to the electric appliance EE, and is important information required for a proper repair and inspection. Specific examples of the identification information are as listed below, but the identification information is not limited thereto. The home electric appliance EE is described in detail subsequently.

(1) Manufacturer name of the home electric appliance EE
(2) Type name
(3) Model number
(4) Rated power consumption
(5) Year, month, and day of purchase (often corresponding to the starting date of a quality assurance period of the manufacturer or the seller)
(6) Year, month, and day of start of usage (corresponding to the starting date of a legal inspection period in the case of a dish washer-dryer)
(7) Warranty number The legal inspection in Item (6) refers to an inspection under the "System for Safety Inspection of Products for Long-Term Use" newly included in the "Consumer Products Safety Act" revised and provided from Apr. 1, 2009. In the separate "Electrical Appliances and Material Safety Act", a system for safety labeling of products for long-term use is established by the revision of the Ministerial Ordinance for Determining Technical Standards for Electrical Appliances, in which, for specific products among the consumer products, labeling is made compulsory for calling the consumer's attention to the design standard usage period and aging deterioration for the promotion of appropriate maintenance and inspection. In view of this, the "identification information" of the home electric appliance EE may include the information of the "manufacturing date of the product" labeled with respect to the consumer or "elapsed years" calculated from the year and month of the manufacture as a reference for the standard usage period.

In the present invention, the term "environment information" collectively refers to "environment data" itself detected by an environment detection unit 202 and "environment evaluation information" created based on such environment data, and includes the following types of information that may affect the degree of comfort of a living space, but the environment information is not limited thereto.

(1) Temperature information
(2) Humidity information
(3) Dust scattering degree information (per unit volume)
(4) Pollen scattering amount information
(5) Light amount (amount of visible light) information, that is, information of brightness of a living space
(6) Noise information, that is, information of quietness of a living space Further, in Embodiment 1, the term "utilization of environment information" refers to utilization of the environment information by various home electric appliances EE to be subsequently described, to realize efficient operation, effective operation, or environment-oriented operation of the home electric appliance EE, examples of which include:

(1) When the temperature is high, the keep-warm function of a rice cooker is activated immediately upon finishing the rice cooking phase.
(2) When the humidity is high, a dehumidifier, which is one of the home electric appliances EE, is activated, or a ventilation fan is activated.
(3) When minute dust that floats in the air is flying, an air purifier is activated, or a ventilation fan is activated.
(4) When a large amount of pollen is flying, an air purifier is activated.
(5) For sand dust or dust from clothes, which is relatively large in diameter or length and falls on the floor, a self-running electric vacuum cleaner is activated.
(6) When the light amount (amount of visible light) is insufficient, illumination apparatus is turned on.
(7) When no noise is detected, it is determined that the current time is in a quiet time period such as midnight, and operation of, for example, a self-running electric vacuum cleaner that generates operation noise of a blower motor and running noise, and a washer-dryer that generates operation noise of an electric motor for rotating a washing-drying drum, is avoided.

Another example is calculating a so-called "discomfort index" based on the relationship between the temperature and the humidity, and activating an air-conditioning apparatus.

The term "environment data" in the present invention refers to data itself representing measured physical states such as temperature and humidity. For example, an air temperature of 35 degrees Celsius corresponds to the environment data. Information subjected to some kind of evaluation or calculation to be classified, ranked, or processed based on the air temperature of 35 degrees Celsius corresponds to the "environment evaluation information". For example, information such as "room temperature is high" or "standard air temperature" corresponds to the "environment evaluation information".

In Embodiment 1, further, the convenience to the occupants is improved through utilization of the environment information, for example as listed below.

(1) Suggestion information is provided about the use of the home electric appliance EE to improve the living environment (e.g., ventilation fan and air purifier). The suggestion information partly overlaps with suggestion information 489 to be subsequently described, and matches therewith in terms of securing the convenience to the occupants and the degree of comfort.
(2) The home electric appliances EE that are currently operating can be identified.
(3) Whether or not a person is present in a separate living space can be detected.
(4) An uncomfortable living space where both of the temperature and the humidity are high can be identified.
(5) A living space unsuitable for exercising can be identified, when an occupant uses an indoor exercise instrument or activity apparatus.
(6) An upper limit of the room temperature may be set for the power instruction apparatus to output a warning. In this case, a room in which the upper limit is exceeded can be identified, and the environment of a separate room can also be recognized.

Such home electric appliances EE that can favorably influence the air in the living space or improve the quality of the air may hereinafter be referred to as "first specific home electric appliance" ("environment improvement apparatus") SP1. A stove with an electric heater and an air-conditioning apparatus that generate heat for heating to maintain or improve the degree of comfort of the room space, thereby, are examples of the environment improvement apparatus. In addition, home electric appliances EE such as an electric heating cooker that give off heat in the room space, but not for the purpose of maintaining or improving the degree of comfort of the room space, may be referred to as "second specific home electric appliance SP2".

Further, a specific appliance of a plurality of home electric appliances EE may be referred to as "first home electric appliance", and another home electric appliance EE may be referred to as "second home electric appliance" for distinction from the first home electric appliance.

The "environment improvement apparatus" SP1 in the present invention refers to apparatus that serve to improve the temperature, humidity, and quality of the air in the living space. By improving the quality of the air, purified air barely containing toxic substances and dust can be obtained.

In Embodiment 1, a "presence detection unit" may be exemplified by the following devices, among which only a typical one is described in detail. Detailed description regarding the other devices is not given in the following.

(1) A device configured to detect coming home of an occupant from an electronic lock (entrance electronic lock) provided outside an entrance (front door) of the house and a PIN code or biological information (such as finger print information) input to an electronic lock 19.

(2) A device configured to cause the power instruction apparatus to directly read personal identification information recorded on a specific ID paper or ID card owned by the occupant magnetically or optically, or by near-field communication or other communication methods, and to determine that the occupant is at home by analyzing the read out information.

(3) A device configured to cause the power instruction apparatus to directly read personal identification information recorded on information terminal devices such as a mobile phone owned by the occupant by near-field communication or other communication methods, and to determine that the occupant is at home by analyzing the read out information.

(4) A device configured to cause the specific home electric appliance EE to read personal identification information recorded on the ID paper, ID card, or information terminal device owned by an individual, or cause the home electric appliance EE to read or input through an input key an ID number or password only known by the individual, so that the power instruction apparatus determines that the individual who has caused the home electric appliance EE to read is at home by analyzing the personal identification information or the password that has been read.

In Embodiment 1, the term "occupant" refers to a person dwelling in a household to be subsequently described and includes parents, children, brothers and sisters related by birth. In addition, a visitor who temporarily stays in a living space HA to be subsequently described for a predetermined period, and other persons who live together are also included. One or a plurality of persons borrowing one or a plurality of living spaces are also included. In Embodiment 1, the occupants are exemplified by a typical four-member family, in which an occupant A is the father, an occupant B is the mother, an occupant C is the older child (10 years), and an occupant is the younger child (7 years). When use of the home electric appliance EE is referred to, the occupant may be called "user", and when there is no need to identify any of the four occupants, the term "person" or "family member" may be used. In addition, when the occupant measures their blood pressure with a healthcare instrument 410 to be subsequently described, such occupant may be called "subject".

In Embodiment 1, the term "household" refers to one house managed by a specific manager, and has a plurality of rooms. The household may include a condominium in which a plurality of families are living. That is, even such a condominium is regarded as the household herein when the upper limit of the commercial power is centrally controlled by a circuit breaker as in the case of one house.

Figure 45:
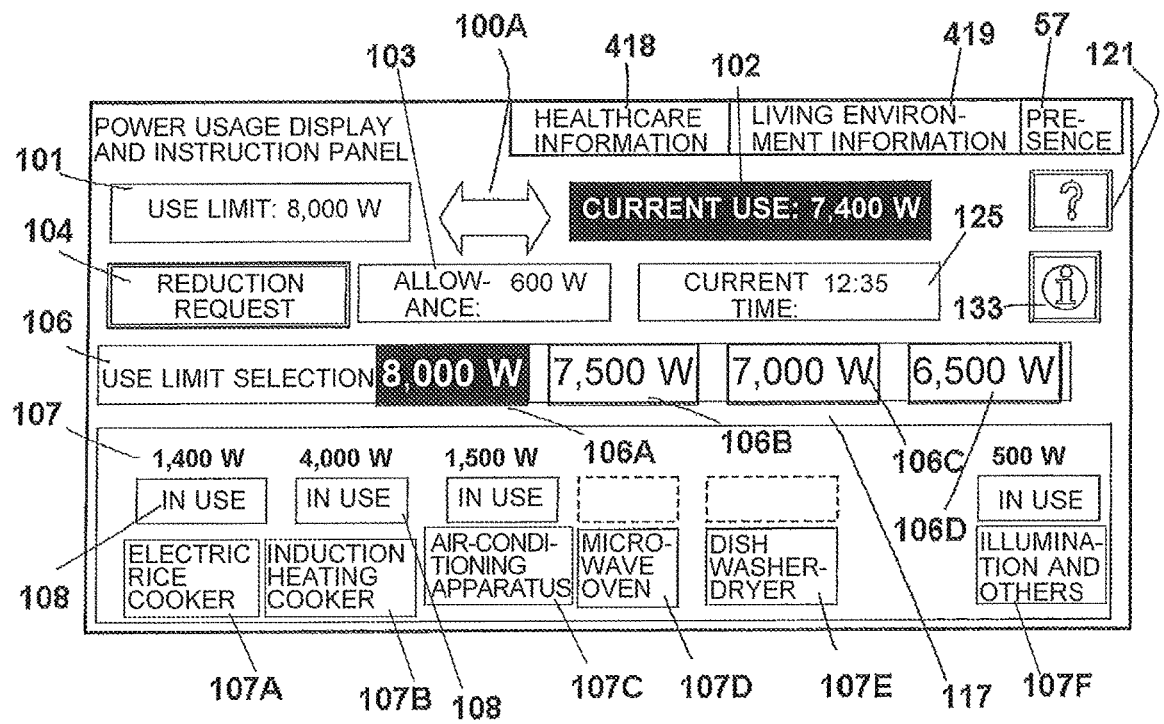
FIG. 45 is a front view for illustrating the display screen of the use limit setting device of the power instruction apparatus according to Embodiment 1 of the present invention.
Figure 46:
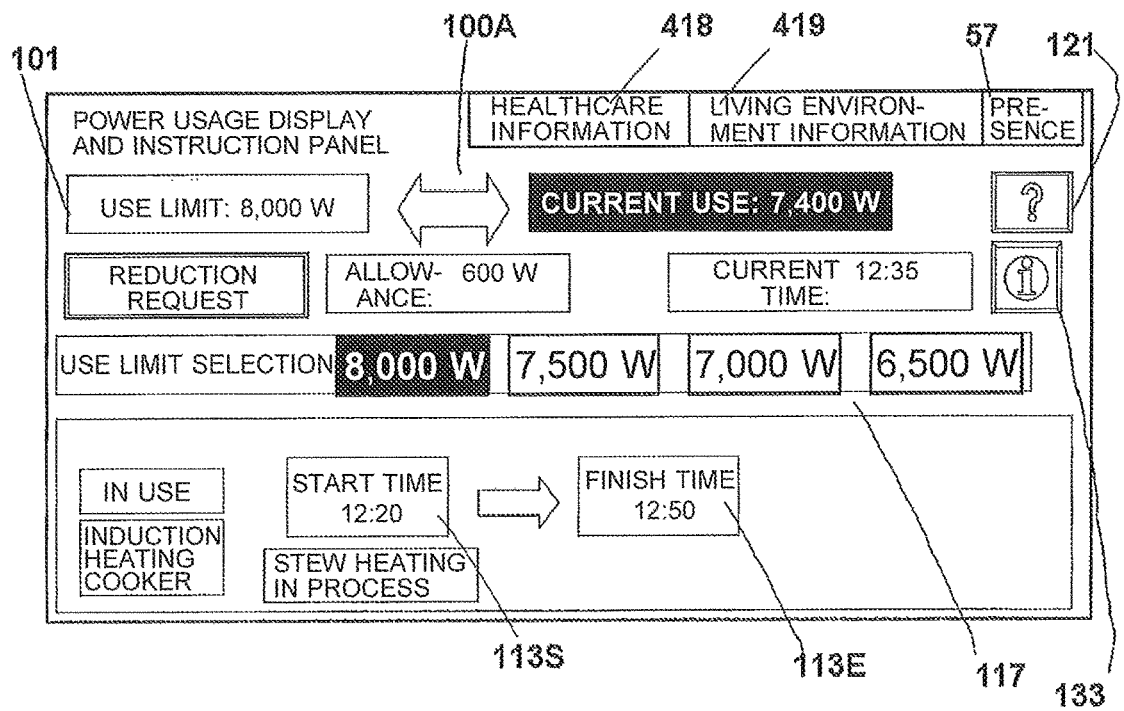
FIG. 46 is a front view for illustrating the display screen of the use limit setting device illustrated in FIG. 45.
Figure 47:
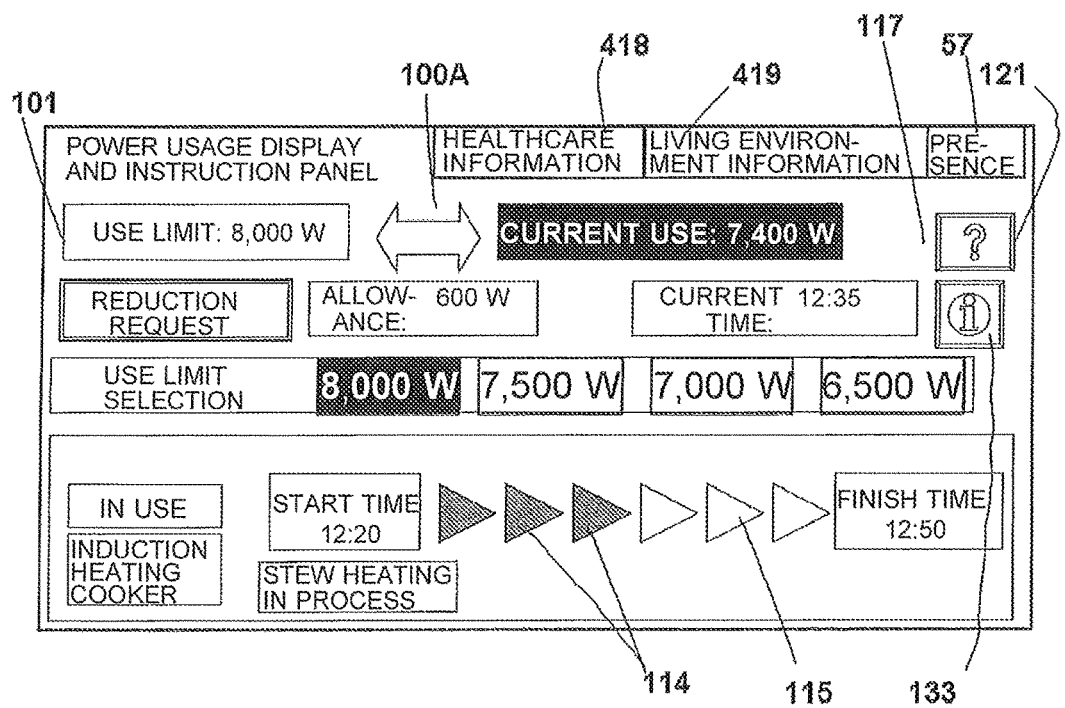
FIG. 47 is a front view for illustrating the display screen of the use limit setting device illustrated in FIG. 45.

In Embodiment 1, the term "operation information" of a power instruction apparatus 9 to be subsequently described refers to, as illustrated in FIG. 45 to FIG. 47, information 101 indicating the upper-limit total electric power set in one household, information 102 indicating the current electric power usage, information 103 indicating a difference between the total electric power and the electric power usage, information 107 for specifically identifying the home electric appliance EE as an object of control by the power instruction apparatus 9, information 108 indicating the usage state of the home electric appliance EE, information of electric power used in each home electric appliance EE (e.g., average electric power for 1 minute), or other information, but the operation information is not limited thereto.

In Embodiment 1, the term "power limitation information of home electric appliance" refers to information relating to some kind of signal regarding the power consumption received by the home electric appliance EE from the power instruction apparatus 9, and includes information relating to an instruction for transmitting a power reduction request signal AS2 and a power reduction instruction signal AS3 to be subsequently described. Those pieces of information include information indicating the reception timing of the signal (year and month, and time to the second) and meaning of the signal, for example, information such as "reception time: Jan. 15, 2014, 17:00:00, reduction of maximum instantaneous power consumption by 2%" in response to the power reduction instruction signal AS3 at a certain time point in the induction heating cooker 2. In the home electric appliance EE, for example, the induction heating cooker 2, the power limitation information of the home electric appliance is stored in time series in a storage device 32R of a controller 32, and is not deleted even when the main power is turned on or off. Turning on and then off the main power is considered as one time of cooking, and the information is stored for at least several times of cooking. The exceeded information is sequentially deleted automatically.

FIG. 1 is an example of a house to which the power control system according to Embodiment 1 is applied. The present invention is also applicable to a condominium, in addition to a detached house. In FIG. 1, reference symbol HA1 denotes a living space in the house. Reference symbol HA2 denotes an adjacent living space partitioned by a wall SB from the living space HA1. When the living spaces are collectively referred to, symbol HA is used. Although not shown in FIG. 1, the living space also includes a "bedroom", a "living room", and a "bathroom", and some rooms may include a toilet. Other rooms may also be included.

Power of, for example, 200 V is supplied to all the living spaces HA from a commercial power source EP of a power company, provided outside the house. The power is introduced into the house through a wattmeter 300. Reference symbol 27 denotes a power supply line (main line) connected to the commercial power source EP of 200 V via a circuit breaker BK. A television receiver (hereinafter referred to as "TV receiver") 75, an air-conditioning apparatus 7, an illumination apparatus 76, and an electric appliance for kitchen (hereinafter referred to as "kitchen electric appliance") KP are connected to the power supply line 27. Although, in FIG. 1, only one TV receiver (display device) 75, one air-conditioning apparatus 7, one illumination apparatus 76, and one kitchen electric appliance KP are illustrated, a plurality of those items may be provided.

Reference symbol 9 denotes a power instruction apparatus to which power is supplied through the circuit breaker BK. The power instruction apparatus 9 is installed on a wall at a position easily accessible by the family member, such as a wall of the living space HA2 (kitchen), or is placed on the floor. A plurality of other home electric appliances are also provided, such as a dish washer-dryer 6 and an automatic laundry-drying machine (not shown), which are subsequently described.

The home electric appliances utilized inside the household, such as the kitchen electric appliance KP and the air-conditioning apparatus 7, are collectively referred to as "home electric appliance" EE.

In the following description, the term "first home electric appliances" refers to the kitchen electric appliances KP other than the dish washer-dryer 6. The first home electric appliances each include a heating unit that consumes electric energy, and are each configured to be independently connected to and disconnected from the power source, and to receive a power reduction instruction from the power instruction apparatus 9 to be subsequently described.

In FIG. 1, reference symbol SL denotes a wall surface constituting the ceiling of the living space HA. Reference symbol 204 denotes a composite sensor (temperature and humidity sensor) configured to detect the temperature and the humidity in the living space HA2, which is an example of the environment sensor. Reference symbol 205 denotes a temperature and humidity sensor configured to detect the room temperature and the room humidity of the living space HA1, which is another example of the environment sensor. Reference symbol 206 denotes a temperature sensor installed outside the house, which also exemplifies the environment sensor. The sensors are hereinafter referred to as environment sensors 204, 205, and 206.

Those environment sensors 204, 205, and 206 including temperature sensors and humidity sensors are configured to transmit, wirelessly or via electrical signals, the measured temperature or humidity to the environment detection unit 202 (see FIG. 6) of the power instruction apparatus 9 to be subsequently described. The power source of the sensors may be a charged cell or power supplied through the power supply line 27. The power consumption of those sensors is as small as 1 watt (W) and hence the sensors are exceptions of the power limitation performed by the power instruction apparatus 9, even when the sensors are operated by power supplied through the power supply line 27. Therefore, the sensors continuously transmit measurement data to the power instruction apparatus 9 at a predetermined timing.

Although not shown, in addition to the temperature sensors and the humidity sensors, environment sensors such as a pollen sensor configured to measure the amount of pollen flying in the air, a dust sensor configured to measure the amount of dust per unit volume in the air, a noise sensor configured to detect the level of a noise in the room, and an illuminance sensor configured to detect the brightness of the room are provided at appropriate positions in each of the living spaces. Further, a temperature sensor and a humidity sensor configured to respectively detect the temperature and the humidity of an outdoor space or outside of the house may be provided in addition to the environment sensor 205. For example, the pollen sensor may be installed not only inside the room but also outside (e.g., outer wall surface of the house, outer frame of a window, and on a porch).

Figure 6:
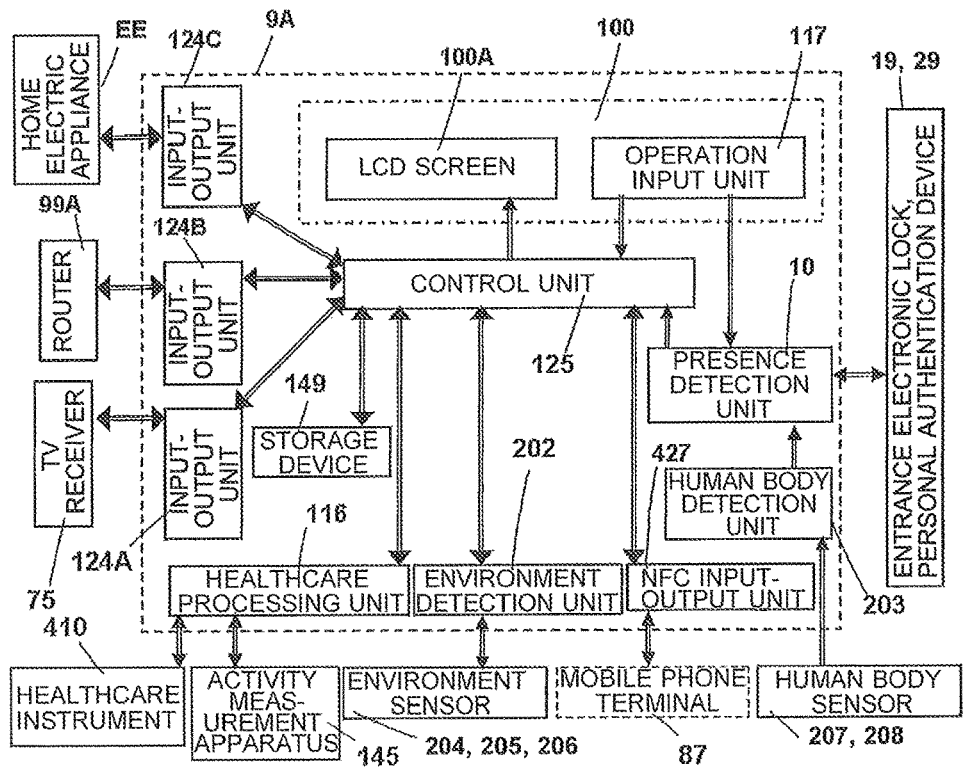
FIG. 6 is a block diagram for illustrating a configuration of the power control system according to Embodiment 1 of the present invention.

FIG. 6 is a block diagram for illustrating the configuration of the power control system according to Embodiment 1. In FIG. 1 and FIG. 6, reference symbol 207 denotes a human body sensor (human body detection sensor) configured to detect infrared rays naturally emitted from a human body to thereby detect whether or not a person is present in the living space HA1. Reference symbol 208 denotes another human body sensor (human body detection sensor) configured to detect infrared rays naturally emitted from a human body to thereby detect whether or not a person is present in the living space HA2. Such a human body sensor may also be installed in other living spaces HA. The human body sensors 207 and 208 are configured to transmit, wirelessly or via electrical signals, the detection result indicating whether a person is present to a human body detection unit 203 of the power instruction apparatus 9 to be subsequently described. The power source of the sensors may be a pre-charged cell or the power branched and supplied from the power supply line 27. The power consumption of those sensors is as small as 1 W to several watts, and hence the sensors are exceptions of the power limitation performed by the power instruction apparatus 9, even when the sensors are operated by power supplied through the power supply line 27. Therefore, the sensors continuously transmit measurement data to the power instruction apparatus 9 at a predetermined timing (e.g., every 10 seconds). The human body sensors 207 and 208 are not limited to infrared sensors, and other sensors such as ultrasonic sensors may be employed.

In FIG. 1, further, reference symbol 77 denotes an outdoor antenna connected to a tuner (not shown) of the TV receiver 75, and reference symbol 99A denotes a router connected to the power instruction apparatus 9. The router 99A connects, via a wide area communication network such as the Internet (may be referred to as "communication network" or "the Internet") 98, the power instruction apparatus 9 to an external organization 78A, e.g., power company or a regional earthquake information agency that distributes information to the region in which the house is located.

Reference symbol 99B denotes a router connected to the TV receiver 75. The router 99B connects the TV receiver 75 to another external organization 78B via the wide area communication network 98. The external organization 78B is, for example, a broadcast station that distributes broadcast programs, or a public agency or a private company that provides medical, healthcare, or activity measurement (activity management) information, but is not limited to such examples. The two external organizations 78A and 78B may be identical or different from each other.

The private company that provides the activity measurement information refers to, for example, an organization that provide full-scale training programs to those who are interested, and manages various types of data on activity (such as walking, running, dancing, and yoga) performed by those who are interested or on body composition balance (e.g., body fat rate) and calorie consumption due to activity of those who worked out. The above-mentioned private company further includes an organization that provides rehabilitation information for improving the motor function of a person with reduced motor function due to injury or disease.

Figure 2:
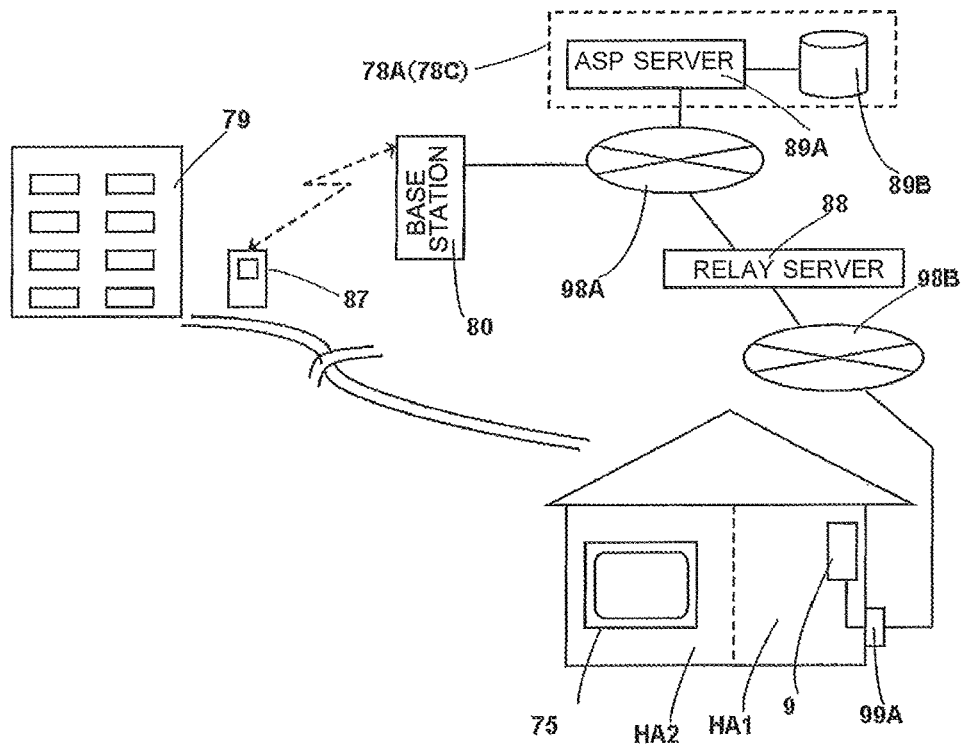
FIG. 2 is a conceptual diagram for illustrating a configuration of an external communication circuit to which the power control system according to Embodiment 1 of the present invention is connected.

Referring now to FIG. 2, a communication environment provided outside the household is described. FIG. 2 is a conceptual diagram for illustrating a configuration of an external communication circuit to which the power control system according to Embodiment 1 is connected. Although the power instruction apparatus 9 according to Embodiment 1 is connected through a network to the external organization 78A via the router 99A, a device generally known as a home gateway may be employed instead. In this case, the home gateway refers to a home-use device provided between digital information media such as the Internet, digital broadcasting, and an IP phone and terminals such as the power instruction apparatus 9 and the digital home electric appliances. The home gateway serves to control the power instruction apparatus 9 and other apparatus as part of the network and transmit information received from the communication or broadcasting medium to the power instruction apparatus 9 and the digital home electric appliances. Providers that supply the IP phone service and content distribution service in addition to the connection to the Internet, through the always-on broadband service, generally call the router rented to the occupant (user) of the household a "home gateway".

Although the power instruction apparatus 9 is connected to the external organization 78A via the wide area communication network 98 in FIG. 1, the wide area communication network 98 actually includes two parts 98A and 98B as illustrated in FIG. 2, and the power instruction apparatus 9 accesses an application service provider (ASP) server 89A of the external organization 78A through a relay server 88 and the wide area communication networks 98A and 98B. The ASP server 89A includes a database 89B configured to store various information to be subsequently described, with respect to a large number of households. The database 89B and the ASP server 89A may be collectively referred to as "information server" ISV in Embodiment 1.

The ASP server 89A functions as a control unit and is installed by the seller or the repairer of the home electric appliance EE or the provider of the information service, and serves to provide, to the user, various types of services related to the home electric appliance EE through the communication networks 98A and 98B. The database 89B also includes a user ID database for identifying the user and an application database storing application software for determining the controlling operation for the home electric appliance EE. The ASP server 89A may be what is generally called "web server". The web server refers to a service program that provides, based on HTTP (protocol used for exchanging data such as HTML documents and images between the web server and a web browser), display information such as HTMLs and objects (such as images) to the web browser of software on the information processing apparatus (client) side, which corresponds to an "information receiving side", such as various mobile phone terminals (information communication terminal devices) 87, the power instruction apparatus 9 having the information communication function and being located in each household, or other personal computers, and also refers to a server computer on which the service operates. The web browser is also referred to as "Internet browser" or "WWW browser", and is a browser to be used to access World Wide Web.

The user ID database stores user-specific information received from the user in the form of so-called user registration, such as the log-in ID and password for the ASP server 89A, setting information including the network address (MAC address) of the router A 99A, and "device-specific information" (including the "identification information" described above) such as the network address, the type, and the model of the specific home electric appliance EE. In other words, the user ID database stores a "user information database" (not shown) that accumulates user information of the home electric appliance EE.

The application database stores control application software that enables remote control of the power instruction apparatus 9 or the home electric appliance EE from outside the living space, for example, remote locations such as the workplace of the occupant and an outside location. With this, the remote control can be performed by accessing the ASP server 89A from the mobile phone terminal 87, which is an example of the information communication terminal device to be subsequently described, thereby downloading (reading) the control application software. The ASP server 89A stores "improved software" obtained by improving the operation program of the home electric appliance EE to be compatible with specific models of the home electric appliances EE. When the power instruction apparatus 9 acquires the improved software via the wide area communication network 98, the power instruction apparatus 9 provides the improved software to the home electric appliance EE via an input-output unit 124C (see FIG. 6).

The mobile phone terminal 87 in Embodiment 1 refers to a terminal device that can be easily carried by the user for making phone calls and performing data communication (including mail transmission) indoors or outdoors, or at a location away from home. A device unable to make a phone call but having the function of downloading information from the Internet, transmitting and receiving mails, and outputting a remote operation signal is referred to as "portable communication device". The "mobile phone terminal" 87 and the "portable communication device" are collectively referred to as "information communication terminal device". A small-sized portable personal computer is also an example of the information communication terminal device.

The "information communication terminal device" in Embodiment 1 has a function of transmitting and receiving signals via short range communication when being brought close to (or into contact with) the input-output unit of each home electric appliance EE within several centimeters. The short range communication is known as an international standard of wireless communication abbreviated as NFC.

In the NFC communication, a so-called wireless tag (NFC tag) is embedded in the home electric appliance EE. The NFC tag includes an NFC communication control IC (hereinafter referred to as "NFC control circuit") 321, an antenna 322 connected to the NFC control circuit 321 and configured to generate power for the NFC control circuit 321 upon reception of a wireless signal of a predetermined frequency from the outside, and a microchip memory (hereinafter referred to as "NFC storage unit") 320 connected to the NFC control circuit 321 (see FIG. 28).

Meanwhile, the information communication terminal device, e.g., the mobile phone terminal 87 can read data (acquire status information) from the NFC storage unit 320 of the home electric appliance EE via the NFC tag, or conversely, the information communication terminal device, e.g., the mobile phone terminal 87 can transmit the control data (also referred to as "control command") to the NFC storage unit 320 of the home electric appliance EE so that the controller 32 (also referred to as "host computer", see FIG. 28) of the home electric appliance EE can operate for control based on the control command stored in the NFC storage unit 320 (the NFC tag in such a form is sometimes called "active tag"). In other words, the NFC of Embodiment 1 has a function of not only reading out information stored in the internal storage device of the home electric appliance EE by the mobile phone terminal 87 (the NFC tag having such a function is sometimes called "simple tag"), but also activating the operation of the home electric appliance EE by the control command from the mobile phone terminal 87 or other devices. In other words, the mobile phone terminal 87 has a function of not only reading out various types of information from the home electric appliance EE, but also writing into the NFC storage unit 320, specifically, has two functions as a reader and a writer. It is said that NFC has advantages in that, in general, there is no limitation on the form of the data exchangeable via communication, and needless to say, text data but also moving images and XML data can be exchanged.

A base station 80 of the mobile phone terminal 87 is connected to the wide area communication network 98B via the relay server 88 and the communication network 98A, so that the mobile phone terminal 87 can access the ASP server 89A and the router A 99A through the base station 80. Accordingly, the occupant of the household can access the ASP server 89A upon connecting the occupant's mobile phone terminal 87 to the wide area communication network 98A from outside locations such as inside of a facility 79 of the occupant's workplace, located at a distant place as illustrated in FIG. 2, and perform the remote control of the power instruction apparatus 9 or the home electric appliance EE from the facility 79 away from the household by downloading the control application software therefor. In Embodiment 1, however, direct remote operation of the electric appliance EE from the mobile phone terminal 87 is disabled. This is because the home electric appliance EE includes appliances that generate high temperature such as the electric heating cooker (second specific home electric appliance SP2), and from the viewpoint of safety, the remote operation performed through the communication circuit which many people utilize outside the houses is not adopted, and all the operations are performed through the power instruction apparatus 9 instead. Inside the house, the mobile phone terminal 87 can only operate the TV receiver 75. The details of the remote control are subsequently described.

Figure 3:
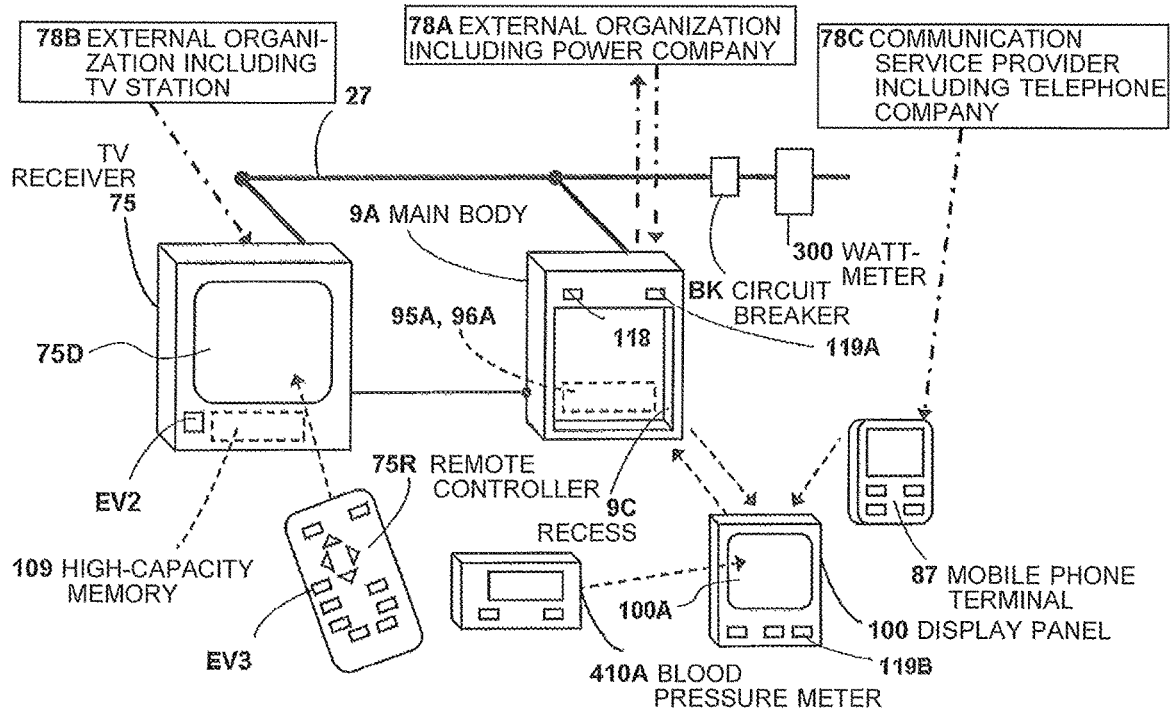
FIG. 3 is a configuration diagram for illustrating a power instruction apparatus and home electric appliances in the power control system according to Embodiment 1 of the present invention.

FIG. 3 is an example of a hardware configuration of the power instruction apparatus 9, the healthcare instrument 410, and so forth, included in the power control system according to Embodiment 1. In FIG. 3, reference symbol 9A denotes a main body of the power instruction apparatus 9, having a box shape. The main body 9A stores therein all of the components of the power instruction apparatus 9 illustrated in FIG. 23, such as a use limit setting device 96, a comparator 92, and a priority order setting unit 95 to be subsequently described. However, a display panel (display device) 100 of the use limit setting device 96 is removable from the main body 9A as illustrated in FIG. 3, and is fitted in a recess 9C formed in the front surface of the main body 9A when mounted thereto. Reference symbol 100A denotes an LCD screen of the display panel 100, and reference symbol 109 denotes a storage device (high-capacity memory) provided inside the TV receiver 75, such as a DVD, a semiconductor memory, or a hard disk drive (HDD). The surface of the display panel 100 is constituted of a touch panel, for example, to serve as a display unit configured to display information, as well as an operation unit configured to accept an input from the user made by touching the screen. As is subsequently described, the display panel 100 configured to display power use information includes an operation input unit 117 (see FIG. 6 and FIG. 20) of the use limit setting device 96 in the power instruction apparatus 9.

In FIG. 3, reference symbol 75R denotes the remote controller configured to operate the TV receiver 75, and reference symbol 410A denotes an electronic blood pressure measurement device (hereinafter referred to as "blood pressure meter") which is an example of the healthcare instrument 410. Reference symbol 87 denotes a high-function mobile phone terminal including a built-in microcomputer that is capable of performing high-speed digital communication, so as to make phone calls via a communication line, connect to a server of a communication service provider 78C such as a telecommunication company or the ASP server 89A, exchange e-mails with other persons, and download various pictures, music, content, and information. The mobile phone terminal 87 also includes a built-in pedometer, so that the user can count their number of steps simply by carrying the mobile phone terminal 87. The information of the number of steps counted by the mobile phone terminal 87 can be input to a healthcare processing unit 116 (see FIG. 4) in the power instruction apparatus 9 via a built-in infrared transmitter or other transmitters. Such an operation is subsequently described in further detail. The mobile phone terminal 87 has the NFC function as described above.

In FIG. 3, reference symbol EV2 denotes an operation button of an operation switch (not shown) for environment confirmation provided in the vicinity of the lower edge of an LCD screen 75D in the front surface of the TV receiver 75. Reference symbol EV3 denotes an operation button of an operation switch (not shown) for environment confirmation provided in the remote controller 75R for the TV receiver 75. When any of those two operation buttons is pressed, the TV receiver 75 is activated if not already activated, and the LCD screen 75D first displays a screen indicating various types of environment information to be subsequently described (illustrated in FIG. 15 or FIG. 16). In other words, without displaying a portal site screen (illustrated in FIG. 11) to be subsequently described, the environment states of all of the living spaces HA in the house can be quickly displayed in a list. Detailed operations of a case where those two operation buttons EV2 and EV3 of the operation switches (not shown) for environment confirmation are operated are subsequently described.

Reference symbol 118 denotes a confirmation button provided on the front surface of the main body 9A of the power instruction apparatus 9, at a position above the recess 9C. When the confirmation button is pressed with the display panel 100 removed from the main body 9A, a search signal is wirelessly output from the main body 9A, so that a receiver circuit (not shown) of the display panel 100 is activated upon reception of the signal and outputs a predetermined sound through an electronic buzzer (not shown). Accordingly, even when the location of the display panel 100 is unknown in the living space HM, the display panel 100 can be easily found by pressing the confirmation button 118.

Reference symbol 119A denotes an emergency cut-off button. When the emergency cut-off button 119A is pressed, the power supply to all of the home electric appliances currently in use (including the kitchen electric appliance KP), except the router 99A, the router 99B, the power instruction apparatus 9, the illumination apparatus 76, and the TV receiver 75 is immediately cut off. Therefore, the emergency cut-off button 119A is useful for immediately cutting off the power supply, for example upon reception of emergency earthquake information through a home electric appliance such as the TV receiver 75 when the display panel 100 is removed from the main body 9A. The display panel 100 itself includes a built-in rechargeable battery (not shown). The main body 9A includes therein a non-contact charger (not shown) located so as to oppose the wall surface of the recess 9C on the front surface of the main body 9A of the power instruction apparatus 9, and therefore the rechargeable battery is automatically charged when the display panel 100 is fitted and retained in the recess 9C on the front surface of the main body 9A of the power instruction apparatus 9.

Reference symbol 119B denotes another emergency cut-off button provided on the LCD screen 100A of the display panel 100. The emergency cut-off button 119B has the same function as the emergency cut-off button 119A. When the emergency cut-off button 119B is pressed, the power supply to all of the home electric appliances currently in use (including the kitchen electric appliance KP), except the power instruction apparatus 9, the illumination apparatus, and the TV receiver 75 can be immediately cut off.

Figure 4:
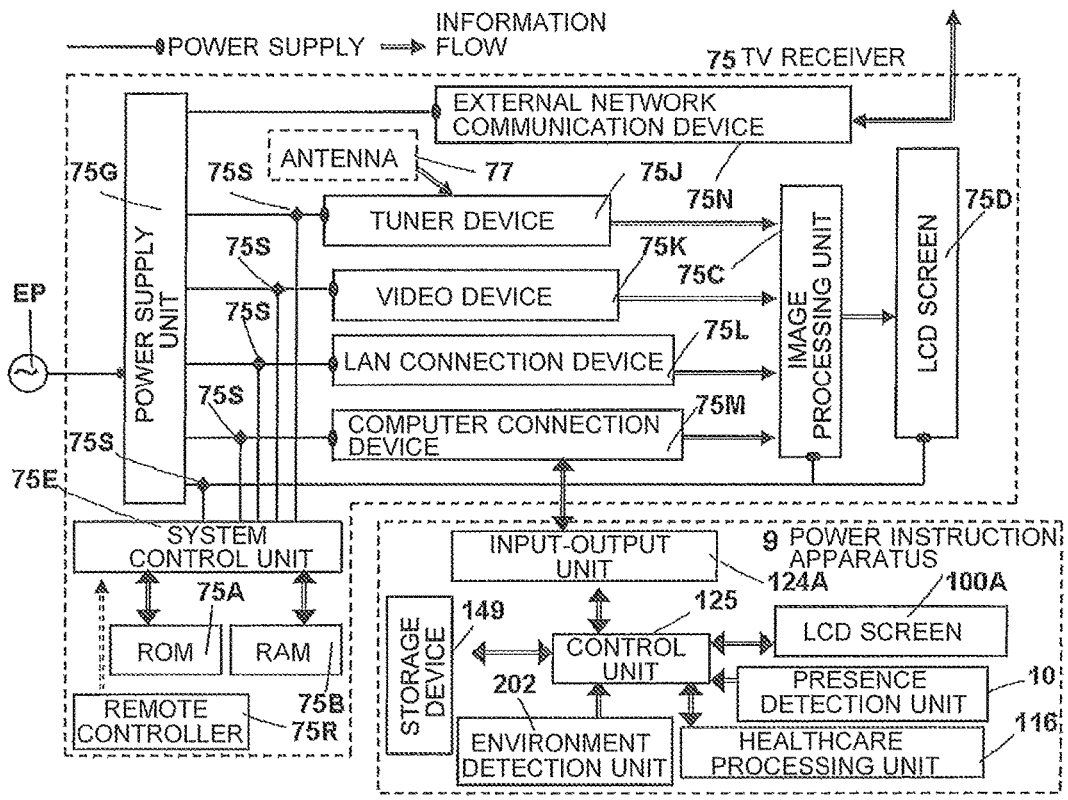
FIG. 4 is a block diagram for illustrating configurations of the power instruction apparatus and a TV receiver in the power control system according to Embodiment 1 of the present invention.
Figure 5:
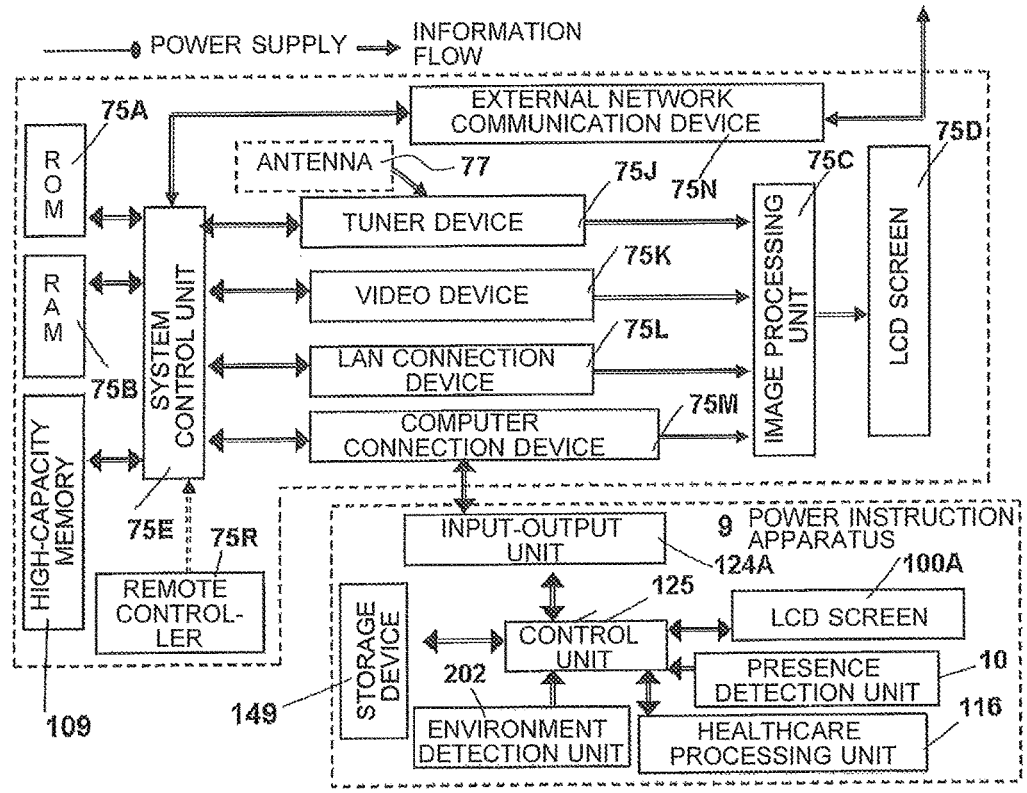
FIG. 5 is a block diagram for illustrating configurations of the power instruction apparatus and the TV receiver in the power control system according to Embodiment 1 of the present invention.

FIG. 4 and FIG. 5 are block diagrams for illustrating the internal configurations of the TV receiver 75 and the power instruction apparatus 9. The TV receiver 75 and the power instruction apparatus 9 are described with reference to FIG. 1 to FIG. 4. The TV receiver 75 includes a read-only memory (ROM) 75A, a random access memory (RAM) 75B, an image processing unit 75C, an LCD screen 75D, a system control unit 75E constituted of a microcomputer, a power supply unit 75G connected to the commercial power source EP via the circuit breaker BK, four input-output functional devices 75J, 75K, 75L, and 75M, power field effect transistors (FETs) 75S, which are an example of a semiconductor element for power control, interposed between the power supply unit 75G and the input-output functional devices 75J, 75K, 75L, and 75M, and an external network communication device 75N.

The system control unit 75E performs signal processing operation of the components of the TV receiver 75 and controls the four input-output functional devices 75J, 75K, 75L, and 75M described above, in accordance with control programs stored in the ROM 75A and RAM 75B. Further, the system control unit 75E controls the input-output functional device 75M upon reception of a specific signal from the power instruction apparatus 9, and provides data specified by the power instruction apparatus 9 from among data stored in the storage device (high-capacity memory) 109 to a control unit 125 of the power instruction apparatus 9 via an input-output unit 124A to be subsequently described.

The four input-output functional devices 75J, 75K, 75L, and 75M are now described. Reference symbol 75J denotes a tuner device configured to receive broadcast waves such as ground waves and satellite waves through the outdoor antenna 77. Reference symbol 75K denotes a video device configured to record and play videos. Reference symbol 75L denotes a LAN connection device configured to process information from devices connected via a LAN. Reference symbol 75M denotes a computer connection device via which a personal computer (hereinafter referred to as "computer") is connected. Different types of input-output functional devices may be additionally provided. For example, a card device may be provided so as to enable the use of a card-type memory such as an SD card, which is a semiconductor recording medium.

As described above, the power FET 75S is inserted between the output terminal of the power supply unit 75G and the power input terminal of each of the four input-output functional devices 75J, 75K, 75L, and 75M. The activation control of the power FET 75S is performed by the output signal of the system control unit 75E. The power supply of each of the four input-output functional devices 75J, 75K, 75L, and 75M can be optionally disconnected by the user. To be more precise, a selection switch (not shown) that can individually disconnect the power supply to the input-output functional devices 75J, 75K, 75L, and 75M may be provided at a predetermined position of the TV receiver 75, or a so-called on-screen switch may be provided on the LCD screen 75D so as to be able to select the input-output functional device to be disconnected, with the remote controller 75R described above.

The power FET 75S described above is not provided between the external network communication device 75N and the power supply unit 75G. In other words, the system control unit 75E performs control so as to prevent the power supply to the external network communication device 75N from being arbitrarily disconnected by the operation of the user, and therefore while the TV receiver 75 is receiving the main power supply, the TV receiver 75 is constantly connected to the external organization 78B by means of the external network communication device 75N via the wide area communication network 98 located outside the house, even if the LCD screen 75D is not turned on and no image is displayed thereon. Accordingly, when emergency information from the external organization 78B, such as request information for prompt reduction of the upper limit of the total electric power of the household for total electric power cut (so-called "peak cut") during the daytime in summer, or emergency earthquake information from the meteorological agency, or a regional disaster prevention center or an earthquake warning center in charge of the living region, is transmitted to the TV receiver 75, the occupant present in the living space HM can be promptly aware of such information. Here, various proposals have thus far been made regarding a TV receiver configured to be turned on by the transmission of such emergency cut-off information and announce the information even when the TV receiver 75 is off, and detailed description of such a system is omitted.

The TV receiver 75 includes exclusive circuits each constituted of an LSI, to which the latest digital signal processing techniques and semiconductor techniques are applied, with respect to each of the functions of the input-output signals as exemplified by the four input-output functional devices 75J, 75K, 75L, and 75M, so that the TV receiver 75 realizes high performance at a relatively low cost. However, because a plurality of high-performance LSIs are incorporated, the power consumption of the TV receiver 75 may be increased. Embodiment 1 is configured, therefore, such that the power supply to one or more of the input-output functional devices 75J, 75K, 75L, 75M that are unused and do not need the power supply can be turned off, on the assumption that the user does not utilize all of the input-output functional devices 75J, 75K, 75L, and 75M incorporated in the TV receiver 75 at a time. In other words, the user is able to turn on and off the power supply to each of the input-output functional devices 75J, 75K, 75L, and 75M, so as to positively reduce the power consumption. For the purpose of the activation control of the power supply, the power FET 75S is inserted in the power supply circuit of each of the input-output functional devices 75J, 75K, 75L, and 75M.

The above-mentioned configuration allows the power supply to the input-output functional devices such as the tuner device 75J and the video device 75K in the TV receiver 75 to be kept off, even when the TV receiver 75, installed in the living space, e.g., the living room where the occupants gather, is set to display, instead of the display screen unit (display panel) 100 of the power instruction apparatus 9, the power supply-related information from the power instruction apparatus 9, such as the current total power usage in the household, and information indicating that a power reduction request has been received from outside. Thus, the power consumption of the TV receiver 75 can be minimized even when the TV receiver 75 is utilized for power control.

In FIG. 4 and FIG. 5, reference symbol 124A denotes an input-output unit for connecting the power instruction apparatus 9 to the input-output functional device (computer connection device) 75M of the TV receiver 75, and reference symbol 125 denotes a control unit of the power instruction apparatus 9, which is configured to intensively control the use limit setting device 96 (and other components illustrated in FIG. 23, such as the comparator 92 and the priority order setting unit 95) of the power instruction apparatus 9, and instruct the home electric appliance to transmit a power reduction request signal AS2 and a power reduction instruction signal AS3. Reference symbol 149 denotes a storage device including a pair of semiconductor memories 95A and 96A for power control to be subsequently described, in which the information related to power control, the healthcare information, and the activity measurement information are stored in separate storage regions at respective exclusive addresses. The storage device 149 may be a random access memory (RAM) or a hard disk. The storage device 149 may also be a USB memory, a CD, a DVD, or an optical card, or a different type of memory provided that the memory is of a non-volatile type that maintains the stored content even when the power supply is disconnected. The memory 96A stores information of the total power usage upper limit specified in the circuit breaker BK, data on power usage upper limit for restricting the power consumption of the home electric appliances EE, and information of the upper power limit specified with respect to each of the occupants.

In FIG. 6, reference symbol 124B denotes an input-output unit for receiving information from the router 99A and transmitting information from the power instruction apparatus 9 to the wide area communication network 98A through the router 99A. Reference symbol 124C denotes an input-output unit for transmitting and receiving information between the power instruction apparatus 9 and the home electric appliance EE. The control unit 125 outputs various instruction signals to power usage control devices (power usage control units) 8A to 8E to be subsequently described via the input-output unit 124C. When the electric appliance EE is configured to read specific computer program software for improving the operation program of the electric appliance EE acquired via the Internet by the power instruction apparatus 9, it is convenient if the input-output unit 124C also has a function of communicating with the power instruction apparatus 9. For example, the improved software for the operation program in the controller 32 of the induction heating cooker 2 to be subsequently described can also be provided from the power instruction apparatus 9 via the input-output unit 124C.

In FIG. 4 to FIG. 6, reference symbol 202 denotes an environment detection unit configured to receive information of temperature and humidity measured by the environment sensors 204, 205, and 206. Reference symbol 203 denotes a human body detection unit configured to receive human body detection information from the human body sensors 207 and 208. Although not shown, each of the living areas described above includes the sensor configured to detect the degree of dust scattering in the space, the pollen scattering amount sensor, the illuminance sensor configured to detect the light amount (visible light amount), and the noise sensor, and the environment detection unit 202 is configured to receive the detection information from the above-mentioned environment sensors. Here, the illuminance sensor serves to distinguish whether the living space is bright or dark, and hence, for example, when the illuminance sensor indicates that a living space where the human body detection unit 203 determines that no occupant is present is bright, it is possible that the occupant has forgotten to turn off the illumination apparatus 76. In such a case, accordingly, the control unit 125 of the power instruction apparatus 9 recommends the user (through the display panel 100 or the LCD screen 75D of the TV receiver 75) to turn off the illumination apparatus 76 from the viewpoint of energy saving, even if the total power usage at that time point is well below the upper limit specified by the use limit setting device 96. Then the control unit 125 of the power instruction apparatus 9 outputs a turn-off instruction signal to the illumination apparatus (provided that the illumination apparatus is connected to the power instruction apparatus 9 as object of power reduction). FIG. 21 is an explanatory diagram for showing appliances that are objects of power reduction by the power instruction apparatus and appliances that are objects of power cut-off upon reception of an Earthquake Early Warning, in the power control system in Embodiment 1.

In FIG. 6, reference symbol 10 denotes the presence detection unit (also referred to as "presence detection device"), configured to receive a detection signal indicating whether presence of a person has been detected, from the human body detection unit 203. In addition, an electronic lock 19 is provided outside the entrance (not shown), which is the doorway common to all of the living spaces HA. The electronic lock 19 includes a personal authentication device 29 configured to detect that the occupant has come home, based on the PIN code or biological information (e.g., fingerprint information) input to the electronic lock 19. The personal authentication device 29 determines whether the person is the occupant based on the password input by the occupant, and the determination result is transmitted to the presence detection unit 10. Here, the electronic lock 19 electronically locking the entrance door and the personal authentication device 29 are only briefly described because many proposals have thus far been made regarding those devices. In Embodiment 1, the four occupants A to D are each given an exclusive password. The rule of the password is, for example, "4-digit number common to all the occupants plus 2-digit number" and should be given to all of the occupants. Thus, the password of the occupant A is "123401", the password of the occupant B is "123402", and the password of the occupant A is "123403". The password is input through 10 input keys (ten key) provided at the electronic lock 19 of the entrance door.

When the occupant goes out through the entrance after inputting the password and entering the living space, it is not necessary to input the password. However, in a case where the human body detection unit 203 does not detect the presence of the occupant in any of the living spaces HA for a predetermined period of time (e.g., 30 minutes), the presence detection unit 10 determines that all of the occupants are away from home, and deletes all the password input records of the occupants input so far and shifts the detection information from the presence state to the absence state. Accordingly, when the occupant comes home thereafter, the occupant has to input the password again. Here, inputting the information that the occupant is going out to the personal authentication device 29 when the occupant goes out of the entrance improves the accuracy of the presence detection. Further, as described above, instead of inputting the password, the coming home of the occupant may be detected based on the biological information (e.g., fingerprint information), or by causing the personal authentication device 29 to directly read, magnetically or optically, the personal identification information recorded on the specific ID paper or ID card owned by the occupant, the detailed description of which is however omitted.

In FIG. 6, reference symbol 427 denotes a wireless input-output unit for the NFC, which is an input-output unit for transmitting and receiving information when a wireless communication unit (also referred to as "wireless input-output unit", not shown) of the mobile phone terminal 87 is brought close to the wireless input-output unit 427 within a predetermined distance (about 10 centimeters) to enter a communication establishment state that enables transmission and reception of information (corresponding to the start of one communication session). The wireless input-output unit 427 constantly displays "NFC" in letters in the vicinity of the lower and outer side of the operation input unit 117 (of the use limit setting device 96) of the display panel 100 in the power instruction apparatus 9 so that the installation position of the wireless input-output unit 427 is clear (see FIG. 20).

Figure 7:
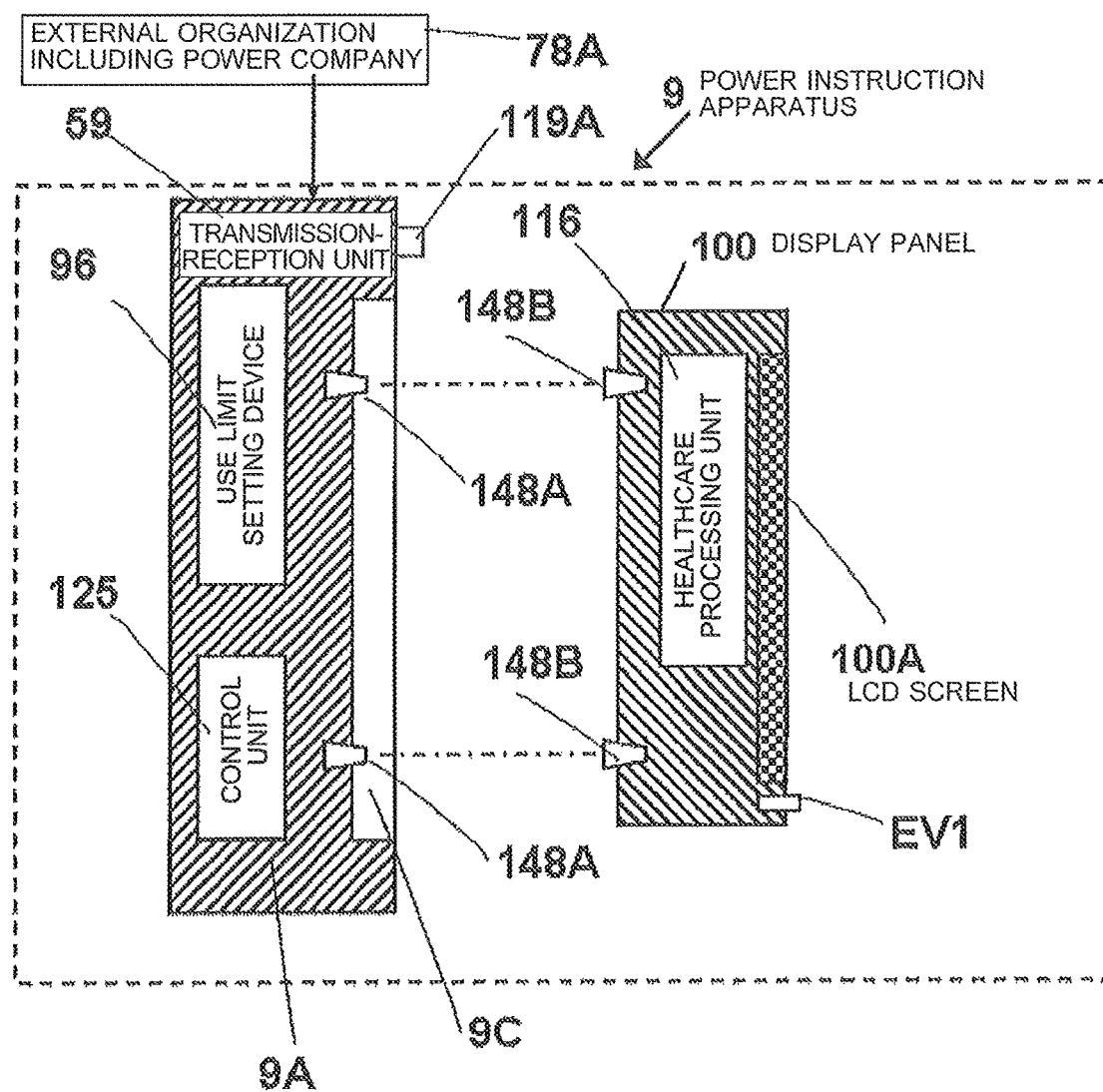
FIG. 7 is a block diagram for illustrating, partially in a vertical cross section, a configuration of a power instruction apparatus main part of the power control system according to Embodiment 1 of the present invention.

FIG. 7 is a block diagram for illustrating, partially in a vertical cross section, the configuration of the main part of the power instruction apparatus 9 illustrated in FIG. 1 to FIG. 5. In FIG. 7, reference symbol 9A denotes the main body of the power instruction apparatus 9 described above. Reference symbol 148A denotes two or more projections respectively formed at an upper position and a lower position in the recess 9C, and reference symbol 148B denotes recesses formed at positions respectively opposing the projections 148A. When the display panel 100 is inserted into a predetermined position in the recess 9C, the projections 148A are fitted in the respective recesses 148B, so that the display panel 100 is retained so as not to readily come off. When the projections 148A and the recesses 148B are fitted to each other, the control unit 125 detects the fitting by signals output from sensing switches (e.g., combination of a magnet and a switch configured to output a signal upon sensing the magnetism) provided on the projection 148A and the recess 148B.

The control unit 125 wirelessly outputs to the display panel 100, a display signal to be displayed on the LCD screen 100A of the display panel 100 and a voice instruction signal for a voice guidance device (not shown) provided inside the display panel 100. Accordingly, even when the display panel 100 is separated from the main body 9A of the power instruction apparatus 9, the display signal and the voice instruction signal can reach the display panel 100 provided that the display panel 100 is located inside the living space HM. Conversely, an input signal is wirelessly transmitted from the display panel 100 to the main body 9A of the power instruction apparatus 9, so that the input signal is recognized by the control unit 125. Such transmission and reception of the wireless signals is performed through input-output units (not shown).

As illustrated in FIG. 6 and FIG. 7, the power usage status of the region in which the household is located, in particular power shortage information, is provided to the main body 9A of the power instruction apparatus 9, from the external organization 78A such as a power company through the wide area communication network 98 and the router 99A. Thus, the main body 9A of the power instruction apparatus 9 is configured to automatically receive a signal, for example, requesting power reduction, from the power company or other public agencies.

In FIG. 3, reference symbol EV2 denotes the press-button operation button of the instruction switch (not shown) for environment confirmation, which is provided in the vicinity of the lower edge of the LCD screen 75D in the front surface of the TV receiver 75. Reference symbol EV3 denotes the operation button of the instruction switch (not shown) for environment confirmation, which is provided in the remote controller 75R of the TV receiver 75. When any of those two operation buttons EV2 and EV3 is pressed, the TV receiver 75 is activated if not already activated, and the LCD screen 75D first displays the screen indicating various types of environment information to be subsequently described (illustrated in FIG. 15 or FIG. 16). Therefore, without displaying the portal site screen (illustrated in FIG. 12) to be subsequently described, the environment states of all of the living spaces HA in the house can be quickly confirmed. Detailed operations of a case where those two operation buttons EV2 and EV3 of the operation switches (not shown) for environment confirmation are operated are subsequently described.

Figure 8:
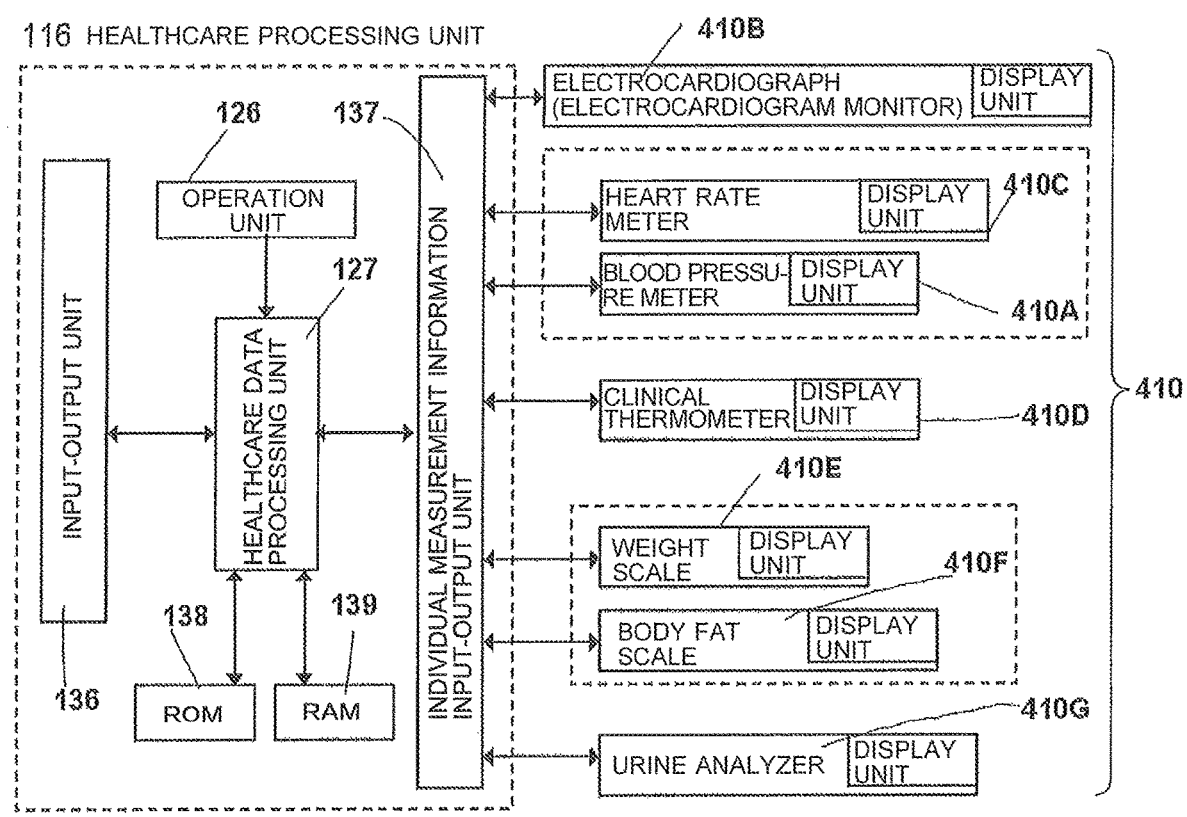
FIG. 8 is a block diagram for illustrating configurations of a healthcare processing unit of the power instruction apparatus and various healthcare instruments in the power control system according to Embodiment 1 of the present invention.
Figure 9:
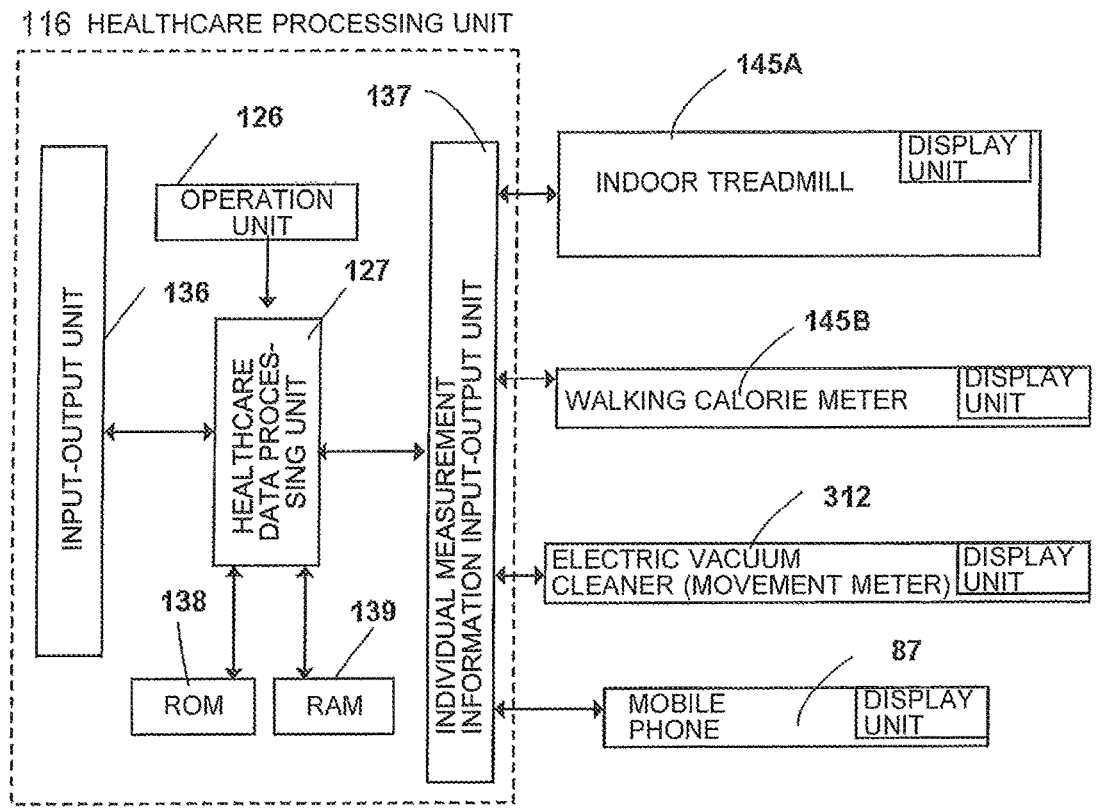
FIG. 9 is a block diagram for illustrating configurations of the healthcare processing unit of the power instruction apparatus and various indoor activity apparatus, an electric vacuum cleaner, and a mobile phone unit according to Embodiment 1 of the present invention.
Figure 20:
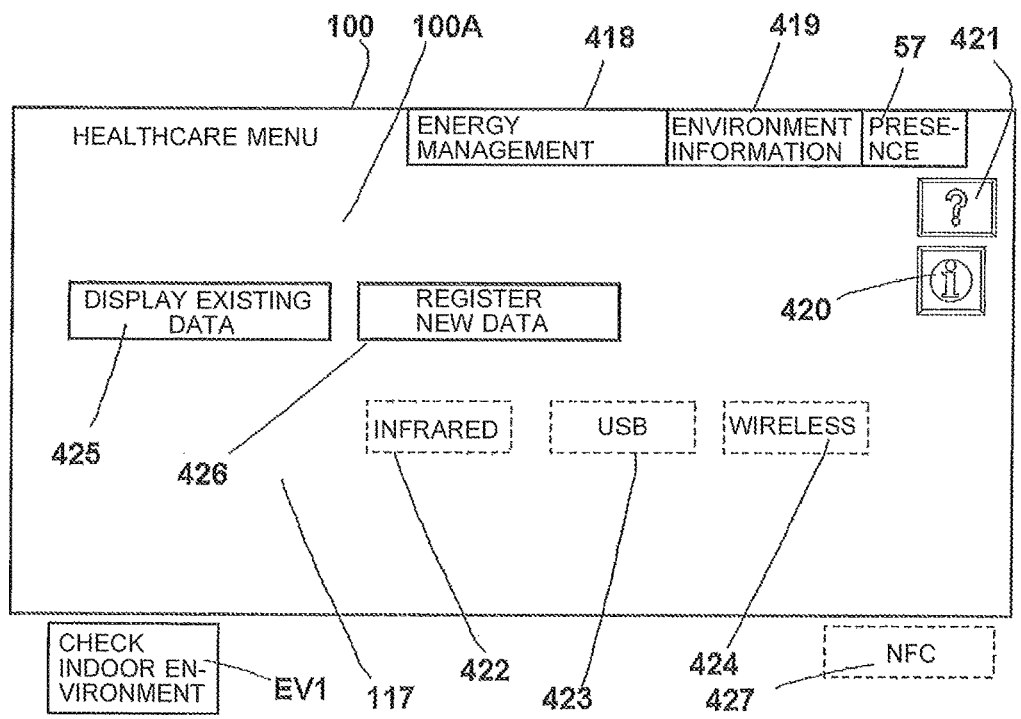
FIG. 20 is a front view for illustrating a display screen of a use limit setting device of the power instruction apparatus constituting a main part of the power control system illustrated in FIG. 1 to FIG. 19.

FIG. 8 and FIG. 9 are block diagrams each for illustrating a configuration of the healthcare processing unit 116 and the various healthcare instruments 410 in the power instruction apparatus 9. In FIG. 8 and FIG. 9, reference symbol 126 denotes an operation unit through which the user inputs various types of information and instructions to the healthcare processing unit 116. For example, to cause the healthcare processing unit 116 to read measurement data of the healthcare instrument to be subsequently described, on-screen switches (corresponding to "icons" to be subsequently described) are displayed on the LCD screen 100A as illustrated in FIG. 20, so that the user can make an input by selecting one of the on-screen switches. Thus, the LCD screen 100A can be utilized by the user to input various types of information and instructions to the healthcare processing unit 116, like the operation input unit 117 of the use limit setting device 96 in the power instruction apparatus 9. Instead of the on-screen switches, for example, touch keys of a static capacitance detection type that enable the user to make an input by touching the LCD screen 100A may be employed.

In FIG. 8 and FIG. 9, reference symbol 127 denotes a healthcare data processing unit configured to process measurement data of the healthcare instrument 410 to be subsequently described. The healthcare data processing unit 127 stores the measurement data of each subject in a memory (RAM) 139, and adds caution information when the measurement data read out from the RAM (memory) 139 and processed indicates a value exceeding a predetermined value, and also converts the measurement data into a graphic conversion signal to generate a table or graph. A ROM 138 stores processing formats of the measurement data and processing programs such as calculation programs for statistical processing.

FIG. 14 is an explanatory diagram for showing configurations of blood pressure data and incidental data acquired by the healthcare instrument used in the power control system according to Embodiment 1. The healthcare data processing unit 127 is configured to process the code for identifying the used healthcare instrument 410, information for identifying the category (e.g., blood pressure) and the subject of the measured measurement data, and information such as measurement date and time, measurement values, and whether or not the values are normal, into matrix-format data as shown in FIG. 14, and to temporarily store the data subjected to the processing in the RAM 139. The healthcare data processing unit 127 is also configured to transfer the measurement data to the storage device 149 of the power instruction apparatus 9 so that the storage device 149 stores the data. When the healthcare data processing unit 127 processes, for example, the blood pressure measurement data of the blood pressure meter (electronic blood pressure meter) 410A to be subsequently described, a blood pressure range of 135 mmHg to 85 mmHg is set as a normal zone in advance, so that the healthcare data processing unit 127 adds, when the blood pressure data from the blood pressure meter 410A is deviated from the normal zone, caution information (caution code) to the data as incidental information. In addition, the user may input in advance a normal zone or a normal value to the blood pressure meter 410A, so that the blood pressure meter 410A transmits the data to the healthcare data processing unit 127 together with some kind of incidental information, when the measurement value is deviated from the zone or value. The above-mentioned process is only required to be performed by adopting a uniform data processing method between the healthcare data processing unit 127 and the healthcare instruments such as the blood pressure meter 410A, and therefore detailed description is omitted.

Reference symbol 136 denotes an input-output unit for connection to the main body 9A of the power instruction apparatus 9, and reference symbol 137 denotes an information reception unit configured to receive the measurement data from the healthcare instruments. In FIG. 8, the healthcare instruments 410 are seven measurement instruments including, for example, the electronic blood pressure meter (hereinafter referred to as "blood pressure meter") 410A, an electrocardiograph 410B, a heart rate meter 410C, a clinical thermometer 410D, a weight scale 410E, a body fat scale 410F, and a urine analyzer 410G, which respectively provide seven types of measurement data to be subsequently described.

Figure 10:
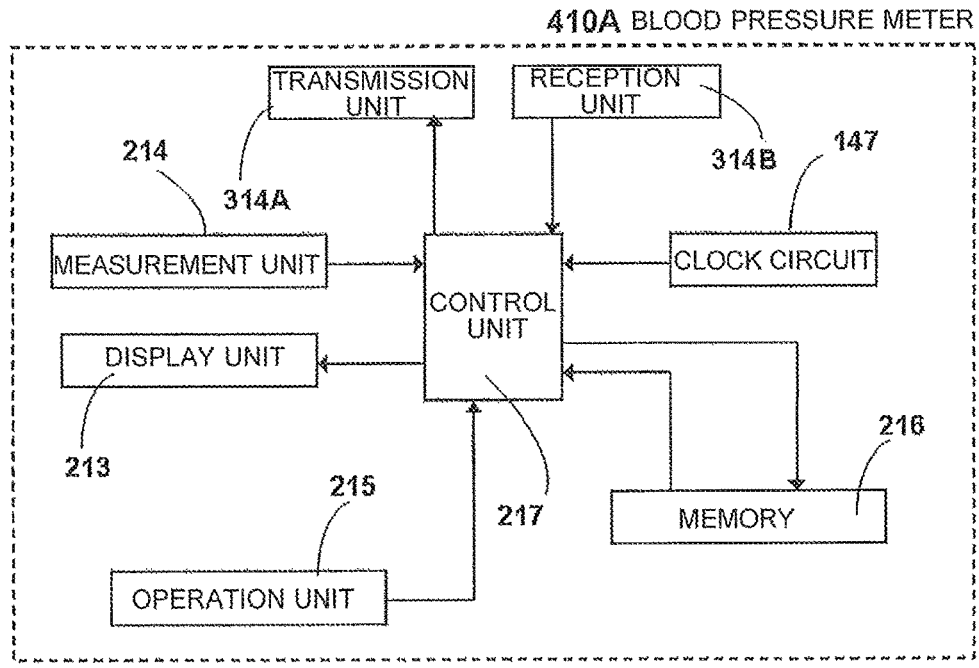
FIG. 10 is a block diagram for illustrating an internal configuration example of an electronic blood pressure meter being an example of the healthcare instruments used for the power instruction apparatus according to Embodiment 1 of the present invention.

FIG. 10 is a block diagram for illustrating a configuration of the blood pressure meter 410A, a typical example of the healthcare instrument 410. In FIG. 10, reference symbol 214 denotes a measurement unit for blood pressure, reference symbol 213 denotes a display unit configured to display the measured blood pressure in figures, and reference symbol 215 denotes an operation unit configured to instruct, for example, starting of the blood pressure measurement. The operation unit 215 includes an input key (not shown) for use to input the healthcare identification data (e.g., 3-digit number) of the subject before the measurement for identifying the subject. The blood pressure meter 410A serves to measure the blood pressure of an artery with a cuff wound around the wrist or arm of the user or an arm cylinder in which the user inserts the arm, and includes the measurement unit 214, a clock circuit 147, the display unit 213, the operation unit 215, a memory 216, a control unit 217, a transmission unit 314A, and a reception unit 314B. The blood pressure refers to the blood pressure in a systole phase and a diastole phase, which are respectively called systolic blood pressure (highest blood pressure) and diastolic blood pressure (lowest blood pressure). The measurement result is displayed, for example, as 140 mmHg (millimeter of mercury). The unit "mmHg" may be omitted, and the highest blood pressure and the lowest blood pressure may be displayed together, such as 140-80. The display unit 213 is, for example, an LCD unit configured to display the measurement result of the blood pressure in figures.

In FIG. 8, reference symbol 410B denotes the electrocardiograph. The electrocardiogram is a graphic record of the electrical activity of the heart which is useful for diagnosis and treatment of heart disease, and is widely used in the daily practice of medical institutions. The electrocardiograph 410B also includes a display unit, such as an LCD unit, configured to display the measurement result in the form of a graph.

In FIG. 8, reference symbol 410C denotes the heart rate meter. The heart rate refers to the number of times that the heart beats per unit time, normally per minute. When the heart pumps out blood, blood pulsation is generated in the artery, and the number of such pulsations is called pulse rate, or simply pulse. The heart rate can be simultaneously measured with the blood pressure meter 410A, and hence the heart rate meter and the blood pressure meter are integrated in many cases. The heart rate meter also includes a display unit, such as an LCD unit, configured to display the measurement result in figures. The heart rate meter 410C may be incorporated in a part of an activity measurement apparatus 145 to be subsequently described.

In FIG. 8, reference symbol 410D denotes the clinical thermometer. The clinical thermometer 410D also includes a display unit, such as an LCD unit, configured to display the measurement result in figures. The clinical thermometer may be incorporated in a part of the activity measurement apparatus 145 to be subsequently described.

Reference symbol 410E denotes the weight scale. The weight scale 410E also includes a display unit, such as an LCD unit, configured to display the measurement result in figures.

In FIG. 8, reference symbol 410F denotes the body fat scale. The body fat scale 410F also includes a display unit, such as an LCD unit, configured to display the measurement result in figures. The body fat scale 410F serves to measure the ratio of fat to the human body (body fat rate), that is, the amount of fat in the body (ratio of fat to the body weight). As the body fat scale 410F, body fat scales that can easily measure the body fat rate by means of a measurement method utilizing the difference in impedance between fat and other components of the human body are commercially available. In addition, some body fat scales include an element configured to detect body weight, which is mounted to an electrode plate for use to measure the impedance of the human body, so as to also measure the body weight at the same time.

In FIG. 8, reference symbol 410G denotes the urine analyzer. A urine examination is generally roughly classified into examination of the color, specific weight, and so forth of the urine itself, and analysis of the components of the urine. In Embodiment 1, the urine analyzer 410G measures whether the urine is acid or alkaline, in the component analysis, because it is known that it is unfavorable if the urine is biased to either acid or alkaline.

It is known that the urine of a person with insufficient vegetable intake tends to be acidic, and the configuration in Embodiment 1 provides such healthcare information to the person who cooks at home through the power instruction apparatus 9. It is preferable that the urine analyzer 410G be incorporated, for example, in a toilet bowl in advance, for the sake of convenience. The urine analyzer 410G also includes a display unit, such as an LCD unit, configured to display the measurement result in figures.

The healthcare instruments 410 may include other measurement instruments than the above-mentioned seven measurement instruments 410A to 410G. A plurality of the cited instruments may be integrated so as to perform multiple functions. The urine analyzer 410G is incorporated in the toilet bowl as described above, and hence the user is unable to freely carry the urine analyzer unlike the blood pressure meter 410A. Therefore, the urine analyzer 410G includes a transmitter (not shown) configured to wirelessly transmit the measurement data to the healthcare processing unit 116 provided in the display panel 100 of the power instruction apparatus 9.

The healthcare instrument 410 may also have the NFC function (short range communication function) as in the mobile phone terminal 87, so that the measurement data may be transmitted via short range communication by the NFC function to the healthcare processing unit 116 built into the display panel 100 of the power instruction apparatus 9.

Referring to FIG. 9, the activity measurement apparatus 145 includes two apparatuses, that is, an indoor treadmill (indoor activity measurement apparatus) 145A and a running calorie meter 145B. The indoor treadmill 145A is installed in the living space HM, and performs calculation based on the product of a period of time that the subject (user) has been running and the body weight of the subject. A calorie consumption calculation program, for example, based on the knowledge that a person having a body weight of 65 kg burns through exercise approximately 480 kcal by jogging for an hour at 120 meters per minute, is incorporated, and when the subject inputs the body weight data and performs the exercise, the calorie consumption is automatically calculated when the subject finishes the exercise.

The running calorie meter 145B also calculates the calorie consumption of the subject based on a similar principle to that of the indoor treadmill 145A. In the case where the running calorie meter 145B has the function of measuring the body weight, the calorie consumption is automatically calculated without the need for the subject to input the body weight. The indoor treadmill 145A and the running calorie meter 145B each include a display unit, such as an LCD unit, configured to display the calorie consumption as a result of exercise in figures.

In FIG. 9, reference symbol 312 denotes a (manual) electric vacuum cleaner, which has a movement measurement function in addition to its original dust suction function, so as to calculate the calorie consumption as a result. Therefore, the electric vacuum cleaner 312 serves not only as the home electric appliance EE, but also as an example of the activity measurement apparatus 145. The activity measurement apparatus 145 and the healthcare instrument 410 are not an object of power reduction of the power instruction apparatus 9, but the electric vacuum cleaner 312 also serves as the home electric appliance EE, and is exceptionally an object of power reduction.

The main body of the electric vacuum cleaner 312 includes therein a movement amount meter (movement meter) configured to sum the forward and backward movement amounts of the vacuum cleaner, and a calculation unit (not shown) configured to calculate calories burned through activity based on information indicating the movement distance detected by the movement amount meter and the weight of the main body of the electric vacuum cleaner 312.

The movement amount meter is configured to calculate the calorie consumption along with the cleaning operation of the user cleaning the room.

The main body of the electric vacuum cleaner 312 includes therein a wireless transmitting unit (not shown) and a control unit (not shown), and has a function of automatically and wirelessly transmitting data of the calorie consumption calculated by the calculation unit to the healthcare processing unit 116 of the power instruction apparatus 9. The timing to wirelessly transmit the data of the calorie consumption is a time point at which the usage of the electric vacuum cleaner 312 is finished. At the time point at which the usage of the electric vacuum cleaner 312 is finished, the control unit (not shown) in the main body of the electric vacuum cleaner 312 detects that the main power of the electric vacuum cleaner 312 is turned off, and instructs the wireless transmitting unit (not shown) to wirelessly transmit the data of the calorie consumption accumulated until the main power was turned off.

In the blood pressure meter 410A illustrated in FIG. 10, reference symbol 217 denotes the control unit configured to combine the blood pressure data measured by the measurement unit 214 with data of the date and time of the blood pressure measurement transmitted from the clock circuit 147 and the healthcare identification data (code), and to record such set of data in the memory 216. Reference symbol 314A denotes the transmission unit configured to transmit the blood pressure measurement data accumulated in the memory 216 to the outside, for example, via an infrared ray signal or a specific low power wireless signal. Reference symbol 314B denotes the reception unit configured to receive the blood pressure measurement data similarly transmitted from another device via an infrared ray signal or a wireless signal, and the measurement data received by the reception unit 314B is associated with the healthcare identification data of the subject by the operation unit 215 and is stored in the memory 216. The memory 216 is a semiconductor memory that retains the storage content regardless if the power is turned off.

The control unit 217 of the blood pressure meter 410A illustrated in FIG. 10 has the following functions. At the time point at which the user turns on the main power of the blood pressure meter 410A, the control unit 217 immediately and wirelessly transmits a predetermined "usage notice signal" 410Y from the transmission unit 314A to the healthcare processing unit 116 of the power instruction apparatus 9. The time point at which the main power is turned on can be recognized by the control unit 217 detecting that the user (subject) has operated the operation unit 215.

The control unit 217 further has the following functions. At a time point at which the user starts measurement of the blood pressure by the measurement unit of the blood pressure meter 410A, the control unit 217 immediately and wirelessly transmits a predetermined "usage start signal" 410S from the transmission unit 314A to the healthcare processing unit 116 of the power instruction apparatus 9. At a time point at which the measurement of the blood pressure is finished, the control unit 217 immediately and wirelessly transmits a predetermined "usage finish signal" 410F from the transmission unit 314A to the healthcare processing unit 116 of the power instruction apparatus 9. In other words, the power instruction apparatus 9 can detect the measurement operation before starting the measurement of the blood pressure. The power instruction apparatus 9 detects the three signals of the usage notice signal 410Y, the usage start signal 410S, and the usage finish signal 410F, and acquires the environment information of the living space HA before the measurement of the blood pressure from the environment detection unit 202. This point is a conspicuous feature of Embodiment 1.

The healthcare instrument 410 of Embodiment 1 is not driven by the commercial power source EP, and thus is not an apparatus whose electric power is to be controlled by the power instruction apparatus 9. The healthcare instrument 410 is driven by a storage battery (including a dry-cell battery) completely different from the commercial power source EP, and hence it is difficult to detect the time point at which the main power is turned on by the power instruction apparatus 9. In view of this, as described above, the usage start signal 410Y is first transmitted, and then the usage start signal 410S and the usage finish signal 410F are transmitted. However, this system may be changed so that the healthcare instrument 410 is supplied with the commercial power source EP via the circuit breaker BK. In this case, like a signal L1 (to be subsequently described in detail) of the induction heating cooker 2, a signal L1 indicating the main power-on may be used instead of the usage notice signal 410Y.

Although the configuration of the blood pressure meter 410A has been described as a typical example of the healthcare instrument 410, the electrocardiograph 410B, the heart rate meter 410C, the clinical thermometer 410D, the weight scale 410E, the body fat scale 410F, and the urine analyzer 410G described above are basically of a similar configuration. The measurement data obtained by the healthcare instruments cited above may be transmitted to the outside via a highly compatible connection method or a recording card, such as a USB cable, a USB memory, and an SD card.

The LCD screen 100A of the display panel 100 illustrated in FIG. 20 indicates that measurement data can be read when new measurement data from the healthcare instruments is registered via any of the infrared ray, the USB memory, and wireless communication. Thus, when the measurement data of the healthcare instrument 410 is read in the healthcare processing unit 116 in the power instruction apparatus 9, the above-described operation input unit 117 can be prepared on the LCD screen 100A of the display panel 100. When, as described above, the healthcare instrument 410 itself has the short range communication (NFC) function, the measurement data such as the blood pressure value can also be read in the healthcare processing unit 116 via the control unit 125 with use of the above-mentioned wireless input-output unit 427. In addition, the healthcare instrument 410 itself may have a wireless communication function to the above-mentioned wireless input-output unit 427, and the healthcare instrument 410 may wirelessly transmit the measurement data after the biological data is measured.

Figure 11:
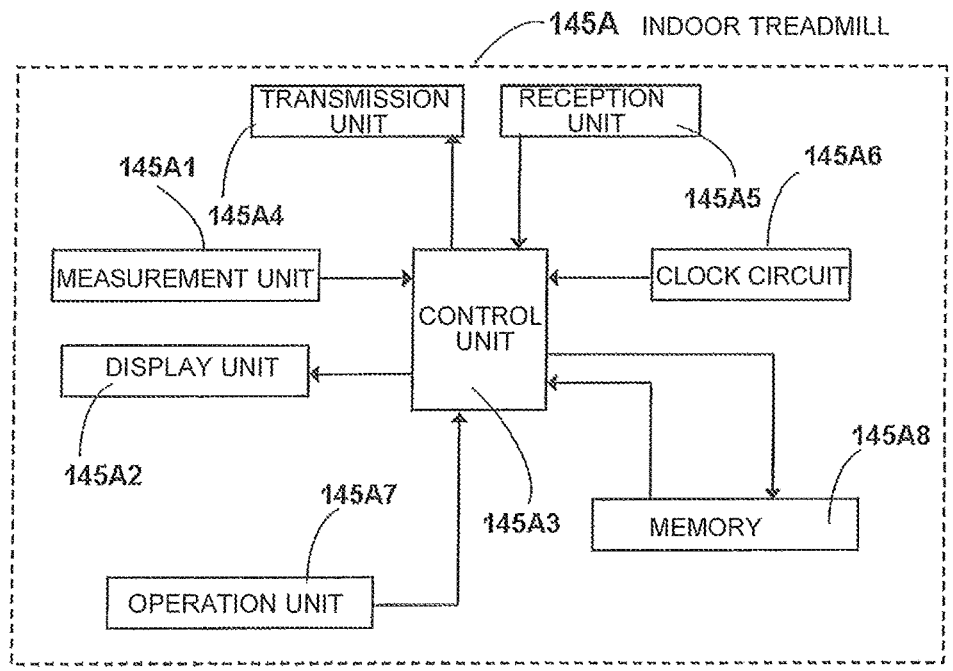
FIG. 11 is a block diagram for illustrating an internal configuration example of an indoor treadmill being an example of the activity measurement apparatus used in the power control system according to Embodiment 1 of the present invention.

FIG. 11 is an illustration of the configuration of the indoor treadmill 145A as a typical example of the activity measurement apparatus 145. In FIG. 11, reference symbol 145A1 denotes a measurement unit configured to measure the amount of activity of the exercising occupant. The indoor treadmill 145A has an infinite tracked belt that rotates in a certain direction in accordance with the running operation of the occupant on the belt. The measurement unit 145A1 measures the accumulated number of rotations of the belt to measure the movement distance of the belt, and calculates calories burned through the running exercise based on the measurement data and the data of the weight of the occupant. Reference symbol 145A2 denotes a display unit configured to display the measured calorie consumption or running distance in figures. Reference symbol 145A7 denotes an operation unit configured to instruct the start of measurement of the running exercise. The operation unit 145A7 includes an input key (not shown) to be used to input exercise measurement identification data (e.g., 3-digit number) of the subject before the measurement for identifying the subject. The exercise measurement identification data is the same as the healthcare measurement identification data described above.

The indoor treadmill 145A includes the measurement unit 145A1, a clock circuit 145A6, the display unit 145A2, the operation unit 145A7, a non-volatile memory 145A8 including a semiconductor similar to that of the memory 216, a control unit 145A3, a transmission unit 145A4, and a reception unit 145A5.

The control unit 145A3 of the indoor treadmill 145A illustrated in FIG. 11 has the following function. At a time point at which the user turns on the main power of the indoor treadmill 145A, the control unit 145A3 immediately and wirelessly transmits a predetermined "usage notice signal" 145Y from the transmission unit 145A4 to the healthcare processing unit 116 of the power instruction apparatus 9. The time point at which the main power is turned on can be recognized by the control unit 145A3 detecting that the user (subject) has operated the operation unit 145A7.

The control unit 145A3 further has the following functions. At a time point at which the user starts measurement of the amount of activity by the measurement unit 145A1 of the indoor treadmill 145A, the control unit 145A3 immediately and wirelessly transmits a predetermined "usage start signal" 145S from the transmission unit 145A4 to the healthcare processing unit 116 of the power instruction apparatus 9. At a time point at which the measurement of the amount of activity is finished, the control unit 145A3 immediately and wirelessly transmits a predetermined "usage finish signal" 145F from the transmission unit 145A4 to the healthcare processing unit 116 of the power instruction apparatus 9. In other words, the power instruction apparatus 9 can detect the measurement operation before starting the measurement of the exercise. The power instruction apparatus 9 detects the three signals of the usage notice signal 145Y, the usage start signal 145S, and the usage finish signal 145F, and acquires the environment information of the living space HA before the measurement of the amount of activity from the environment detection unit 202. This point is a conspicuous feature of Embodiment 1.

The activity measurement apparatus 145 of Embodiment 1 is not driven by the commercial power source EP, and thus is not an apparatus whose electric power is to be controlled by the power instruction apparatus 9. The activity measurement apparatus 145 is driven by a storage battery (including a dry-cell battery) completely different from the commercial power source EP, and hence it is difficult to detect the time point at which the main power is turned on by the power instruction apparatus 9. In view of this, as described above, the usage start signal 145S is first transmitted, and then the usage start signal 145S and the usage finish signal 145F are transmitted.

The above system may be changed so that the activity measurement apparatus 145 is supplied with the commercial power source EP via the circuit breaker BK. In this case, as the signal L1 (to be subsequently described in detail) of the induction heating cooker 2, the signal L1 indicating the main power-on may be used instead of the usage notice signal 145Y.

Figure 12:
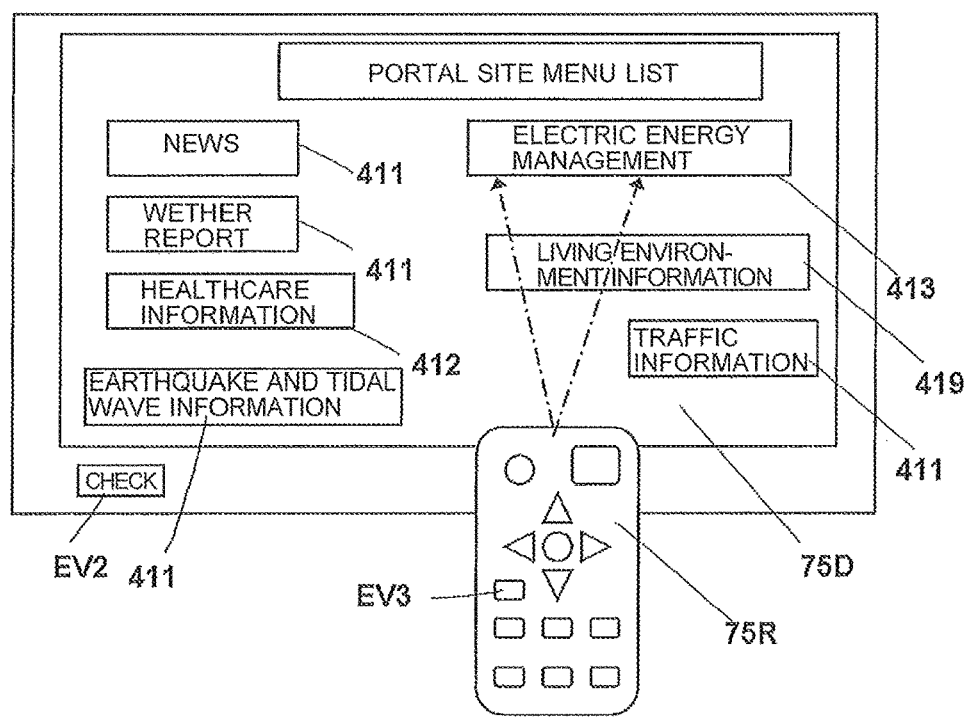
FIG. 12 is a schematic diagram for illustrating an example of a TV receiver screen and a remote controller in the power control system according to Embodiment 1 of the present invention.

FIG. 12 is a schematic diagram for illustrating an example of a screen of the TV receiver 75 and the remote controller. In FIG. 12, a TV portal site is displayed on the TV receiver 75. When a specific power source ON button provided on the remote controller 75R is pressed once, the TV receiver 75 is turned on and the system control unit 75E displays the TV portal site on the LCD screen 75D. Here, the TV portal site refers to a portal site for providing various types of services, mainly provided for a TV set connectable to the Internet.

As illustrated in FIG. 12, the TV portal site displays a menu of a portal site including icons (on-screen input switches) 411 surrounded by a substantially rectangular frame indicating, for example, "news", "weather report", "traffic information", "earthquake and tidal wave information". The TV portal site also displays a special icon 412 indicating "healthcare information", a special icon 413 indicating "electric energy management", and a special icon 419 indicating "living environment information".

Those three special icons 412, 413, and 419 may be displayed in a larger size or in a color that stands out, for clearer visual recognition compared with other ordinary icons. The term "icon" herein referred to is displayed on the display screen and used for selecting a specific function, and includes those representing the letters indicating the specific function, not only symbols. In addition, an input display unit (often called "tab" or "thumbnail") that indicates a purpose or a function only in letters such as "healthcare information", for example as illustrated in FIG. 13, is also referred to as icon. FIG. 13 is a schematic diagram for illustrating an example of the screen of the TV receiver 75 in the power control system according to Embodiment 1.

When the remote controller 75R is directed to the special icon 413 indicating "electric energy management" displayed on the LCD screen 75D of the TV receiver 75 as illustrated in FIG. 12 and a specific button (input confirmation button) on the remote controller 75R is pressed, the remote controller 75R emits an infrared ray signal. When the TV receiver 75 detects the signal, the screen of "electric energy management" is selected, and the LCD screen 75D displays a single-purpose screen titled "electric energy management".

Here, the input signal is generated not because the infrared ray signal from the remote controller 75R is emitted only to the specific icon; when the remote controller 75R emits the infrared ray signal after the specific icon is selected with the remote controller 75R, such emission is detected so that the selection of the icon is confirmed. Such an icon is widely known, and hence detailed description of the operation principle thereof is omitted.

When the remote controller 75R is directed to the special icon 412 indicating "healthcare information" displayed on the LCD screen 75D and the specific button (input confirmation button) on the remote controller 75R is pressed, the LCD screen 75D displays a single-purpose screen titled "healthcare information". Through further operation of the remote controller 75R, the blood pressure measurement data of the subject A measured at a certain date and time as illustrated in FIG. 13 is displayed, as an example of the healthcare information 412. In the case where the blood pressure exceeds the target set in advance by the subject, the highest blood pressure exceeds 135 mmHg, or the lowest blood pressure is below 85 mmHg, a suggestion or caution for improving the blood pressure is displayed at the same time, so as to call the attention of the subject. Such suggestion or caution may be stored in advance in the ROM 138 of the healthcare processing unit 116, or stored in advance in the memory 216 in the healthcare instrument 410.

Reference information may be acquired from an external specialized medical institution with the mobile phone terminal 87, to transmit such information from the mobile phone terminal 87 to the power instruction apparatus 9 through the wide area communication network 98A. Then, the information may be stored in the healthcare processing unit 116 and the information may be read out whenever necessary.

Upon operating the remote controller 75R further, as shown in FIG. 14, the measurement results of all the family members (in FIG. 14, only the subjects A and B are displayed, though the family includes two other members) who underwent the measurement in a certain period are displayed on the LCD screen 75D in the form of a list. The subject A corresponds to the occupant A to be subsequently described, and the subject B corresponds to the occupant B to be subsequently described.

In FIG. 14, reference symbol LS1 denotes the column displaying the instrument code for identifying the healthcare instrument 410, reference symbol LS2 denotes the column displaying the category of the measurement, and reference symbol LS3 denotes the column for identifying the subject, and any desired form may be adopted, for example, letters, numerals, or a nickname, provided that the subject can be identified. Reference symbol LS4 denotes the column displaying the date and time that the metabolic data was measured with the healthcare instrument, and reference symbols LS5 and LS6 denote the columns displaying the measured values, and the number of columns may be just one, or three or more, depending on the type of the metabolic data. Reference symbol LS7 denotes the column for a predetermined mark displayed when the measurement data is deviated from a normal range or close to a border line and precaution is required, in different forms depending on the extent of the deviation.

As shown in FIG. 14, when the measurement result is deviated from the normal range, a symbol "E" indicating that precaution is necessary is displayed in the column of "abnormality" (LS7). In Embodiment 1, the information accompanied by such a symbol is hereinafter referred to as "caution data". The display panel (display device) 100 is configured to display the caution data stored in the storage device 149 of the power instruction apparatus 9. In FIG. 14, data indicating abnormal blood pressure is exemplified as the caution data, but the caution data is not limited thereto. For example, information for calling the user's attention, such as data indicating abnormal uric acid or high body fat rate, may be adopted.

Further, the caution data may include cooking reference data indicating useful suggestions regarding a cooking method or mode of the induction heating cooker (heating cooker) 2. The cooking reference data is information indicating cooking methods for people who have high blood pressure, high uric acid, or high body fat rate, seasoning modes (e.g., level of salt), or recipes (e.g., recipes that use less salt, recipes that promote salt excretion, and recipes that include calorie values). The display panel 100 may display the cooking reference data when the caution data includes the cooking reference data. In addition, when the family members are registered as the subjects, the display panel 100 may display words such as "A family member has high blood pressure" as the cooking reference data.

Here, the measurement data of a specific subject alone can be displayed by operating the remote controller 75R. The healthcare information 412 represents the information displayed as LS1 to LS7 including, for example, the measurement data.

Figure 15:
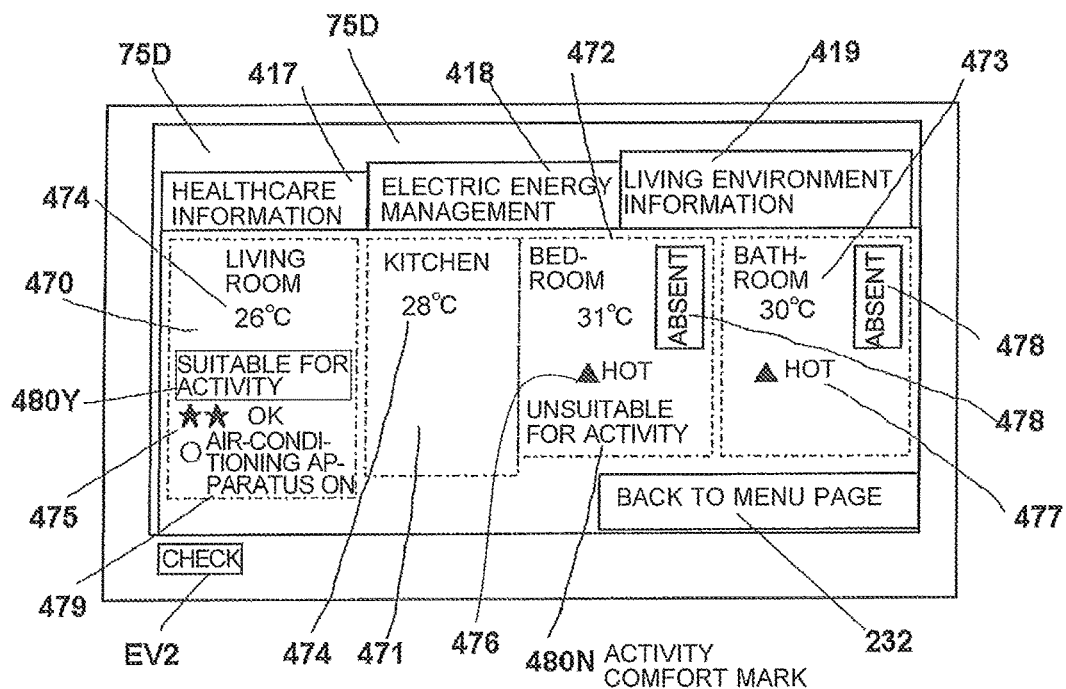
FIG. 15 is a schematic diagram for illustrating an example of the TV receiver screen in the power control system according to Embodiment 1 of the present invention.

When the remote controller 75R is directed to the special icon 419 indicating "living environment information" displayed on the LCD screen 75D illustrated in FIG. 12 and the specific button (input confirmation button) on the remote controller 75R is pressed, the LCD screen 75D displays a single-purpose screen titled "environment information" as illustrated in FIG. 15.

Figure 18:
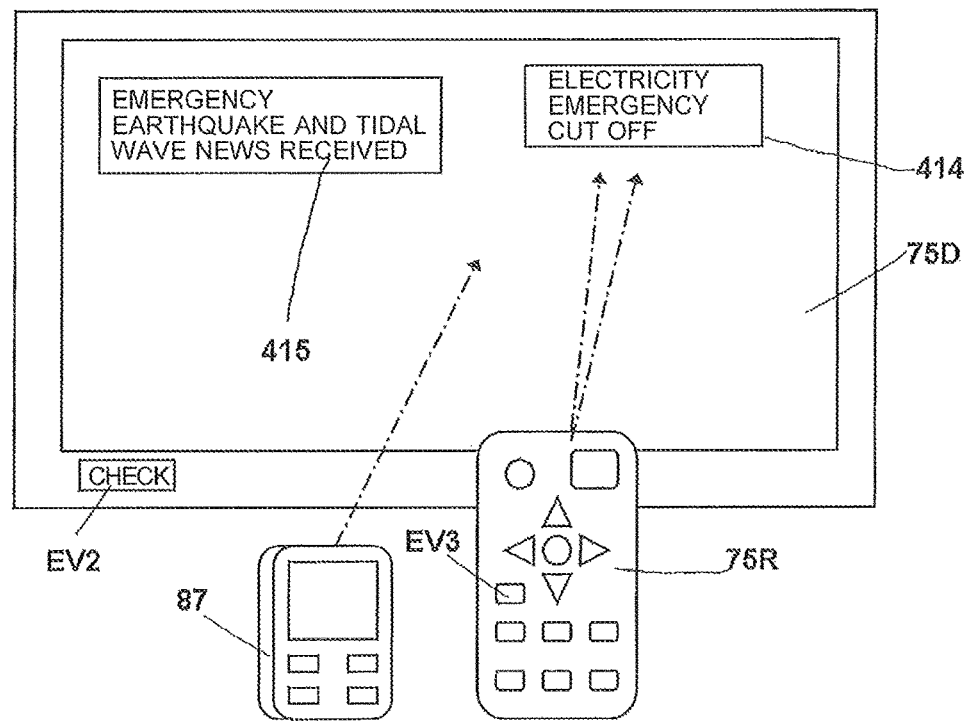
FIG. 18 is an explanatory diagram for illustrating an example of the TV receiver screen and the operation thereof in the power control system according to Embodiment 1 of the present invention.
Figure 19:
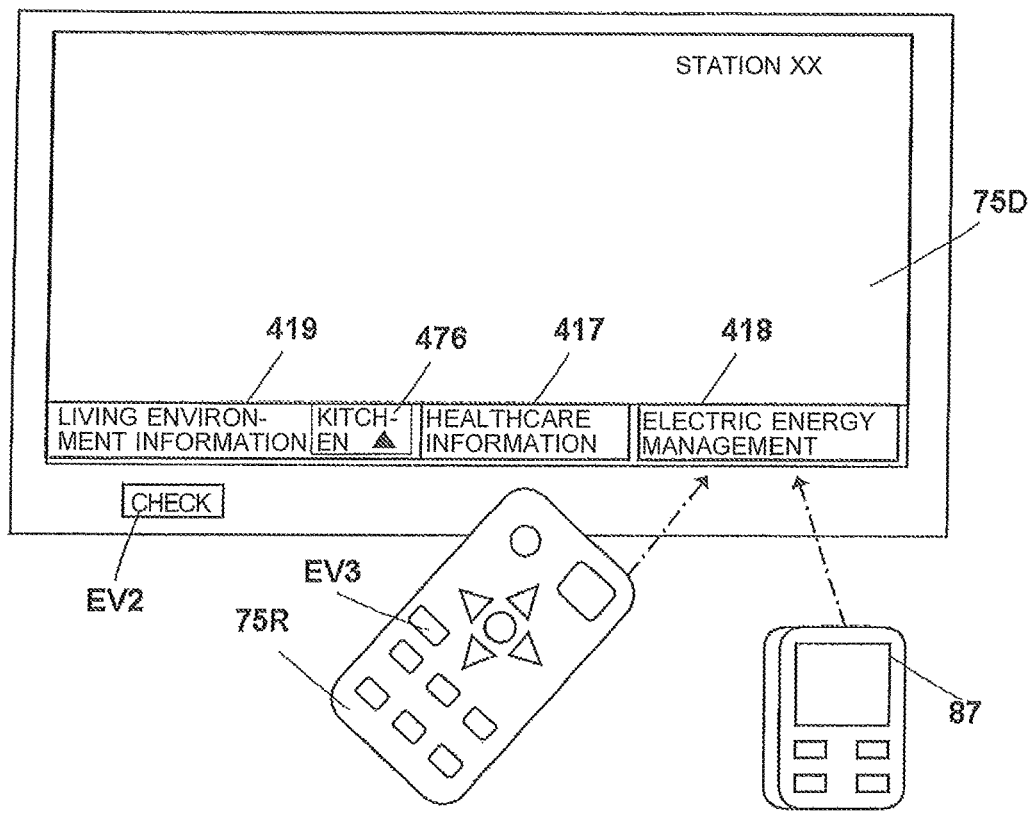
FIG. 19 is an explanatory diagram for illustrating an example of the TV receiver screen and the operation thereof in the power control system according to Embodiment 1 of the present invention.

Although the remote controller 75R of the TV receiver 75 is used to select the icons 411, 414, 415, 417, and 418 in the examples illustrated in FIG. 18 and FIG. 19, the mobile phone terminal 87 can also be used for selection inside the house. With the mobile phone terminal 87, the ASP server 89A can be accessed through the base station 80, and therefore upon downloading control application software for the TV receiver 75 in the ASP server 89A, the mobile phone terminal 87 can be used to control the TV receiver 75 inside the living space (house).

Although the mobile phone terminal 87 is unable to perform a direct remote operation of the home electric appliance EE from outside locations in Embodiment 1 as described above, the mobile phone terminal 87 may be allowed to operate the home electric appliance EE other than the TV receiver 75, inside the house. Therefore, the mobile phone terminal 87 can be brought close to (or in contact with) the input-output unit of each home electric appliance EE, so that information or an instruction signal can be transmitted or received via short range wireless communication (NFC).

FIG. 15 is a schematic diagram for illustrating an example of the screen of the TV receiver 75 in the power control system according to Embodiment 1. In FIG. 15, reference symbol 470 denotes a region for displaying information of the living room environment, reference symbol 471 denotes a region for displaying information of the kitchen environment, reference symbol 472 denotes a region for displaying information of the bedroom environment, and reference symbol 473 denotes a region for displaying information of the bathroom environment. Those regions are virtually formed by the system control unit 75E of the TV receiver 75 when the display screen of the "living environment information" is displayed. The term "virtually" refers to the state where the control program of the system control unit 75E divides the image display region of the LCD screen 75D, instead of each of the regions being physically independent. The display regions 470 to 473 each indicate the name of the corresponding living space in letters, such as "living room" and "kitchen".

Reference symbol 474 denotes a temperature and humidity information sign indicating at least one of the temperature or humidity in the room in letters, and reference symbol 475 denotes a comfort mark that appears when the room temperature of the living space is within a temperature range set by the user, and the mark of three stars indicates the best of the three degrees of comfort, the mark of two stars indicates the medium degree, and the mark of one star indicates the lowest degree. The comfort mark 475 is an example of the information indicating the degree of comfort. The criteria of the degree of comfort can be changed by the user any time, and the occupant can freely determine the setting depending on whether it is winter or summer, or according to the climate of the district of the household. As the initial setting, default values in a range of comfort (three stages) are set to 26 degrees Celsius for temperature and below 50% for humidity. The processing of determining the degree of comfort in the environment detection unit 202 is referred to as "comfort degree determination". Instead of displaying the degree of comfort in the form of stars as the comfort mark 475, indication of the degree of comfort using letters may be employed.

Reference symbol 476 denotes a caution mark (information sign) displayed when the temperature and humidity deviate from the comfort conditions and the environmental condition is uncomfortable or close thereto. The mark of one triangle indicates "slightly uncomfortable", and the mark of two triangles indicates "uncomfortable". The caution mark 476 is also an example of the information indicating the degree of comfort. In Japan, a discomfort index calculated based on temperature and humidity is sometimes employed. For example, when the temperature is 29 degrees Celsius and the humidity is 70%, the discomfort index is 80. It is said that when the discomfort index exceeds 75, 10% of the population feels uncomfortable, and when the discomfort index exceeds 80, everybody feels uncomfortable. Accordingly, the caution mark 476 of one triangle may be defined as below 75 in discomfort index, and the caution mark 476 of two triangles may be defined as 75 or higher in discomfort index.

Although the caution mark 476 of one triangle indicates "slightly uncomfortable" and the mark of two triangles indicates "uncomfortable" in this example, when the room temperature exceeds 30 degrees Celsius and the humidity exceeds 75%, the discomfort index exceeds 80, in which case there is a risk of heat stroke even inside the room. It is known that, in terms of the location of heat stroke, a large number of people aged 65 years and higher, both male and female, suffer from heat stroke indoors (Reference Literature: "Heat Stroke Environmental Health Manual" by Ministry of the Environment of Japan, revision of May, 2011).

The environment detection unit 202 transmits a signal of "level 1 warning" to the control unit 125 when the temperature reaches 29 degrees Celsius and the humidity reaches 70%, and transmits a signal of "level 2 warning" to the control unit 125 when the room temperature becomes 30 degrees Celsius or higher and the humidity exceeds 75%. When the signal of "level 1 warning" is output in the living space where the presence of a person, e.g., an occupant is detected by the human body detection unit 203, the control unit 125 takes the following measures (remedy 1 and remedy 2) corresponding to "level 1 warning".

Remedy 1: Display the warning on the display screen 100A of the display panel 100 of the power instruction apparatus 9

Remedy 2: Display the warning in letters on the display screen 75D of the TV receiver 75, when the TV receiver 75 is being viewed In the case where the temperature does not fall below 29 degrees Celsius or the humidity does not fall below 70% within five minutes after the operation instructions of the remedy 1 and remedy 2 are output, it can be assumed that the person in the living space may not be feeling the heat. In such a case, therefore, the control unit 125 takes the following measure corresponding to "level 2 warning" (remedy 3).

Remedy 3: Forcibly turn on the air-conditioning apparatus 7 which has cooling capacity (effect of suppressing increase of temperature) in the environment improvement apparatus in the living space (target room temperature in this case is, for example, 27 degrees Celsius).

In Embodiment 1, the expression that the air-conditioning apparatus 7 is available in the living space naturally includes the case where the apparatus itself is installed inside the living space. In addition, the case where the apparatus is located outside the living space and the conditioned air is supplied into the living space is also included. In the case where the air-conditioning apparatus 7 is not available inside the living space, or when it is detected that the air-conditioning apparatus 7 is unusable because, for example, the power cord is removed from the power outlet, another environment improvement apparatus to be subsequently described, for example, a ventilation device or an air purifier, is activated.

It is known that causing air in a room to circulate is also effective for preventing heat stroke. In Embodiment 1 of the present invention, therefore, an occupant located outside the living space (e.g., occupant A or B) is made aware that the environmental condition is hazardous to health. To be more detailed, the caution information is transmitted from the input-output unit 124B (see FIG. 6) of the power instruction apparatus 9 to the outdoor communication network (communication network) 98 through the router 99A, so that the information reaches the mobile phone terminal 87 of the occupant B. Then the occupant B is supposed to turn on the air-conditioning apparatus 7 by remote operation through the power instruction apparatus 9, however when this is unfeasible, the occupant B may communicate with a relative or a home helper service office, to let someone actually visit the household (in this case, the occupant B tells the visitor how to unlock the electronic lock of the entrance). Thus, in the case where the temperature and the humidity do not return to the state of less than a first predetermined value within a predetermined time after reception of the level 2 warning signal, the control unit 125 notifies the occupant located outside the living space that the environmental condition has become hazardous. With the above-mentioned configuration, the detection unit 202 monitors the environment even while a senior person or a child unfamiliar with the use of the environment improvement apparatus is in the room alone, and therefore the safety level of the indoor living space can be improved.

The environment detection unit 202 immediately outputs "level 2 warning" to the control unit 125 when the room temperature reaches 30 degrees Celsius or higher and the humidity exceeds 75%, irrespective of whether "level 1 warning" has been output. When the "level 2 warning" is output with respect to the living space where the presence of a person, e.g., an occupant is detected by the human body detection unit 203, the control unit 125 instructs the execution of the remedy 3. The environment detection unit 202 measures and monitors the latest environmental condition of the living space where the warning has been output, at intervals of one minute after the instruction of the remedy 3 is output.

The operation of the environment improvement apparatus forcibly activated as above, for example, the air-conditioning apparatus 7, is automatically stopped by an instruction from the control unit 125 output to the use limit setting device 96, when the environmental condition in the living space returns to the predetermined condition set by the occupant. Alternatively, the environment improvement apparatus may be automatically stopped after operating for 30 minutes. This is because operating the environment improvement apparatus longer than is necessary is undesirable from the viewpoint of energy saving.

Reference symbol 477 denotes a cold-hot information sign displayed close to the caution mark 476, to indicate whether it is hot or cold in letters. In FIG. 15, "hot" is displayed in the cold-hot display section with respect to the bedroom and bathroom. In the environment detection unit 202, the processing for determining the states of "hot" and "cold" is referred to as "cold-hot determination".

Reference symbol 478 denotes an absence mark (absence information sign) that is displayed when the human body detection unit 203 of the power instruction apparatus 9 detects that no one is in the living space. As illustrated in FIG. 15, it is easily identified that no one is in the bedroom and the bathroom by viewing the LCD screen 75D.

Reference symbol 479 denotes an operation information sign of the first specific home electric appliance SP1, for displaying the operation status of the "environment improvement apparatus", which is the home electric appliance EE configured to condition the air in the living space so as to maintain and improve the degree of comfort, for example, the air-conditioning apparatus 7, the air purifier (not shown), and the ventilation device (not shown). Although the air purifier and the ventilation device are not shown, the air purifier generally includes a box-shaped main body having an intake port and an exhaust port, an electric air-sending device (electric fan) provided inside the main body to suck the air in the room through the intake port and discharge the air through the exhaust port, and a dust-removing filter mounted across the air passage between the intake port and the exhaust port. More preferably, the air purifier may be configured to emit negative ions or minute particle ions composed of water particles and said to be effective for suppressing mold germs, allergens, and odor, to the air passing through the air passage. The ventilation device is typically exemplified by a ventilation fan with a hood, mounted right above the induction heating cooker 2 in the kitchen.

Reference symbols 480N and 480Y denote an activity caution mark (activity caution information sign) indicating in letters whether the living space has a high degree of comfort and is suitable for performing indoor activity. This mark may be included in the display regions 470 to 473 for all of the living spaces. However, when the activity measurement apparatus 145 configured to transmit information, wirelessly or by wired communication, to the healthcare processing unit 116 of the power instruction apparatus 9, for example, the indoor treadmill 145A or the running calorie meter 145B (in a standby state or in a currently-used status) is present in at least the living space, the activity caution mark 480 may be displayed in the display region of the living space that includes the activity measurement apparatus 145.

The standby state can be detected by receiving the usage notice signal 145Y to be subsequently described by the power instruction apparatus 9. Further, in this case, the electric vacuum cleaner 312 also serving as the activity measurement apparatus 145 is also an object of activity caution determination, and hence FIG. 15 indicates that it is not appropriate to operate the electric vacuum cleaner 312 in the bedroom. Reference symbol 480Y denotes an activity recommendation mark indicating that the environment is suitable for activity, and reference symbol 480N denotes a non-recommendation mark indicating that the environment is unsuitable for activity. In the following description, those two marks are collectively referred to as the activity caution mark 480.

The information that can be displayed on the LCD screen 75D of the TV receiver 75 illustrated in FIG. 12 to FIG. 19 is basically the same as the information that can be displayed on the LCD screen 100A of the display panel 100. In other words, the "operation information" of the power instruction apparatus 9, the "environment information" of the environment detection unit 202, the health measurement information (healthcare information) of the healthcare instrument 410, and the activity measurement information of the activity measurement apparatus 145 can be displayed similarly whether on the LCD screen 75D of the TV receiver 75 or on the LCD screen 100A of the display panel 100. However, the size of the LCD screen 75D is 20 inches to 60 inches while that of the display screen 100A is 10 inches to 15 inches, and hence the effective display area of the latter is only a quarter or less of the former. Therefore, it is impossible to display the same content at the same size. However, the temperature and humidity information sign 474, the comfort mark 475, the caution mark 476, and the activity caution mark 480 described above, and further a change information sign 483, an unsuitable environment information sign 484, a pollen scattering amount information sign 485, and an operation information sign 482 to be subsequently described in detail, are all displayed, though naturally the size of the displayed letters is reduced.

With the above-mentioned configuration, the same type of information is displayed on the LCD screen 75D of the TV receiver 75 and the display screen 100A of the display panel 100, so that the same information can be confirmed, in whichever of the kitchen or the living room without difference in information to be displayed. Here, the display of the information on the display screen 100A is realized by execution of the display control program of the control unit 125.

When contradictory inputs are simultaneously made from both the TV receiver 75 and the display panel 100, the input of the display panel 100, that is, the power instruction apparatus 9 is given priority. For example, when the power instruction apparatus 9 is operated to set the total electric power of the home electric appliances EE to a certain value (second capacity limit, e.g., 7,000 W) less than the capacity limit restricted by the circuit breaker BK (first capacity limit, e.g., 8,000 W), and when the TV receiver 75 is simultaneously operated to input increase of the second capacity limit to 78,000 W, the input of the power instruction apparatus 9 is given priority, so that the setting to 7,000 W is enabled in the above example. However, the limitation of viewing of a broadcast program or image quality adjustment of the LCD screen 75D, which are original functions of the TV receiver 75, cannot be made from the power instruction apparatus 9.

Figure 16:
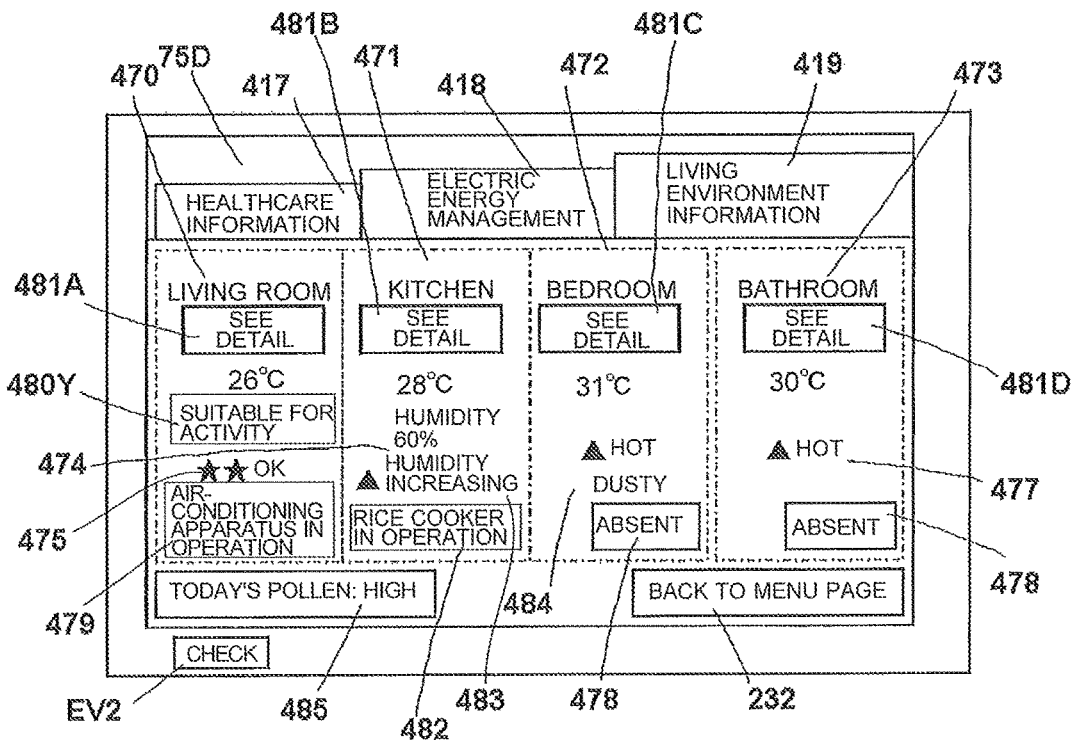
FIG. 16 is a schematic diagram for illustrating an example of the TV receiver screen in the power control system according to Embodiment 1 of the present invention.

FIG. 16 is a variation of the screen configuration displaying the environment information illustrated in FIG. 15. A distinctive feature of the screen illustrated in FIG. 16 is that icons 481A to 481D for viewing detailed information are respectively included in the four display regions 470 to 473. Another feature is that the screen includes, in addition to the operation information sign 479 allocated to the first specific home electric appliance SP1, an operation information sign 482 for displaying the operation status of the second specific home electric appliance SP2, for example, the rice cooker (electric rice cooker) 3, which may adversely affect the air in the living space by, for example, emitting heat to the air thereby increasing the temperature.

Reference symbol 483 denotes the change information sign that appears when the temperature or the humidity fluctuates (increases or decreases) by a larger range than a predetermined ratio. For example, when the temperature increases or decreases by 1 degree Celsius or more within five minutes or two minutes, the change information sign 483 displays "increasing" or "decreasing". The living spaces such as the living room, the kitchen, the bedroom, and the bathroom may be colored differently depending on the actually measured temperature. For example, in the example of FIG. 16, the bedroom having the highest temperature is colored in warm colors such as orange, the bathroom is colored in yellow, and the living room having the lowest temperature is colored in blue. As above, it is further preferred that the level of the temperature may be directly imaged by colors.

Reference symbol 484 denotes an unsuitable environment information sign indicating that the space is in a physical environment undesirable for the health of the occupant but improvable by operating the first specific home electric appliance SP1, that is, the environment improvement apparatus. FIG. 16 represents an example of a case where one liter of air contains more than a predetermined number of dust particles larger than a predetermined size in diameter. For example, when bedding is moved or beaten after the occupant wakes up, dust is temporarily stirred up and stagnated in the air, in which case the unsuitable environment display section displays some letters or a mark. The unsuitable environment information sign 484 is also an example of the information that indicates the degree of comfort of a specific living space.

Reference symbol 485 denotes a pollen scattering amount information sign for indicating whether or not a large amount of pollen is flying in the air outside the house, which is useful because, for example, an occupant suffering from a pollen allergy can determine whether to refrain from going out. The basic data for the pollen scattering amount display section is available from the Japan Meteorological Agency or other meteorological institutions and TV stations. Therefore, in addition to the information from the pollen sensor described above, or instead of utilizing the pollen sensor, the information from one of the cited external organizations may be used. The information from the external organizations can be acquired by the power instruction apparatus 9 or the TV receiver 75 from the external organizations 78A and 78B.

Figure 17:
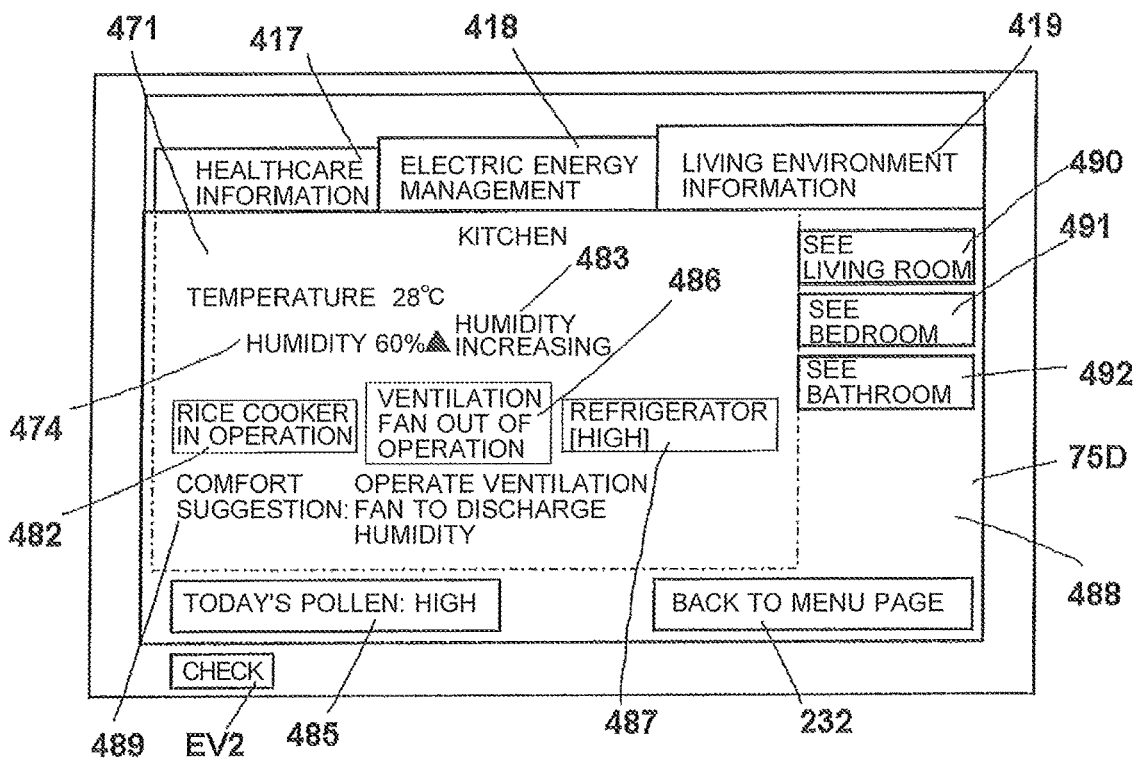
FIG. 17 is a schematic diagram for illustrating an example of the TV receiver screen in the power control system according to Embodiment 1 of the present invention.

When the remote controller 75R is further operated so as to select, for example, the icon 481B when the screen is set as illustrated in FIG. 16, the screen is switched as illustrated in FIG. 17. In FIG. 17, reference symbol 486 denotes an information sign indicating whether the ventilation fan (not shown) provided in the kitchen is operating, and reference symbol 487 denotes an operation intensity information sign indicating to which of the three stages of refrigerating operation modes an electric refrigerator (not shown) also provided in the kitchen is set, "high", "medium", or "low". It is widely known that the operation intensity largely affects the power consumption of the refrigerator, and therefore further description is omitted.

As illustrated in FIG. 17, the kitchen display region 471 is automatically enlarged in area to the largest possible size. Such an enlarged display can be realized as a result of the change in display mode of the LCD screen 75D by the control program in the system control unit 75E. Reference symbol 488 denotes a blank section secured along the right edge of the display region 471, and an icon 490 for selecting viewing of the environment information of the living room, an icon 491 for selecting viewing of the environment information of the bedroom, and an icon 492 for selecting viewing of the environment information of the bathroom are displayed in the blank section 488. Therefore, upon selecting one of those icons 490 to 492, the environment information of the living room, the bedroom, or the bathroom can be displayed in detail on the LCD screen 75D.

Reference symbol 489 denotes suggestion information. In the suggestion information 489, whether the home electric appliance, in particular, the first specific home electric appliance SP1 may be operated, or a suggestion regarding the operating condition of the appliance, is displayed in letters in accordance with the current situation of the living space. Such a display contributes to enabling more effective control of the environment of the living space. The example illustrated in FIG. 17 is urging the occupant to turn on the ventilation fan, as a suggestion for improving the situation in the kitchen where humidity is increasing. In other words, the suggestion to use the ventilation fan, which is an example of the environment improvement apparatus, is being made to purify the air in the kitchen.

The basic data for such suggestions is stored in the storage device 149 serving as a storage unit for the healthcare processing unit 116. The same data is also stored in the storage device (high-capacity memory) 109 of the TV receiver 75. Accordingly, to display the environment information on the TV receiver 75, the system control unit 75E reads out the information from the storage device 109 and transmits the information to the LCD screen 75D to display the information. In this process, the control unit 125 of the power instruction apparatus 9 collects the operation information of each of the home electric appliances EE as a set on a real-time basis, and therefore the information from the control unit 125 can be utilized for the display on the LCD screen 75D. To display the environment information on the display panel 100 of the power instruction apparatus 9, the control unit 125 reads out the information from the storage device 149 and transmits the information to the display panel 100 to display the information. In this case also, the information from the control unit 125 of the power instruction apparatus 9 can be utilized for the display on the LCD screen 100A, because the control unit 125 collects the operation information of each of the home electric appliances EE as a set on a real-time basis.

Upon operating the remote controller 75R to select the icon 411 indicating the "earthquake and tidal wave information" when the icon 411 indicating the "earthquake and tidal wave information" is displayed in the TV portal site as illustrated in FIG. 12, or suddenly displayed while viewing an ordinary TV program, a special icon 414 indicating "emergency cut off" and a special icon 415 indicating "emergency earthquake and tidal wave information received" are displayed as illustrated in FIG. 18. FIG. 18 is an explanatory diagram for illustrating an example of the screen of the TV receiver 75 and the operation thereof in the power control system according to Embodiment 1. In this case, when the icon 414 of the "emergency cut off" is selected, the TV receiver 75 transmits an emergency cut-off instruction to the power instruction apparatus 9 and the power supply to the predetermined home electric appliances EE is cut off within a few seconds, without the need for the user to go to the place where the main body 9A of the power instruction apparatus 9 is installed. The power supply to an "exclusive electric appliance" to be subsequently described is also cut off within a few seconds.

As described above, the emergency cut-off is not performed with respect to the illumination apparatus 76 provided in a corridor that serves as an evacuation passage, in each room and the bath tub, the TV receiver 75, the power instruction apparatus 9, the router 99A, and the router 99B. The two special icons 414 and 415 may be displayed in a larger size or in a color that stands out, for clearer visual recognition compared with other ordinary icons, as for the special icons 412, 413, and 419.

FIG. 19 is a front view of the LCD screen 75D, displayed while the user is viewing an ordinary TV program on the TV receiver 75. As illustrated in FIG. 19, a special icon 418 indicating "electric energy management" is constantly displayed in the right lower corner of the LCD screen, even while the ordinary TV program is being displayed. However, the user cannot display the icon 418 if so desired.

In FIG. 13, FIG. 15, FIG. 16, FIG. 17, and FIG. 19, reference symbol 417 denotes an icon for switching to the single-purpose screen for the healthcare information, displayed in the form of a tab. The icon 418 is used to switch the display to the single-purpose screen for the electric energy management as described above, and is displayed in a rectangular frame shape. In FIG. 17, reference symbol 232 denotes an icon for returning to the initial screen of the TV portal site illustrated in FIG. 12.

FIG. 20 is a front view of the LCD screen 100A of the display panel 100 in the power instruction apparatus 9 and a peripheral region thereof. In the situation illustrated in FIG. 20, reference symbol 420 denotes an information key. Each time the user touches the information key, healthcare-related information and information for effectively performing healthcare, which are useful for the user in that situation, are displayed on the LCD screen 100A. To secure a sufficient display region, for example, the measurement data of the blood pressure meter 410A is not displayed.

Reference symbol 421 denotes a help mode key. When the user touches the key 421, information that assists the user's operation in the situation is displayed, and a correct operation method is audibly announced through a voice guide device (not shown) separately provided. For example, when the blood pressure data is displayed, the keys are located in the periphery of the blood pressure data display, and when the key is pressed, the meaning of the blood pressure data and explanation of the normal range are displayed on the LCD screen 100A, in schematic figures and letters.

In FIG. 20, reference symbol 425 denotes an icon for displaying existing data. When this icon is selected, the measurement data, the activity data, and the calorie consumption data for healthcare are retrieved into the display panel 100 of the power instruction apparatus 9 from the healthcare instruments 410 including the blood pressure meter 410A, the electrocardiograph 4106, the heart rate meter 410C, the clinical thermometer 410D, and the weight scale 410E, the activity measurement apparatus (indoor treadmill 145A, running calorie meter 145B), the electric vacuum cleaner 146, the mobile phone terminal 87, and other instruments or apparatuses. In addition, reference symbol 57 in FIG. 20 denotes a presence management menu selection key, which is subsequently described in detail with reference to FIG. 63.

In FIG. 20, reference symbol EV1 denotes the press-button operation button of the instruction switch (not shown) for environment confirmation. The operation button EV1 is provided in the vicinity of the lower edge of the display screen 100A of the display panel 100 in the front surface of the main body 9A of the power instruction apparatus 9. When the operation button EV1 is operated, an instruction signal for acquiring the environment information is input to the control unit 125 of the power instruction apparatus 9. The control unit 125 acquires with the environment detection unit 202 the environment information such as the temperature and the humidity of the living space HA, and displays the result of the acquired environment information on the LCD screen 100A. The display mode is similar to that of the screen for displaying various types of environment information to be subsequently described (see FIG. 15 or FIG. 16).

When an icon indicating "registration" (not shown) is selected with the screen for healthcare being displayed by selecting the icon 417 illustrated in FIG. 15, FIG. 17, and FIG. 19, an icon (input key) 426 indicating "register new data" and the icon (input key) 425 for retrieving and displaying existing measurement data are displayed, as illustrated in FIG. 20.

When the icon 426 for new data registration is selected, upon bringing, for example, the blood pressure meter 410A close to the display panel 100 and pressing the transmission button on the blood pressure meter 410A, the measurement data stored in the memory 216 of the blood pressure meter 410A is transferred to the RAM 139 from the information reception unit 137 of the healthcare processing unit 116, to be stored therein. As described above, the measurement data of the healthcare instruments can be read by the healthcare processing unit 116 by any of infrared ray communication, a USB memory, and wireless communication, as illustrated in FIG. 20. Further, the measurement data of the various healthcare instruments 410 can be read into the healthcare processing unit 116 via the wireless input-output unit 427 for the NFC. Though not shown, a connection port for inserting the USB memory is provided on the front surface or the side surface of the main body 9A of the power instruction apparatus 9.

Each time the measurement data is received from the healthcare instrument 410, the healthcare processing unit 116 transmits the entire data to the power instruction apparatus 9. When any of the measurement results is deviated from the normal range, the healthcare processing unit 116 adds a special code (hereinafter referred to as "abnormal value code") to the data including the abnormal value (e.g., highest blood pressure), the subject, the date and time of measurement (see FIG. 14 as an example), and transmits the entirety of such data to the power instruction apparatus 9. Accordingly, the "caution data" is kept from being erased and is maintained in the memory. The abnormal value code is different for each type of the healthcare instruments 410, and a plurality of numbers of codes are prepared depending on the measurement target of the healthcare instrument 410 such that, in one healthcare instrument 410, for example, in the blood pressure meter 410A, different codes are respectively added to the highest blood pressure and the lowest blood pressure.

The healthcare processing unit 116 transmits the measurement data and the abnormal value code to the system control unit 75E through the input-output functional device 75M, and the measurement data and the abnormal value code are finally stored in the storage device (high-capacity memory) 109 (see FIG. 5) of the TV receiver 75. The storage device 109 has a storage capacity of several tens of gigabytes, for example, so as to store the healthcare data of one year or more, when more than 10 pieces of measurement data are daily accumulated.

The high-capacity memory also stores the recorded pictures with sounds of broadcast programs received by the TV receiver 75, and the information from the TV receiver 75 and the information from the healthcare processing unit 116 are stored in separated memory regions, so that the data in each region can be independently updated or deleted. The storage device 109 (high-capacity memory) may be composed of two portions that can be physically separated from each other, so as to store the picture information from the TV receiver 75 in a first portion and the information from the healthcare processing unit 116 in a second portion. In this case, either of the first or second portion can be repaired or replaced without affecting the other, which facilitates the maintenance work.

Figure 24:
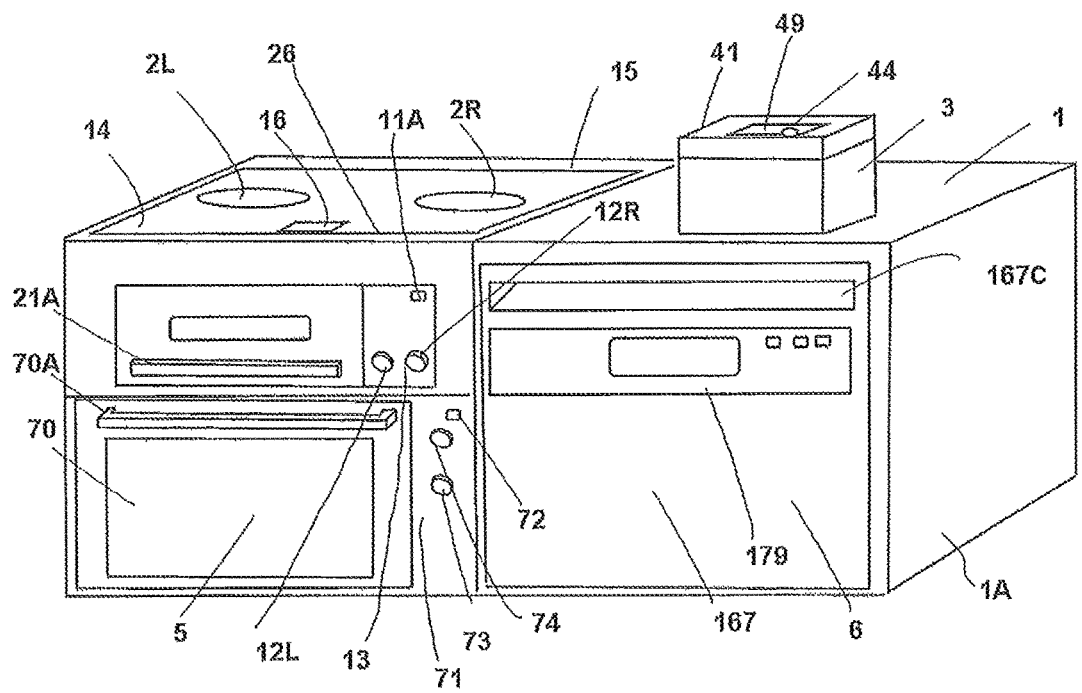
FIG. 24 is an external view for illustrating a kitchen electric appliance used in the power control system according to Embodiment 1 of the present invention.
Figure 25:
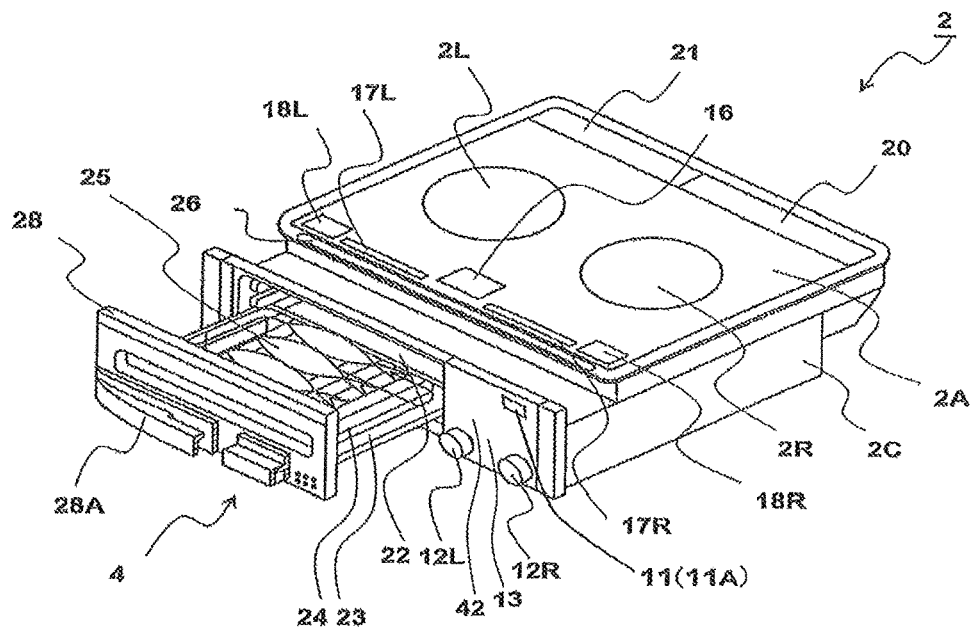
FIG. 25 is an external view for illustrating an induction heating cooker used in the power control system according to Embodiment 1 of the present invention.
Figure 26:
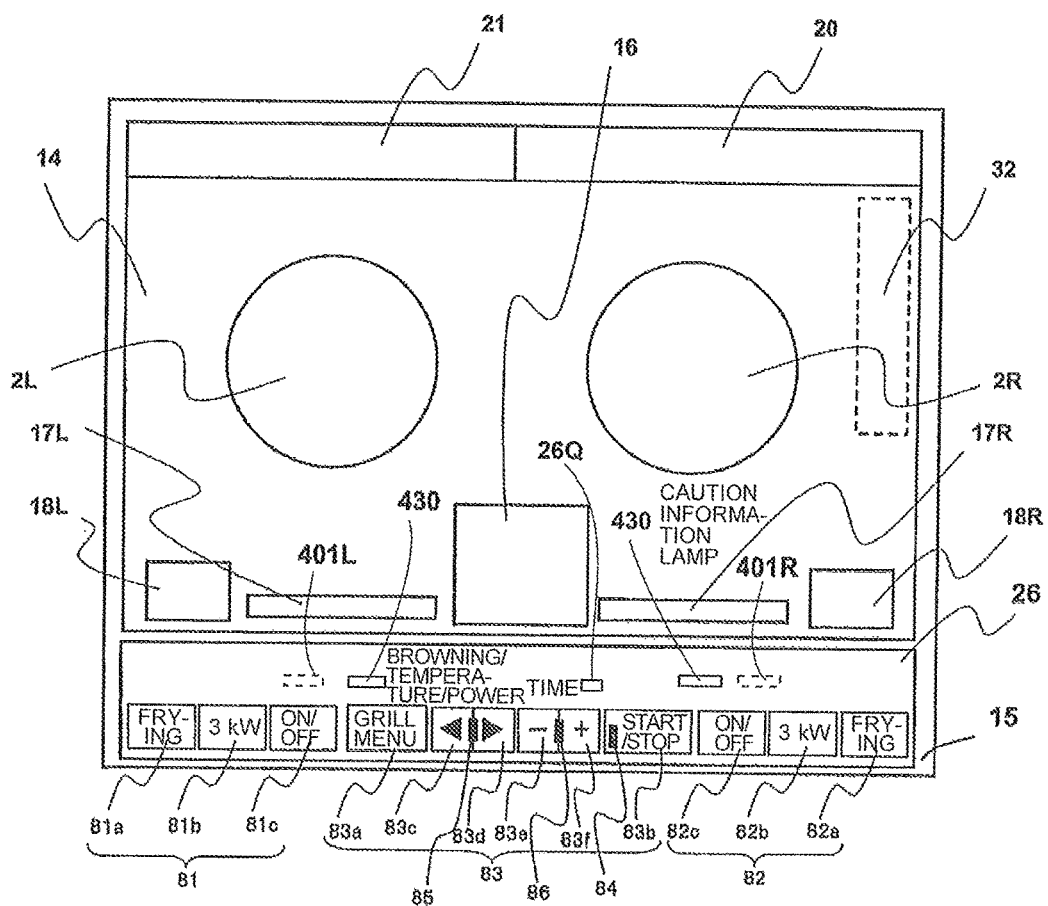
FIG. 26 is a plan view of the induction heating cooker illustrated in FIG. 25.
Figure 27:
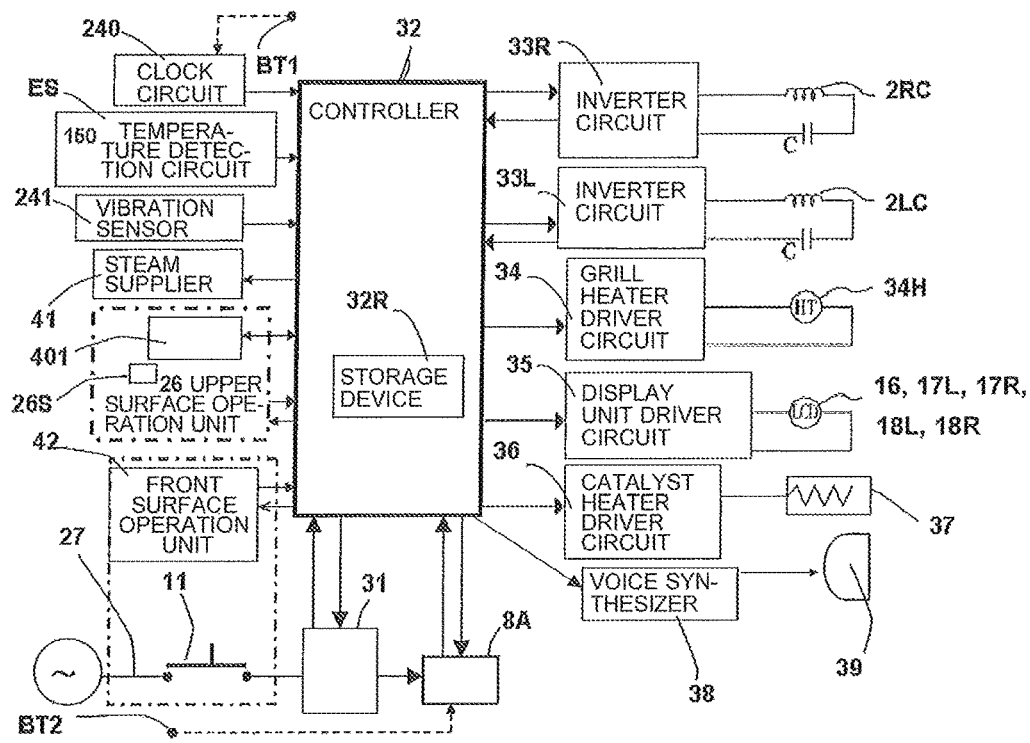
FIG. 27 is a block diagram for illustrating a configuration of a controller of the induction heating cooker illustrated in FIG. 25.
Figure 28:
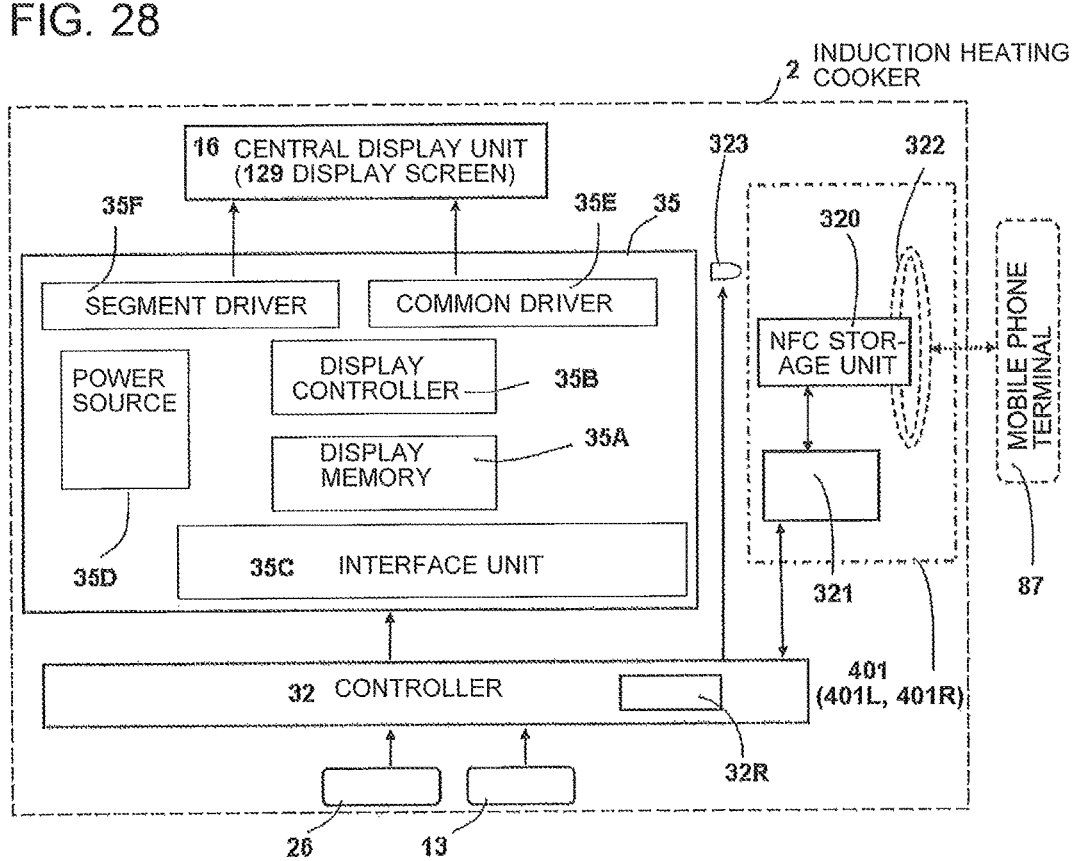
FIG. 28 is a block diagram for illustrating a configuration of a driver circuit for a display unit and a near-field communication input-output unit in the induction heating cooker illustrated in FIG. 25.

Next, the power control system of the home electric appliances EE including the induction heating cooker 2 and the rice cooker 3 is described with reference to FIG. 24 to FIG. 28. First, description is given focusing on a system kitchen (kitchen sink) 1 used in the "kitchen" illustrated in FIG. 24, which is one of the living spaces. FIG. 24 is a perspective view for illustrating an appearance of the kitchen electric appliance used in the power control system according to Embodiment 1, FIG. 25 is a perspective view for illustrating an appearance of the induction heating cooker 2 used in the power control system according to Embodiment 1, FIG. 26 is a plan view of the induction heating cooker 2 illustrated in FIG. 25, FIG. 27 is a block diagram for illustrating a configuration of a control circuit of the induction heating cooker 2, and FIG. 28 is a block diagram for illustrating a configuration of a driver circuit for a display unit and a near-field communication input-output unit in the induction heating cooker 2.

The system kitchen (also called "kitchen sink" or "kitchen furniture") 1 includes five home electric appliances described below, installed in a casing 1A constituting the outer shell of the system kitchen 1. The kitchen electric appliances are the induction heating cooker 2 having two (left and right) heaters (first heater 2L and second heater 2R), the electric rice cooker 3, a grill cooker (electric fish roaster) 4, an electronic oven with electric heater (hereinafter referred to as "microwave oven") 5, and the dish washer-dryer 6. Here, the "kitchen electric appliance" KP collectively represents those plurality of home electric appliances provided in the kitchen (induction heating cooker 2, rice cooker 3, grill cooker 4, and microwave oven 5). The electric rice cooker 3 is hereinafter simply referred to as "rice cooker". Although there are cases where the grill cooker 4 is independently provided, in Embodiment 1, the grill cooker 4 is integrally incorporated in the induction heating cooker 2, so as to constitute a heating unit in a composite induction heating cooker employing electrothermal and induction heating methods. Accordingly, when the main power supply circuit of the induction heating cooker 2 is disconnected, the power supply to the grill cooker 4 is also disconnected at the same time. Hereunder, description of other kitchen electric appliances such as the refrigerator and the ventilation fan is omitted.

Before proceeding to the description of "time period-classified electricity rate information" according to Embodiment 1 of the present invention, an actual example of the household electricity rate scheme is described hereunder.

According to the household electricity rate scheme of Tokyo Electric Power Company as of Jan. 1, 2014, the electricity unit rate is classified into two seasons and three time periods. Because of the difference in unit rate depending on the season and time period, it is recommended to reduce the electricity rate by, for example, using home electric appliances having high thermal efficiency in morning and evening hours, or shifting the use of home electric appliances normally used in daytime to night hours or morning and evening hours.

Here, the seasonal rate is classified into "summer" and "other seasons", the former being July 1 to September 30 each year, and the latter being October 1 each year to June 30 of the next year.

The "time period rate" scheme is classified into the following three time periods.

"Daytime hours": 10 a.m. to 5 p.m. each day. The electricity unit rate (tax included) per kWh is 37.56 yen for summer and 30.77 yen for the other seasons.

"Morning and evening hours": 7 a.m. to 10 a.m. and 5 p.m. to 11 p.m. each day. The electricity unit rate (tax included) per kWh is 25.20 yen.

"Night hours": 11 p.m. each day to 7 a.m. next morning. The electricity unit rate (tax included) per kWh is 11.82 yen.

Thus, it is understood that, in terms of the electricity unit rate, the night rate is the lowest, the morning and evening rate is the second lowest, and the daytime rate is the highest.

The "time period-classified electricity rate information" is such information of the "time period rate" scheme, an example of which is the electricity unit rate per kWh. Another example is the information that, for example, "the night rate is the lowest, the morning and evening rate is the second lowest, and the daytime rate is the highest". Accordingly, for example, in terms of the electricity rate scheme, the information "the electricity rate is the lowest in a day during the night hours from 11 p.m. each day to 7 a.m. of the next morning" corresponds to the time period-classified electricity rate information. It is not mandatory that the information provides specific values of the hourly electricity rate, and it suffices that the information allows the user to recognize whether the electricity rate of a certain time period is higher or lower in comparison with a predetermined reference (for example, the daytime rate).

Regarding the induction heating cooker 2 referred to in Embodiment 1, although the user sets the power supply start time for the heating unit, the user may not set the power supply finish time. Accordingly, in a strict sense, the time period may not be set. However, the induction heating cooker 2 according to Embodiment 1 is configured as follows:

(1) A maximum continuous heating time is automatically set to 60 minutes, so that the heating operation is automatically finished after 60 minutes unless a specific operation is performed during the cooking. With employment of such control, the time period may be set when the user sets the time of day for starting the heating.

(2) The cooking menu of the induction heating (e.g., "frying", "boiling", "stewing", and "water heating") includes, as experience shows, those that finish in 15 minutes to less than 30 minutes (e.g., "water heating") and those that last an hour or more, and the power consumption also varies depending on the menu. Therefore, the cooking menu that is presumed to require a power of 500 W or more and last 30 minutes or longer (hereinafter referred to as "specific menu") is selected in advance, and the time period-classified electricity rate information is displayed when the specific menu is about to be cooked.

A reason for the above-mentioned configuration is that displaying the time period-classified electricity rate information each time the cooking menu that finishes in a short time and requires only a small amount of power is selected does not make much sense because the information is actually seldom utilized. Therefore, the above-mentioned configuration simplifies the control program of the induction heating cooker 2, as well as the operation of the user. In Embodiment 1, "boiling", "stewing", and "rice cooking" are selected as specific menus, however the present invention is not limited to such a setting.

Reference symbol 7 denotes the home-use air-conditioning apparatus which, though may be sometimes installed in the kitchen where the kitchen electric appliances KP are located, is assumed to be installed in another room (e.g., living room) in Embodiment 1. In addition, a plurality of air-conditioning apparatus 7 in total, instead of just one, may be respectively installed in a plurality of rooms; however, the following description is based on the assumption that there is only one air-conditioning apparatus 7. In the air-conditioning apparatus 7, a power usage control device 8E of the power instruction apparatus 9 is incorporated. Accordingly, information about the power requirement, the cooking status of the cooking devices, and permitted power usage is exchanged with the power instruction apparatus 9, so that the power usage control device 8E controls the power of the air-conditioning apparatus 7 within a power usage permitted by the power instruction apparatus 9.

Further, the air-conditioning apparatus 7, the dish washer-dryer 6, and a washing-drying machine (washing machine unified with clothes dryer) or a clothes dryer configured to blow air heated by an electric heater while forcibly rotating clothes thereby drying the clothes (neither shown) are hereinafter referred to as "second home electric appliance". The cited appliances each include a motor unit that consumes electric energy, and are configured to be turned on and off independently from one another and receive a power reduction instruction from the power instruction apparatus 9 as is subsequently described. The "second home electric appliance" also includes such appliances that include a motor that consumes power and a heating unit that consumes electric energy, and is configured to generate hot airflow by the heating unit. The electric clothes dryer and the washing-drying machine that also works as a washing machine are such examples and, for example, the washing-drying machine includes a basket-shaped air-permeable container (drum) in which washed but not dried clothes are placed, a motor configured to rotationally drive the container, and an electric heater serving as the heat source of the hot air supplied to the container. Some washing-drying machines include an electric compressor to collect heat from ambient air and generate hot airflow by a heat pump method.

Figure 23:
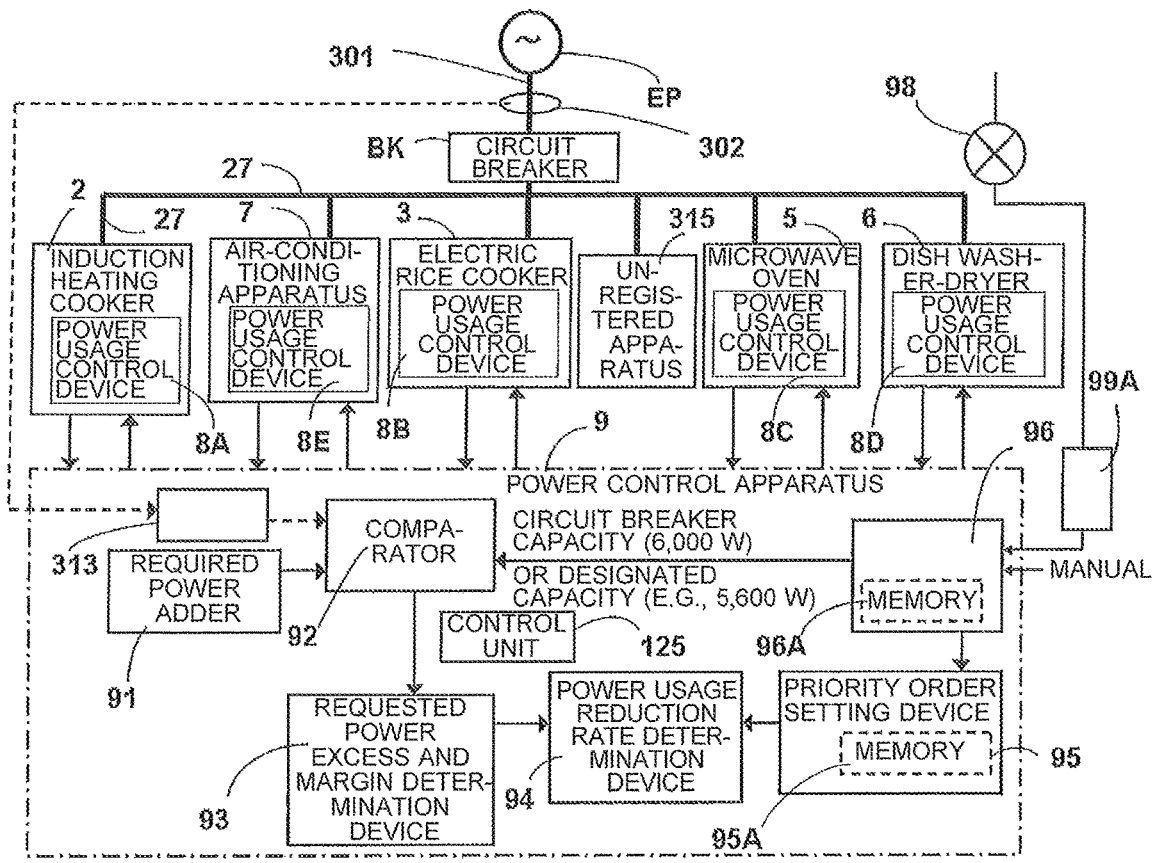
FIG. 23 is a block diagram for illustrating a general configuration of the power control system according to Embodiment 1 of the present invention, except for the healthcare instruments and the activity measurement apparatus.

As illustrated in FIG. 23, the kitchen electric appliances KP are connected to the commercial power source EP of AC 200 V via the single circuit breaker BK. The kitchen electric appliances KP are configured to exchange infrared ray signals or wireless signals with the power instruction apparatus 9. Accordingly, information about the power requirement, the cooking status of the cooking devices, and permitted power usage is exchanged between the power instruction apparatus 9 and power usage control devices 8A, 8B, 8C, 8D of the kitchen electric appliances KP, respectively, so that the power usage control devices 8A to 8D respectively control the power of the kitchen electric appliances KP within a power usage permitted by the power instruction apparatus 9.

Examples of the kitchen electric appliance KP also include devices having a rated maximum power of 1,000 W or so, such as a toaster oven, a table-top hot plate, and a water boiler (electric thermos pot), which are however excluded from the drawings for the sake of simplicity of the description. In addition, the kitchen electric appliances (induction heating cooker 2, rice cooker 3, and microwave oven 5) and the power instruction apparatus 9 may be connected to each other via a signal line that also serves as a power line, so as to use power line transport technology for the control.

(Induction Heating Cooker 2)

As illustrated in FIG. 25 and FIG. 26, the induction heating cooker 2 is what is known as a dual-heater built-in induction heating cooker including two left and right induction heating units that can independently operate. An operation button 11A of a main power switch 11, and power control dials 12L and 12R for the first heater (left heater) 2L on the left and the second heater (right heater) 2R on the right, respectively, are provided on an operation panel 13 on the right of the front surface of the induction heating cooker 2. The user turns on the main power switch 11 and adjusts the power control dial 12L or 12R depending on the cooking state to perform cooking. Thus, with the power control dials 12L and 12R, the heating power of the first heater 2L and the second heater 2R can be independently controlled when performing the induction heating.

The rated power consumption (maximum power consumption) of the induction heating cooker 2 is 5,800 W. Unlike a free-standing induction heating cooker, a built-in induction heating cooker is installed by a specialized installer so that a power source plug of a power cord led out from the induction heating cooker 2 cannot be easily inserted into or removed from a power outlet (power connection port) connected to the power supply line 27 by a user of a general household. Therefore, commercial power (e.g., 200 V) is constantly supplied to a position just before the main power switch 11.

The first heater 2L and the second heater 2R are covered with a top plate (glass top plate) 14 made of heat-resistant reinforced glass, and ring-shaped heating units (induction heating coils 2LC and 2RC) serving as the heating source for the first heater 2L and the second heater 2R are installed in the space under the top plate.

Reference symbol 2C denotes a box-shaped main body casing constituting the outer shell of a main body 2A of the induction heating cooker 2, and a frame-shaped metal frame 15 covers the perimeter of the top plate 14 and fixes the top plate 14 onto the upper surface of the main body casing 2C.

Along the forward end portion of the upper surface of the main body 2A, the following units are provided: a central display unit (central display panel) 16 serving as a display unit and including an LCD substrate configured to display set values of cooking conditions, a warning, and abnormal condition; a left display panel 17L and a right display panel 17R each including an LCD substrate configured to display a heating power value and a heating power level (high, medium, and low) during the induction heating; a left display unit 18L configured to indicate a heating time and oil temperature during oil cooking with the first heater 2L in LCD letters or a plurality of LEDs (light emitting body); a right display unit 18R configured to indicate a heating time and oil temperature during oil cooking with the second heater 2L in the same way as the left display unit 18L; and an upper surface operation unit 26 for use to start the heating operation.

The upper surface operation unit 26 is used to input drive conditions of the induction heating cooker 2. The "drive conditions" herein refer to conditions for determining heating capacity and heating power, such as a high-frequency current value to be applied to the induction heating coil 2LC of the first heater 2L to be subsequently described. Physical conditions such as the supply time of the high-frequency current and the frequency thereof are also examples of the drive conditions. In other words, the drive conditions are conditions for driving two inverter circuits 33L and 33R and a grill heater driver circuit 34 to be subsequently described.

The central display unit 16, the left display panel 17L, the right display panel 17R, the left display unit 18L, and the right display unit 18R are located close to the lower surface of the top plate 14.

The display on the central display unit 16, the left display panel 17L, the right display panel 17R, the left display unit 18L, and the right display unit 18R is controlled by a display unit driver circuit 35 illustrated in FIG. 28.

Referring now to FIG. 28, the display unit driver circuit 35 is described. Although FIG. 28 only includes the central display unit 16 out of the display units, the left display panel 17L, the right display panel 17R, the left display unit 18L, and the right display unit 18R are also controlled in the same way as the central display unit 16.

In Embodiment 1, the central display unit 16 is shared by all the heating sources and hence is also called an integrated display unit. Here, the heating sources include the first heater 2L, the second heater 2R, and a plurality of electric radiation heaters, for example, sheath heaters 34H, provided inside a grill chamber 22 of the grill cooker 4.

A display screen 129 constituting the central display unit 16 is a known dot matrix LCD screen, and is capable of displaying high-definition images (equivalent to QVGA having resolution of 320×240 pixels or VGA of 640×480 dots capable of displaying 16 colors) and a multitude of characters even when displaying characters. The LCD screen may have a single-layer structure, or may have an upper and lower dual-layer structure or a structure with more layers to display a larger amount of information. In addition, the LCD screen may be constituted of a super twisted nematic (STN) LCD driven by a simple matrix method.

In Embodiment 1, the display region of the display screen 129 is a rectangular region of approximately 40 mm (or 80 mm) in the vertical (front-back) direction and approximately 100 mm (or 120 mm) in the transverse direction.

In FIG. 27, reference symbol 35 denotes a display unit driver circuit. The display unit driver circuit 35 is connected to the controller 32. As illustrated in FIG. 28, the display unit driver circuit 35 includes a display memory 35A, a display controller 35B, an interface unit 35C, a power source 35D, a common driver 35E, and a segment driver 35F.

As illustrated in FIG. 28, the display unit driver circuit 35 is activated by the power from the power source 35D, and acquires image information to be displayed from a storage device (built-in memory) 32R of the controller 32 through the interface unit 35C. The display memory 35A stores the image information acquired from the controller 32. As illustrated in FIG. 28, the display controller 35B reads out the image information stored in the display memory 35A, and continuously drives the common driver 35E and the segment driver 35F based on the image information. The common driver 35E and the segment driver 35F apply a voltage to electrodes intersecting each other respectively corresponding to the pixels of the display screen 129, to thereby drive the liquid crystal. Thus, the display unit driver circuit 35 causes the image information stored in the display memory 35A to be displayed on the display screen 129 whenever necessary. The image information to be displayed and the driving current for light emission are also provided to the right display panel 17R, the left display panel 17L, the left display unit 18L, and the right display unit 18R. The information to be displayed on the display screen 129 by the display controller 35B includes text data in writing so that types and causes of the abnormality can be known as subsequently described.

For example, after the controller 32 brings any one of the two induction heating units (induction heating coil 2LC or 2RC) to emergency stop due to occurrence of abnormality, the display unit driver circuit 35 performs display of the abnormality occurrence in response to the instruction from the controller 32. At this time, the controller 32 analyzes the abnormality content based on the detection output of an abnormality detection unit ES, and causes the central display unit 16 to display information classified in advance so that the causes corresponding to the abnormality types (e.g., abnormal high-temperature state of the top plate 14, abnormal voltage of the inverter circuit 33R) can be known. The text (text data) as the base of such display is stored in advance in the display memory 35A.

In FIG. 28, reference symbol 321 denotes the NFC communication control IC (NFC control circuit) constructing a part of the NFC tag arranged at predetermined positions (two NFC input-output units 401L and 401R illustrated in FIG. 26). Reference symbol 322 denotes the antenna connected to the NFC control circuit 321 and configured to generate inductive power being power for the NFC control circuit 321 upon reception of a wireless signal of a predetermined frequency from the outside. Reference symbol 320 denotes the microchip memory (equal to the "NFC storage unit" described above) connected to the NFC control circuit 321. The two NFC input-output units 401L and 401R (also collectively referred to as "NFC input-output unit 401") are each provided with the dedicated antenna 322, NFC control circuit 321, and NFC storage unit 320. Therefore, for example, the abnormality monitoring information relating to the first heater 2L, which is generated during heat cooking with the first heater 2L, cannot be acquired by the mobile phone terminal 87 unless via the left NFC input-output unit 401L. However, the above-mentioned identification information can be acquired from any one of the left and right NFC input-output units 401. The identification information can be acquired not only when an abnormality occurs, but also during operation stop, immediately after operation start, and other various timings. Detailed description is given subsequently.

In FIG. 28, reference symbol 323 denotes a light emitting diode element (LED) installed so as to surround the vicinity of a part of the antenna 322 constituting each of the two NFC input-output units 401L and 401R. The LED 323 illuminates the antenna 322 from below so as to surround the vicinity of the part of the antenna 322 in a rectangular frame shape in the upper surface operation unit 26. Therefore, the user easily recognizes the part of the antenna 322. Such an LED 323 cooperates with the operation of the display unit driver circuit 35 by the controller 32, and hence is turned on by the display unit driver circuit 35 at a predetermined timing in synchronization with the display that the detailed abnormality content and the information for countermeasures can be obtained by, for example, the mobile phone terminal 87 having the short range communication (NFC) function. The specific turn-on timing is a start time point of an "abnormality occurrence notification section ET3" illustrated in FIG. 64. The turn-off timing is the end of the abnormality occurrence notification section ET3, that is, the time point at which the main power is turned off, but the LED 323 may be automatically turned off after an elapse of a certain time period from the turn-on.

An information sign PU representing "unusable" with the words "UNUSABLE BECAUSE EXCLUSIVE TO ANOTHER PERSON" in FIG. 32 to be subsequently referred to, which appears when an occupant other than the occupant registered in the power instruction apparatus 9 attempts to use the induction heating cooker 2, is stored in the display memory 35A. The controller 32 instructs, upon reception of a predetermined signal from the power instruction apparatus 9, the display controller 35B to display the information sign PU on the display screen 129. In addition, when a help mode key 111 to be subsequently described is pressed, the display indicating in illustrations and letters the correct way to view the display screen 129 and the operation method of the display screen 129, which appears all over the display screen 129, and a reduction display section 36C (see FIG. 36) indicating in letters that power reduction has been forcibly done, are displayed on the display screen 129 through the same process as the information sign PU indicating the message of "unusable".

Although the display unit driver circuit 35 is constituted of an exclusive microcomputer independent from the microcomputer constituting the controller 32, the display unit driver circuit 35 may be constituted of the same microcomputer.

(Basic Operation of Induction Heating Cooker 2)

Figure 29:
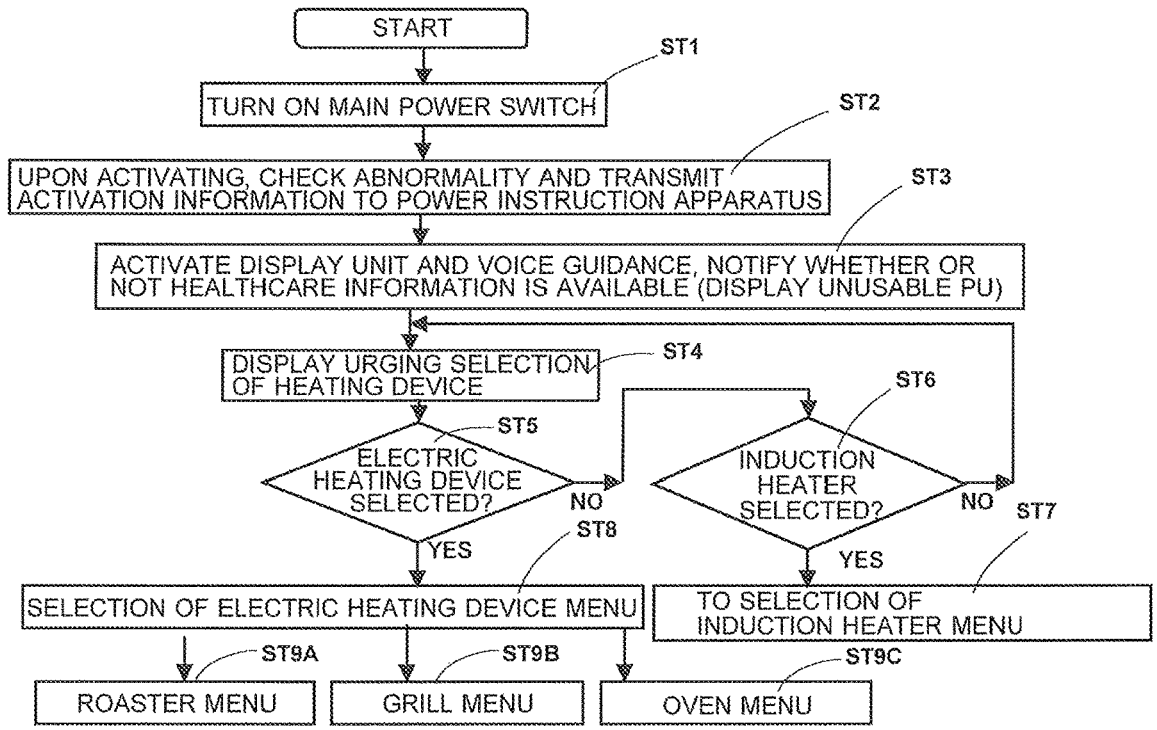
FIG. 29 is a control step explanatory diagram for illustrating basic operations of the induction heating cooker illustrated in FIG. 25.
Figure 30:
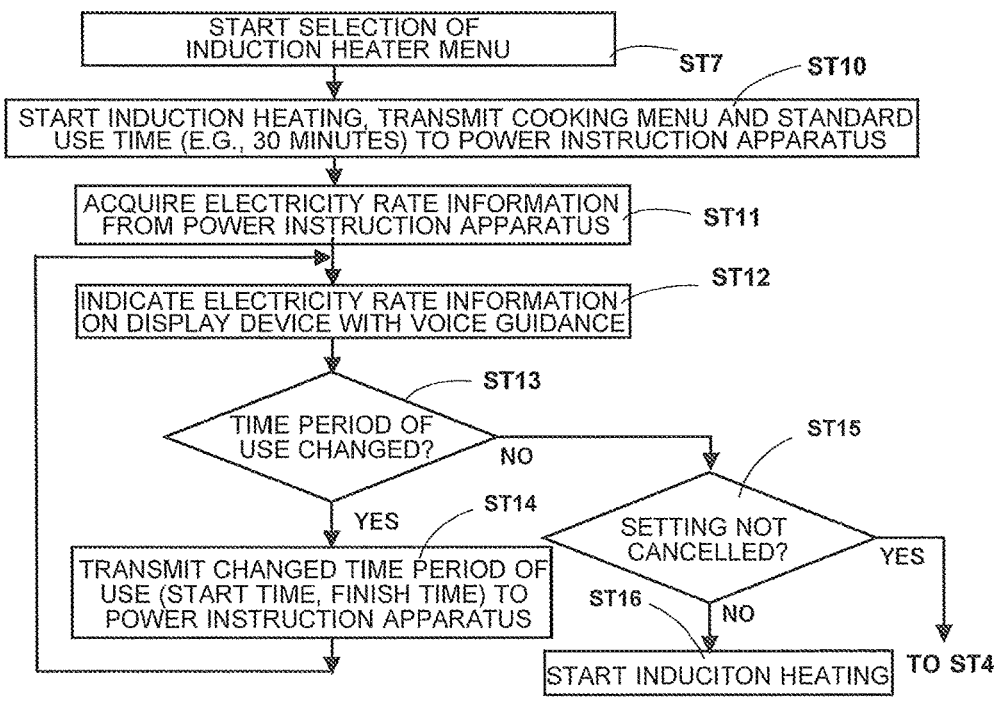
FIG. 30 is a control step explanatory diagram for illustrating a cooking menu selection process of the induction heating cooker illustrated in FIG. 25.
Figure 31:
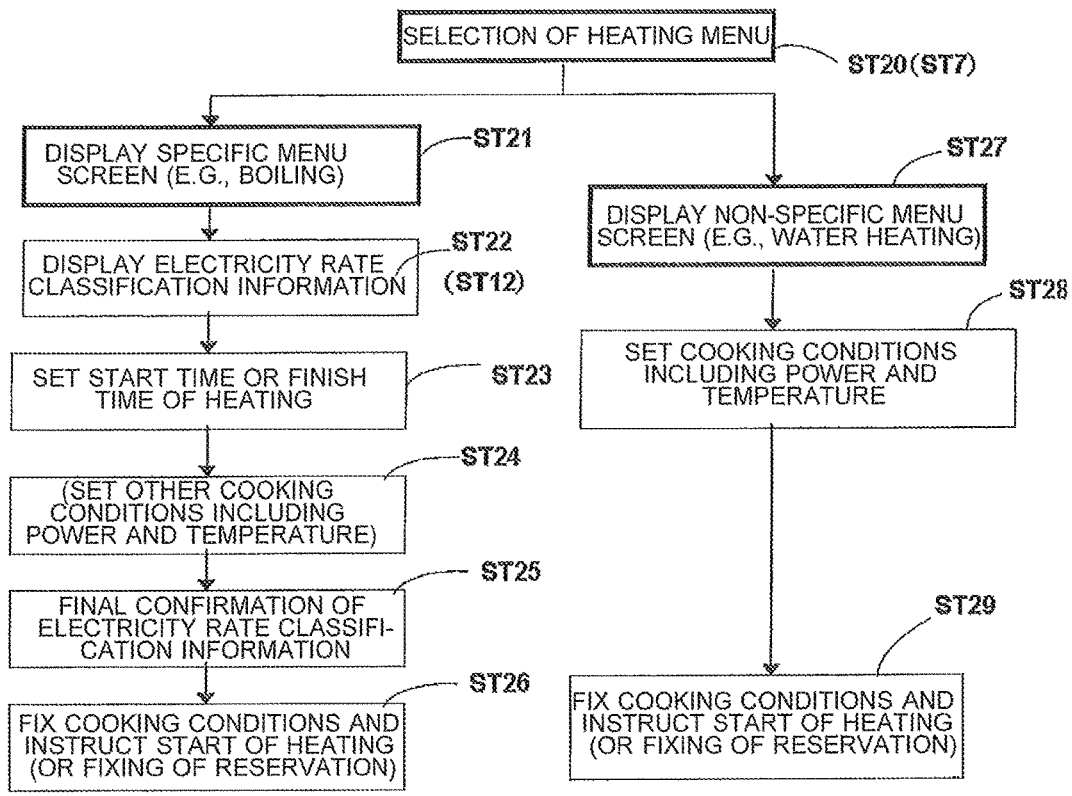
FIG. 31 is a control step explanatory diagram for illustrating the cooking menu selection process of the induction heating cooker illustrated in FIG. 25.

Hereunder, the induction heating operation performed by the induction heating cooker 2 according to Embodiment 1 is described with reference to FIG. 29 to FIG. 31. FIG. 29 is a control step explanatory diagram for illustrating basic operations of the induction heating cooker 2. FIG. 30 is a control step explanatory diagram for illustrating a cooking menu selection process of the induction heating cooker 2. FIG. 31 is a control step explanatory diagram for illustrating the cooking menu selection process of the induction heating cooker 2.

The flowchart of FIG. 29 represents the basic operation process of the induction heating cooker 2. Referring to FIG. 29, when the user touches the operation button 11A of the main power switch 11, the power is turned on (ST1). Then the power is applied to the controller 32, which acquires temperature information from a temperature detection circuit 150 and performs a self-check to confirm whether the temperature of main parts of the cooker is not abnormally high (ST2). Further, an ammeter or a voltmeter installed on each of the primary side and the secondary side of the inverter circuits 33L and 33R configured to supply high-frequency currents to the two induction heating coils 2LC and 2RC perform a self-check to confirm whether or not abnormal current is flowing.

The "abnormality detection unit" ES in Embodiment 1 of the present invention includes the temperature detection circuit 150 and electric sensors (not shown) such as the ammeters or the voltmeters installed on each of the primary side and the secondary side of the inverter circuits 33L and 33R. As subsequently described, a plurality of temperature sensors (not shown) are arranged so as to detect the temperature of the heating object N on the top plate 14, the temperature of the top plate 14 itself, the ambient temperature in the grill chamber 22, the inverter circuits 33L and 33R, and the central display unit 16. The temperatures detected by those temperature sensors are also transmitted to the temperature detection circuit 150, and hence those temperature sensors also configure a part of the "abnormality detection unit".

In the case where abnormality is not detected, the controller 32 activates the display unit driver circuit 35 to operate, for example, the central display unit 16, and displays in the central display unit 16 a message indicating that cooking can be started because there is no abnormality, and outputs a voice message to the same effect as that of the central display unit 16 by using a voice synthesizer 38 (ST3). When specific caution information (e.g., highest blood pressure exceeding upper limit) is generated as healthcare information, an exclusive caution information light 430 illustrated in FIG. 26 is turned on as an alarm to the user, instead of utilizing the display units such as the central display unit 16. In FIG. 27, the caution information light 430 is not illustrated.

The exclusive caution information light 430 is turned on as described above as an alarm to the user each time the main power of the induction heating cooker 2 is turned on, within a predetermined period of time after the above-described specific caution data is added to the healthcare information, that is, after the caution data is transferred from the healthcare processing unit 116 to the power instruction apparatus 9. Such a configuration ensures that the subject is made aware of the caution data. For example, when the blood pressure was measured the day before and the highest blood pressure exceeded the upper limit, the exclusive caution information light 430 is lit up for seven days after the day of the measurement to notify the user that the caution data has been made, and such notification period may be extended or shortened by the user as desired.

The caution information light 430 includes a press-button switch and a light source such as an LED that illuminates the switch button from below, and when the user further presses the button while the light source is on, the content of the caution information is displayed in the central display unit 16. The display may indicate, for example, that the highest blood pressure of the subject A exceeded 140 mmHg the day before yesterday and last night successively. Such a display is automatically erased after a predetermined time (e.g., 10 seconds), and the operation proceeds to Step ST4.

After that, the central display unit 16 then displays letters urging the user to place a heating object N, e.g., a metal pan on the first heater 2L or the second heater 2R, whichever the user desires to use (ST4).

At this point, the above-described first information sign 210A showing letters of "object of power reduction" appears on the display screen of the central display unit 16, to indicate that the induction heating cooker (heating cooker) 2 may receive a power reduction request signal to be subsequently described, during the operation.

When the user presses an on/off button 81c in a left heater operation unit 81, the first heater 2L on the left is selected. When the user presses an on/off button 82c on the right, the second heater 2R on the right is selected (ST6). Then the menu of the induction heating is to be selected (ST7). For example, when a frying button 81a is pressed thereafter, the fry cooking is selected, and when a 3 kW button 81b is pressed, water heating can be performed with a maximum heating power of 3 kW.

When a start/stop button 83b in the central position is pressed, the grill cooker 4 is selected (ST5). In other words, the heat cooking with use of a heating source of electric radiation heat is selected. After selecting the heat cooking with use of a heating source of electric radiation heat, one of the roaster cooking, the grill cooking, and the oven cooking is selected (ST9A, ST9B, ST9C).

When the user rotates a power control dial 12L for the first heater 2L provided on an operation unit 43 of the main body 2A, a signal representing the rotating operation is transmitted to the controller 32. The controller 32 controls the output of the inverter circuit 33L based on the received rotation signal, to thereby adjust the induction heating power of the induction heating coil 2LC of the first heater 2L being used. In this process, the controller 32 displays the intensity of the heating power, for example, in numerals indicating the power value, on the left display panel 17L for the first heater 2L.

After the heat cooking is finished, the user presses the on/off button 81c again, to finish the induction heating operation. In the case of the heating operation with the electric radiation heat with the grill cooker 4, the start/stop button 83b is pressed to finish the operation.

When the user places the heating object N on the second heater 2R, the induction heating can be similarly performed by using the heating unit (induction heating coil 2RC) provided in the main body casing 2C at a position under the second heater 2R. In this case, the operation of the on/off button 82c and the power control dial 12R by the user, and the display on the left display panel 17L are the same as the operation of the on/off button 81c and the power control dial 12L, and the display on the left display panel 17L for the first heater 2L described above.

After high-frequency current is supplied to the above-mentioned two induction heating coils 2LC and 2RC to start full-scale induction heating, the ammeter or the voltmeter installed on each of the primary side and the secondary side of the inverter circuits 33L and 33R monitors whether or not abnormal current is flowing. Even after the power is supplied to the electric heaters (sheath heaters) 34H to start electric radiation heat cooking, whether or not abnormal current or abnormal voltage is generated in the driver circuit 34 is monitored. In other words, in any of the induction heating and the electric radiation heat cooking, whether or not the state is electrically abnormal is monitored by the controller 32. The controller 32 further obtains temperature information from the temperature detection circuit 150 to monitor whether or not the main part of the cooker is in an abnormal high-temperature state. The abnormality monitoring is subsequently described in detail.

The flowchart of FIG. 30 represents the basic operation process of the induction heat cooking. In FIG. 30, ST7 represents the step of selecting the induction heating menu as described with reference to FIG. 29.

In the induction heat cooking, first the heat cooking menu is selected. The heat cooking menu includes, for example, "frying", "boiling", "stewing", and "water heating" as described above. When the cooking menu is selected, predetermined activation information is transmitted to the power instruction apparatus 9 to be subsequently described, so that the power instruction apparatus 9 recognizes that the induction heat cooking is about to be started with the induction heating cooker 2 (ST10). Then, the induction heating cooker 2 acquires the time period-classified electricity rate information from the power instruction apparatus 9 (ST11), and stores the information in the internal memory. The time period-classified electricity rate is not frequently revised, and hence the information may be acquired every several days so as to utilize the information stored in the built-in memory each time for the several days.

The induction heating cooker 2 then displays the time period-classified electricity rate information on the display screen of the central display unit 16, and outputs a voice message indicating the operation method to follow, through the voice synthesizer 38 to be subsequently described. More specifically, in the case where the time to use the induction heating cooker 2 is unchanged, the message urges the user to press a start key 212 to be subsequently described (ST12).

In the case where the time period of use of the induction heating cooker 2 is unchanged (ST13, NO), it is determined whether or not the setting has been cancelled (ST15), and in the case where cancelling has not been input, the operation proceeds to Step ST16 to start the induction heating operation. In the case where the time period of use has been changed (ST13, YES), information of the new time period of use is transmitted to the power instruction apparatus 9 (ST14). Then the electricity rate information corresponding to the changed time period of use is displayed on the display screen of the central display unit 16. At Step ST10, a predetermined standard time, for example, 45 minutes for "boiling", is transmitted to the power instruction apparatus 9, however when the user inputs both of the start time and finish time of use and sets a specific time period (e.g., 30 minutes), the information of the scheduled time period of use is transmitted to the power instruction apparatus 9 at Step ST14.

The flowchart of FIG. 31 also represents the basic operation process of the induction heat cooking. In FIG. 31, ST20 represents a first step of selecting the induction heating menu, which is the same as Step ST7 for selection described with reference to FIG. 29. As described above, when a "specific menu" such as "boiling" or "stewing" is selected, the time period-classified electricity rate information is displayed on the display screen of the central display unit 16 (ST22). Then the start time and the finish time of the heating are set (ST23), the heating power and the temperature are set if necessary (ST24), the time period-classified electricity rate information corresponding to the time period of use is finally confirmed (ST25), and the start key 212 is pressed provided that the electricity rate is acceptable to confirm the cooking conditions, so as to start the induction heating operation (ST26).

When a non-specific menu is cooked as illustrated in the flowchart of FIG. 31, the time period-classified electricity rate information is not displayed. More specifically, in the case where the heating power and the temperature have to be specified, such data is input (ST28), and when the start key 212 is pressed provided that the heating power and the temperature are acceptable, the cooking conditions are confirmed and the induction heating operation is started (ST29). Here, the finish time of the induction heating may be reserved before the induction heating operation is started. Such a method is generally known as timer cooking, in which the timer is set (e.g., 15 minutes) before starting the cooking, so that 15 minutes are subtracted from the time point at which the induction heating is started, and the induction heating is automatically finished when 15 minutes elapses.

Figure 32:
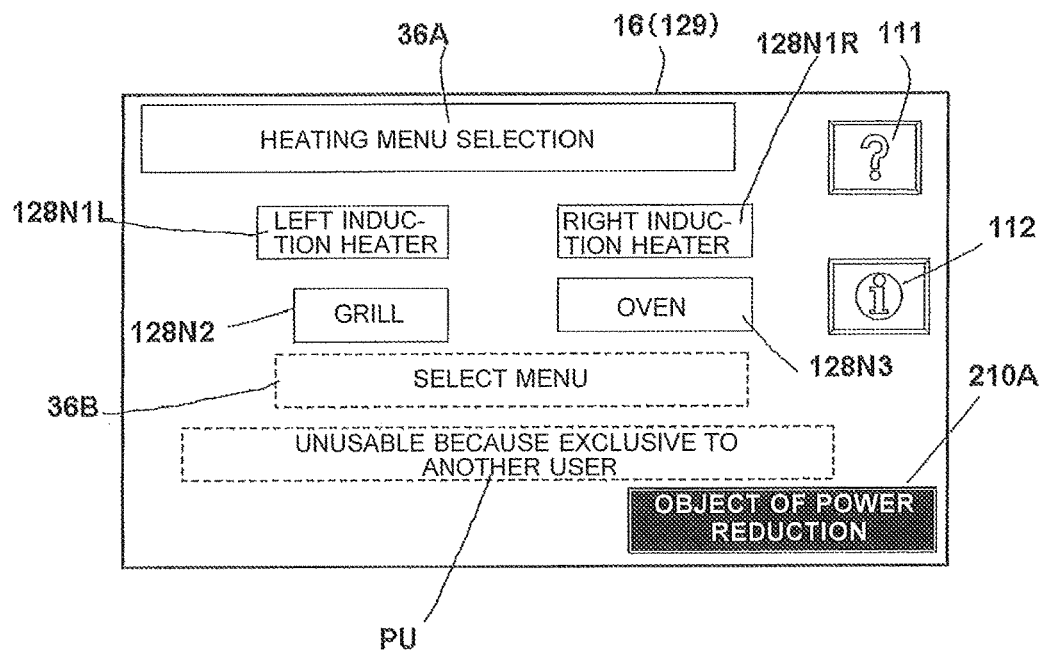
FIG. 32 is a plan view for illustrating a display unit of the induction heating cooker illustrated in FIG. 25.
Figure 33:
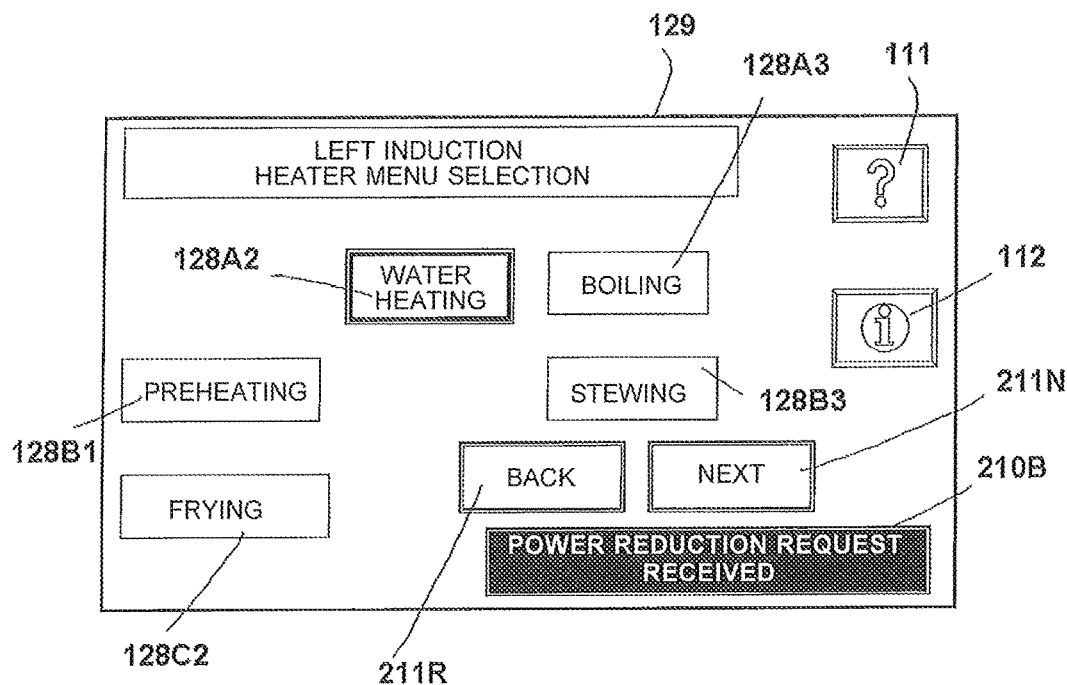
FIG. 33 is a plan view for illustrating the display unit of the induction heating cooker illustrated in FIG. 25.
Figure 34:
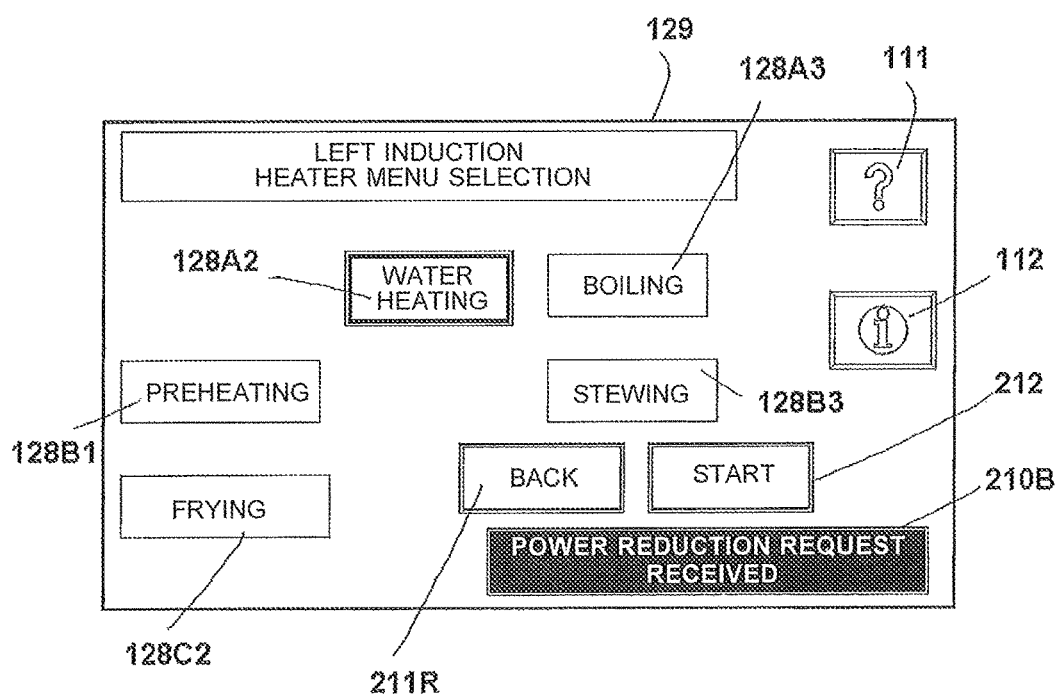
FIG. 34 is a plan view for illustrating the display unit of the induction heating cooker illustrated in FIG. 25.
Figure 35:
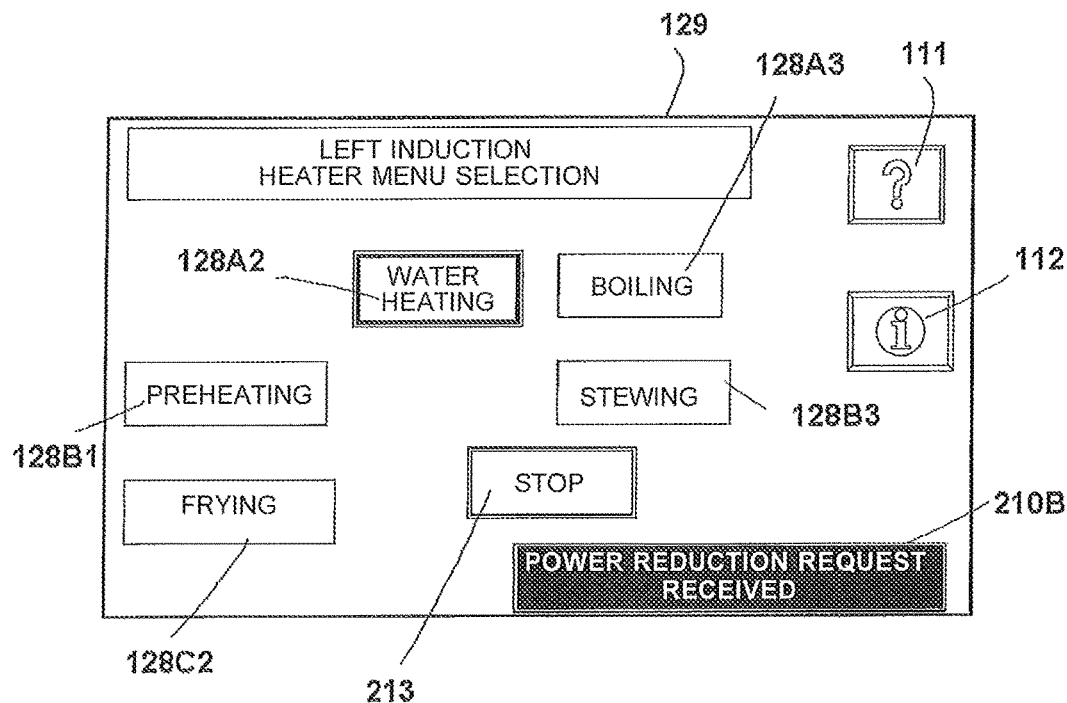
FIG. 35 is a plan view for illustrating the display unit of the induction heating cooker illustrated in FIG. 25.
Figure 36:
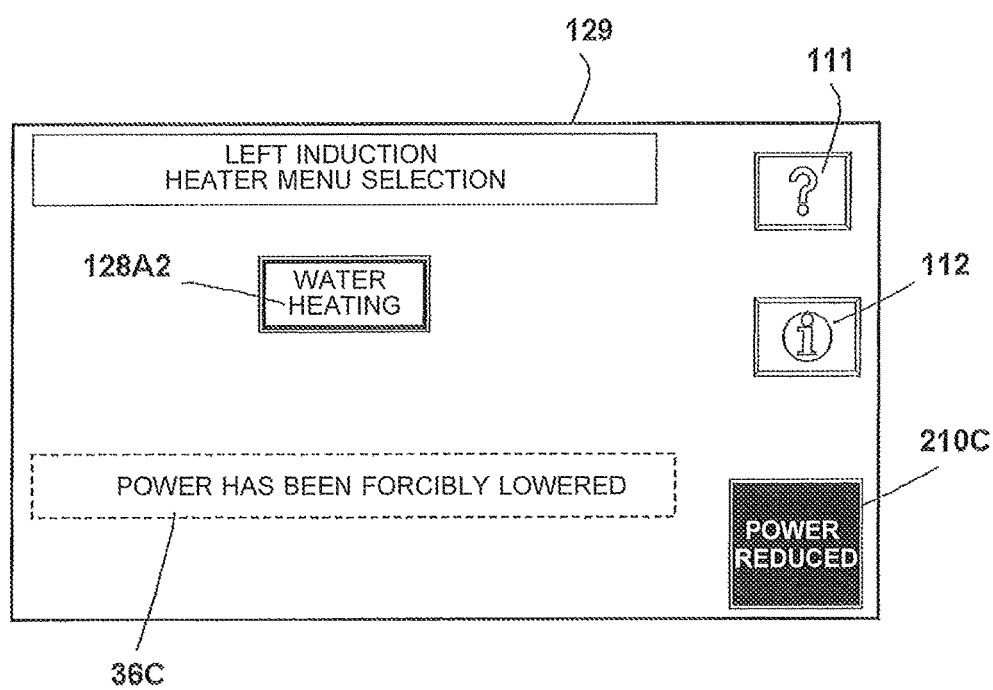
FIG. 36 is a plan view for illustrating the display unit of the induction heating cooker illustrated in FIG. 25.
Figure 37:
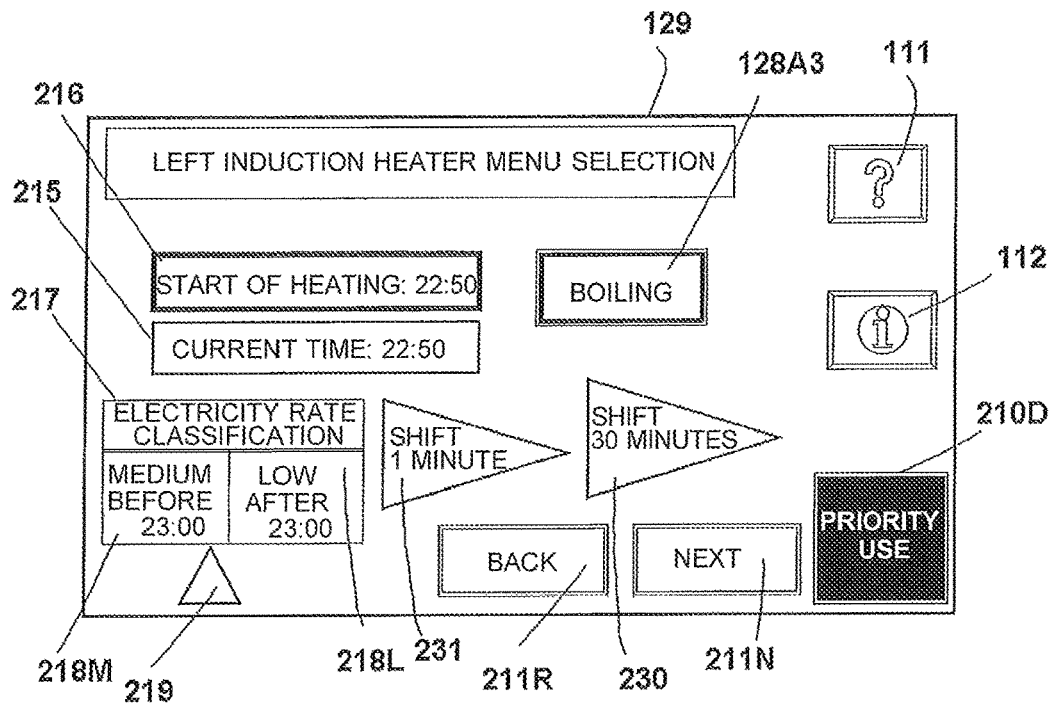
FIG. 37 is a plan view for illustrating the display unit of the induction heating cooker illustrated in FIG. 25.
Figure 38:
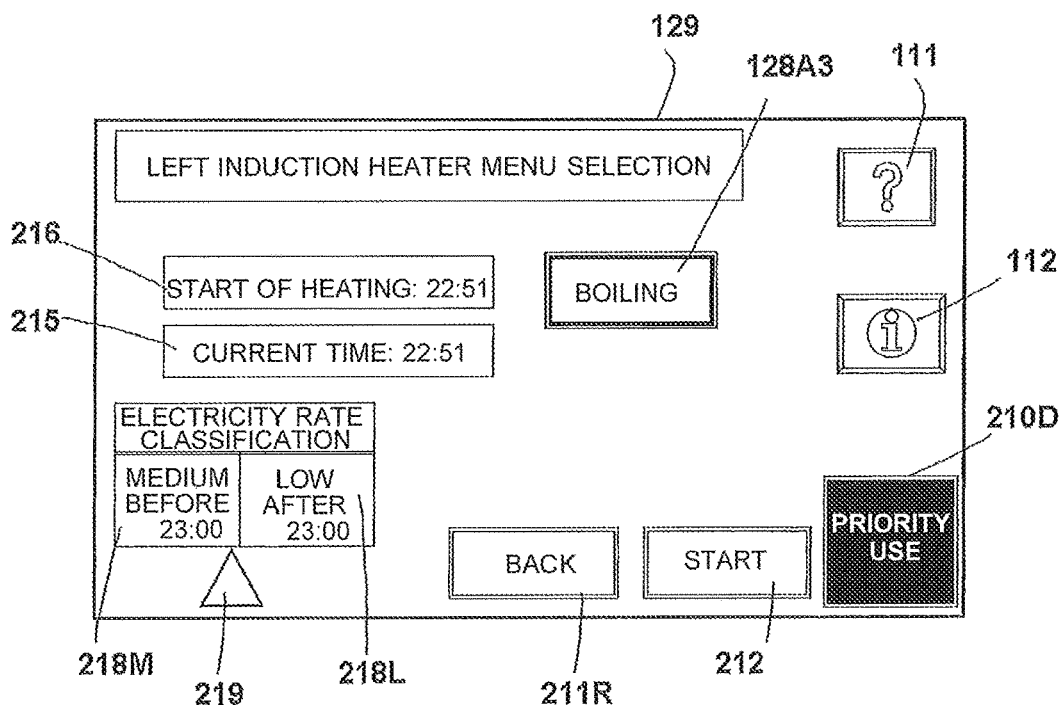
FIG. 38 is a plan view for illustrating the display unit of the induction heating cooker illustrated in FIG. 25.
Figure 39:
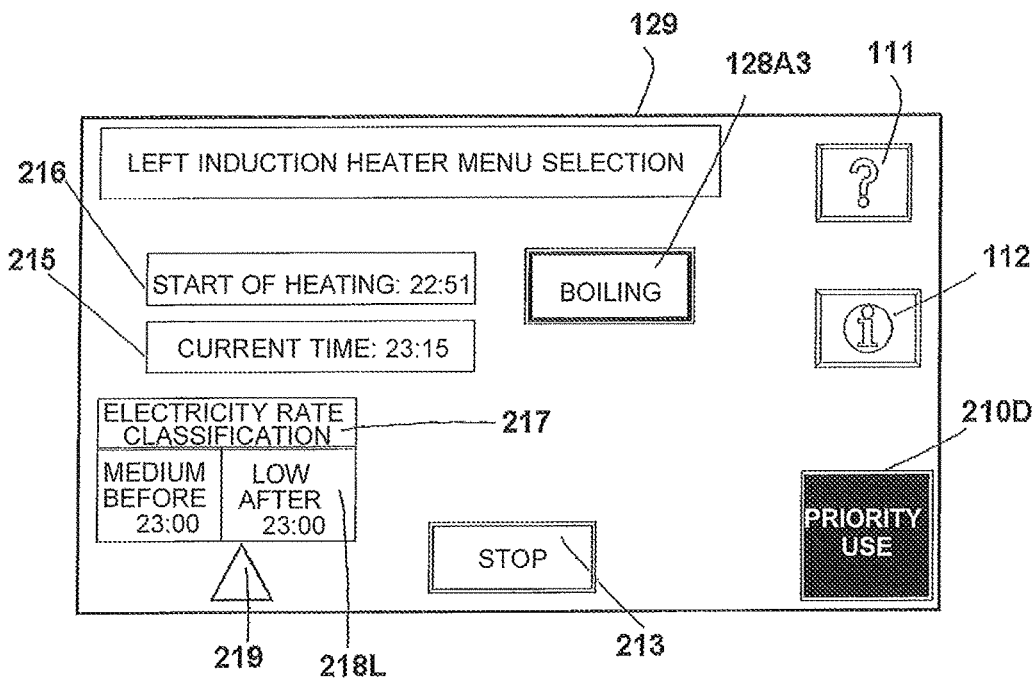
FIG. 39 is a plan view for illustrating the display unit of the induction heating cooker illustrated in FIG. 25.

FIG. 32 to FIG. 39 are display examples of the display screen 129. FIG. 32 is a plan view for illustrating the display unit of the induction heating cooker 2, FIG. 33 is a plan view for illustrating the display unit of the induction heating cooker 2, FIG. 34 is a plan view for illustrating the display unit of the induction heating cooker 2, FIG. 35 is a plan view for illustrating the display unit of the induction heating cooker 2, FIG. 36 is a plan view for illustrating the display unit of the induction heating cooker 2, FIG. 37 is a plan view for illustrating the display unit of the induction heating cooker 2, FIG. 38 is a plan view for illustrating the display unit of the induction heating cooker 2, and FIG. 39 is a plan view for illustrating the display unit of the induction heating cooker 2. When the operation button 11A of the main power switch 11 is pressed, the screen illustrated in FIG. 32 is displayed first. As illustrated, a left induction heating selection key 128N1L, a right induction heating selection key 128N1R, a grill cooking selection key 128N2, and an oven cooking selection key 128N3 are displayed at a time (in the list form) for selection of the cooking menu that uses the induction heater and the grill chamber 22. The oven cooking refers to raising the ambient temperature in the grill chamber 22 to a predetermined temperature to cook food, for example baking a cake. Then, when the left induction heating selection key 128N1R is pressed, the menu screen for the induction heating is displayed, and when the grill cooking selection key 128N2 is pressed, the display is switched to the menu screen for the grill cooking. Here, instead of the left induction heating selection key 128N1R, the frying button 81a or the 3 kW button 81b in the left heater operation unit 81 may be pressed.

In FIG. 32, the four keys 128N1 (L, R), 128N2, and 128N3 are touch input keys that incur a fluctuation of static capacitance upon being touched by the user with the finger, and when the user lightly touches the upper surface of the top plate 14 covering the upper surface of the display screen 129 at the position corresponding to the selected key surface, an effective signal to be input to the controller 32 is generated. Those keys are different from the icons 411 to 413 illustrated in FIG. 12. In the following, when both the keys 128N1L and 128N1R are referred to, reference symbol 128N1 is employed.

To be more detailed, no display indicating the input function of the keys is provided, neither in letters nor in illustrations printed or carved, on the surface of the top plate 14 on which the regions (sections) corresponding to the respective input keys 128N1 to 128N3 are defined. However, the letters and figures representing the input function of the keys are displayed on the display screen 129 located under the mentioned keys when one of those keys is to be operated, so that when the display screen 129 is touched, the key located at the touched position is selected.

Reference symbol 36A denotes a menu selection display section, and reference symbol 36B denotes a display section for urging the user in letters to select the menu. The menu selection display section 36A and the display section 36B do not possess the input key function, and hence no input is made to the controller 32 by touching those display sections.

Reference symbol 111 denotes a help mode key. When the user touches the key 111, information that assists the user's operation at that time is displayed, and the correct operation method is audibly announced through the voice synthesizer 38 (see FIG. 27) separately provided. When the key 111 is pressed a plurality of times, the information of how to view the display screen 129 and the operation method of the display screen 129 is displayed all over the display screen 129 in illustrations and letters. Reference symbol 112 denotes an information key. Each time the key 112 is touched, the information of the heating object N being used and the cooking method, and suggestions for better cooking are displayed in detail in letters on the display screen 129. Reference symbol 36C illustrated in FIG. 36 denotes a reduction display section for displaying a message in letters that the power reduction has been forcibly done, on the display screen 129.

In FIG. 32, reference symbol 210A denotes a first information sign indicating that the induction heating cooker 2 may receive a power reduction request signal. In the example of FIG. 32, the message of "object of power reduction" is displayed in the display screen 129 in white letters on a colored background in a rectangular frame, which appears immediately after a non-specific menu, for example, "water heating", is selected, and is not displayed until "water heating" is selected. In the case where the power is actually reduced while performing "water heating", a third information sign 210C to be subsequently described is displayed, which may display the words "power reduced". In either case, the user can recognize, by viewing the first information sign 210A, that the power to the induction heating cooker 2 may be forcibly reduced.

In FIG. 32, reference symbol PU denotes an information sign of "unusable" which appears first when an occupant other than the occupant registered as "exclusive user" to be subsequently described in the power instruction apparatus 9 attempts to use the induction heating cooker 2. This display appears at Step ST2 where the display unit such as the display screen 129 illustrated in FIG. 29 is activated. When such use restriction display associated with "exclusive user" appears, the operation process illustrated in FIG. 29 does not proceed any further. In other words, when the use restriction display appears, an input by any of the four keys 128N1 (L, R), 128N2, and 128N3 appearing on the display screen 129 is invalid (controller 32 does not recognize an input signal) even if the user presses the keys. However, in the case where the user desires to obtain permission to use the induction heating cooker 2 from the exclusive user (occupant B), as exemplified by the occupant C referred to in the description of the operation process illustrated in FIG. 62 to be subsequently described, a "permission request key" (not shown) for selecting whether to ask for the permission may be displayed on the display screen 129. When an occupant other than the exclusive user operates the "permission request key" (not shown), a specific signal is transmitted from the induction heating cooker 2 to the power instruction apparatus 9, and inquiry information is transmitted from the power instruction apparatus 9 to the external wide area communication network 98 to which the mobile phone terminal 87 is connected.

FIG. 33 is a display example of the display screen 129 that appears immediately before "water heating" is started by the induction heating cooker 2. Reference symbol 210B denotes a second information sign indicating that a predetermined power reduction request signal AS2 is being received from outside while the water heating is in process. The first information sign 210A displayed in the display screen 129 as the words "object of power reduction" as illustrated in FIG. 32 disappears. In its place, the second information sign 210B notifying "power reduction request received" in white letters on a colored background is displayed at the same position as illustrated in FIG. 33.

In FIG. 33, reference symbol 211R denotes an input key formed on the top plate 14 covering the upper surface of the display screen 129. When the key 211R is pressed, the display returns to the state of the display screen 129 illustrated in FIG. 32. Reference symbol 211N also denotes an input key, a touch of which advances the display to the state illustrated in FIG. 34.

In FIG. 34, reference symbol 212 denotes an input key (also referred to as "start key") formed on the top plate 14 covering the upper surface of the display screen 129. When the input key 212 is touched, the induction heat cooking with the first heater 2L is started. FIG. 35 is an illustration of a display state that appears on the display screen 129 after the water heating operation is started. Reference symbol 213 denotes an input key for stopping (the water heating).

The input keys 211R, 211N, 212, and 213 are touch input keys that incur fluctuation of static capacitance upon being touched by the user with the finger, and when the user lightly touches the upper surface of the top plate 14 covering the upper surface of the display screen 129 at the position corresponding to the selected key surface, an effective signal to be input to the controller 32 is generated. To be more detailed, no display indicating the input function of the keys is provided, neither in letters nor in illustrations printed or carved, on the surface of the top plate 14 on which the regions (sections) corresponding to the respective input keys 211R, 211N, 212, and 213 are defined. However, the letters and figures representing the input function of the keys are displayed on the display screen 129 located under the mentioned keys when one of those keys is to be operated.

In FIG. 36, reference symbol 210C denotes the third information sign indicating that the power to the induction heating cooker 2 has actually been reduced after reception of the predetermined power reduction request signal from outside, while the induction heat cooking menu of "water heating" is in process with the induction heating cooker 2. In the example of FIG. 36, the first information sign 210A (see FIG. 32) or the second information sign 210B (see FIG. 33, FIG. 34) displayed in the display screen 129 is erased, and instead the third information sign with the message of "power reduced" is displayed in white letters on a colored background at the same position.

In FIG. 37, reference symbol 210D denotes a fourth information sign indicating that the power reduction is not applied, which is displayed as "priority use" in white letters on a colored background, at the same position as the first information sign 210A instead thereof. The user can recognize, by viewing the fourth information sign 210D, that the power for the heat cooking currently in process with the induction heating cooker 2 is maintained, without being forcibly reduced. A "priority cooking menu time period" is specified in the induction heating cooker 2 to perform a heating process with priority as is subsequently described, and therefore when the cooking is performed within the mentioned time period, the fourth information sign 210D of "priority use" appears on the right in the display screen 129. FIG. 37 represents the case where the cooking menu of "boiling" is being performed.

In FIG. 33 to FIG. 35, reference symbol 128A2 denotes a key for selecting "water heating" displayed in the display screen 129, reference symbol 128A3 denotes a key for selecting "boiling", reference symbol 128B1 denotes a key for selecting "preheating", reference symbol 12B83 denotes a key for selecting "stewing", and reference symbol 128C2 denotes a key for selecting "frying". Those five keys are touch input keys that incur fluctuation of static capacitance upon being touched by the user with the finger, and when the user lightly touches the upper surface of the top plate 14 covering the upper surface of the display screen 129, an effective signal to be input to the controller 32 is generated. In other words, the five keys 128A2, 128A3, 128B1, 128B3, and 128C2 each include an input electrode, which is a transparent electrode bonded or vapor-deposited to the lower surface of the top plate 14, at the predetermined position on the display screen 129 immediately above the letters indicating the input function of the key, such as "water heating".

In the case where letters indicating the input function of the key such as "water heating" are not displayed at the predetermined position on the display screen 129 corresponding to one of the five keys 28A2, 128A3, 128B1, 12B83, and 128C2, the input function of the key is invalid and hence the input is unable to be made even if the user touches that position. Although the input keys 128A2 and 128A3 of the selected cooking menu remain displayed as illustrated in FIG. 36 and FIG. 37 even after the heating operation is started, the display screen is controlled by the controller 32 so as not to abruptly shift to a different screen despite the key being touched again.

Referring now to FIG. 37 to FIG. 39, display examples of the time period-classified electricity rate information and the use time period information of the induction heating cooker are described. In FIG. 37, reference symbol 215 denotes a time display section indicating the heating start time that appears on the display screen 129 of the central display unit 16 when the boil cooking menu is selected. The display section 215 shows the current time of day read out by the controller 32 from a clock circuit 240 to be subsequently described. Reference symbol 216 denotes a time display section indicating the time that the boil cooking is to be started, which displays the current time of day unless the user sets a different time. This time of day is also displayed in the display screen 129 by the controller 32 based on the information from the clock circuit 240 to be subsequently described. Reference symbol 217 denotes an information sign for displaying the classification of the time period-classified electricity rate. The example illustrated in FIG. 37 displays two columns, which are electricity rate classification information 218M indicating the time period up to 23:00 to which a medium electricity rate is applied, and a display section 218L indicating the time period after 23:00 to which a lower electricity rate is applied.

A triangular mark 219 indicates which of the electricity rate classification is applied if the heating is started right now. In the example illustrated in FIG. 37, it can be intuitively understood that, because the current time is 22:50, which is close to "night hours" from 23:00 but still earlier than that time, the electricity rate per kWh is relatively high (23.13 yen tax included), however after 23:00, the rate of "morning and evening hours" is applied and the electricity rate per kWh is reduced to 9.17 yen (tax included). Here, the electricity rate per kWh itself may be displayed; however, misunderstanding may be incurred if the actual power usage is not strictly accurate. In Embodiment 1, therefore, the rate is displayed as three levels, namely "high", "medium", and "low".

In FIG. 37, reference symbol 211R denotes a return key to be touched to return to the previous display screen, reference symbol 230 denotes a key to delay (shift to a later time) the heating time by one minute, and reference symbol 231 denotes a key to delay (shift to a later time) the heating time by 30 minutes.

Those two keys are also electrostatic touch input keys formed on the top plate 14 covering the display screen 129. The letters indicating the function of the key ("shift one minute", "shift 30 minute") are displayed on the display screen. To revise the heating start time from 22:50 to 23:00 in the screen of FIG. 37, the key 230 is touched 10 times. Then, upon touching the key 211N, the display is shifted to the state illustrated in FIG. 38, and upon touching the start key 212, the cooking conditions are confirmed and the heating operation is started. To return to the screen in FIG. 37 from that in FIG. 38, the key 211R may be touched.

The structure of the induction heating cooker 2 is described again. In FIG. 25, an intake port 20 for introducing air into the grill chamber 22 of the grill cooker 4 to be subsequently described, and an exhaust port 21 for discharging the smoke and the like generated from a cooking object 25 in the grill chamber 22 are formed in the rear portion of the upper surface of the main body 2A. Through the intake port 20, the air in the room is introduced into the inner space of the main body 2A by a fan (not shown), and a part of the introduced air is used for cooling the induction heating coils 2LC and 2RC, and such air is discharged with the room through the exhaust port 21 after being used for cooling. In addition, as illustrated in FIG. 26, the controller 32 configured to control the overall operation of the induction heating cooker 2 is provided inside the main body 2A.

(Configuration of Grill Cooker 4)

Referring to FIG. 25 and FIG. 26, the configuration of the grill cooker 4 is described hereunder.

The grill cooker 4 is mounted inside the main body 2A of the induction heating cooker 2, in a left lower region thereof. The grill cooker 4 includes at least a grill lid 28 openably mounted to the left region of the front surface portion of the main body 2A, the grill chamber 22 which is a cooking space having a front opening openably covered with the grill lid 28, a receiving tray 23 placed on the bottom portion of the grill chamber 22, and a gridiron 24 placed on the receiving tray 23 for the cooking object 25 such as fish to be placed thereon. The grill lid 28 includes a handle 28A to be held by the user to open and close the grill lid.

In addition, an exhaust duct (not shown) communicating between the grill chamber 22 and the exhaust port 21 is connected to the rear portion of the grill chamber 22, to discharge the air introduced through the intake port 20, from the grill chamber 22 through the exhaust port 21 to the outside together with the smoke generated from the cooking object 25.

(Configuration of Upper Surface Operation Unit 26)

Hereunder, the configuration of the upper surface operation unit 26 is described with reference to FIG. 26. In a plan view of the induction heating cooker 2 illustrated in FIG. 26, the upper surface operation unit 26 has an elongate strip shape transversely extending along the front edge of the upper surface of the induction heating cooker 2. The upper surface operation unit 26 is disposed at a position directly behind a front side of the frame-shaped metal frame 15, at a position forward of the front edge of the top plate 14.

In FIG. 26, the upper surface operation unit 26 includes, from the left, a left heater operation unit (first heater operation unit) 81 on the left configured to operate heating of the first heater 2L, a grill chamber operation unit 83 configured to operate the grill heating, and a right heater operation unit 82 configured to operate the heating of the second heater 2R on the right. In addition, a pair of caution information lights 430 is provided on the upper surface operation unit 26.

Reference symbol 26Q is a press-button provided at a central portion of the upper surface operation unit 26. When this button is pressed, an operation signal of an assistance request switch 26S is generated. Thus, the controller 32 causes the display screen 129 to display information for guidance of the operation of the upper surface operation unit 26, and as necessary, the voice synthesizer 38 outputs voice guidance as well. The assistance request switch 26S has a function similar to that of the help mode key 111 to be subsequently described. In other words, when the user presses this key, information that assists the user's operation in that situation is displayed, and a correct operation method is audibly announced through the voice synthesizer 38 (see FIG. 27) separately provided. When the key is pressed a plurality of times, displays indicating in illustrations and letters how to view the display screen 129 or the operation method of the display screen 129 appear all over the display screen 129.

Further, the NFC input-output units 401L and 401R are provided at two locations. The right NFC input-output unit 401R is used to read abnormality monitoring data of the second heater 2R on the right, and the left NFC input-output unit 401L is used to read abnormality monitoring data of the first heater 2L on the left. The common identification information of the induction heating cooker 2 can be read from any of the left and right NFC input-output units 401L and 401R.

As described above, each of those NFC input-output units 401L and 401R is illuminated from below by the light emitting diode element (LED) 323 illustrated in FIG. 28. Upon reception of the instruction from the controller 32, the display unit driver circuit 35 turns on the LED at an appropriate timing. At least when abnormality occurs in electric circuits and electric components relating to the first heater 2L, the left NFC input-output unit 401L is illuminated, and at least when abnormality occurs in electric circuits and electric components relating to the second heater 2R, the right input-output unit 401R is illuminated by the right LED 323. Thus, the user can accurately read out the information indicating the abnormality content by the mobile phone terminal 87.

In FIG. 26, the NFC input-output units 401L and 401R are represented by broken-line frames, and those frames schematically represent the positions of the antennas (NFC antennas) 322. The size of the antenna 322 is actually different from that illustrated in FIG. 26, and the NFC antenna cannot be visually observed directly on the upper surface operation unit 26 in appearance. Therefore, on the surface of a translucent structural plate (not shown) that forms the outer shell of the upper surface operation unit 26, the antenna positions of the NFC input-output units 401L and 401R are indicated by some kind of letters or illustrations so that the antenna positions of the NFC input-output units 401L and 401R can be known even when the light emitting diode element (LED) is not turned on.

The left heater operation unit 81 includes the frying button 81a, the 3 kW button 81b, and the on/off button 81c. The right heater operation unit 82 includes the frying button 82a, the 3 kW button 82b, and the on/off button 82c. The grill chamber operation unit 83 includes a grill menu button 83a, a start/stop button 83b, a left arrow button 83c, a right arrow button 83d, a time-down button 83e, and a time-up button 83f.

The start/stop button 83b includes a start/stop button LED 84. An arrow button LED 85 is provided between the left arrow button 83c and the right arrow button 83d. A time button LED 86 is provided between the time-down button 83e and the time-up button 83f.

Details of the function of the buttons and LEDs are subsequently described. The types and layout of the buttons provided on the upper surface operation unit 26 illustrated in FIG. 26 are merely exemplary, and different configurations may be adopted.

(Control Unit of Induction Heating Cooker 2)

In FIG. 27, reference symbol 27 denotes the power supply line connected to the commercial power source EP of 200 V via the circuit breaker BK, reference symbol 11 denotes a main power switch to be turned on and off by the user, reference symbol 31 denotes a power supply circuit to which electric energy is supplied through the main power switch 11, and reference symbol 32 denotes the controller mainly constituted of a microcomputer to which a predetermined constant-voltage current is supplied from the power supply circuit 31. The microcomputer is constituted of four components, namely, an input terminal, an output terminal, a storage unit, and a central processing unit (CPU), and a power supply control program designed for various cooking menus is stored in advance in the storage unit. In addition to the storage unit (ROM, RAM) of the microcomputer, the controller 32 includes the high-capacity storage device 32R configured to record the abnormality monitoring information.

As described above, in any of the induction heating and the electric radiation heat cooking, whether or not the state is electrically abnormal is monitored by the controller 32. The controller 32 further obtains temperature information from the temperature detection circuit 150 to monitor whether or not the main part of the cooker is in an abnormal high-temperature state. For example, the display screen 129 of the central display unit 16 is formed of an LCD substrate, and hence has a relatively low heat resistance. Therefore, the temperature is monitored via the temperature detection circuit 150 so that the temperature does not exceed a predetermined temperature (e.g., 60 degrees Celsius). At a time point at which the temperature exceeds the predetermined temperature, the controller 32 determines the state as a preliminary abnormal state (only in the case where the temperature falls within the range of 60 degrees Celsius to 65 degrees Celsius). In the preliminary abnormal state, the heating operation is not immediately stopped, and the state is solved by increasing the air sending capacity of the cooling fan that cools the internal space of the main body casing 2C. At a time point at which the temperature exceeds 65 degrees Celsius, however, the controller 32 determines the state as an abnormal state. Then, the heating operation is immediately stopped, and hence, for example, the power supply to the inverter circuit 33L (subsequently described) operating for drive is cut off.

At least information (abnormality monitoring information) indicating the electrical or physical change situation (e.g., temperature of the central display unit 16 described above) of the main part of the induction heating cooker during a period from the preliminary abnormal state to the emergency stop is stored in the storage device 32R of the controller 32. The abnormality monitoring information stored in the storage device 32R is started to be acquired from when the main power switch 11 is turned on, and reflects the history of the electrical or physical change until the cooking is stopped. Therefore, the information of the cooking menu ("water heating", "stewing", "frying", etc., to be subsequently described) selected thereafter and information of the induction heating power are recorded in time series. When the emergency stop occurs part way through due to an abnormal state, the abnormality monitoring information up to the time point is stored in the storage device 32R.

In Embodiment 1, in order to acquire data in a wider range by monitoring the operation of the induction heating cooker 2, monitoring is performed from the time point prior to the preliminary abnormal state. Specifically, although described in detail with reference to FIG. 64, the controller 32 can acquire monitoring information during a period from when the main power is turned on to when the induction heating cooking is brought to emergency stop (called "abnormality monitoring data acquisition section ET1" in FIG. 64).

Reference symbol 33L denotes an inverter circuit configured to supply a high-frequency current to the left induction heating coil 2LC. The induction heating coil 2LC is included in a known resonance circuit in which a resonance capacitor is connected.

Reference symbol 33R denotes an inverter circuit configured to supply a high-frequency current to the right heating unit (induction heating coil 2RC). The heating unit (induction heating coil 2RC) is included in a known resonance circuit in which a resonance capacitor is connected.

The two inverter circuits 33L and 33R are driven by the controller 32 independently from each other.

Reference symbol 34 denotes a driver circuit configured to drive a plurality of electric radiation heaters provided inside the grill chamber 22 of the grill cooker 4, for example, the sheath heaters 34H. The sheath heaters 34H are horizontally mounted inside the grill chamber 22 at a position close to the ceiling and close to the bottom surface respectively, so as to heat the gridiron 24 from above and from below.

Reference symbol 37 denotes a catalyst heater configured to heat a catalyst (not shown) located at the inlet of or halfway from the exhaust duct (not shown) provided from the grill chamber 22 to the exhaust port 21, to thereby promote the removal of the smoke generated from the grill chamber 22. By heating the catalyst (not shown), oxidation and reduction are promoted.

Reference symbol 38 denotes the voice synthesizer configured to synthesize voices electronically generated, and output voice messages, such as operation guidance and notice of abnormality, to the user each time through a voice notification unit (speaker) 39.

Reference symbol 150 denotes a temperature detection circuit. The temperature detection circuit receives the temperature of the heating object N placed on the top plate 14 to be heated by the induction heating coil 2LC or 2RC, the temperature of the top plate 14 itself, the ambient temperature inside the grill chamber 22, and temperature detection information from a plurality of temperature sensors (not shown) configured to detect the inverter circuits 33L and 33R and the central display unit 16, and transmits the temperature detection result to the controller 32. The temperature sensors (not shown) may be of a non-contact type such as an infrared ray sensor or a contact type such as a thermistor, and may be used independently or in combination.

Reference symbol 41 denotes a steam supply device configured to supply high-temperature steam into the grill chamber 22, so as to perform steam cooking with the grill chamber 22 with the high-temperature steam. Reference symbol 43 denotes a front operation unit provided on the operation panel 13 and including the operation button 11A of the main power switch 11 and the pair of power control dials 12L and 12R.

Reference symbol 240 denotes a clock circuit, also called a real-time clock, supplied with power from an exclusive power supply (built-in battery) BT1 different from the power supply circuit 31 connected to the main power switch 11 to be subsequently described, and driven for a long period of time. The clock circuit, which may be a radio-wave clock for example, serves to tell the current day and the correct time to the unit of seconds to the controller 32 whenever requested, and is set to the correct date and time at the stage when the induction heating cooker 2 is manufactured. Therefore, even when the main power of the induction heating cooker 2 is once turned off and again turned on, the time information of the clock circuit is not thereby affected, and the latest correct time can be constantly provided to the controller 32. Therefore, the abnormality monitoring information is always recorded and stored in the storage device 32R of the controller 32 together with the correct time. Therefore, the occurrence time information is added to the abnormality monitoring data to be read to the outside by the mobile phone terminal 87 from the NFC input-output units 401L and 401R. With this, the correct elapsed time can be known when the data is analyzed thereafter.

Reference symbol 241 denotes a vibration sensor configured to detect vibration generated upon occurrence of an earthquake, which transmits a vibration detection signal to the controller 32 once seismic intensity (acceleration) higher than a predetermined level is detected. The controller 32 determines that an earthquake has occurred upon reception of the signal, and instantly cuts off the power supply to all of the heating units currently in use. Such emergency cut-off information is immediately transmitted also to the power instruction apparatus 9 to be subsequently described, so that in the case where any other home electric appliances (in particular, those having an electric heat source) is in use, the power instruction apparatus 9 performs the emergency cut-off of the power supply to such home electric appliances all at once.

Hereunder, oil cooking performed with the induction heating cooker 2 illustrated in FIG. 24 and FIG. 25 is described. The oil cooking refers to the fry cooking of tempura, for example. The fry cooking is not included in the specific cooking menu described above.

The user places a frying pan loaded with cooking oil on the first heater 2L. When the user presses the on/off button 81c provided in the upper surface operation unit 26, the heating operation for the frying pan is started in the same way as the induction heating operation described above. Then the user presses the frying button 81a a predetermined number of times to thereby input the amount of oil in the frying pan to the controller 32 and stores therein the oil amount. The user then rotates the left power control dial 12L so as to set a desired oil temperature. In this process, the oil amount and the oil temperature that have been set may be displayed, for example, in numerals in the left display unit 18L.

When the user presses the on/off button 81c again after the oil cooking is finished, the oil cooking can be finished. As described above, in the fry cooking, the heating power is controlled by the controller 32 such that the oil temperature is automatically increased to the target oil temperature as described above, which is defined as "automatic frying" in the cooking menu. The frying can be performed while manually controlling the heating power, which is defined as "manual frying". In the description given below, "fry cooking" refers to "automatic frying", unless otherwise noted.

When the user places the frying pan on the second heater 2R on the right, the induction heating of the frying pan can be similarly performed. In other words, the operation of the on/off button 82c, the frying button 82a, and the right power control dial 12R by the user, as well as the display operation of the right display unit 18R, are the same as the operation of the on/off button 81c, the frying button 81a, and the left power control dial 12L, and the display operation of the left display unit 18L.

Here, at the time that the fry cooking is started, the first information sign 210A indicating the words "object of power reduction" is displayed on the display screen of the central display unit 16.

The power supply control pattern for the fry cooking is now described hereunder. Although the description is given with respect to the first heater 2L, the same control pattern can be applied to the second heater 2R on the right.

Figure 48:
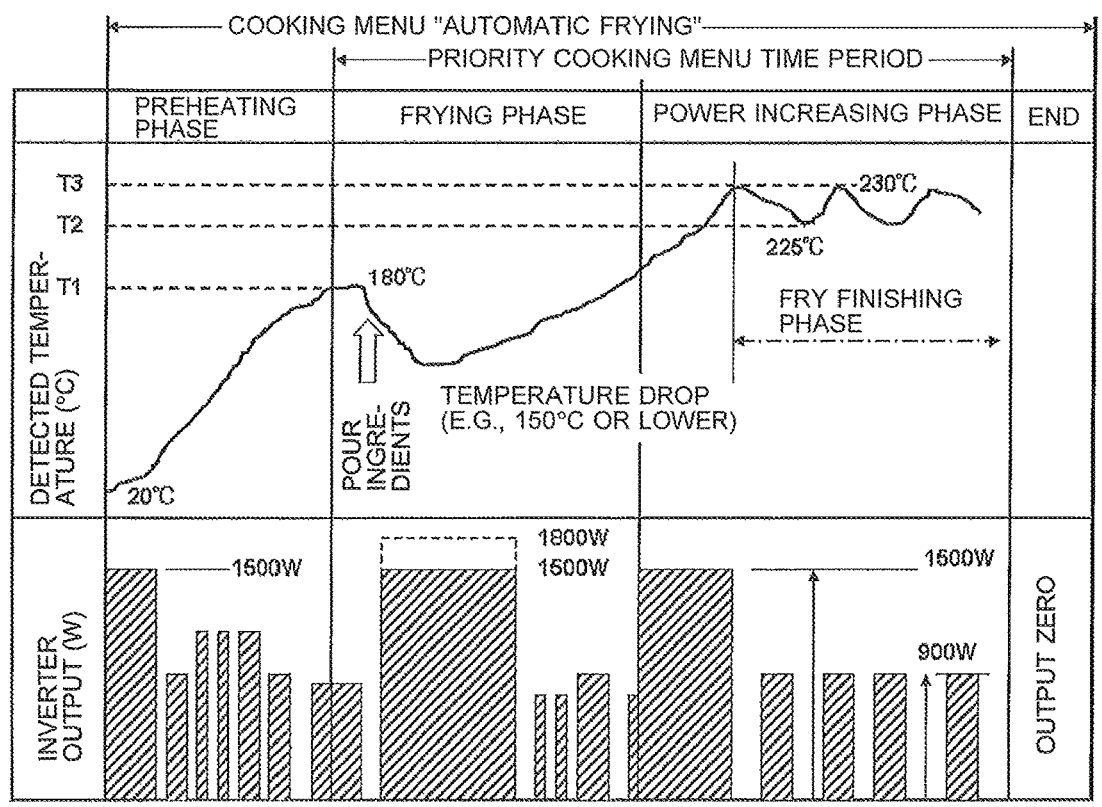
FIG. 48 is an explanatory diagram for illustrating a basic process in fry cooking performed by the induction heating cooker according to Embodiment 1 of the present invention.

When the user selects the (automatic) fry cooking in the cooking menu, the controller 32 sequentially performs a preheating phase, a frying phase, and a power increasing phase as illustrated in FIG. 48. FIG. 48 is an explanatory diagram for illustrating a basic process in fry cooking performed by the induction heating cooker 2 according to Embodiment 1. The fourth information sign 210D showing the words "priority use" appears on the display screen of the central display unit 16. Accordingly, the user can recognize that, in the cooker, the power for the fry cooking is secured with priority, even when the power reduction request signal to be subsequently described is received.

In the preheating phase, when the target oil temperature set by the user is 180 degrees Celsius, the inverter circuit 33L starts to be driven by a predetermined heating power (maximum 1,500 W) so as to rapidly increase the oil temperature from the room temperature (e.g., 20 degrees Celsius), up to the target temperature T1 which is 180 degrees Celsius.

The temperature increase is monitored on a real-time basis by the temperature detection circuit 150 described above, and therefore when the temperature detection circuit 150 detects that the target temperature T1 (first temperature) of 180 degrees Celsius has been reached, the controller 32 adjusts the induction heating amount, that is, the inverter output so as to maintain the target temperature (the automatic control of the high-frequency heating power based on the temperature detection information, so as to bring the temperature close to the target temperature, is hereinafter referred to as "temperature feedback control").

When the process of "temperature feedback control" is begun, the first information sign 210A indicating the words "object of power reduction" disappears from the display screen of the central display unit 16, and instead the fourth information sign 210D indicating the words "priority use" is displayed. Therefore, the user can easily recognize, by viewing the display screen 129, that the power for "frying phase" which is the main part of the fry cooking is secured with priority even though the power reduction request signal to be subsequently described is received.

In addition, the voice synthesizer 38 outputs a voice message to the user, for example saying "Target oil temperature has been reached. Please put in the ingredients".

When the user puts the ingredient in the oil, for example, a croquette that has been frozen, the oil is quickly cooled by the cold ingredient from when the ingredient is input, and therefore the temperature sharply drops as illustrated in FIG. 48. However, the temperature detection circuit 150 is monitoring the fluctuation of the oil temperature, and hence the heating power of the inverter circuit 33L is immediately increased to the predetermined heating power of 1,500 W or 1,800 W, and therefore the oil temperature is again increased (temperature feedback control). Immediately after the oil temperature thus reaches the target temperature T1 again (or when a predetermined time has elapsed), the cooking proceeds from the frying phase to the power increasing phase.

In the power increasing phase illustrated in FIG. 48, the controller 32 controls the inverter circuit 33L so as to maintain the oil temperature between a second temperature T2 of 225 degrees Celsius, which is higher than the target temperature T1, and a still higher upper limit temperature (third temperature) T3 of 230 degrees Celsius. As illustrated in FIG. 48, the heating power of approximately 900 W is intermittently supplied. The process that follows the point when the third temperature T3 is reached is called "fry finishing phase", and is an important phase for obtaining a crispy finish of the fried food. The food may fail to be finished as desired unless a sufficient heating power is applied in the power increasing phase. The frying phase is not specifically limited to be within a predetermined time, and therefore the entire process of the fry cooking is finished when the user presses the on/off button 81c.

As illustrated in FIG. 48, in the cooking menu of the (automatic) fry cooking, the period including the frying phase and the power increasing phase is defined as "priority cooking menu time period", during which the power is restricted from being reduced by an operation or command from outside. In other words, the controller 32 of the induction heating cooker 2 constantly recognizes whether the cooking menu in process is in the "priority cooking menu time period", and when the cooking process is in this time period, the controller 32 notifies the outside of this state. In addition, the third information sign 210C indicating the words "priority use" continues to be displayed on the display screen of the central display unit 16, and therefore the user can recognize that the controller 32 automatically performs the operation for securing the power with priority.

The water heating operation is now described. As described above, the "water heating" menu is not included in the specific cooking menu either. The user places the heating object N such as a pan or a kettle loaded with water on the first heater (left heater) 2L. When the user presses the on/off button 81c provided in the upper surface operation unit 26, the heating operation is started in the same way as the induction heating operation described above. Then the user presses the 3 kW button 81b a predetermined number of times to thereby set the heating time. In this process, the heating time that has been set may be displayed, for example, in the left display unit 18L. The heating operation is automatically finished when the heating time set as above has elapsed after the heating operation is started.

When the user places the heating object N such as the pan or kettle loaded with water on the second heater 2R on the right, the induction heating can be similarly performed. In other words, the operation of the on/off button 82c and the 3 kW button 82b by the user, as well as the display operation of the right display unit 18R, are the same as the operation of the on/off button 81c and the 3 kW button 81b, and the display operation of the left display unit 18L described above.

(Heating Operation with Grill Cooker 4 of Induction Heating Cooker 2)

Still referring to FIG. 24 to FIG. 26, the heat cooking operation in the grill chamber 22 of the induction heating cooker 2 according to Embodiment 1 is described.

First, the user holds the handle 28A of the grill lid 28 and pulls it toward the user, to thus draw out the receiving tray 23 and the gridiron 24 from the grill chamber 22. Then, the user places the cooking object 25 such as fish on the gridiron 24 which has been drawn out. The user again holds the handle 28A and pushes the grill lid 28 forward into the grill chamber 22 of the main body 2A, thereby introducing the receiving tray 23 and the gridiron 24 into the grill chamber 22, and closes the grill lid 28. The user then presses the grill menu button 83a located in the upper surface operation unit 26 a predetermined number of times, to select one of the grill menus of "whole grilling", "grilling", and "oven cooking".

Hereunder, the grill heating operation performed when the user selects the grill menu of "whole grilling" is described.

The user presses the left arrow button 83c and the right arrow button 83d a predetermined number of times to thereby set a browning degree of the cooking object 25. The signal representing the browning degree setting is transmitted to the controller 32, which displays the browning degree which has been set in the central display unit 16 based on the setting signal. When the user presses the start/stop button 83b, the grill heating operation for "whole grilling" is started. To be more detailed, the press-down signal of the start/stop button 83b by the user is transmitted to the controller 32 and, upon reception of the press-down signal, the controller 32 calculates the cooking time for the cooking object 25, based on the browning degree setting signal received earlier. Then the controller 32 causes the grill heater driver circuit 34 (see FIG. 27) to supply power to the sheath heaters 34H provided inside the grill chamber 22, so as to heat the cooking object 25 with the heaters until the browning degree set as above is obtained. When the calculated cooking time has elapsed after the heating operation is started, the controller 32 finishes the heating operation.

The grill heating operation performed when the user selects the grill menu of "grilling" is described.

The user presses the left arrow button 83c and the right arrow button 83d a predetermined number of times to thereby set the heating power to be employed in the heating operation of the cooking object 25. The signal representing the heating power setting is transmitted to the controller 32, which displays the heating power which has been set in the central display unit 16 based on the setting signal.

The user presses the time-down button 83e and the time-up button 83f a predetermined number of times to thereby set a heating time for the cooking object 25. The signal representing the heating time setting is transmitted to the controller 32, which displays the heating time which has been set in the central display unit 16 based on the setting signal. When the user presses the start/stop button 83b, the grill heating operation for "grilling" is started. To be more detailed, the press-down signal of the start/stop button 83b by the user is transmitted to the controller 32 and, upon reception of the press-down signal, the controller 32 causes the grill heater driver circuit 34 to supply power to the sheath heaters 34H provided inside the grill chamber 22, so as to heat the cooking object 25 with the heaters. When the heating time set as above has elapsed after the heating operation is started, the controller 32 finishes the heating operation.

The grill heating operation performed when the user selects the grill menu of "oven cooking" is described.

The user presses the left arrow button 83c and the right arrow button 83d a predetermined number of times to thereby set the heating temperature in the heating operation of the cooking object 25. The signal representing the heating temperature setting is transmitted to the controller 32, which displays the heating temperature which has been set in the central display unit 16 based on the setting signal.

The user presses the time-down button 83e and the time-up button 83f a predetermined number of times to thereby set a heating time for the cooking object 25. The signal representing the heating time setting is transmitted to the controller 32, which displays the heating time which has been set in the central display unit 16 based on the setting signal. When the user presses the start/stop button 83b, the grill heating operation for "oven cooking" is started. To be more detailed, the press-down signal of the start/stop button 83b by the user is transmitted to the controller 32 and, upon reception of the press-down signal, the controller 32 causes the grill heater driver circuit 34 to supply power to the sheath heaters 34H provided inside the grill chamber 22, so as to heat the cooking object 25 with the sheath heaters 34H at the heating temperature set as above. When the heating time set as above has elapsed after the heating operation is started, the controller 32 finishes the heating operation. In the grill menu of "oven cooking", the controller 32 automatically controls the heating power of the sheath heaters 34H such that the ambient temperature inside the grill chamber 22 matches the heating temperature set by the user (temperature feedback control).

(Configuration of Rice Cooker 3)

Figure 40:
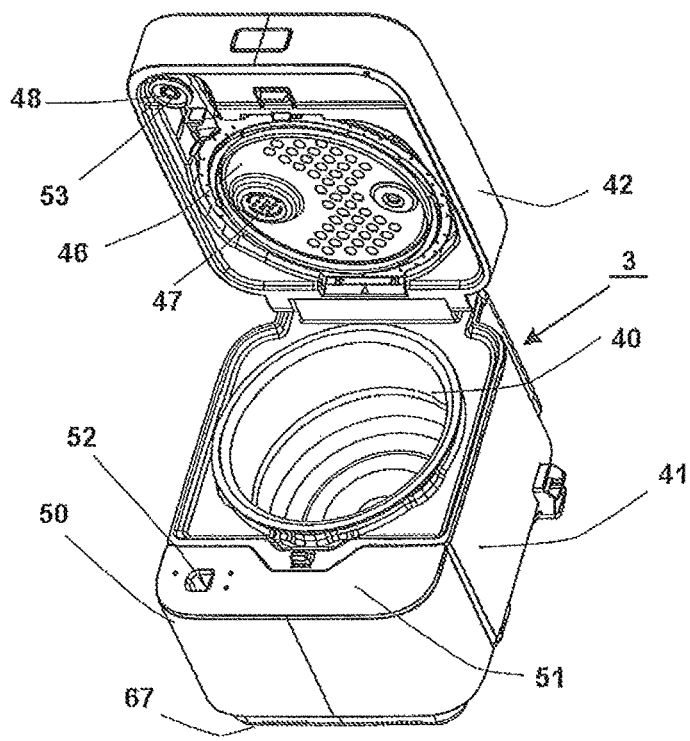
FIG. 40 is a perspective view for illustrating a rice cooker according to Embodiment 1 of the present invention, with its lid opened.
Figure 41:
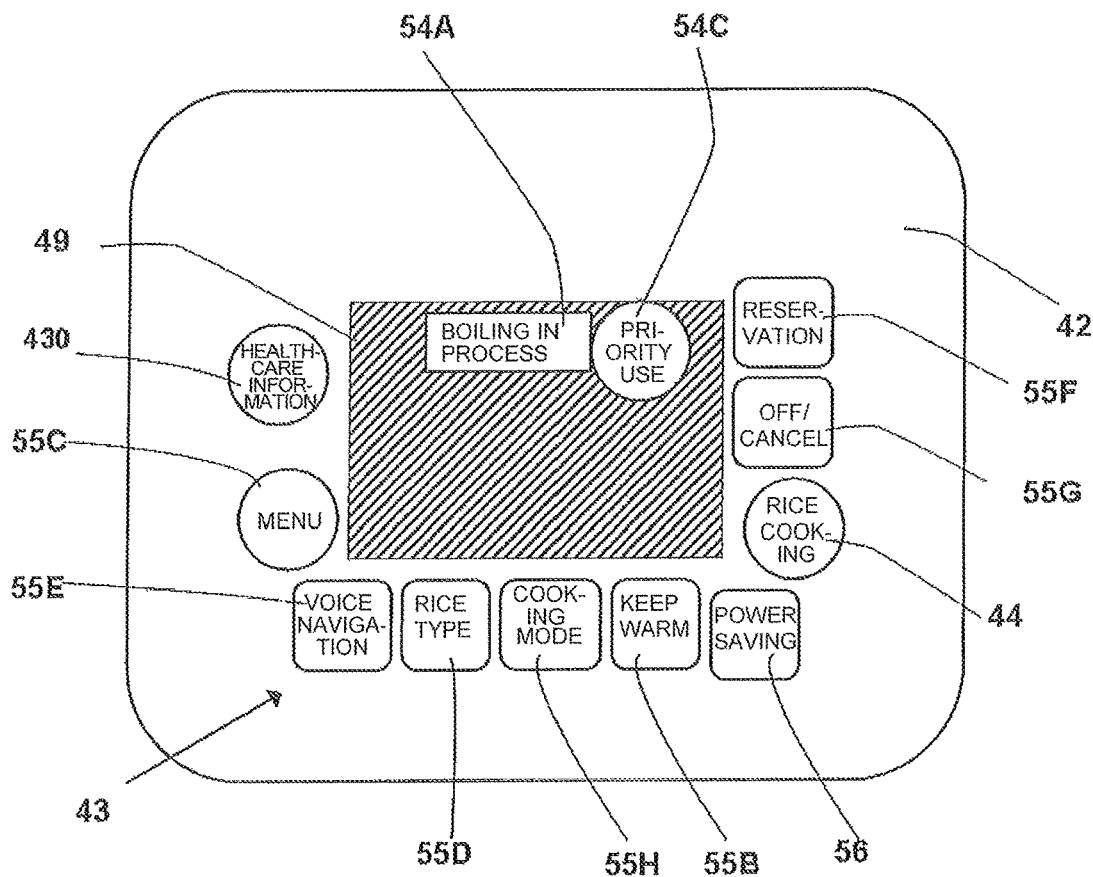
FIG. 41 is a plan view of the lid of the rice cooker according to Embodiment 1 of the present invention.
Figure 42:
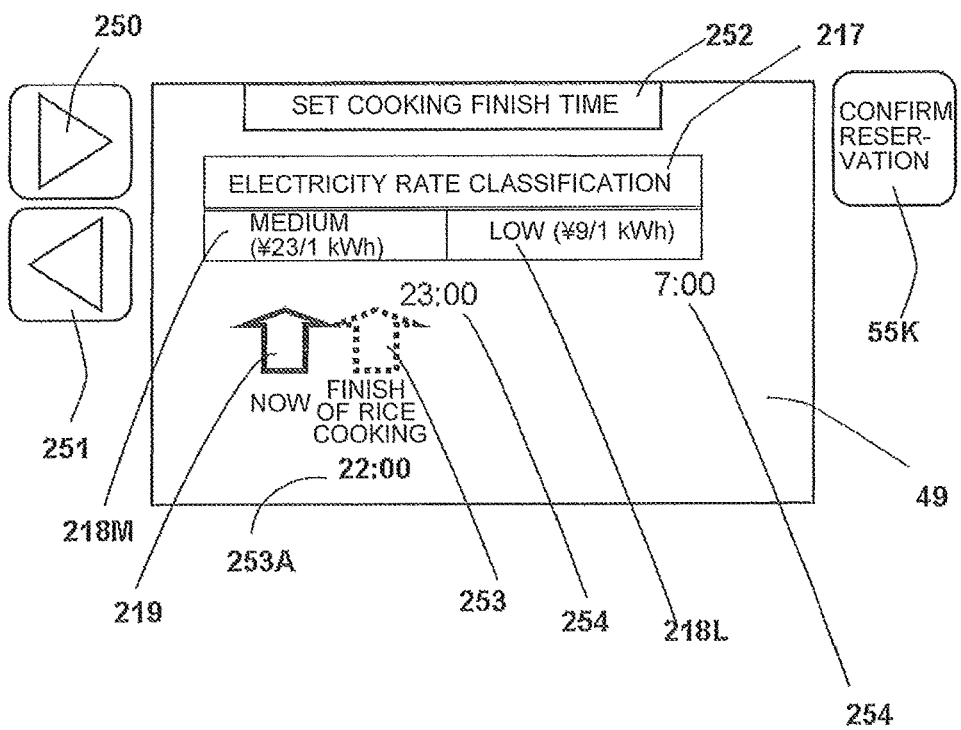
FIG. 42 is an enlarged plan view for illustrating a part of the lid of the rice cooker according to Embodiment 1 of the present invention.
Figure 43:
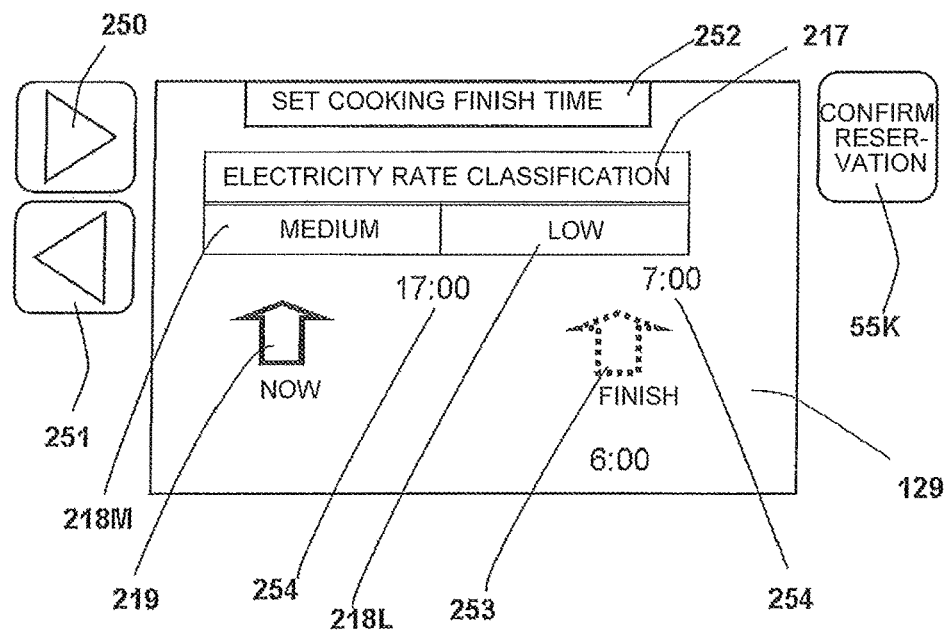
FIG. 43 is an enlarged plan view for illustrating a part of the lid of the rice cooker according to Embodiment 1 of the present invention.

The rice cooker 3 according to Embodiment 1 includes, as illustrated in FIG. 23, FIG. 24, FIG. 40, FIG. 41, FIG. 42, and FIG. 43, a box-shaped main body casing 41 of the rice cooker 3, a lid 42, and a steam processor 50. An operation unit 43 to be operated by the user is provided on the surface of the lid 42 or the main body casing 41, and the operation unit 43 includes a rice cooking start button 44. As widely known, when the rice cooking start button 44 is pressed, the rice cooking is automatically started, and the rice is subjected to a water absorption phase and then quickly cooked through a boiling phase. FIG. 40 is a perspective view for illustrating the rice cooker 3, with its lid opened, FIG. 41 is a plan view of the lid of the rice cooker 3, FIG. 42 is an enlarged plan view of part of the lid of the rice cooker 3, and FIG. 43 is an enlarged plan view of part of the lid of the rice cooker 3.

After the rice cooking is finished, the rice is kept warm by a keep-warm heater (not shown) so as to maintain a predetermined temperature (e.g., 70 degrees Celsius) for a predetermined time (e.g., 7 hours). The rice cooker 3 can be carried by the user to a desired place, and is hence usable in a location other than the system kitchen 1.

The main body casing 41 of the rice cooker 3 has a vertically long rectangular shape or a square shape, in a plan view. The main body casing 41 includes an inner pot 40 made of a magnetic metal and having a circular shape in a plan view with an open upper surface, the lid 42 supported by a hinge mechanism at the rear edge of the main body casing 41 so as to freely open and close the upper opening of the inner pot, and a heating device (heating unit) 45 configured to heat the inner pot 40. The heating device 45 uses a heater based on the induction heating method, and includes an induction heating coil that serves as the actual heating body, which is composed of a multitude of fine copper wires of several tens of microns in diameter, bundled and twisted and then formed into a disk (or annular) shape. The heating coil is provided over a broad area of the outer bottom surface of the inner pot 40, so as to face the outer bottom surface in close contact with or with a fine gap from the outer bottom surface.

A circular inner lid 46 made of a highly heat-conductive metal is removably fixed to the inner surface of the lid 42, the inner lid 46 having an annular lid sealing material made of rubber for preventing leakage of steam to the outside through between the lid 42 and the upper surface of the inner pot 40 when the lid 42 is closed. The inner lid 46 includes a steam port 47 for discharging the steam generated in the inner pot 40 to the outside.

An LCD unit 49 (see FIG. 41 to FIG. 43) is fitted in the lid 42 and exposed in the upper surface thereof. The display screen of the LCD unit is configured to display letters, symbols, and illustrations, so as to enable visual recognition of various condition setting information specified before starting the rice cooking and information of the rice cooking process being performed. In addition, incidental information indicating the operation status of the heating device 45 and useful suggestions regarding the rice cooking (including information for pointing out abnormal use and notifying the user of irregularity in operation) is also displayed on the display screen of the LCD unit 49 as the case may be.

In FIG. 41, reference symbol 54A denotes a sixth information sign for indicating that a "high heat" phase to be subsequently described in the "rice cooking process" is being performed, in which the words "boiling in process" are displayed. Reference symbol 54C denotes a seventh information sign for indicating, like the fourth information sign 210D, that the process for which the power has to be secured with priority (cooking with high heat in the rice cooking process) is being performed, because an abrupt power reduction is undesirable. Further, a fifth information sign 54B (not shown) for indicating, like the first information sign 210A of the induction heating cooker 2, that the power supply may be reduced, and an eighth information sign 54D (not shown) for indicating, like the third information sign 210C, that the power supply has been reduced, may also be displayed in the LCD unit 49.

Reference symbol 43 denotes the operation unit of the rice cooker 3 as illustrated in FIG. 41, which includes: a "rice cooking start button" 44 for starting the rice cooking and confirming reservation; a "keep-warm key" 55B for starting the keep-warm mode in which the cooked rice is kept warm at a predetermined temperature; a "menu key" 55C for selecting one of various rice cooking menus, for example, ordinary rice, porridge, and mixed rice; a "rice type key" 55D for selecting and inputting the type of the rice to be cooked, for example, polished rice or unpolished rice; a "voice navigation key" 55E for notifying the user of the status of the rice cooker 3 and the next necessary step to be followed by voice message, controlling the volume of the voice message, and turning on and off the voice mode; a "reservation key" 55F for setting details of rice-cooking reservation; a "stop/cancel key" 55G for suspending or cancelling input operations and modes; and a "cooking mode key" 55H for selecting one of "normal finish" and "hard finish" indicating the cooking mode (how well the rice is cooked), and "porridge", which is different from the ordinary rice cooking. Those keys may be a mechanical switch configured to close a built-in electrical contact so as to generate an input signal upon being pressed by the user, or an electrostatic touch switch like the one provided in the induction heating cooker 2, and different types of switches may be employed in combination.

Reference symbol 56 denotes a power saving switch that reduces the power consumption by a predetermined rate with each press. When the power saving switch is pressed, for example, in the preheating phase, the power consumption can be reduced for the initial several minutes, however the duration of the preheating phase will be proportionally prolonged. Therefore, a message to this effect is displayed on the display screen of the LCD unit 49, and also voice guidance such as "Energy saving mode has been selected. Preheating time is prolonged by several minutes" is output, without the need to press the voice guidance (navigation) key 55E each time.

Reference symbol 48 denotes a steam duct having an end portion connected to the steam port 47 and including a steam outlet 53 formed at the other end portion, the steam duct 48 being routed through the lid 42.

The steam processor 50 includes a water tank (not shown) having an opening directed upward and configured to store water for condensing the steam discharged from the steam port 47, and a tank lid 51 formed so as to cover the upper opening of the water tank while being able to be opened and closed.

Reference symbol 52 denotes a steam inlet provided in the tank lid 51 at a position corresponding to the steam outlet 53. A communication pipe (to be subsequently described) is connected to the lower portion of the steam inlet in communicating therewith. When the lid 42 is closed, the inner lid 46 tightly closes the upper opening of the inner pot 40 and the steam inlet 52 is brought into close contact with the steam outlet 53.

The communication pipe (not shown) has its upper end portion fixed to the lower surface of the tank lid 51 and is vertically disposed such that the majority of the pipe is submerged in the water in the water tank (not shown). The vertical length of the communication pipe and the size (height) of the water tank are determined such that the lower end of the communication pipe is located at a predetermined depth (H) from the surface of the water in the water tank. Accordingly, the steam emitted from the lower end opening of the communication pipe can be efficiently brought into contact with the water in the water tank to thus be condensed.

Therefore, the predetermined depth (H) is determined so as to condense the entirety of the steam emitted from the steam port 47 even when the maximum heating power is supplied to the heating device 45. To be more detailed, the predetermined depth (H) is determined based on the velocity of steam bubbles blowing up in the water when the high-temperature steam is emitted to the water from the lower end opening of the communication pipe, and the condensation rate of the steam being cooled and condensed. The "steam" refers to the steam generated inside the inner pot 40 in "rice cooking phase" and "steaming phase" to be subsequently described and conducted into the communication pipe. In Embodiment 1, the entirety of the steam generated from "water absorption phase" to "keep-warm phase" can be collected. Although the keep-warm phase is set to 7 hours after "steaming phase" in Embodiment 1, the duration of the keep-warm phase may be changed as desired.

When the lid 42 is closed, a seal member provided at the steam outlet 53 in the end portion of the steam duct 48 is brought into close contact with the steam inlet 52 of the tank lid 51, so as to ensure that the high-temperature steam passing through the lid 42 flows into the communication pipe in the water tank (not shown), without leaking to the outside halfway.

When the reservation key 55F for setting the rice-cooking reservation function is pressed, the operation unit displays the reservation setting screen as illustrated in FIG. 42. The rice cooker 3 is one of the first electric appliances capable of setting the finish time of the rice cooking operation. In other words, the time of day that the rice cooking operation is to be finished (reserved finish time A) can be set with the rice cooker 3.

Reference symbols 250 and 251 denote a pair of time-setting keys displayed on the left of the LCD unit 49 on the upper surface of the lid 42 as illustrated in FIG. 42, when the finish time of the rice cooking operation is to be reserved (hereinafter referred to as "reserved rice cooking"). The keys 250 and 251 are electrostatic touch switches. The outline and the triangular shape of those keys are made visible with light from an LED provided under the keys, when the input function of the switch is effective. One of the keys 250 is used for delaying the time and the other key 251 is used for reversing the time.

An upward arrow mark 219 indicates, as those of the induction heating cooker 2 illustrated in FIG. 36 and FIG. 37, which of the electricity rate classification is applied if the power supply to the rice cooker 3 is started at that moment. The word "now" is displayed close to the mark 219 together (on the screen of the LCD unit 49). Reference symbol 253 denotes a rice-cooking finish time indicator displayed at a predetermined position depending on a time deviation from the mark 219, and the words "rice cooking finish" are displayed in the vicinity of the indicator 253 on the screen of the LCD unit 49. In the case where the rice cooking is started at the mark 219 corresponding to the current time, the rice-cooking finish time indicator 253 is displayed at a position corresponding to approximately 40 minutes later, when the amount of rice to be cooked is about 0.54 liters. The cooking finish time varies depending on the amount of rice to be cooked. Reference symbol 254 denotes an indication of the time boundary at which the electricity rate classification is switched. With the time indication 254 and the electricity rate classification information 218M, the user can easily recognize that, for example, the rate of "morning and evening hours" is applied from 17:00 to 23:00, and the rate of "night hours", which is lower, is applied after 23:00 and before 7:00 next morning. The longest time of the rice cooking reservation is 10 hours in this example.

By each touch of one of the pair of time-setting keys 250 and 251, for example, the key 250, the rice-cooking start time can be delayed by 30 minutes, and the indicator 253 moves to the right each time as illustrated in FIG. 43. Reference symbol 253A denotes a time indicator displaying the time corresponding to the position of the indicator. For example, when the time indicator 253A is displaying 10 p.m. (22:00), the rice-cooking finish time can be delayed by 30 minutes from 22:00 each time the key 250 is touched. Upon touching the key 250 so as to move the time indicator until the indicator shows 6:00, the reservation for finishing the rice cooking by the time desired by the user (6:00) can be set, though the start time of the rice cooking is unclear. Reference symbol 55K denotes the key for confirming the reservation, displayed at the same position as the reservation key 55F with the input function being switched to "confirm reservation". After the reservation (of rice cooking finish time) is confirmed, the key 55K remains lit up by the LED provided thereunder, until the rice cooking is finished.

Figure 44:
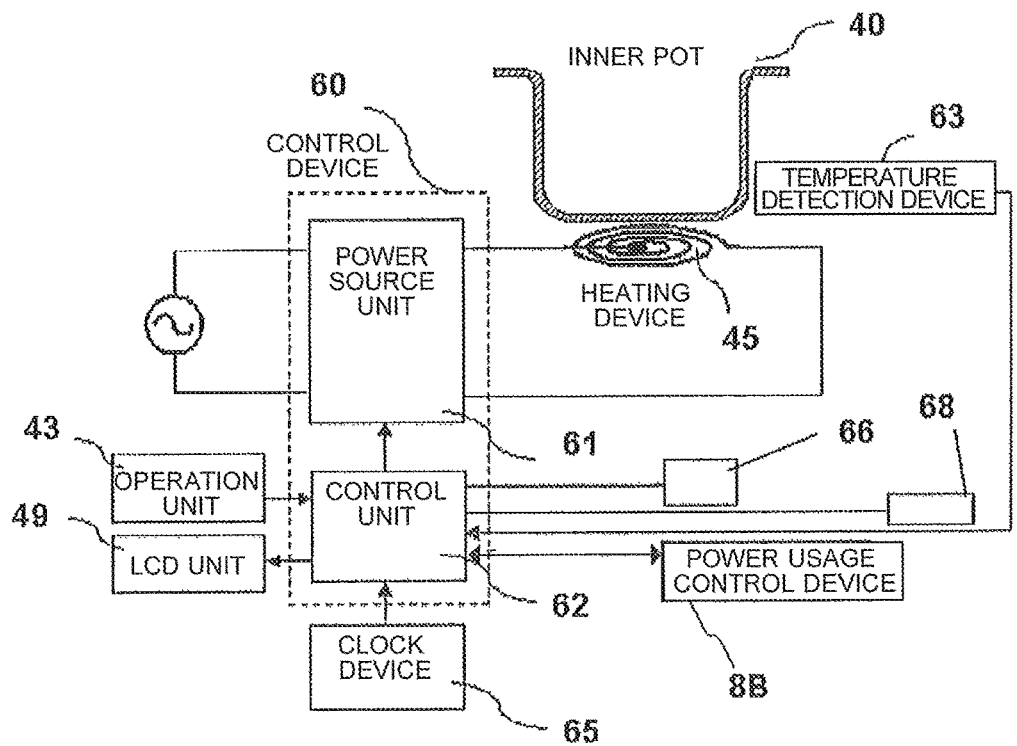
FIG. 44 is a block diagram for illustrating a configuration of a control circuit of the rice cooker used in the power control system according to Embodiment 1 of the present invention.

Referring primarily to FIG. 44, a control device (controller) 60 of the rice cooker 3 is described below. FIG. 44 is a block diagram for illustrating a configuration of a control circuit of the rice cooker 3 used in the power control system according to Embodiment 1. The control device 60 includes a power source unit 61 and a control unit 62. The control unit 62 mainly includes one or a plurality of microcomputers. The microcomputer includes four parts, that is, an input terminal, an output terminal, a storage unit, and a central processing unit (CPU), and is driven by DC power supplied from the power source unit 61 so as to mainly serve to control the heating device 45 and the LCD unit 49 serving as the display unit.

The control unit 62 stores, as operating conditions of the heating device 45, a cross-reference table of the temperature of the bottom surface of the inner pot 40 and the temperature of rice, and cooking menus (selection of polished rice and wash-free rice, "normal finish" and "hard finish" indicating how well the rice is cooked, and "porridge", which is different from ordinary rice cooking). In addition, the control unit 62 stores a control program specifying the rice cooking process including four phases of "preheating phase", "rice cooking phase", "steaming phase", and "keep-warm phase" to be sequentially performed. One of the "operating conditions" is a power supply condition related to electrical and physical conditions of the heating device 45, and collectively specifying the time and amount of power supply to the heating device 45, and power supply patterns (continuous, intermittent, and ED percent).

Referring to FIG. 44, a temperature sensor (temperature detecting unit) 63 is pressed against the bottom surface of the inner pot 40 from below by a compression spring or the like, to detect the temperature of the bottom surface of the inner pot 40 and output a signal of that detection. The temperature sensor 63 is a thermistor-based temperature sensor. Reference symbol 43 denotes the operation unit provided in the forward portion of the upper surface of the lid 42 of the rice cooker 3 as illustrated in FIG. 41. The operation unit 43 includes the plurality of press keys 55D and 55H formed on the surface of the lid 42. The operating conditions of the heating device 45 can be set by operating the plurality of press keys 55D and 55H. The operation unit 43 is located forward of the LCD unit 49. The rice cooking start button 44 is located obliquely right of the front end of the LCD unit 49.

In FIG. 44, reference symbol 65 denotes a clock device (clock circuit) constituted of a timer or the like, and the clock signal output by the clock device 65 is input to the control unit 62. The clock device 65 also outputs information of the current time of day and rice cooking reservation setting time to the LCD unit 49, so that such information is displayed on the display screen of the LCD unit 49. The clock device 65 continues to work for a long period of time with a built-in battery in the rice cooker, regardless of whether the power cord of the rice cooker is disconnected. The clock device 65 may be given a function to acquire the time-of-day information from outside during operation, as does a radio-wave clock, to thereby eliminate error and self-correct the current time of day.

In FIG. 44, reference symbol 66 denotes a water level sensor configured to detect the amount of water in the water tank from the water level, and is configured to detect the water level of the water tank based on light, weight, or other physical conditions. The water level sensor 66 is located either on the forward portion of the main body casing 41 so as to oppose the water tank, or in the forward region of the upper surface of a bottom plate 67 on which the water tank is placed.

In FIG. 44, reference symbol 68 denotes a water temperature sensor configured to detect the temperature of the water in the water tank, which is located either on the forward portion of the main body casing 41 so as to oppose the water tank to detect the water temperature through the sidewall of the water tank, or in the forward region of the upper surface of the bottom plate 67 on which the water tank is placed as illustrated in FIG. 40.

Figure 49:
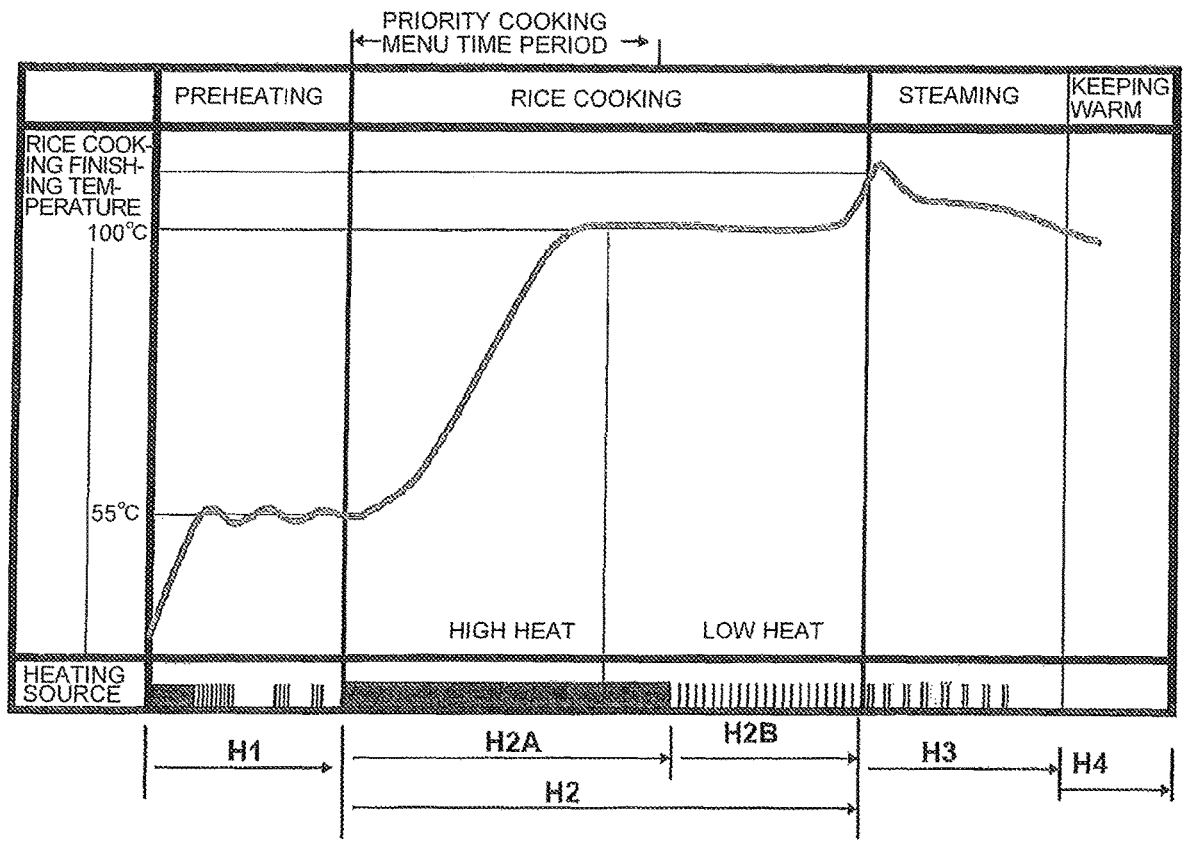
FIG. 49 is an explanatory diagram for illustrating a rice cooking operation performed by the rice cooker according to Embodiment 1 of the present invention.

The rice cooking operation with the rice cooker 3 is now described, regarding the case where the rice cooking is immediately started by the user, instead of the reserved rice cooking. FIG. 49 is an explanatory diagram for illustrating the rice cooking operation performed by the rice cooker 3 according to Embodiment 1. As illustrated in FIG. 49, the control unit 62 of the rice cooker 3 according to Embodiment 1 possesses the control program for sequentially executing four phases of a preheating phase, a rice cooking phase, a steaming phase, and a keep-warm phase.

First, the tank lid 51 of the water tank taken out of the main body casing 41 is removed, and water is introduced to the water tank from outside. Then a predetermined amount of rice and water is introduced to the inner pot 40, and the rice cooking start button 44 on the upper surface of the lid 42 of the main body casing 41 is pressed, to start the rice cooking. Accordingly, the heating device 45 is heated up and the rice cooking is performed. In an initial stage where the water absorption phase is performed, the fifth information sign 54B (not shown) indicating that the power supply may be reduced is displayed in the LCD unit 49. Therefore, the user can recognize that the power supply to the rice cooker may be reduced by an instruction from outside in the initial stage of use of the rice cooker 3.

Referring to FIG. 49, in the preheating phase H1, the heating device 45 starts to receive power in the continuous power supply pattern to obtain high heating power at first. When the temperature sensor 63 detects that the temperature in the inner pot 40 has reached a predetermined temperature (55 degrees Celsius), the information to this effect is input to the control unit 62, which suppresses the power supply so as to maintain 55 degrees Celsius and also shifts the pattern to the intermittent power supply. Therefore, steam is barely generated and the steam processing (condensation) is not yet performed in the water tank. The temperature of 55 degrees Celsius is maintained for a certain period of time. The clock device 65 measures the time that has elapsed after the temperature reached 55 degrees Celsius, so that the control unit 62 controls the finish time of the preheating phase based on the clock signal input thereto.

When the rice cooking phase H2 is entered, the heating power of the heating device 45 is increased during a high heat phase H2A performed in the initial stage, so that the water temperature in the inner pot 40 is gradually increased, until the water in the inner pot 40 is boiled. When the boiling becomes more intense and the amount of steam increases, the pressure in the inner pot 40 exceeds the atmospheric pressure and therefore the steam generated in the inner pot 40 is driven out by the pressure through the steam port 47 and enters the closed passage in the steam duct 48 inside the lid 42. The steam then spouts through the steam duct 48 into the water tank serving as part of the steam processor. Thus, the rice cooking phase H2 includes two phases of the high heat phase H2A in which the maximum heating power, for example, 1,300 W, is supplied for heating, and a low heat phase H2B which follows the high heat phase H2A.

In the rice cooking phase, the fifth information sign 54B (not shown) disappears from the LCD unit 49 and instead the seventh information sign 54C appears in the LCD unit 49. Accordingly, the user recognizes that the power supply for the rice cooking operation is secured with priority. Here, the same message may be audibly output by a voice guidance (navigation) device such as a voice synthesizer. Alternatively, the fifth information sign 54B (not shown), the sixth information sign 54A, the seventh information sign 54C, or a ninth information sign 54E (not shown) indicating that the power reduction request has been received may be displayed, instead of in the LCD unit 49, in the form of a "light emitting button" or the like located in the vicinity of the LCD unit 49.

The steam which has entered the water tank serving as part of the steam processor spouts out into the water from the lower end opening of the communication pipe (not shown), to make contact with the water in the water tank to thus lose heat and be condensed, and turns into water.

The steam generated in the inner pot 40 is thus processed and hence prevented from leaking outward. Therefore, the steam generated during the rice cooking operation is prevented from being directly emitted to the room space, and an increase in humidity, which degrades the comfortableness, can be suppressed.

At a certain point halfway through the rice cooking phase (determined by the control unit 62 monitoring the time elapsed after the boiling has begun), the heating power of the heating device 45 is reduced to enter the low heat phase H2B. At the end of the low heat phase H2B, the moisture in the inner pot 40 is decreased because the water has been evaporated and discharged, and the temperature in the inner pot 40 sharply increases from 100 degrees Celsius or so to approximately 130 degrees Celsius. Such sharp increase in temperature is detected by the temperature sensor 63, and the control unit 62 determines that the rice cooking has been finished upon reception of the temperature detection information from the temperature sensor 63.

When the low heat phase H2B is entered, the seventh information sign 54C displayed in the LCD unit 49 disappears. In the case where the power reduction request signal is received from the power instruction apparatus 9 in the low heat phase H2B or the preheating phase, the ninth information sign 54E (not shown) notifying the user of this effect is displayed in the LCD unit 49.

The low heat phase H2B is followed by the steaming phase H3, in which, as the rice cooking progresses, the generation of steam gradually decreases with the lapse of time, and when the rice cooking is finished, the inside of the inner pot 40 is cooled and the pressure decreases. Although at this point the pressure in the steam duct 48 decreases, because the communication pipe (not shown), which is located under the tank lid 51 and mostly submerged in the water in the water tank (not shown), includes a check valve (not shown) at an upper portion thereof, ambient air is introduced through the check valve, so that the pressure in the inner pot 40 is recovered to a level close to the atmospheric pressure. Therefore, the water in the water tank can be prevented from being sucked up toward the lid 42 and flowing inside the lid 42.

The amount of steam generated during the rice cooking process varies depending on combinations of the type of rice (polished rice, wash-free rice), the cooking mode (hard, viscous), and the menu (ordinary rice cooking, porridge), and the amount of water in the water tank is determined such that, in any of the cases, the steam processing is performed without fail before the cooking operation is finished, and that the temperature of the water in the water tank falls to a level that prevents scalding, for example, below 55 degrees Celsius, after the cooking is finished.

The rice cooking phase is followed by the keep-warm phase H4, in which a keep-warm heater (not shown) provided independent of the heating device 45 is employed to maintain the temperature in the inner pot 40 at a predetermined temperature, for example, 70 degrees Celsius.

The steam is mainly generated in the rice cooking phase H2 and the steaming phase H3 as described above. Therefore, in Embodiment 1 of the present invention, the amount of steam emitted through those phases has been studied through calculations and experiments, and the amount of water to be put in the water tank and the water level have been accordingly determined. It has been discovered that, even if a sufficient amount of water is provided, in the case where the steam spouts into the water at a shallow position in the water, the steam is unable to make sufficient contact with the water and therefore floats up to the water surface maintaining the form of bubbles, thus being emitted to the ambient air. In Embodiment 1, therefore, the water level sensor 66 is employed so that the control unit 62 determines whether a sufficient amount of water is in the water tank based on the detection information from the water level sensor 66, before the water absorption phase, which is the first step of the rice cooking process, is started.

Further, the water temperature sensor 68 configured to detect the temperature of the water in the water tank is provided, and therefore the control unit 62 can determine whether the temperature of the water in the tank is higher than a predetermined temperature, based on the output from the water temperature sensor. In the case where the water temperature is excessively high, the control unit 62 does not begin to supply power to the heating device 45, and therefore even the preheating phase is inhibited.

Further, once the cooking process enters the rice cooking phase, the temperature of the water in the water tank is to be maintained within a predetermined temperature range until the rice cooking is finished. However, in the case that the temperature of the water in the water tank exceeds the predetermined temperature for some reason (e.g., room temperature of the space where the cooker is placed has suddenly increased), the water temperature sensor detects such increase, and the control program of the control unit 62 is designed so as to, in the mentioned case, change the power supply condition for the heating device 45 and substantially reduce the heating power. The extent of the heating power reduction is determined within a range that does not affect the intended finish quality of the rice cooking operation. To lower the heating power, an appropriate method may be employed, for example, reducing the power supply itself or lowering the ED percent. In Embodiment 1, the rice cooker is programmed so as to start the rice cooking operation when the water temperature is 35 degrees Celsius or lower at the time to start the rice cooking operation, and not to start the rice cooking operation when the water temperature is higher than 35 degrees Celsius. Such programming prevents the temperature of the water in the water tank from increasing up to an abnormal level at the end of the rice cooking operation.

Regarding the rice cooker 3, it is the high heat phase H2A in the rice cooking phase H2 performed in the initial stage that most affects the quality of the rice cooking operation. In the rice cooker 3, accordingly, the control unit 62 designates the high heat phase H2A as "priority cooking menu time period". In other words, the control unit 62 constantly monitors whether the cooking menu currently being performed is in the "priority cooking menu time period", and in the affirmative case, the control unit 62 has a function to notify the power instruction apparatus 9 of this effect through the power usage control device 8B. Therefore, abrupt power reduction can be prevented. In addition, when the high heat phase H2A is entered, the seventh information sign 54C is displayed in the LCD unit 49, so that the user can recognize that the rice cooking operation is being performed with the power supply secured with priority.

Although the rice cooker 3 according to Embodiment 1 is configured to collect the steam generated in the rice cooking process using the steam processor 50, the rice cooker may not include the steam processor 50, and emit the steam to the room space during the rice cooking operation.

(Microwave Oven 5)

Referring to FIG. 24, the microwave oven (electronic oven with electric heater) 5 includes a heating chamber (not shown) made of a metal in which a microwave of a frequency of, for example, 2,450 MHz is introduced, a main body casing (not shown) of the electronic oven accommodating therein the heating chamber, and a door 70 for use to open and tightly close the outlet of the heating chamber made of a metal. Reference symbol 70A denotes a handle of the door 70.

An operation unit 71 to be operated by the user is provided in a right region of the front surface of the main body casing of the microwave oven 5, and the operation unit includes a power source switch 72, a start button 73, and a heating time setting dial (for timer setting) 74. When the heating time is set with the heating time setting dial 74 and the start button 73 is pressed, the predetermined power is output for the time that has been set, to finish the cooking. The microwave oven 5 may include a heat sensitive element (not shown) such as an infrared ray sensor configured to detect the temperature of the heating object placed in the heating chamber, so that the oscillation source of the microwave is automatically turned off when the temperature of the heating object reaches a target temperature.

(Dish Washer-Dryer 6)

A basic configuration of the dish washer-dryer according to Embodiment 1 of the present invention is described hereunder. Referring to FIG. 24, the dish washer-dryer 6 includes a main body (not shown) constituting the outer shell, and a washing unit (not shown) mounted inside the main body.

The main body has a box shape, and includes a front door 167 mounted on the front side and integrally coupled to the front wall of a washing tank (not shown), and a cover (not shown) mounted to the outer side of the washing tank so as to cover outer sides of various functional components.

A handle 167C to be held by the user to draw out the washing tank (not shown) from the main body, and an operation unit 179 for inputting various operations of the dish washer-dryer 6 are provided on the front surface at an upper portion of the front door 167.

(Air-Conditioning Apparatus 7)

A basic configuration of the air-conditioning apparatus according to Embodiment 1 of the present invention is described hereunder. The air-conditioning apparatus 7 may be installed in the kitchen in which the kitchen electric appliances KP are provided, however in Embodiment 1, the air-conditioning apparatus 7 is provided in another room, for example, the living room. In the air-conditioning apparatus 7, the power usage control device 8E of the power instruction apparatus 9 is incorporated. Therefore, information about requested power, cooking status of the cooking appliances, usable power, and so forth can be exchanged with the power instruction apparatus 9, so that the power usage control device 8E controls the power supplied to the air-conditioning apparatus 7 within the power consumption permitted by the power instruction apparatus 9.

The air-conditioning apparatus 7 includes an indoor unit (not shown) to be installed inside the room, an outdoor unit (not shown), a refrigerant circuit (pipe path) configured to connect the indoor unit and the outdoor unit in a closed loop arrangement, and a motor (not shown) serving as a drive source for an electric compressor configured to circulate the refrigerant in the refrigerant circuit. In the air-conditioning apparatus 7, a mode selection switch (not shown) is provided in an operation unit (not shown) or a remote controller (not shown) so as to enable selection of one of at least four operation modes, namely, cooling, heating, dehumidifying, and ventilating.

For the air-conditioning apparatus 7, a current capacity is specified so as to secure the rated cooling capacity when a maximum load is imposed. Under load conditions lower than the maximum load, the upper limit of the driving current of the electric compressor (not shown) is lowered based on the load condition.

One of the detection methods of the air-conditioning load is providing an outdoor temperature sensor (not shown) to determine the load condition based on the outdoor temperature detected by the sensor. With this, for example, in the cooling operation, when the outdoor temperature is low, that is, when the operation load is low, a cooling capacity is set based on that load from the viewpoint of stability of the room temperature and energy saving, and therefore operation is possible with reduced power consumption. Here, the outdoor temperature sensor may utilize the information from the environment sensor (outdoor temperature sensor) 206 illustrated in FIG. 1.

An indoor temperature detection unit (not shown) supplies the temperature detection information to determine the load condition based on the detected indoor temperature. In this case, for example, in the cooling operation, when the indoor temperature is low, or when the indoor temperature is low and also the cooling target temperature is low, that is, when the operation load is low, a cooling capacity is set based on that load from the viewpoint of stability of the room temperature and energy saving, and therefore the power consumption can be reduced. In general, the majority of the power consumption of the air-conditioning apparatus 7 configured as above is occupied by the electric compressor, and therefore decreasing the rotation speed of the electric compressor leads to reduced power consumption.

The air-conditioning apparatus 7 is one of the first electric appliances in which the operation start time can be set using a built-in timer (not shown), and therefore the user can set the operation start time (reserved start time A) of, for example, the cooling operation. Therefore, the cooling operation can be automatically started while the occupant is away from home.

Further, the air-conditioning apparatus 7 is one of the first electric appliances in which the operation finish time can be set using the built-in timer (not shown), and therefore the user can set the operation finish time (reserved finish time A) of, for example, the cooling operation. Therefore, when the occupant starts the cooling operation at home and the reserved finish time is reached while the occupant is away, the cooling operation can be automatically finished.

(Internal Configuration of Mobile Phone Terminal 87)

FIG. 22 is a block diagram for illustrating an internal configuration of the mobile phone terminal used in the power control system according to Embodiment 1. In FIG. 22, the mobile phone terminal 87 includes a display unit 180 including an LCD screen 180A, an operation input unit (operation unit) 181 including a plurality of input keys to be operated by the user, a wireless interface (wireless input-output unit) 182, a posture detection unit (posture sensor) 183, a control unit 184 including a microcomputer, and a notification unit 194 configured to output synthetic voice messages of a plurality of types depending on the operation situation, and including a small-sized vibrator configured to vibrate the mobile phone terminal 87 as necessary. The vibrator can vibrate the mobile phone terminal 87 itself in synchronization with the output (sound) of the voice messages from the notification unit 194. With this, even under a state in which the user cannot reliably know the operation situation or the incoming of the notification by the display unit 180 alone, sound and vibration can be used to complement.

The wireless input-output unit 182 includes two input-output units. One is an apparatus-side near-field communication unit 182A configured to perform short range wireless communication with the short range wireless communication input-output unit 427 of the power instruction apparatus 9 and the antenna 322 (see FIG. 28) forming each of the short range wireless communication input-output units 401L and 401R of the induction heating cooker 2. The other is an NFC wireless input-output unit 182B configured to perform predetermined communication with the wide area communication network (communication network) 98.

The display unit 180 and the operation input unit 181 are connected by signal circuits to the wireless input-output unit 182, the posture detection unit 183, the control unit 184, and the notification unit 194, although not shown. The posture detection unit 183 includes a gyro sensor, and is configured to detect the posture of the mobile phone terminal 87 when being inclined (in a right-left or front-rear direction) by the user, and to output a signal indicating the posture to the control unit 184.

The control unit 184 roughly includes a central processing unit (CPU) 185 and a storage unit 186 mainly formed of a semiconductor storage element. The CPU 185 is configured to execute processing of the entire mobile phone terminal 87 based on the control program stored in the storage device (ROM/RAM unit) 187 in the storage unit 186, and is also configured to read out data required in the process of executing the processing from the ROM/RAM unit 187 or store the data generated in the process of executing the processing to the ROM/RAM unit 187. Reference symbol 209 denotes a semiconductor non-volatile memory forming a part of the storage unit 186. The memory 209 can store various types of information read from the wireless input-output unit 182. Further, the memory 209 temporarily stores information indicating the operation states of the various electric appliances EE, which are read from the power instruction apparatus 9, environment information provided from the environment detection unit 202, "abnormality occurrence information", and information transmitted from the ASP server 89A. The meaning of "temporarily" refers to the case where the user does not particularly input a deletion instruction, or the case where the information is automatically stored and held for a certain period, e.g., 1 month or 1 week, and is automatically deleted after the elapse of this period.

The storage unit 186 includes an application software unit 188. The application software unit 188 includes a reception processing unit 189, a transmission processing unit 190, a communication establishment unit 191, a display control unit 192, a selection determination unit 193, and the memory 209.

The "abnormality occurrence information" refers to special information newly generated when the control unit 125 of the power instruction apparatus 9 receives from the home electric appliance EE, for example, the induction heating cooker 2, an operation information signal L6E (see FIG. 64) indicating the emergency stop of the heating source. The abnormality occurrence information is exclusive information to be recognized by the mobile phone terminal 87 and the information server ISV. In other words, the abnormality occurrence information is information for notifying the outside of the household of the occurrence of the abnormality in the home electric appliance EE.

The storage unit 186 includes the application software unit (application processing unit) 188 capable of storing application software for the home electric appliance EE (in Embodiment 1, at least the induction heating cooker 2). The application software unit 188 further stores application software for the display panel 100 of the power instruction apparatus 9. The software of the application software unit 188 may be installed from the outside of the mobile phone terminal 87, or may be stored in the storage unit 186 from the time when the mobile phone terminal 87 is shipped. In other words, the countermeasure software program transmitted from the ASP server 89A is also stored in the storage unit 186.

When the CPU 185 executes the processing based on the application software unit 188, respective functions of the predetermined reception processing unit 189, transmission processing unit 190, communication establishment unit 191, display control unit 192, and selection determination unit 193 are realized. Operations of those units are subsequently described.

(Power Instruction Apparatus 9)

Referring to FIG. 23, the power instruction apparatus 9 constituting the core device of Embodiment 1 is now described. FIG. 23 is a block diagram for illustrating the general configuration of the power control system according to Embodiment 1, except for the healthcare instruments and the activity measurement. The power instruction apparatus 9 is configured to exchange information about operating status or the cooking status of the home electric appliances, usable power, and so forth with the power usage control devices 8A, 8B, 8C, and 8D of the kitchen electric appliances KP. Accordingly, the power usage control devices 8A to 8D control the power of the respective kitchen electric appliances KP within the power usage permitted by the power instruction apparatus 9. The power usage control devices 8A, 8B, 8C, and 8D may be incorporated in the respective kitchen electric appliances KP, or may be mounted to the power supply circuit units of the kitchen electric appliances KP in the form of adapters as subsequently described. In Embodiment 1, the power usage control devices 8A, 8B, 8C, and 8D are incorporated in the respective kitchen electric appliances KP as described above. Those power usage control devices 8A to 8D are supplied with power from an exclusive power supply (built-in battery) BT2 different from the power supply circuit 31 connected to the main power switch 11 to be subsequently described, and are driven for a long period of time. The power usage control devices 8A to 8D may be driven with power branched from the power supply circuit 31 connected to the main power switch 11, but it is necessary to prevent the power supply from being affected even after automatic stop upon an abnormality occurrence to be subsequently described. This is because a signal is transmitted to or received from the power instruction apparatus 9 through wireless communication even after the emergency stop due to the abnormality occurrence. The power usage control device 8E of the air-conditioning apparatus 7 not installed in the kitchen is configured similarly to the power usage control devices 8A, 8B, 8C, and 8D.

Further, the power usage control devices 8A, 8B, 8C, 8D, and 8E are each allocated with unique identification information with respect to the control unit 125 of the power instruction apparatus 9. In other words, in order to receive an "object appliance registration signal" AS1 to be subsequently described, the power usage control devices 8A, 8B, 8C, 8D, and 8E are each a "registered appliance" with respect to the power instruction apparatus 9. When the device is registered as the registered appliance, a power usage reduction rate determination device 94 to be subsequently described can recognize a "priority order" (subsequently described in detail) of power supply.

Further, each of the power usage control devices 8A, 8B, 8C, 8D, and 8E registers the information of the installation position with respect to the power instruction apparatus 9. In other words, "installation position information" of the kitchen electric appliances KP and the air-conditioning apparatus 7 is stored in the control unit 125 of the power instruction apparatus 9. Further, the installation position information can be changed by the user as needed by the operation input unit 117 (see FIG. 6) provided on the display panel 100 of the power instruction apparatus 9. Therefore, when the air-conditioning apparatus 7 is moved from the living room to the kitchen to be used, the installation position information of the air-conditioning apparatus 7 may be changed to the kitchen. Instead of such manual input of the installation position information, the power instruction apparatus 9 may be configured to be able to automatically recognize the change of the installation position. For example, a position sensor configured to receive, for example, a wireless signal indicating the position information output from the home electric appliance EE may be installed in each of the living spaces such as the kitchen, the living room, and the bedroom, and the control unit 125 of the power instruction apparatus 9 may receive the reception signal of the position sensor so that the power instruction apparatus 9 can recognize the home electric appliance EE as the output source and the latest information of the installation position of the home electric appliance EE.

Likewise, the power supplied to the air-conditioning apparatus 7 and the dish washer-dryer 6 is also collectively controlled by the power instruction apparatus 9. Here, the "adapter" refers to a control device provided between each of the home electric appliances and the power source thereof. Examples of the adapter herein referred to include the one according to Japanese Unexamined Patent Application Publication No. 2012-83453, which includes a power source plug and a power outlet. An electric appliance, the power to which is to be controlled, is connected to the power outlet. Upon reception of the power instruction signal through a wireless or wired communication device unit, the adapter limits or cuts off the power supply to the home electric appliance to be controlled. Thus, the adapter is connected to the existing home electric appliance and the power instruction signal is transmitted to the adapter from the power instruction apparatus 9 so that the adapter controls the home electric appliance in accordance with the signal. Therefore, the power instruction apparatus 9 can integrally control the power supply, by providing the adapter also on the power source side of the existing home electric appliances.

The power instruction apparatus 9 includes: a required power adder 91 configured to sum the requested power from the power usage control devices 8A to 8D of the kitchen electric appliances KP and the requested power from the power usage control device 8E of the air-conditioning apparatus 7; a comparator 92 configured to compare a total power summed by the required power adder 91 and a first capacity limit (e.g., 8,000 W) of the circuit breaker BK; a requested power excess determination device 93 configured to determine an excess amount of the total power based on the comparison result from the comparator 92, and detain the comparison result when the total power is 8,000 W or lower and output the excess amount when the total power exceeds 8,000 W; a power usage reduction rate determination device 94 configured to (i) return the same usable power as the requested power to each of the power usage control devices 8A to 8D of the kitchen electric appliances KP and the power usage control device 8E of the air-conditioning apparatus 7 when no output is made from the requested power excess determination device 93 (i.e., excess amount is 0), and (ii) determine, when the excess amount is output, a reduction amount of the power consumption of each of the kitchen electric appliances KP and the air-conditioning apparatus 7 based on the excess amount of the total power and a predetermined priority order and respond to the power usage control devices 8A to 8E of the kitchen electric appliances KP and the air-conditioning apparatus 7; a priority order setting device 95 configured to read out "priority order" registered in advance in the built-in semiconductor memory (semiconductor non-volatile memory) 95A and transmit "priority order" information of the power reduction to the power usage reduction rate determination device 94; and the control unit 125 configured to control the healthcare processing unit 116 and the use limit setting device 96.

In FIG. 1 and FIG. 3, reference symbol 300 denotes a wattmeter to which the power of AC 200 V from the power company is supplied through a single-phase S-wire power line 301 (see FIG. 23). The power line 301 includes three wires respectively allocated to a first phase, a second phase, and a third phase, and a current clamp 302 is inserted in each of the first phase and the second phase, and the current value is detected on the power source side (upstream side) of the circuit breaker BK. The current clamp 302 is interposed between the wattmeter 300 and the circuit breaker BK.

Reference symbol 313 denotes a power detector configured to calculate power consumption based on the current from the current clamp 302, and the output from the power detector is input to the comparator 92 of the power instruction apparatus 9. Reference symbol 315 denotes small and portable home electric appliances used in the household, other than the kitchen electric appliances KP, the air-conditioning apparatus 7, and the dish washer-dryer 6. Examples of the home electric appliances 315 include a hair dryer, an electric iron, and an electric vacuum cleaner, which consume electric energy of approximately 1,000 W with a built-in heater or motor, and do not possess the self power-limitation device like the power usage control devices 8A to 8E. In FIG. 23, such appliances are denoted as "unregistered apparatus" because the rated maximum power information and the names of those appliances are unable to be registered in the power instruction apparatus 9. Not only one but a plurality of the unregistered apparatus may be utilized at a time. The unregistered apparatus 315 are not the object of the power limitation directly subjected to power reduction or power increase by the power instruction apparatus 9, and hence the power supplied through the circuit breaker BK is directly applied to the unregistered apparatus 315. The healthcare instruments 410 and the activity measurement apparatus 145 described above are also included in the "unregistered apparatus". In the case of utilizing an oxygen inhaler or other electric medical device for home medical care or nursing, such devices are also categorized as "unregistered apparatus" so as to prevent abrupt reduction of power usage.

The power usage reduction rate determination device 94 determines the power usage reduction amount with respect to the kitchen electric appliances KP and the air-conditioning apparatus 7 to which the power requests have been made, such that the total power does not exceed the capacity of the circuit breaker BK (8,000 W), and also that power usage of the power usage control devices 8A to 8E of the kitchen electric appliances KP and the air-conditioning apparatus 7 at lower ranks of "priority order" is reduced. The rated capacity originally given to the circuit breaker BK in advance (for example, 8,000 W as described above) may be referred to as "first capacity limit".

The "priority order" refers to the order determined so as to supply power to those kitchen electric appliances KP to which the power has to be supplied with priority in order to maintain the expected cooking quality and cooking work efficiency, within the limited first capacity (8,000 W) of the circuit breaker BK. Accordingly, the priority order is registered in advance such that the kitchen electric appliances that do not cause much inconvenience to the user even when the power is reduced are given lower ranks. Among the "first home electric appliances", the priority to secure the power is determined in the order of the rice cooker 3, the induction heating cooker 2, and the microwave oven 5, so as to prevent the work efficiency of the user from being degraded. However, in the process of determining the priority, in the case where the kitchen electric appliance KP in which the "priority cooking menu time period" is specified is currently in use in the "priority cooking menu time period", the power supply to such a kitchen electric appliance KP is not reduced by the power instruction apparatus 9 until the time period is over.

The information sign indicating that the power reduction is avoided, such as the fourth information sign 210D and the sixth information sign 54A may be individually provided to all of the "first home electric appliances". Likewise, the first information sign 210A and the fourth information sign 210D indicating that the appliance is an object of power reduction may be provided to all of the "first home electric appliances". Further, the information sign indicating that the appliance is an object of power reduction and the information sign indicating that the power supply is actually being reduced may each be provided to the "second home electric appliances" such as the air-conditioning apparatus 7. In addition, a display unit corresponding to the second information sign 210B indicating that the power reduction request has been received may be provided to the first home electric appliances other than the induction heating cooker 2 and the second home electric appliances. In the case of the air-conditioning apparatus 7, the mentioned displays may be visibly provided on the surface of the indoor unit (not shown), or in the display screen (where the indoor temperature and the operation mode are displayed) of the indoor remote controller configured to operate the indoor unit.

In the case where, in an independent kitchen electric appliance KP having a plurality of heating units (heaters), one of the heating units is actually performing the cooking in the "priority cooking menu time period" while the other heating units are not in the "priority cooking menu time period", the power for the heating unit in the "priority cooking menu time period" is maintained, and the power for the remaining heating units is designated as an object of power reduction.

In the "second home electric appliances", the priority for securing the power supply is given in the order of the air-conditioning apparatus 7 and the dish washer-dryer 6, so as to prevent the work efficiency of the user from being degraded.

Although the air-conditioning apparatus 7 is not installed in the kitchen, the power thereto is cut off via the same circuit breaker BK, and therefore the air-conditioning apparatus 7 is given a lower rank than the rice cooker 3 and the induction heating cooker 2 which are the "first home electric appliances". However, the air-conditioning apparatus 7 is given a higher priority than the dish washer-dryer 6, which is also one of the second home electric appliances. Although the "second home electric appliances" also include the washing-drying machine for clothes, detailed description thereof is omitted for the sake of simplicity.

In FIG. 23, reference symbol 96 denotes the power use limit setting device configured to instruct revision of the total power to be used as a basis for comparison by the comparator 92 to a designated power value. The power use limit setting device 96 is optionally operated by the user to set a second capacity limit lower than 8,000 W, and the value can be selected, for example, from 7,500 W, 7,000 W, and 6,500 W. In FIG. 23, the designated power value is denoted as "designated capacity". The designated capacity may hereafter be referred to as "second capacity". Here, although the designated capacity corresponds to the "second capacity limit" (e.g., 7,500 W) in this embodiment, it is not mandatory in this embodiment that the user is able to recognize the absolute value of the "second capacity". For example, the "second capacity" may be set to a desired ratio in regards to the "first capacity limit", such as "98% of the rated capacity (first capacity limit)" (i.e., reduction by 2%).

Reference symbol 99A denotes the router described above with reference to FIG. 1. Via the router, the power instruction apparatus 9 is connected to the server of a power company or other external organization 78A outside the house. Accordingly, for example, when the power shortage information is transmitted from a public agency or the power company in the district, the information is displayed on the display panel 100 of the use limit setting device 96. The use limit setting device 96 and its display screen 100A are subsequently described in detail. The power shortage information is classified into at least two types, that is, a compulsory instruction to reduce the power consumption of each household, and a non-compulsory request to optionally reduce the power consumption. Here, a communication unit 97 is also configured to transmit information on the power instruction apparatus 9 side to the external wide area communication network. Therefore, the occupant of the household can access the wide area communication network 98 from the mobile phone terminal 87 or another information communication terminal device when the occupant is away from home, to find out the power usage status of the household, and also input the upper limit of the power usage to the use limit setting device 96 from outside.

FIG. 45 and FIG. 46 are the details of the LCD screen 100A of the use limit setting device 96. In those drawings, reference symbol 101 denotes maximum allowable power information indicating in figures the rated capacity (first capacity limit: 8,000 W) of the circuit breaker BK allocated to the household, and reference symbol 102 denotes a current power consumption information sign indicating in figures the current power consumption of the household. Reference symbol 103 denotes a power allowance information sign indicating a degree of allowance of the power being consumed with respect to the maximum allowable power. The allowance may be indicated in words such as "allowance: large" or "allowance: small", instead of indicating the figure of "600 W" as it is, as illustrated in FIG. 45.

Reference symbol 104 denotes a power reduction request notification section to be lit up when the power shortage information is received from the wide area communication network 98 through the router 99A, and reference symbol 105 denotes an information sign of the current time of day. Reference symbol 106 denotes an information sign indicating the setting keys of the use limit setting device 96 and the figure of each setting key, the use limit setting device 96 being configured to instruct revision of the total power value used as a basis for comparison by the comparator 92 to a designated power value. In the state illustrated in FIG. 45 and FIG. 46, only the key of 8,000 W is displayed in white letters on colored background, which indicates that the power use limit is 8,000 W which is the same as the rated capacity of the circuit breaker BK. As illustrated in FIG. 45, four setting keys are provided, namely, a setting key 106A for 8,000 W, a setting key 106B for 7,500 W, a setting key 106C for 7,000 W, and a setting key 106D for 6,500 W.

Those four setting keys 106A to 106D are touch keys of a static capacitance detection type, and the outline of the key and the letters representing a part of the function (e.g., 6,500 W) are visibly displayed only when inputting by touch is effective. In other words, when the key is unusable for input by touch, the input key itself is not displayed, or barely visibly displayed. Basically, the static capacitance-based input keys are formed on the glass plate covering the surface of the display screen 100A, so that when the key of a predetermined position is touched, an input signal corresponding to the touched key is given to the use limit setting device 96.

Reference symbol 107 denotes a use status information sign indicating the list of the home electric appliances EE in the household that are the objects of the control by the power instruction apparatus 9, such as reference symbol 107A representing the name of the induction heating cooker 2 and reference symbol 107B representing the name of the rice cooker 3. The use status information sign 107 is arranged such that the appliance given the higher priority for securing the power supply is located on the left side. Reference symbol 108 denotes a use display section to be lit up when the corresponding appliance is supplied with power, that is, currently in use. From FIG. 45, it can be recognized that the induction heating cooker 2, the rice cooker 3, the air-conditioning apparatus 7, and the illumination apparatus are in use. The figures displayed close to the use information sign 108 indicate the power consumption of the corresponding appliance. For example, an average power value for the past one minute is displayed, and updated every minute. The screen display layout may be designed such that, when the priority of the home electric appliances EE in the household is set, the names of the set home electric appliances are automatically displayed from the left to the right in the order of priority, the farthest left being the highest (every time the priority of the home electric appliances EE is set, the names of the home electric appliances are rearranged as needed). In this manner, the user can instantly recognize the home electric appliances given a higher priority order.

Reference symbol 110 denotes an information key. Each time the user touches the information key 110, power supply-related information useful to the user in that situation, and information about cooking methods for effectively utilizing the power and how to set a temperature of the air-conditioning apparatus, are displayed on the display screen 100A. To secure a sufficient display region, the information sign 105 of the current time of day and the power allowance information sign 103 are not displayed.

Reference symbol 121 denotes a help mode key. When the user touches the key 121, information that assists the user's operation in that situation is displayed, and a correct operation method is audibly announced through a voice guide device (not shown) separately provided. When the key 121 is further pressed a plurality of times, displays indicating in illustrations and words how to view the display screen 100A, a use limit setting method, and so forth appear all over the display screen 100A. Reference symbol 133 denotes an information key. Each time the user touches the information key 133, the caution for when the operation of power limitation is input, or how to view the display screen 100A is displayed in detail in letters on the display screen 100A. The information that assists the user's operation is stored in the control unit 125.

In FIG. 46, reference symbol 57 denotes a presence management menu selection key displayed on the display screen 100A of the use limit setting device 96. The presence management menu selection key is touched when the user intends to switch the display screen, like the icon 419 for selecting the screen of the living environment information. When the user touches the presence management menu selection key, the screen is switched to a single-purpose display screen showing the list of all the family members indicating the presence or absence status at the current time of each member (see FIG. 63). Therefore, the presence status of all the family members can be recognized by viewing the mentioned display screen.

Figure 63:
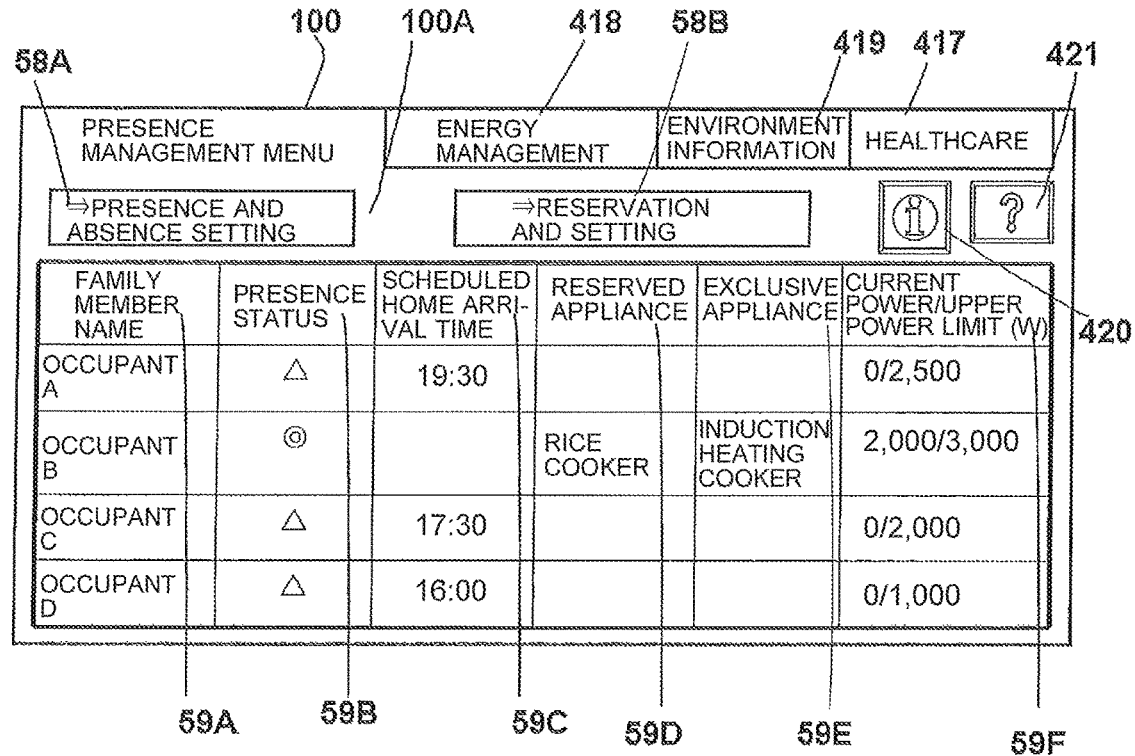
FIG. 63 is a front view for illustrating a state in which a presence management menu is displayed on the display screen of the use limit setting device of the power instruction apparatus according to the present invention.

FIG. 63 is a front view for illustrating a state in which a presence management menu is displayed on the display screen of the use limit setting device of the power instruction apparatus 9 according to Embodiment 1. In FIG. 63, reference symbol 58A denotes a selection key for switching to the input screen for use by the occupant who is at home. When the occupant touches the key 58A, the input screen appears in which an updated presence or absence status, the time known in advance that the occupant is away, scheduled home arrival time, and the absence period (month, date) can be input, with respect to each of the occupants. Reference symbol 58B denotes a selection key for switching to the input screen for setting the home electric appliance in which the occupant can reserve the operation start time or finish time in advance (e.g., rice cooker), and setting the exclusive electric appliance of the occupant. When the occupant touches the key 58B, the input screen appears in which the electric appliance that the occupant intends to reserve, and the designated exclusive electric appliance can be specified and input, with respect to each of the occupants.

In FIG. 63, reference symbol 59A denotes a family name column for displaying the names or nicknames for identifying each of the family members, and reference symbol 59B denotes a current presence status display column for displaying in symbols or letters the presence status of each of the occupants. In the example illustrated in FIG. 63, a circle indicates that the corresponding occupant is at home and a blank triangle indicates that the corresponding occupant is absent. Reference symbol 59C denotes a scheduled home arrival time display column for displaying the scheduled home arrival time with respect to each of the occupants, and reference symbol 59D denotes a reserved appliance display column for displaying the exclusive electric appliance in letters, symbols, or illustrations with respect to each of the occupants, so that the home electric appliance for which the reservation time (operation start time or operation finish time) has been set can be identified. With the mentioned columns, the presence status, the scheduled home arrival time, and so forth of each of the family members can be easily confirmed on the display screen 100A of the power instruction apparatus 9.

In FIG. 63, reference symbol 59E denotes an exclusive electric appliance display column for displaying the exclusive electric appliance in letters, symbols, or illustrations with respect to each of the occupants, so that the home electric appliance registered as an exclusive electric appliance can be identified. Reference symbol 59F denotes a power value display column for displaying the power consumption and the upper power limit of the exclusive electric appliance being used, with respect to each of the occupants. The "power" referred to here may be, for example, an average power of one minute, instead of an instantaneous maximum power. The "upper power limit usage" of each occupant can only be set by the occupant A or occupant B, on a different input screen.

In FIG. 63, the home electric appliances that may be used by any of the occupants, such as the illumination apparatus in the kitchen, the home electric appliance in the living room, and the air-conditioning apparatus in the living room, are common home electric appliances, and therefore the use of such common home electric appliances is not included in the power usage of the occupant who is using the home electric appliance, whoever of the occupants A and B may be using it. In the case where the occupant A registers the air-conditioning apparatus in the bedroom of the occupant A as an exclusive electric appliance, the upper power limit usage of the occupant A (2,500 W) is applied when the occupant A uses the air-conditioning apparatus, and therefore the occupant A is not permitted to use the air-conditioning apparatus if the total power exceeds 2,500 W (i.e., the power instruction apparatus 9 restricts the use so as not to exceed the upper power limit usage).

The control unit 125 sums the monthly power usage (kWh) of the exclusive electric appliances with respect to each occupant, and the result is displayed in figures or illustrations on the display screen 75D of the TV receiver or the display screen 100A of the power instruction apparatus 9 as appropriate. With the above-mentioned configuration, the existence of the exclusive electric appliance and the power consumption thereof can be easily confirmed with respect to each occupant.

Description is given referring back to FIG. 46. FIG. 46 is an illustration of the state of the screen that first appears when the user touches the name (display part) 107B of the induction heating cooker 2 on the display screen 100A in the state illustrated in FIG. 45. By viewing the display screen 100A illustrated in FIG. 46, it is understood that the induction heating cooker 2 is currently performing the stew heating operation, which is estimated to finish at 12:50. Further, it is understood that cooking is further continued for 15 minutes from the current time. Reference symbol 113S denotes the use start time information sign, and reference symbol 113E denotes the estimated finish time information sign.

Thus, by utilizing the display screen 100A of the use limit setting device 96, the outline of the status of the home electric appliances currently in use can be recognized, without taking the trouble of going to the actual place where the individual home electric appliance is located.

FIG. 47 is an illustration of the screen that automatically appears after a predetermined time, for example, 10 seconds, after the screen of FIG. 46 is displayed. In view of FIG. 47, it is understood that the induction heating cooker 2 is currently performing the stew heating operation, and that the process is still halfway through in view of marks 114 and 115 showing the degree of progress. With the progress of the cooking, the marks 114 sequentially increase to the right, and finally the marks 114 are aligned up to the left end position of the estimated finish time information sign 113.

A distinctive feature of Embodiment 1 is that the limitation can be determined so as to allow the user to spontaneously reduce the power consumption of the household collectively, by viewing the display screen 100A of the use limit setting device 96, regardless of whether the first capacity limit of the circuit breaker BK (8,000 W) is exceeded.

To be more detailed, the user can select the power usage limit from a plurality of levels, at a desired time. For example, when the power shortage information is received from the wide area communication network 98, the power reduction request notification section 104 is lit up, and therefore the user can spontaneously set an appropriate power usage limit by viewing the power reduction request notification section 104. Alternatively, when the user decides to reduce the power consumption based on information from a different source, the user can set the upper limit of power consumption through the use limit setting device 96 at any desired time. As described above, the user can select a power limit, for example, from 7,500 W, 7,000 W, and 6,500 W (the "second capacity limit" can be optionally determined).

Accordingly, although considerable allowance is available with respect to the first capacity limit of the circuit breaker BK (e.g., 8,000 W), the second capacity limit can be set as desired. The user can spontaneously set the upper limit to 7,500 W for example, in which case the power consumption of the home electric appliances in the household can be automatically suppressed by the power instruction apparatus 9, within the limit of 7,500 W. Further, the signals received from the wide area communication network 98 may be automatically classified so as to select a specific signal if any, and when the specific signal is received, the power instruction apparatus 9 may execute power reduction so as to reduce the power consumption by 5%, or revise the upper limit to a value one stage lower, for example, to 7,500 W when the capacity of the circuit breaker BK is 8,000 W, to thereby limit the power consumption.

Figure 50:
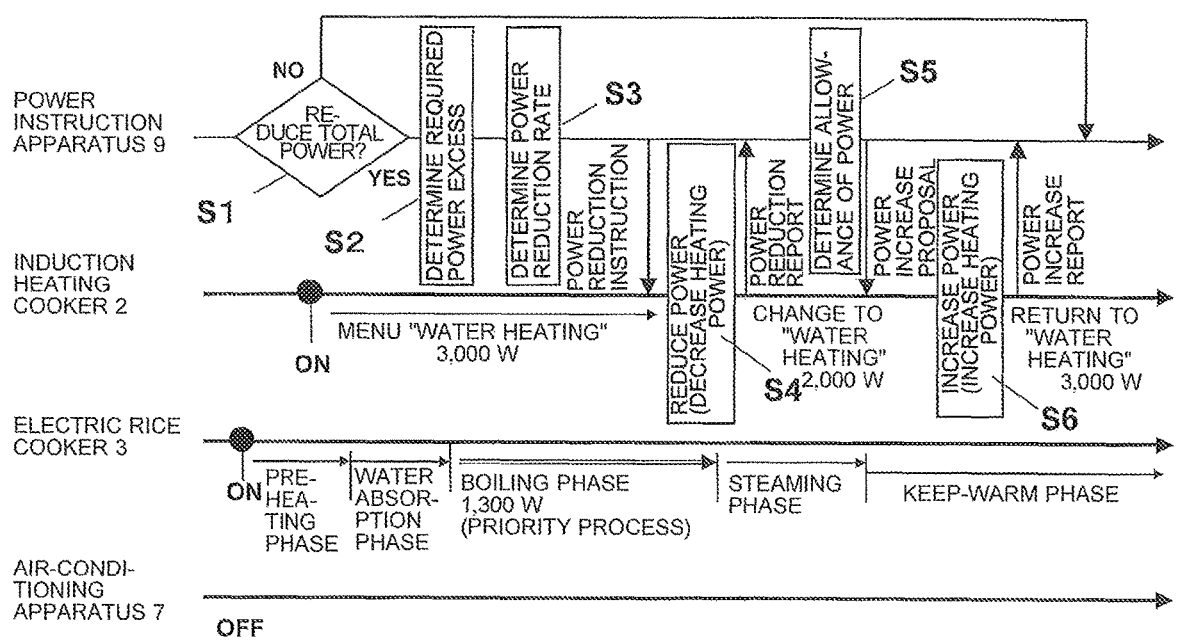
FIG. 50 is an explanatory diagram for illustrating a power controlling operation performed by the power instruction apparatus according to Embodiment 1 of the present invention.

Referring to FIG. 50, the operation of the power control system of the electric appliance of Embodiment 1 having the configuration described above is described. FIG. 50 is an explanatory diagram for illustrating the power controlling operation performed by the power instruction apparatus 9 according to Embodiment 1. Here, it is assumed that some home electric appliances EE, which are kitchen electric appliances KP, are about to be used by the user. Specifically, the kitchen electric appliances KP other than the rice cooker 3 and the induction heating cooker 2 have already started to work, the rice cooker 3 is to start working next, and the operation of the induction heating cooker 2 follows.

At the time point immediately before the induction heating cooker 2 starts the heating operation, the power instruction apparatus 9 has already received the information about the power necessary for performing the scheduled operation, for example, at the time point of starting the cooking, from the kitchen electric appliances KP, and then from the induction heating cooker 2. Accordingly, in the power instruction apparatus 9, the required power adder 91 sums the power values requested by each of the kitchen electric appliances KP and the comparator 92 compares the summed total power with the circuit breaker capacity (e.g., 8,000 W), and the comparison result is output to the requested power excess determination device 93.

The requested power excess determination device 93 does not output a signal when the total power is within 8,000 W (excess amount is 0), and when the total power is equal to or larger than 8,000 W, the requested power excess determination device 93 outputs the excess amount to the power usage reduction rate determination device 94. The power usage reduction rate determination device 94 returns the same usable power as the requested power to each of the power usage control devices 8A to 8D of the kitchen electric appliances KP when no output is made from the requested power excess determination device 93, and determines, when the excess amount is output, a reduction amount of the power consumption of each of the kitchen electric appliances KP based on the excess amount of the total power and the priority order determined by the priority order setting device 95, and responds to the power usage control devices 8A to 8D of the kitchen electric appliances.

The first time point at which the power instruction apparatus 9 receives the power request from the respective kitchen electric appliance KP is when the main power of one of the kitchen electric appliances KP has been turned on or a cooking start instruction has been made. For example, when the plug at the distal end of the power cord of the rice cooker 3 is inserted into a power supply port (power outlet or receptacle) and then a predetermined operation is performed (e.g., press rice cooking start key), the rated maximum power of the rice cooker 3 is requested. In the case of the induction heating cooker 2 constituted of a built-in type induction heating cooker, when the main power switch 11 is pressed so as to turn on the main power supply and then the heater is selected and the heating power is set (or, at the latest, when the heating operation is started after the heating power is set), the power request is received.

A specific heating power such as 1,000 W may be automatically set as a default value (initial value) when the heater of the induction heating cooker 2 is first selected, however, in this case, the power including the power required by the internal electric parts of the induction heating cooker 2 (e.g., rated maximum power of the motor for the cooling fan) in addition to the heating power 1,000 W (e.g., 1,050 W) is determined as the requested power transmitted to the power instruction apparatus 9. Unless permission is received from the power instruction apparatus 9 in response to the transmitted power request, the operation with the requested power is unable to be started. This is because the power usage control devices 8A to 8D each restrict the power supply to the corresponding kitchen electric appliance KP.

In other words, the power usage control devices 8A to 8D each control the power of the corresponding kitchen electric appliance KP within the power consumption permitted by the power instruction apparatus 9, and reduce the power consumption in the case where the power consumption reduction instruction is received from the power instruction apparatus 9 so as to control the power of the kitchen electric appliance KP within the reduced power consumption limit. The power instruction apparatus 9 is configured to permit the upper power limit usage for each individual kitchen electric appliance KP, taking into account the total electric power in advance, instead of collectively setting the total electric power for the plurality of kitchen electric appliances KP. Accordingly, for example, in the case of the induction heating cooker 2, a specific value of the upper power limit is determined, such as 4,000 W in response to the power request of 4,800 W.

Likewise, when the air-conditioning apparatus 7 is in use, the power usage control device 8E transmits the power request signal to the power instruction apparatus 9, and when the power consumption reduction instruction is received from the power instruction apparatus 9 in response, the power usage control device 8E accordingly reduces the power consumption of the air-conditioning apparatus 7. This also applies to the dish washer-dryer 6.

As described above, in the power control system for an electric appliance according to Embodiment 1, the power instruction apparatus 9 determines the reduction amount of power consumption with respect to each of the kitchen electric appliances KP based on the predetermined priority order, so that the total of the requested power from the power usage control devices 8A to 8D of the respective kitchen electric appliances KP does not exceed the capacity of the circuit breaker BK, and outputs the instruction to the power usage control devices 8A to 8D of the respective kitchen electric appliances. Consequently, the power consumption can be prevented from exceeding the capacity of the circuit breaker. Unlike the related-art mechanical method of limiting the power supply, the power supply to the kitchen electric appliances KP, which require sufficient power in order to maintain the cooking quality and cooking work efficiency, can be secured with priority.

In addition, the power instruction apparatus 9 instructs the kitchen electric appliance KP of a lower priority order to reduce the power consumption, which facilitates other kitchen electric appliances KP to maintain the cooking quality and cooking work efficiency.

As described above, the kitchen electric appliances KP are given a priority order. Specifically, as described above, the priority for securing power is given in the order of the rice cooker 3, the induction heating cooker 2, and the microwave oven 5, such that the kitchen electric appliances that do not cause much inconvenience to the user even when the power is reduced are given lower ranks. In other words, when the power is required to be reduced, the power is reduced in the order of the microwave oven 5, the induction heating cooker 2, and the rice cooker 3.

However, in the case where the power is reduced based on the priority order of those home electric appliances, but reducing the power of the microwave oven 5 is not sufficient for achieving the required power reduction, the induction heating cooker 2 is designated as the object of power reduction, among the specific kitchen electric appliances KP in which the "priority cooking menu time period" is specified. In this case, however, until the "priority cooking menu time period" is over, the power instruction apparatus 9 does not exceptionally reduce the power for the heating source of the kitchen electric appliance KP currently cooking the priority cooking menu. In this case, the power reduction instruction is output to the rice cooker 3, which is currently in the next rank in priority order. When the air-conditioning apparatus 7 and the dish washer-dryer are both being used, the dish washer-dryer 6 is designated as the object of power reduction before the induction heating cooker 2 is. When the power reduction of the dish washer-dryer 6 is still insufficient, the air-conditioning apparatus 7 may also be designated as the object of power reduction.

Description is now given regarding the case where the total value of the power request from the kitchen electric appliances KP summed by the required power adder 91 does not exceed the circuit breaker capacity (e.g., 8,000 W) and hence the power reduction instruction is not output, but the user has spontaneously reduced the power consumption upper limit in view of the display screen 100A of the use limit setting device 96. In other words, the case where the user sets the "second capacity limit" is described.

Referring to FIG. 50, at a first step (hereinafter "step" is abbreviated as "S"), the power instruction apparatus 9 determines that the instruction of total power reduction has been given from the outside (S1). The power instruction apparatus 9 compares the new upper limit (e.g., 7,000 W) and the power request from the kitchen electric appliances KP with the comparator 92 (S2), and determines the power reduction amount with the power usage reduction rate determination device 94 when the power request exceeds the upper limit (S3).

The power instruction apparatus 9 outputs the power reduction instruction to the kitchen electric appliances KP being used. The induction heating cooker 2, which had started the heat cooking prior to Step S1, reduces its power consumption in response to the instruction. When the power reduction amount is 1,000 W, and the total power usage of the induction heating cooker 2 is 4,200 W, for example, when the heating power of the first heater 2L alone is 3,000 W, the heating power of the second heater 2R alone is 1,000 W, and both the heaters perform the water heating menu (non-priority cooking menu), the induction heating cooker 2 reduces the total heating power to 3,000 W (S4), thereby reducing the power consumption to 3,200 W. Here, 200 W corresponds to the power consumption of the built-in electric parts such as the fan. Then, induction heating cooker 2 notifies the power instruction apparatus 9 that the power consumption has been reduced by 1,000 W.

Thereafter, in the power instruction apparatus 9, the power requests from the kitchen electric appliances KP are summed again (S5), and when the total of the power requests is still small and allowance exceeding the power reduction amount of 1,000 W is available, for example, when the total power request at this point is not more than 5,900 W while the new upper limit is 7,000 W, in which case an allowance of 1,100 W is available, the power instruction apparatus 9 proposes (notifies) the induction heating cooker 2 in advance that the power consumption of the induction heating cooker 2 reduced as above may be recovered to the original level. The induction heating cooker 2 does not automatically recover the heating power for safety's sake unless an operation for increasing the heating power is performed within a predetermined time after reception of the notification, however in the case where the user operates the induction heating cooker 2 so as to recover the heating power, for example, increases the heating power, the induction heating cooker 2 increases the (total) heating power to the initial level of 4,000 W (S6). To simplify the operation to increase the heating power in such a case, a key of "recovery" may be provided in the upper surface operation unit 26 of the induction heating cooker 2, so that upon pressing the "recovery" key once, the original heating power is easily regained, provided that the allowance is available.

In the case where, in the independent induction heating cooker 2, the first heater 2L is performing "frying" and has entered the "priority cooking menu time period" in which a maximum power of 1,800 W may be used, while the second heater 2R is performing "water heating" (non-priority cooking menu) which consumes 2,000 W at maximum, when the power reduction amount instructed by the power instruction apparatus 9 is 1,000 W, the second heater 2R performing the water heating is subjected to the power reduction, and the heating power for the water heating is reduced such that the power consumption of the induction heating cooker 2 as a whole is reduced by 1,000 W.

In the case where the induction heating cooker 2 is not in use in the situation of FIG. 50, the reduction of power consumption with the induction heating cooker 2 is unfeasible, and therefore the rice cooker 3 is designated as the object of power reduction based on the priority order. However, in the case where the rice cooker 3 is in the "priority cooking menu time period" as illustrated in FIG. 50 when the power usage reduction rate determination device 94 determines the power reduction amount (S3), the rice cooker 3 is not subjected to the power reduction.

In the kitchen, relatively small electric heaters that receive power through the same circuit breaker BK and consume approximately 1,000 W for 10 minutes to 60 minutes are also provided, for example a thermos pot, a hot plate, and an oven toaster. An electric refrigerator is also provided. Accordingly, even though the induction heating cooker 2 is used at 4,000 W in the kitchen as above, the power consumption of the induction heating cooker 2 may be limited as described above, if the user reduces the total power consumption to 7,000 W (sets the second capacity limit) through the use limit setting device (power use limit setting device) 96.

Figure 51:
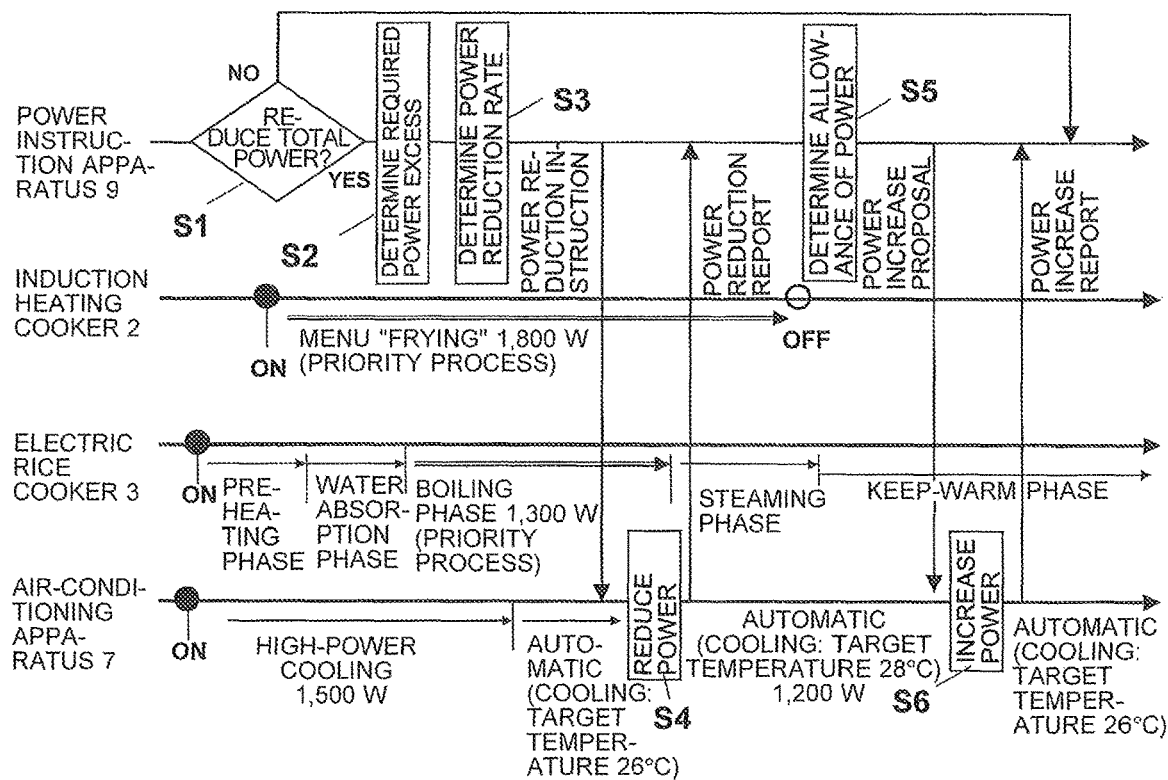
FIG. 51 is an explanatory diagram for illustrating the power controlling operation performed by the power instruction apparatus according to Embodiment 1 of the present invention.

Now, description is given regarding the case where the power instruction apparatus 9 has output an instruction to reduce the total electric power, when one air-conditioning apparatus 7, the induction heating cooker 2, and the rice cooker 3 are being used at the same time. FIG. 51 is an explanatory diagram for illustrating the power controlling operation performed by the power instruction apparatus 9 according to Embodiment 1. Referring to FIG. 51, description is given regarding the case where the total value of the power requests from the respective kitchen electric appliances KP and the air-conditioning apparatus 7 summed by the required power adder 91 does not exceed the circuit breaker capacity (e.g., 8,000 W), but the user has spontaneously reduced the power consumption upper limit after viewing the display panel 100 of the use limit setting device 96.

Referring to FIG. 51, the power instruction apparatus 9 determines in the first step that the instruction of total power reduction has been given from outside (S1).

The power instruction apparatus 9 compares the new upper limit (second capacity limit, e.g., 7,000 W) and the power requests from the kitchen electric appliances KP and the air-conditioning apparatus 7 with the comparator 92 (S2), and determines the power reduction amount with the power usage reduction rate determination device 94 when the power request exceeds the upper limit (S3).

The power instruction apparatus 9 then outputs the power reduction instruction to the air-conditioning apparatus 7 in use, based on the priority order. The air-conditioning apparatus 7 reduces its power consumption accordingly (S4). In the case where the power reduction amount is 300 W, the air-conditioning apparatus 7 revises the cooling target temperature from 26 degrees Celsius to 28 degrees Celsius to decrease the rotation speed of the electric compressor (not shown) which consumes the most power in the air-conditioning apparatus 7, thereby changing to an energy-saving operation in which the power consumption is reduced. Here, the power consumption of the electric compressor at a lower rotation speed is determined in advance based on the correlation between the target temperature and the actual indoor temperature obtained through experiments, and such data is stored in the air-conditioning apparatus 7. Therefore, the operation condition of the electric compressor (not shown) for the power reduction can be instantaneously determined based on the power reduction request from the power instruction apparatus 9.

In the case where the air-conditioning apparatus 7 is not in use, neither the rice cooker 3 nor the induction heating cooker 2 are designated as the object of power reduction immediately. This is because the rice cooker 3 is performing the high heat phase (boiling phase) H2A and the induction heating cooker 2 is performing the fry cooking, and therefore both are in the "priority cooking menu time period".

Then, the air-conditioning apparatus 7 notifies the power instruction apparatus 9 that the power consumption has been reduced by 300 W. In the power instruction apparatus 9, the power requests from the kitchen electric appliances KP and the air-conditioning apparatus 7 are summed again (S5), and when the total of the power requests is still small and an allowance exceeding the power reduction amount of 300 W is available, for example, when the total power request at this point is not more than 6,500 W while the new upper limit is 7,000 W, in which case the allowance of 500 W is available, the power instruction apparatus 9 proposes (notifies) the air-conditioning apparatus 7 in advance that the power consumption of the air-conditioning apparatus 7 reduced by 300 W may be recovered to the original level.

The air-conditioning apparatus 7 automatically resumes the operation of reducing the target temperature to 26 degrees Celsius, within a predetermined time after reception of the notification (S6). The air-conditioning apparatus 7 transmits, upon reducing the power consumption and upon increasing the power, the information about the power consumption to the power instruction apparatus 9 as illustrated in FIG. 50.

As described above, the kitchen electric appliance KP transmits the operation information (selection of cooking menu, setting of heating power) to the power instruction apparatus 9 at each occasion, throughout the process from turning on to turning off of the power supply. The air-conditioning apparatus 7 also transmits the operation information (selection of cooling-heating operation menu, setting of target temperature) to the power instruction apparatus 9 at each occasion, throughout the process from turning on to turning off of the power supply. Therefore, the power instruction apparatus 9 can constantly recognize the power usage status of a plurality of home electric appliances EE. This aspect is described in further detail hereunder.

Figure 52:
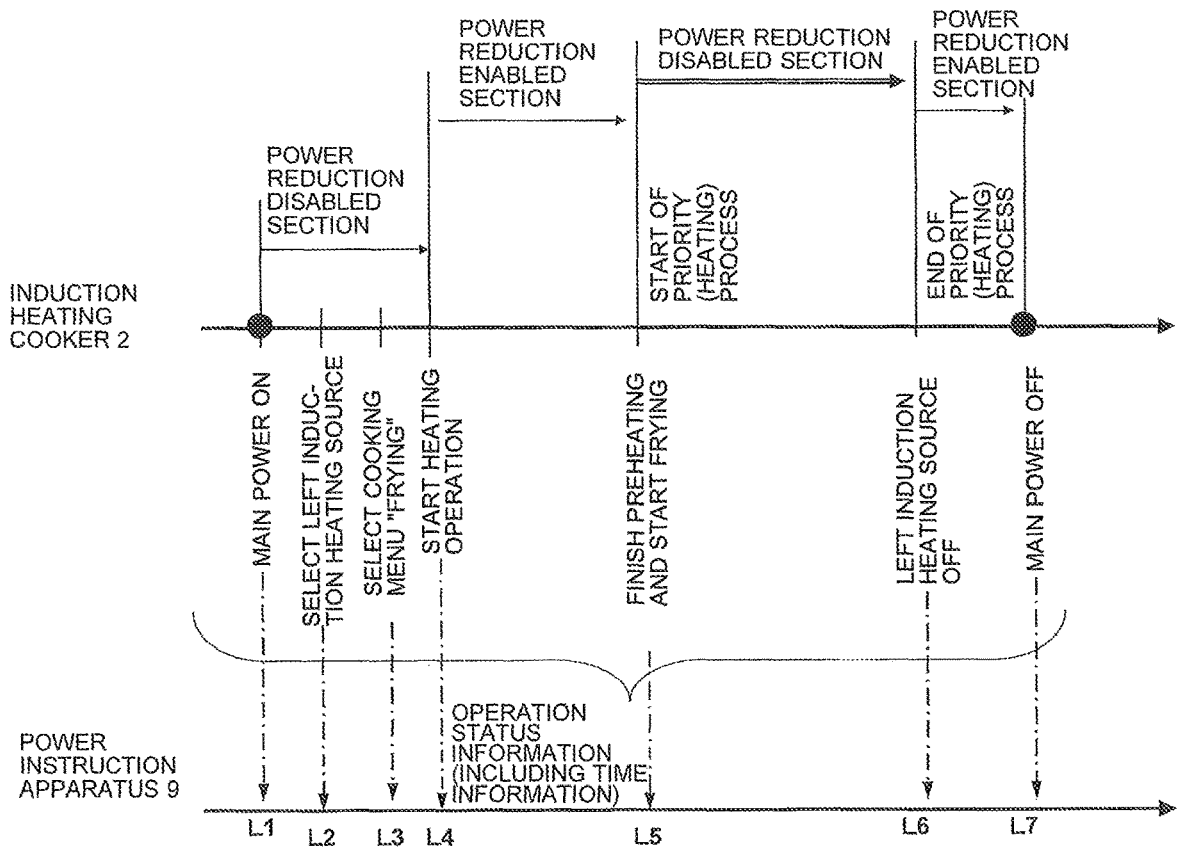
FIG. 52 is an explanatory diagram for illustrating a relationship between operation information from the induction heating cooker and a heating process, according to Embodiment 1 of the present invention.
Figure 53:
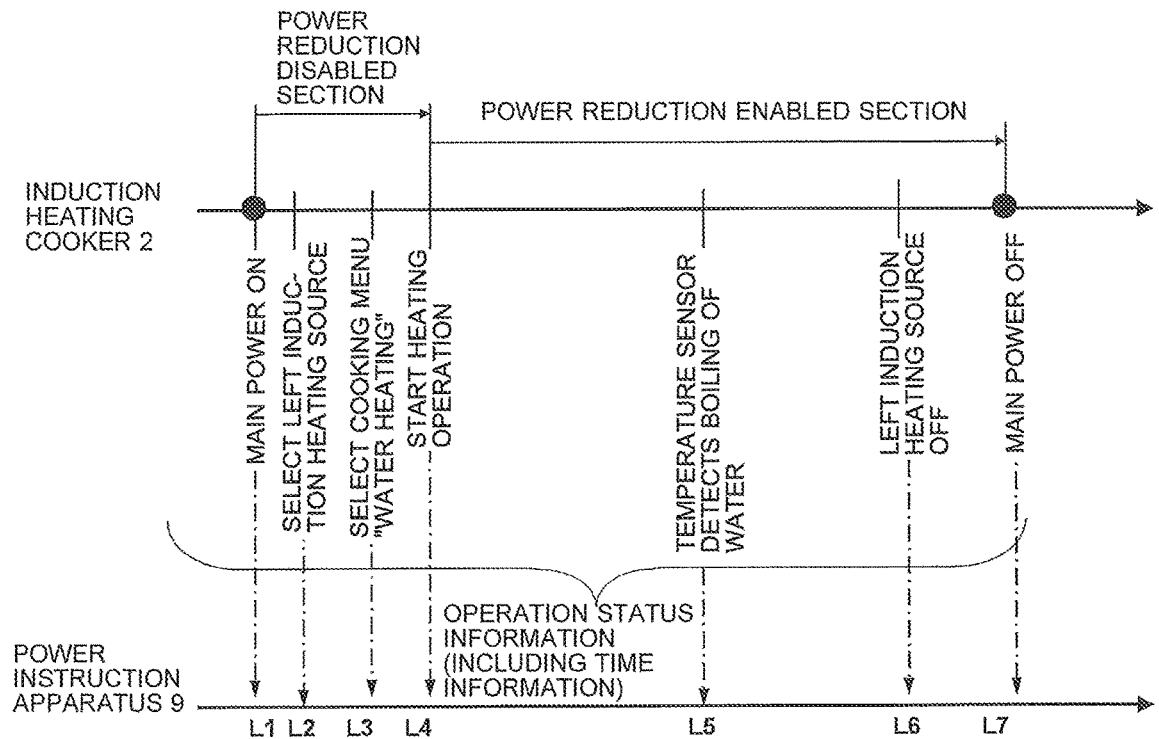
FIG. 53 is an explanatory diagram for illustrating the relationship between the operation information from the induction heating cooker and the heating process.
Figure 54:
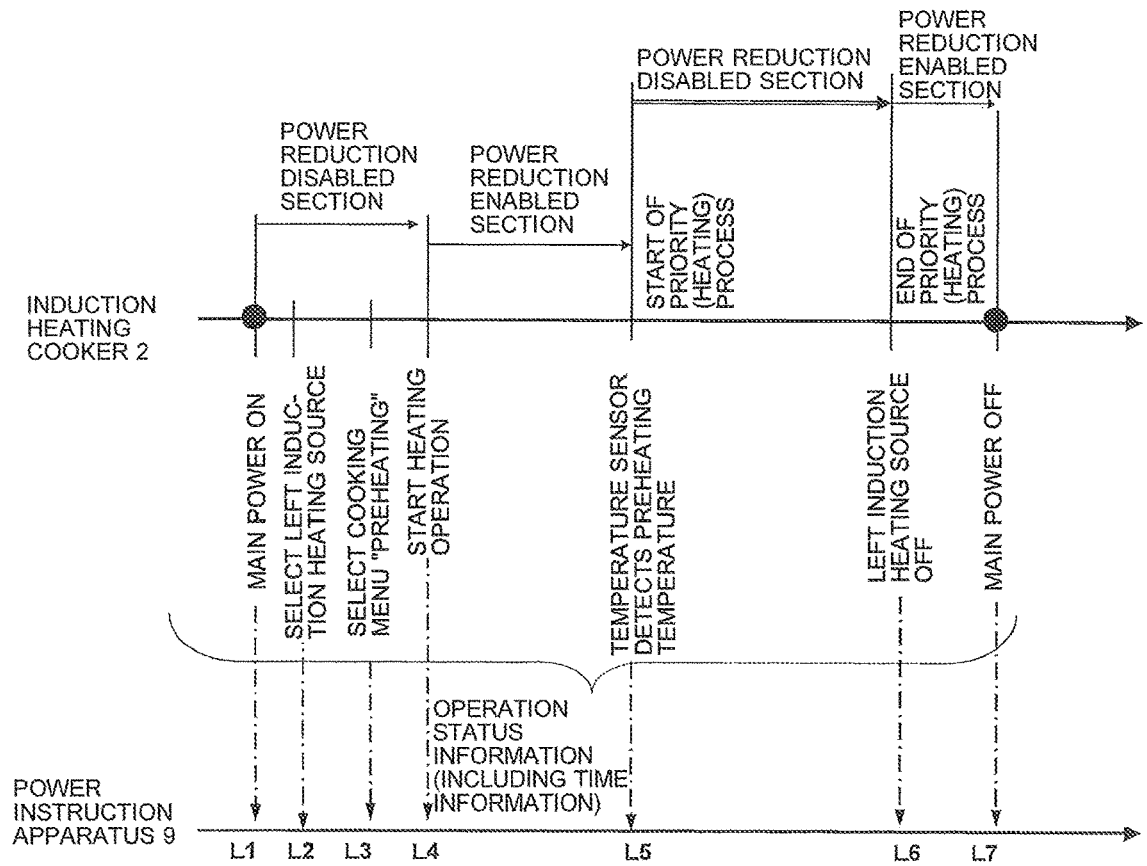
FIG. 54 is an explanatory diagram for illustrating the relationship between the operation information from the induction heating cooker and the heating process.

FIG. 52 to FIG. 54 are time charts for illustrating how the operation information (selection of cooking menu, setting of heating power) is transmitted to the power instruction apparatus 9 at each occasion throughout the process from turning on to turning off of the power supply, with respect to the induction heating cooker 2 as a typical example. That is, FIG. 52 to FIG. 54 are explanatory diagrams for illustrating the relationship between the operation information from the induction heating cooker 2 and the heating process according to Embodiment 1. The other kitchen electric appliances KP and the air-conditioning apparatus 7 are also transmitting the operation information to the power instruction apparatus 9 at each occasion, basically in the same way. As described above, the operation information is also used as information for monitoring abnormality by the controller 32. In other words, the controller 32 adds information for knowing the occurrence timing such as time to the operation information when the operation information is transmitted to the power instruction apparatus 9, and the obtained information is sequentially stored in the storage device 32R incorporated in the controller 32.

In FIG. 52, reference symbols L1 to L7 denote the operation information signals transmitted from the induction heating cooker 2 to the power instruction apparatus 9. Reference symbol L1 denotes the signal indicating the turning on of the main power supply, and reference symbol L2 denotes the selection information of the heater, indicating that the first heater 2L has been selected in FIG. 53. Reference symbol L3 denotes the selection information of the cooking menu, indicating that "frying" has been selected from among the cooking menus of water heating, stewing, fry cooking, and so forth. As described above, the induction heating cooker 2 is configured to acquire the time period-classified electricity rate information as described above, however it is not necessary to acquire the rate each time the main power supply to the induction heating cooker 2 is turned on. In addition, when "frying", a non-specific menu, is selected as illustrated in FIG. 52, the time period-classified electricity rate information is not notified to the user. However, if the time period-classified electricity rate information is to be acquired, the time point of the acquisition is between the signals L3 and L4 in FIG. 52. The induction heating cooker 2 transmits a signal requesting the information to the power instruction apparatus 9, and analyzes the signal returned from the power instruction apparatus 9, thereby acquiring the time period-classified electricity rate information.

Reference symbol L4 denotes the information indicating that the inverter circuit 33L has actually been activated and the induction heating has been started. Reference symbol L5 denotes the information indicating that the frying phase has been started. As described above, the process including the frying phase and the power increasing phase is defined as the "priority cooking menu time period", and the power reduction is not performed by operation or instruction from outside in this time period. Accordingly, whether the induction heating cooker 2 is actually in the "priority cooking menu time period" is determined depending on whether the operation information signal L5 has been transmitted (but before transmission of the operation information signal L6). Reference symbol L6 denotes the information indicating that the operation of the inverter circuit 33L has actually been stopped and the induction heating has been finished. Reference symbol L7 denotes the information indicating that the main power supply has been turned off. The operation information signals L1 to L7 are accompanied with the time of day of the transmission, to the second.

As is apparent from FIG. 52, in the entire process of the induction heating cooker 2 from turning on to turning off of the power supply, the operation with reduced power can be performed based on the power reduction request from the power instruction apparatus 9, in the time period other than the period between the signals L1 and L4 and the "priority cooking menu time period". The period between the signals L1 and L4 is the phase where the cooking menu has not been fixed and "frying" may be selected immediately thereafter, and therefore this phase is designated as a preliminary period exempted from the power reduction. During the period from L1 to L4, the heating operation has not started substantially, and therefore the power consumption is small. Thus, a visible effect of power reduction can barely be expected even though the period from L1 to L4 is designated as the period for power reduction.

Therefore, in the process of, for example, "water heating", in which the "priority cooking menu time period" is not specified, the power supply can be reduced any time, whenever the power reduction request is received. Even when the heating operation is started in the process of performing "water heating" as the cooking menu as illustrated in FIG. 53, the power can be reduced at any desired time.

FIG. 54 is a time chart for illustrating the process of performing the cooking menu for which a different "priority cooking menu time period" is specified. FIG. 54 represents an example where the induction heating cooker 2 is performing the cooking menu of "preheating". The operation information signal L3 is information indicating the selected cooking menu, and in this case, indicates that the cooking menu of "preheating" has been selected out of various cooking menus. Reference symbol L4 denotes the information indicating that the inverter circuit 33L has actually been activated and the induction heating has been started. Here, although "preheating" requires a heating power of approximately 1,500 W at maximum, "preheating" is not classified as a specific menu because the timing for such a menu is unable to be shifted.

Reference symbol L5 denotes the information indicating that the temperature detection circuit (temperature detection device) 150 has detected that the temperature of the heating object N, for example, the frying pan, has reached a preheating temperature set by the user (e.g., 160 degrees Celsius). After the preheating temperature is detected, the controller 32 automatically adjusts the heating power for the inverter circuit 33L so as to maintain the preheating temperature.

At the point of the operation information signal L5, the "priority cooking menu time period" is entered. Accordingly, the power reduction based on operation or instruction from outside is invalid after the point of L5. In the case that the heating power accidentally falls in the "priority cooking menu time period", the preheating temperature is unable to be maintained, and therefore when the user starts to cook (e.g., rolled egg) believing that the desired preheating temperature has been reached, the user is unable to satisfactorily perform the cooking because the temperature of the frying pan is only 140 degrees Celsius or so.

Reference symbol L6 denotes the information indicating that the operation of the inverter circuit 33L has actually been stopped and the induction heating has been finished. Reference symbol L7 denotes the signal indicating that the main power supply has been turned off.

As is apparent from FIG. 54, in the entire process of the induction heating cooker 2 from turning on to turning off of the power supply, the operation with reduced power can be performed based on the power reduction request from the power instruction apparatus 9, in the time period other than the period between the signals L1 and L4 and the "priority cooking menu time period". The period between the signals L1 and L4 is the phase where the cooking menu has not been fixed and "automatic stewing" may be selected immediately thereafter, and therefore this phase is designated as a preliminary period exempted from the power reduction. During the period from L1 to L4, the heating operation has not substantially started, and therefore the power consumption is small. Thus, a visible effect of power reduction can barely be expected even though the period from L1 to L4 is designated as the period for power reduction.

Although not described in detail above, in the power control system according to Embodiment 1, the power instruction apparatus 9 gives the highest priority order to the power request from the rice cooker 3, so as to secure the power for the rice cooker 3 with highest priority. Accordingly, the power for the rice cooker 3 is kept from being reduced once the boiling phase is entered despite the total power usage being about to exceed the capacity of the circuit breaker BK (8,000 W) or the upper limit set by the user (e.g., 7,000 W), and therefore excellently finished rice can be enjoyed.

In the case of the dish washer-dryer 6, when the power is reduced during the washing process, the rotation speed of the motor driving a washing pump (not shown) is decreased, and the supply capacity of water or hot water significantly declines. Accordingly, the power of water flow jetted from a jetting nozzle (not shown) configured to jet washing water toward the dishes is weakened, and grime such as rice grains become unable to be completely removed.

In Embodiment 1, the power necessary for the washing process is maintained, and hence the time period of the washing process corresponds to the "priority cooking menu time period" specified in the induction heating cooker 2 and the rice cooker 3, and is exempted from the power reduction by the power instruction apparatus 9. Accordingly, during the washing process, the jet water flow from the washing nozzle (not shown) can be secured and the stain removing performance can be kept from being degraded. However, the priority for securing the power for the dish washer-dryer 6 is lower than that of the induction heating cooker 2 and the rice cooker 3. Thus, the dish washer-dryer 6 is subjected to the power reduction in the case where the capacity of the circuit breaker BK is about to be exceeded. In addition, the power consumption of an electric heater (not shown) configured to increase the temperature of the washing water is considerably large, for example, 800 W, and reducing the power for the electric heater barely affects the washing performance itself, though it takes longer before the temperature of the washing liquid is sufficiently increased. Therefore, the control unit of the dish washer-dryer 6 is programmed in advance such that the washing process is not specified as a zone corresponding to the "priority cooking menu time period" of the induction heating cooker 2 and the rice cooker 3.

When the power is reduced, the washing process is temporarily suspended, and therefore even when the power is recovered again and the washing process is resumed, the temperature of the washing water may have dropped because of the suspension. In such a case, time for heating the washing liquid so as to increase the temperature to a predetermined temperature is needed, and hence the overall operation time is prolonged. Therefore, the fact that the washing is temporarily suspended is displayed on a display unit (not shown) of the dish washer-dryer 6 when the washing process is suspended, and also the fact that it takes longer before the predetermined washing is completed even when the washing is resumed is notified to the user, with a specific indication of the time prolonged.

The cooking time is required to be prolonged because power has been reduced in the process other than the "priority cooking menu time period". For example, in the case of the induction heating cooker 2, the initially set cooking time is prolonged based on the amount of power reduction and a notice to this effect is output to the user. On the side of the power instruction apparatus 9, the progress of the heating process has been recognized in view of the signals L1 to L4 from before the power reduction, and therefore misrecognition of the finish time of the heating operation, as well as increase of power usage based on the misrecognition can be avoided.

Figure 55:
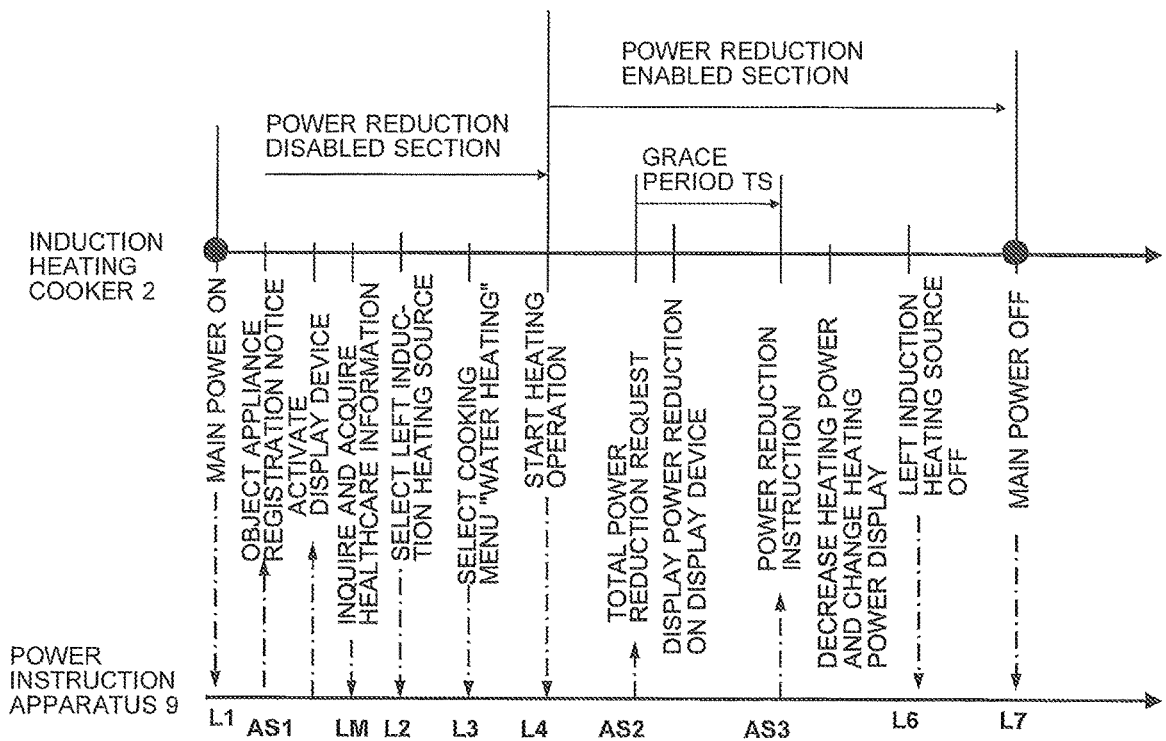
FIG. 55 is an explanatory diagram for illustrating the relationship between the operation information from the heating cooker and the heating process.

FIG. 55 is an explanatory diagram for sequentially illustrating how the home electric appliance, e.g., the induction heating cooker 2 can recognize whether the home electric appliance is the object of power control of the power instruction apparatus 9. Reference symbols L1 to L7 in FIG. 55 each denote the operation information signal transmitted from the induction heating cooker 2 to the power instruction apparatus 9, as described above. Reference symbol LM denotes a signal for inquiring whether the healthcare information is stored in the power instruction apparatus 9.

Reference symbol AS1 denotes an object appliance registration signal transmitted from the power instruction apparatus 9 to the induction heating cooker 2 upon reception of the operation information signal L1 from the induction heating cooker 2. The operation information signal L1 contains the appliance code for identifying the induction heating cooker 2, and therefore the power instruction apparatus 9 transmits the object appliance registration signal AS1 only to the induction heating cooker 2.

The object appliance registration signal AS1 indicates that the induction heating cooker 2 is electrically connected to the power instruction apparatus 9 and may receive the power instruction signal from the power instruction apparatus 9 to thus be subjected to power reduction.

The object appliance registration signal AS1 output from the power instruction apparatus 9 is received by the power usage control device 8A of the induction heating cooker 2, and enters the interface unit 35C of the display unit driver circuit 35 illustrated in FIG. 27 through the controller 32. Then the display controller 35B recognizes the reception of the object appliance registration signal AS1, and the words "object of power reduction" as illustrated in FIG. 32 are displayed in the display screen 129 of the central display unit 16, as the first information sign 210A.

Before the reception of the object appliance registration signal AS1, the display unit driver circuit 35 is driven by the controller 32 so as to display necessary information in advance in the display screen 129 as illustrated in FIG. 32, because the main power is turned on. Accordingly, in the case where the exclusive caution information light 430 also serving as the display instruction switch is lit up as illustrated in FIG. 26, the healthcare data stored in the power instruction apparatus 9, in particular the caution data, is retrieved to the induction heating cooker 2 and notified to the user through the display screen already activated by the display controller 35B, when the user presses the caution information light 430. After the generation of the signal LM illustrated in FIG. 55 also, the caution data can be displayed in the display screen 129 by pressing the caution information light 430.

Then, the operation information signal L4 indicating that the inverter circuit 33L has actually been activated and the induction heating has started is transmitted to the power instruction apparatus 9 through the power usage control device 8A. Further, the display unit driver circuit 35 changes the display content on the central display unit 16, when the induction heating cooker 2 receives a request signal (advance notice signal) AS2 from the power instruction apparatus 9 indicating that the total electric power of all the home electric appliances connected to the power instruction apparatus 9 is to be reduced. When the request signal is received, the first information sign 210A in the central display unit 16 of the induction heating cooker 2 disappears and instead the second information sign 210B is displayed at this position in order to notify the user that the power is desired to be reduced. For example, such a message as "power reduction request received" or "requested to reduce power" is displayed in white letters on colored background.

The power reduction request signal AS2 is a signal from the power instruction apparatus 9 urging prompt power reduction, and in the case where the total electric power is not reduced within a predetermined time after the transmission of the signal AS2, the power instruction apparatus 9 forcibly reduces the power. Accordingly, the power instruction apparatus 9 transmits a power reduction instruction signal AS3 to the power usage control device 8A within a predetermined time (e.g., a few seconds to 10 seconds) after the transmission of the power reduction request signal AS2. When any of the home electric appliances have spontaneously reduced the power within the predetermined time, and sufficient allowance of the power is secured with respect to the setting by the user to reduce the total power to 7,000 W through the use limit setting device 96, for example, the request signal AS2 may be revoked and the power supply to other home electric appliances may be maintained unchanged. Even though the request signal AS2 is revoked, the first information sign 210A of "object of power reduction" is again displayed in letters and remains on all the electric appliances that had received the object appliance registration signal AS1 earlier.

In the case where the power reduction instruction signal AS3 is output, the display unit driver circuit 35 changes the display content of the central display unit 16 and displays the third information sign 210C such as "power reduced" in the display screen 129 (see FIG. 36).

As illustrated in FIG. 55, the period between the time that the power reduction request signal AS2 requesting reduction of the total electric power is received and the time that the power reduction is actually executed is referred to as "grace period" TS. The grace period is provided in expectation of spontaneous power reduction by the user of the home electric appliance, and set in a minimum time necessary to do so. The grace period may be displayed in increments of 1 second, for example. For example, the remaining time may be displayed in the display screen 129 in a count-down mode, such as 10 seconds, 9 seconds, 8 seconds, and so on. Alternatively, a figure like a bar-graph that becomes shorter every second may be displayed, to visually notify the user that the grace period is about to end.

In the examples described above, the first information sign 210A and the second information sign 210B are displayed on the central display unit 16 of the induction heating cooker 2, however such information may be displayed at a different position. Further, the first information sign 210A and the second information sign 210B may each be displayed similarly on the display unit unique to other home electric appliances EE such as the rice cooker 3.

In Embodiment 1, as may be understood from the foregoing description, for example, the induction heating cooker 2 is configured to accept, throughout the entire process from turning on to turning off of the power supply except for the "priority cooking menu time period", the power reduction in compliance with the power reduction request from the power instruction apparatus 9. Therefore, the first information sign 210A of "object of power reduction", indicating that the induction heating cooker 2 may receive the power reduction request signal during the operation, is displayed in the display screen 129 of the central display unit 16. In addition, when the power reduction request is received, the second information sign 210B appears on the display screen. When the power is actually reduced, the third information sign 210C is displayed on the display screen 129.

Further, the fourth information sign 210D is displayed for indicating that, in the "priority cooking menu time period", the power reduction is avoided despite an instruction having been received from outside the induction heating cooker 2. Therefore, the user can recognize the influence of the power restriction instruction on the heating cooker being used, by viewing the first to fourth information signs. To be more detailed, when the induction heating cooker 2 receives the object appliance registration signal AS1, the first information sign 210A of "object of power reduction" is displayed in words first in the display screen 129 of the central display unit 16 as illustrated in FIG. 32. However, when the induction heating cooker 2 starts the boil cooking, thereby entering the heating operation in the "priority cooking menu time period", no message is displayed on the display screen 129 and no voice guidance is output, even though the induction heating cooker 2 has received the power reduction request signal AS2 in this time period. Such an arrangement prevents the user from being induced to reduce the heating power in haste during the boiling process.

Alternatively, during the time that the heating operation in the "priority cooking menu time period" is being performed, voice guidance such as "Power reduction request has been received but power is automatically maintained for this important cooking process. Power may be reduced when the current process is over" may be output so as to ensure that the user further recognizes the situation. Naturally, such a message may be displayed as words on the display screen 129.

In the examples described above, the time period-classified electricity rate information and the information of the time that power is supplied to the heating unit are displayed at the same time. Here, the expression "at the same time" means that both pieces of information are displayed together for a predetermined period of time so that the user can visually compare the electricity rate classification information and the power supply time information, and not that the electricity rate classification information and the information of the time that power is supplied to the heating unit appear exactly simultaneously.

Now, the case of revising a reservation time of the "operation start time (reserved start time A)" of the first home electric appliance, and the case of revising a reservation time of the "operation finish time (reserved finish time A)" of the first home electric appliance are described, as one of the distinctive features of Embodiment 1.

Figure 56:
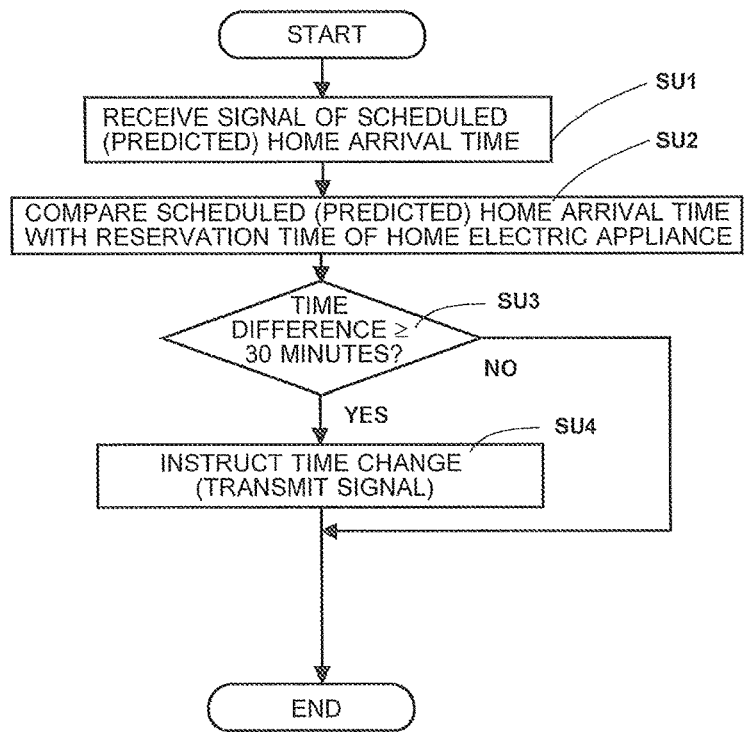
FIG. 56 is a flowchart for illustrating a changing process of a reservation time of a home electric appliance.

FIG. 56 is a flowchart for illustrating an operation of the control unit 125 of the power instruction apparatus 9. The basic operation program (information processing program) illustrated in the flowchart is stored in the semiconductor memory (ROM) in the microcomputer (not shown) constituting the control unit 125 of the power instruction apparatus 9.

The following description refers to the case where the occupant B (user B) made a rice cooking reservation with the rice cooker 3 beforehand, and set the "operation finish time" to 20:00 (8 p.m.). When the occupant B, who went out after making the rice cooking reservation, changes the predicted home arrival time to 22:00 from a remote facility 79 as illustrated in FIG. 2 using the mobile phone terminal 87 exclusive to the occupant B, the information of the scheduled (predicted) home arrival time is transmitted from the mobile phone terminal 87 and reaches the power instruction apparatus 9 through the wide area communication network (communication network) 98. More specifically, the information reaches the control unit 125 through the input-output unit 124B (Step 1; "step" is hereinafter denoted by "SU").

Then, the control unit 125 of the power instruction apparatus 9 identifies the home electric appliance EE in which the reservation time (operation start time or operation finish time) acquired in advance from the home electric appliances EE is set, and compares the reservation time with the scheduled home arrival time (SU2).

It is determined through the comparison whether there is a time deviation of 30 minutes or more (SU3), and when the time deviation is 30 minutes or more, the control unit 125 outputs an instruction to change the reservation time so as to match the scheduled (predicted) home arrival time, to the home electric appliance (SU4). Accordingly, the reserved cooking finish time of the rice cooker 3 is revised to 22:00.

A reason of setting the threshold to 30 minutes is that revising the reservation time each time a minor schedule change is made may force the home electric appliance to perform an operation that may impose thereon an adverse impact. For example, it generally takes approximately 30 minutes before the rice cooker finishes the boiling phase after the rice cooking has started and therefore, although "operation finish time" is advanced by 20 minutes because the home arrival time is unexpectedly advanced by 20 minutes, the rice cooking is unable to be completed before the scheduled home arrival time. Accordingly, in the case where the difference is less than 30 minutes as result of the comparison at SU3, SU4 is skipped, that is, the reservation time revision instruction is not output.

Figure 57:
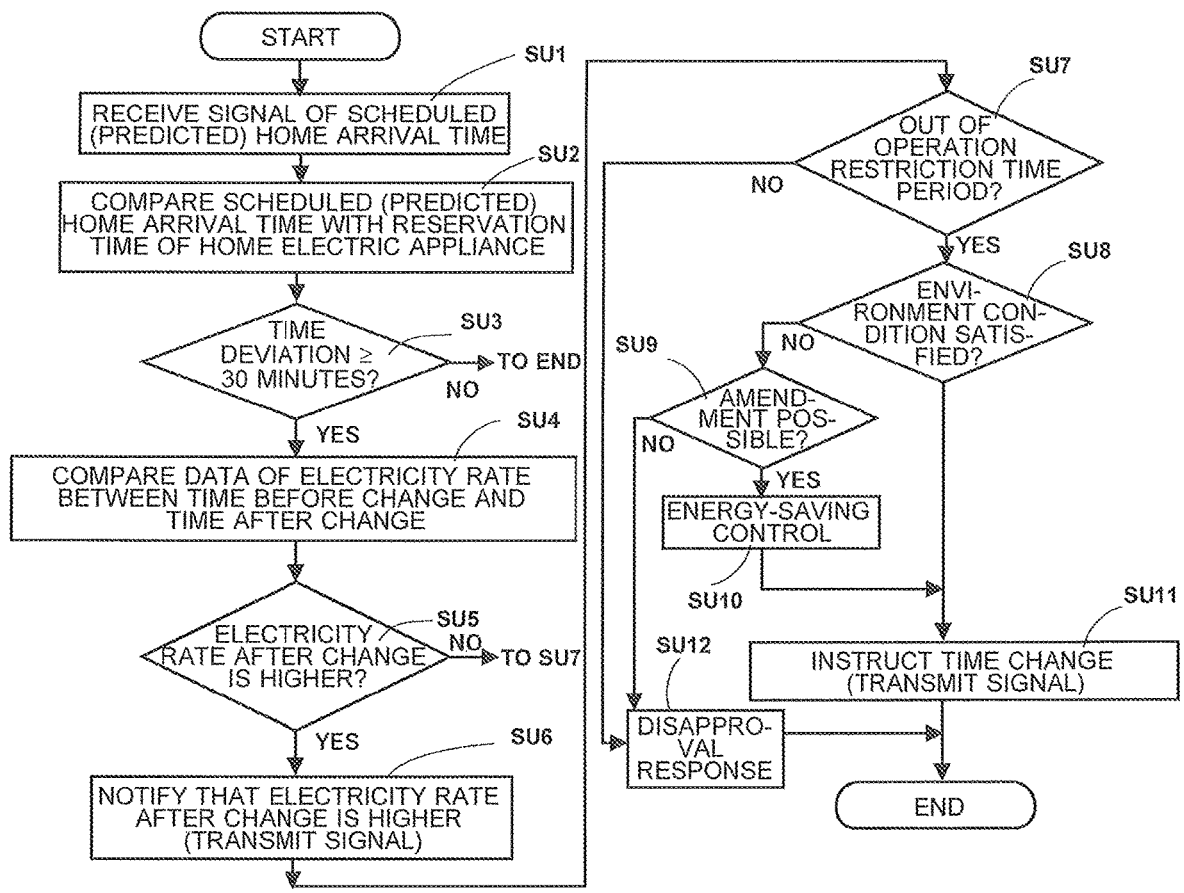
FIG. 57 is a flowchart for illustrating the changing process of the reservation time of the home electric appliance.

FIG. 57 is a flowchart for illustrating an actual operation of the control unit 125 of the power instruction apparatus 9. The basic operation program (information processing program) illustrated in this flowchart is stored in the semiconductor memory (ROM) in the microcomputer (not shown) constituting the control unit 125.

The following description refers to the case where the occupant B (user B) made a rice cooking reservation with the rice cooker 3 beforehand, and set the "operation finish time" to 20:00 (8 p.m.). When the occupant B, who went out after making the rice cooking reservation, changes the predicted home arrival time to 22:00 using the mobile phone terminal 87, the information of the scheduled (predicted) home arrival time reaches the control unit 125 of the power instruction apparatus 9 (SU1).

Then, the control unit 125 of the power instruction apparatus 9 identifies the home electric appliance EE in which the reservation time (operation start time or operation finish time) acquired in advance from the home electric appliances EE is set, and compares the reservation time with the scheduled home arrival time (SU2). To be more detailed, in the case where reservation has been made only with the rice cooker 3, the control unit 125 compares the reservation time (operation finish time in the case of the rice cooker) 20:00 of the rice cooker 3 with the scheduled home arrival time 22:00 (SU2).

It is determined through the comparison whether there is a time deviation of 30 minutes or more (SU3), and when the time deviation is 30 minutes or more, the control unit 125 compares the electricity unit rate applied to the time period before the change with the electricity unit rate applied to the time period after the change (SU4), before outputting to the rice cooker 3 the instruction to change the reservation time so as to match the scheduled (predicted) home arrival time of 22:00. In this case, indices of "high" and "low" may be prepared with reference to the time period-classified electricity unit rate for comparison purposes, instead of comparing the specific values of the electricity unit rates.

In the case where the reservation time is changed to the time period where the unit rate is increased (economically disadvantageous time period) as a result of the comparison, the control unit 125 notifies the mobile phone terminal 87 of the occupant who transmitted the information of the scheduled (predicted) home arrival time (22:00) that the changed home arrival time corresponds to the time period where the electricity rate is disadvantageous. For example, a predetermined message such as "With the change of rice cooking reservation time of rice cooker because of the delay of home arrival time, electricity rate is increased from 'low' to 'medium'" is transmitted to the mobile phone terminal 87 (SU6). The occupant B may transmit a revised home arrival time in view of such a message.

Here, in the example of the rice cooker 3 described above, although the reserved cooking finish time is changed from 20:00 to 22:00, "morning and evening hours" encompass both before 20:00 and before 22:00 and hence there is no gain or loss due to the change in terms of the electricity rate.

The control unit 125 then determines whether the revised reservation time (operation start time or operation finish time) of the electric appliance adjusted to the scheduled home arrival time overlaps with the "operation restriction time period" specified in specific home electric appliances (SU7). The "operation restriction time period" is, for example, in the case of the self-running electric vacuum cleaner (also referred to as "cleaning robot"; not shown), from 10 p.m. (22:00) to 6 a.m. next morning. The home electric appliances for which the "operation restriction time period" is to be specified and the hours thereof can be individually set by the user (occupant) in the power instruction apparatus 9. This is because when the self-running electric vacuum cleaner is operated, the blower motor generates operation noise, which not only disturbs the slumber of the occupants but also causes annoyance to the neighborhood, especially in a condominium.

The "operation restriction time period" is not specified for the rice cooker 3, and therefore the determination step (SU7) is YES, and the operation proceeds to the next step (SU8). At SU8, it is determined whether the environmental conditions are satisfied when the relevant electric appliance is operated at the revised reservation time. In the case of the rice cooker 3, for example, the control unit 125 determines the condition as "suitable" when the room temperature is between 2 degrees Celsius and 35 degrees Celsius, based on the information in the environment detection unit 202 as illustrated in FIG. 58. FIG. 58 is a table for showing examples of various reservation statuses of the home electric appliances EE and examples of correspondence relationships of permission criteria specified by the environment detection unit. In other words, as in the example shown in FIG. 58, when the temperature of the kitchen is 4 degrees Celsius at the rice cooking start time (e.g., 21:20), the rice cooking operation is started at 21:20 (the water absorption phase is first started at 21:20). When the temperature is 0 degrees Celsius, the water in the steam collection device of the rice cooker may be frozen and the collection of the generated steam may be impossible, due to which the temperature range shown in FIG. 58 is adopted to determine whether or not to start the rice cooking.

As shown in FIG. 58, normally the rice cooking operation is automatically shifted to the keep-warm phase after the rice cooking phase is over, and the keep-warm phase continues 7 hours at maximum. In the rice cooker 3, whether to perform the keep-warm phase can be selected before the rice cooking is started, and in the case where the keep-warm phase is cancelled, the power consumption is accordingly reduced by the amount of power supply to the keep-warm heater. In this case, however, the cooked rice may go bad when the room temperature is high, and therefore the control unit 125 determines the condition as "suitable" when the room temperature is between 2 degrees Celsius and 23 degrees Celsius, based on the information in the environment detection unit 202. For example, in the case where the room temperature of the kitchen is 30 degrees Celsius at the time that the boiling phase is over and the keep-warm phase is about to be entered, the keep-warm operation is not cancelled despite the "keep-warm cancel" mode being selected, and the cooking operation is automatically shifted to the keep-warm phase.

At SU9 in FIG. 57, it is determined whether to change the reservation time, based on the environmental conditions such as room temperature in the living room where the home electric appliances are provided, that is, the "environmental condition acceptability" is determined. The "permission criteria" that serve as a reference for this determination are specified by the control unit 125 of the power instruction apparatus 9 and stored in advance in the storage device 149.

At SU10 in FIG. 57, amendment possibility is examined. Regarding the air-conditioning apparatus 7 for example, when the reserved operation does not satisfy the environmental condition (e.g., room temperature is too low to perform cooling operation), the operation may be shifted to the energy-saving mode, for example, by raising the target room temperature or lowering the cooling capacity. Accordingly, it is determined whether such operating conditions (heating amount, motor output, cooling capacity, and so on) can be amended. When the amendment is possible, the amendment is performed (SU10), and the control unit 125 of the power instruction apparatus 9 outputs the operating condition change instruction to the relevant home electric appliance (in this case, air-conditioning apparatus 7).

In the case where it is determined that the environmental conditions are satisfied at Step SU8, and after the operation is switched to the energy-saving mode (SU10), the reservation time (operation start time or operation finish time) is revised. To be more detailed, the control unit 125 of the power instruction apparatus 9 outputs the change instruction for the operation start time or the operation finish time to the relevant home electric appliance (SU11), and the home electric appliance revises the operation start time or the operation finish time in accordance with the change instruction. In the case of the rice cooker 3, the reservation is rewritten such that the rice cooking is to finish at 22:00.

At SU9 in FIG. 57, it is determined whether to change the reservation time, based on the environmental conditions such as room temperature in the living space where the home electric appliances are provided, that is, the "environmental condition acceptability" is determined. The "permission criteria" that serve as a reference for this determination are specified by the control unit 125 of the power instruction apparatus 9 and stored in advance in the storage device 149.

In contrast, in the case where the operation of the home electric appliance enters the operation restriction time period if the reservation time (operation start time or operation finish time) is changed, such a change of the reservation time is not permissible, and therefore a response of disapproval is output (SU12). To be more detailed, the control unit 125 of the power instruction apparatus 9 transmits information indicating the reason of the disapproval to the mobile phone terminal 87 through the wide area communication network (communication network) 98. Accordingly, the occupant who intends to use the self-running electric vacuum cleaner can recognize, in view of the information from the power instruction apparatus 9, that the home arrival time is close to midnight and hence the self-running electric vacuum cleaner (not shown) will not start operation from the viewpoint of noise problem.

Also in the case where the "environmental condition acceptability" is denied at SU8 and the amendment at SU10 is impossible, the operation similarly proceeds to Step SU12 and the power instruction apparatus 9 transmits the information indicating the reason of the disapproval, and the sequential process is finished. When the response of disapproval is output at SU12, various response messages may be used depending on the type of the electric appliance and the environmental conditions. Such responses are prepared in predetermined patterns in advance and stored in the storage device 149, and the control unit 125 selects an appropriate message each time and transmits the selected message. The responses may preferably be briefly composed, such as "Use prohibited because of midnight time period" or "Unusable due to low indoor temperature" when the disapproval is based on, for example, the operation restriction time period.

As described above, the purpose of transmitting the reason of the disapproval is to provide the occupant (user) with exact information. To be more detailed, in the case where notifying the home arrival time does not automatically achieve the change of the reservation time (operation start time or operation finish time) of the home electric appliance, the power instruction apparatus 9 notifies the occupant (user) to this effect, and therefore the occupant (user) can be made aware before arriving home that the notification of disapproval has been received, and predict the operation status of the home electric appliance. Depending on the case, the user may think of expediting the home arrival time, or revise the details of the reservation of the home electric appliance in response to the notification of the disapproval.

In the case where it is determined throughout the mentioned steps that the reservation time is to be changed, the control unit 125 outputs the instruction to change the initially set reservation time (operation start time or operation finish time) so as to match the scheduled home arrival time that has been notified, to the applicable home electric appliance (SU11 in FIG. 57).

The power control system according to Embodiment 1 includes the presence detection unit 10 configured to detect the presence of the occupants, the exclusive user information storage unit (storage device 149) configured to store the exclusive user information in which the specific home electric appliance (hereinafter referred to as "exclusive home electric appliance") exclusive to the occupant B among the electric appliances EE and the information for identifying the occupant B are associated with each other, the use limit setting device 96 configured to limit the power usage of each of the home electric appliances EE, and the control unit 125 configured to permit or restrict the operation of the home electric appliances EE. The control unit 125 has a function of determining, upon reception of the signal requesting the permission of use from the exclusive home electric appliance, whether the exclusive user and the occupant B at home are the same, based on the exclusive user information in the exclusive user information storage unit and the occupant information detected by the presence detection unit 10, and outputting the signal permitting the exclusive home electric appliance (e.g., induction heating cooker 2) to start the operation, in the case where the exclusive user and the occupant at home are the same. This is subsequently described in detail with reference to FIG. 59 to FIG. 62.

FIG. 59 to FIG. 62 are explanatory diagrams for illustrating the controlling operation performed by the power instruction apparatus according to Embodiment 1 of the present invention, triggered by an occupant coming home. The examples illustrated in FIG. 59 to FIG. 62 are based on the situation where the occupant A, the occupant B, the occupant C, and the occupant D are all away from home. As described above, the occupant A is the father, the occupant B is the mother, the occupant C is the elder child (10 years), and the occupant is the younger child (7 years). The occupant B carries the mobile phone terminal 87 when she goes out. In the kitchen, a thermos pot (also called "electrical hot-water pot") (not shown) is provided, which is also subjected to reduction of the power consumption by the power instruction apparatus 9 like the induction heating cooker 2 (the thermos pot is not shown in FIG. 23).

Figure 59:
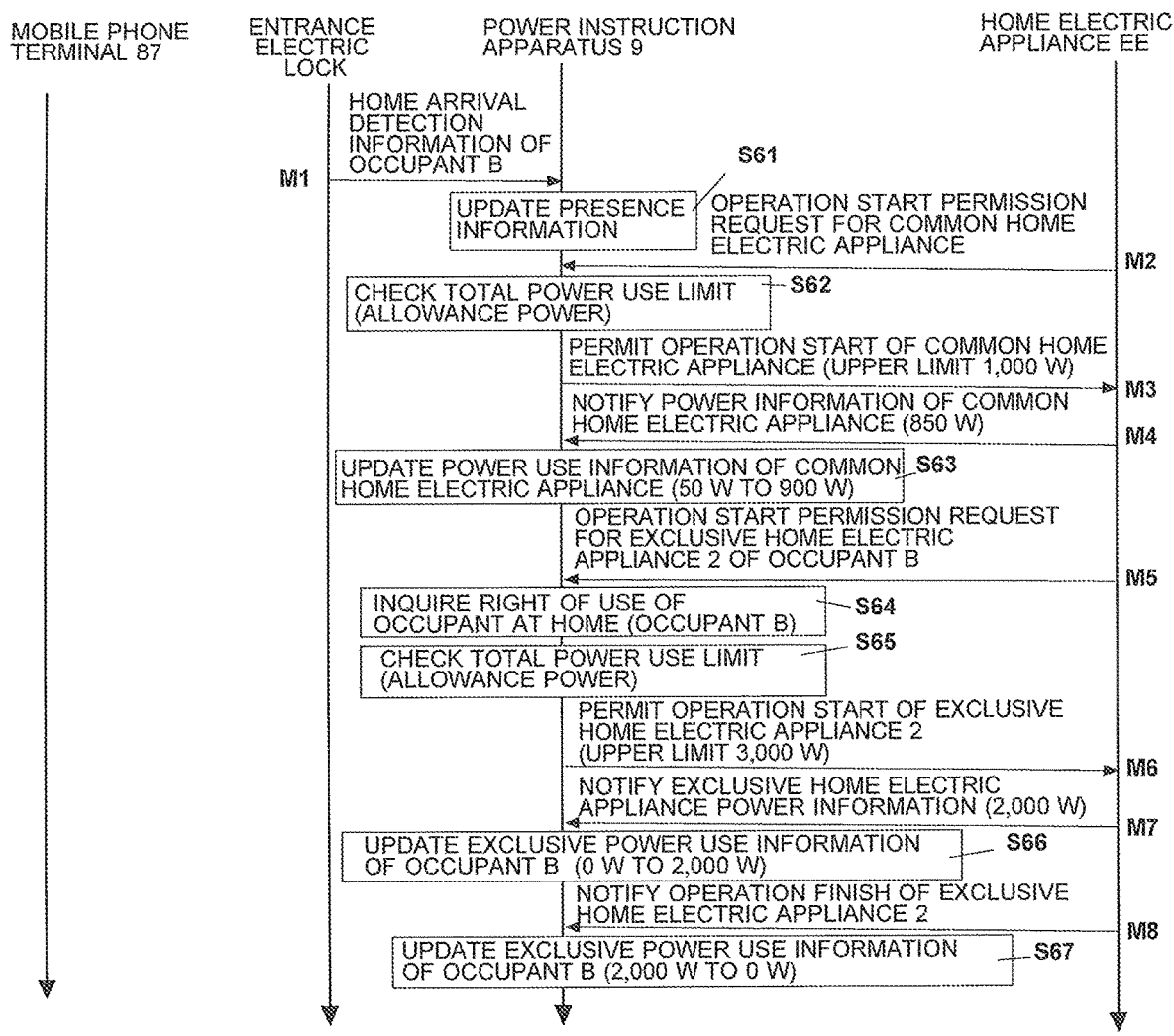
FIG. 59 is an explanatory diagram for illustrating a controlling operation performed by the power instruction apparatus according to Embodiment 1 of the present invention, triggered by an occupant coming home.

FIG. 59 is first described based on the premise mentioned above. FIG. 59 represents the case where the occupant B comes home first. The steps performed by the power instruction apparatus 9 are denoted by S61 to S67. Arrows in FIG. 59 to FIG. 62 represent that notifications or instructions have been made. The timing of the notifications and the instructions is sequentially denoted by M1, M2, M3 . . . in FIG. 59 to FIG. 62.

When the occupant B comes home first and unlocks the electronic lock of the entrance (inputs the password or biological information authentication), the electronic lock 19 transmits an unlock signal to the personal authentication device 29 (M1), and a signal representing the determination result as to whether or not the person is the occupant B is input to the presence detection unit 10. The presence detection unit 10 transmits a home arrival signal of the occupant B to the control unit 125, to thereby update the presence information in the storage device 149 (in this case, "all are absent" is updated to "only occupant B is at home") (S61).

In the case where the living space is dark, the control unit 125 turns on the light located outside and inside of the entrance, out of the common electric appliances designated in advance, to facilitate the occupant B safely walking into the room. Here, although the environment detection unit 202 may detect whether the living space is dark, the control unit 125 may automatically instruct to turn on the light depending on the home arrival time.

Next, the occupant B goes to the kitchen and uses the thermos pot (not shown) which is one of the common home electric appliances and has the rated maximum power of 1,000 W. When the occupant B operates the operation unit of the thermos pot or connects the power cord, the thermos pot first transmits an operation start permission request signal (M2), and the control unit 125 of the power instruction apparatus 9 determines whether to permit the request. This determination corresponds to Step S62 in FIG. 59. To be more detailed, the requested power excess determination device 93 determines the power excess amount. When allowance is available with respect to the total power usage, the control unit 125 transmits the operation start permission instruction signal to the common home electric appliance (M3). In this case, the upper power limit is set to 1,000 W. In response, the home electric appliance (thermos pot) transmits the operation start information indicating that the maximum power value is 850 W, to the control unit 125 of the power instruction apparatus 9 (M4). The control unit 125 of the power instruction apparatus 9 updates the power consumption of the common home electric appliances to 900 W, by adding the power consumption of the thermos pot to that of the illumination apparatus (50 W) (S63).

When the use of the thermos pot is finished (power consumption of the common home electric appliances returns to 50 W in total), the occupant B uses the induction heating cooker 2 registered in advance as the exclusive electric appliance of the occupant B. As described above with reference to FIG. 25 to FIG. 27, when the occupant B first touches the operation button 11A of the main power switch 11, thereby turning on the power supply, normally the controller 32 activates the display unit, e.g., the central display unit 16, and at the same time, the induction heating cooker 2 transmits the operation permission request to the power instruction apparatus 9 (M5). In other words, as described with reference to FIG. 53, the induction heating cooker 2 transmits the operation information signal L1 first, and therefore the first operation information signal L1 indicates that the main power supply has been turned on.

Then, the control unit 125 of the power instruction apparatus 9 determines whether to permit the request. This determination corresponds to Steps S63 and S64 in FIG. 59. At this step (S63), because the induction heating cooker 2 is one of the exclusive electric appliances, the control unit 125 looks up the memory data stored in advance, to check the usage right of the occupant B at home, and proceeds to the next step S64 upon confirming that the occupant B has the right to use the appliance, where the requested power excess determination device 93 determines the power excess amount as done at the step described above (S62). When allowance is available with respect to the total power usage, the control unit 125 transmits the operation start permission instruction signal to the exclusive electric appliance (in this case, induction heating cooker 2). In this case, the maximum power consumption of the induction heating cooker 2 is 3,000 W, and the upper limit of the power consumption allocated to the occupant B is also 3,000 W at the maximum, and therefore the operation permission signal is output, with an upper limit of 3,000 W (M6).

When the occupant B actually starts using the induction heating cooker 2 with the power of 2,000 W, the information indicating the power of 2,000 W is transmitted to the power instruction apparatus 9 (M7), to be used by the requested power excess determination device 93 for subsequent determination. When the occupant B stops using the induction heating cooker 2, the induction heating cooker 2 transmits the notification signal indicating that the operation has finished to the power instruction apparatus 9 (M8). At this point, the control unit 125 updates the power usage information of the exclusive electric appliance of the occupant B (2,000 W to 0 W), and inputs this information to the storage device 149.

Figure 60:
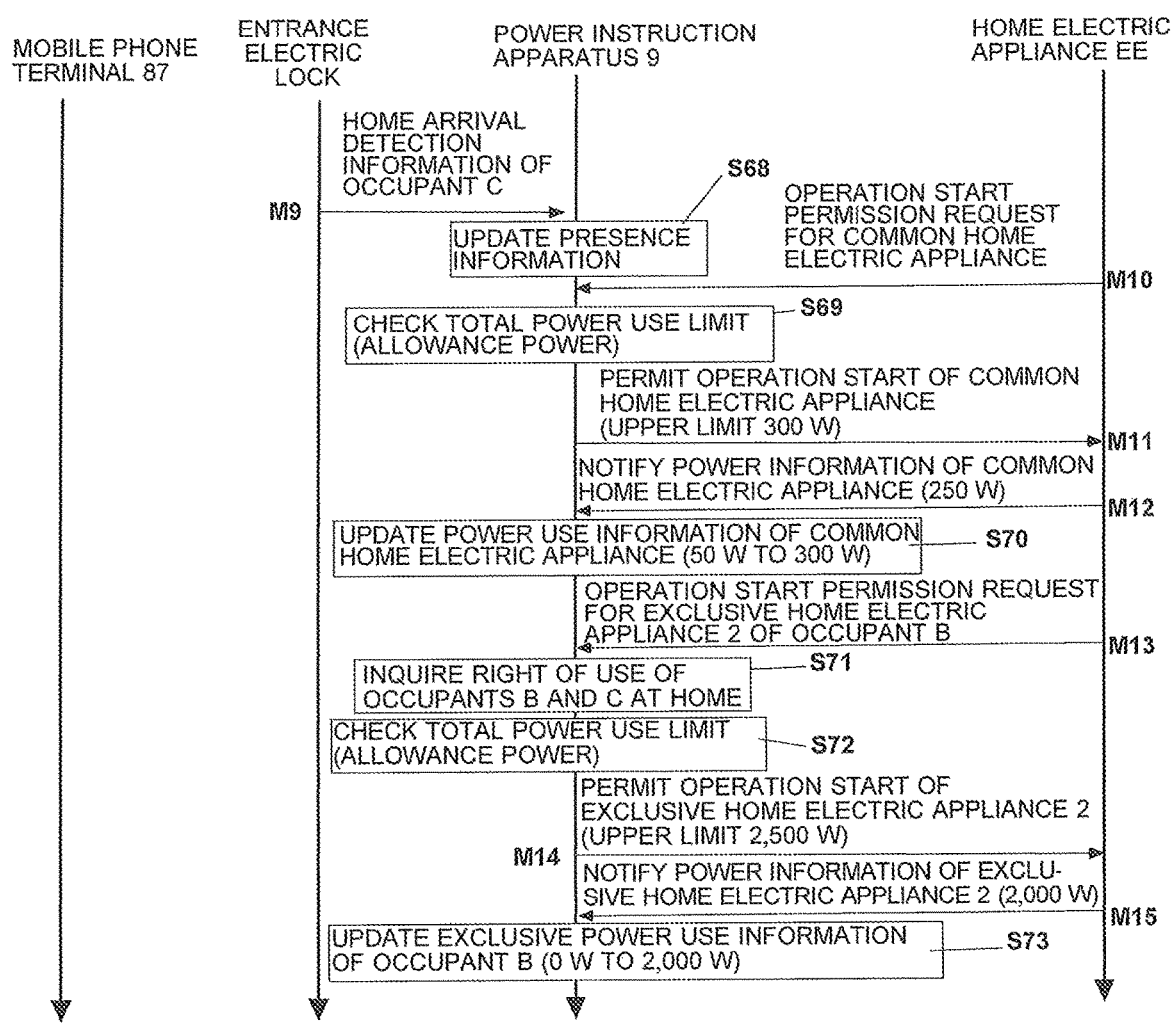
FIG. 60 is an explanatory diagram for illustrating the controlling operation performed by the power instruction apparatus according to Embodiment 1 of the present invention, triggered by the occupant coming home.

Referring now to FIG. 60, description is given regarding the case where the occupant C (child) has come home while the occupant B is at home. When the occupant C (child) unlocks the electronic lock of the entrance (inputs the password or biological information authentication), the signal representing the personal authentication determination result is input to the presence detection unit 10 as in the case of the occupant B. The presence detection unit 10 transmits the home arrival signal of the occupant C to the control unit 125 (M9), to thereby update the presence information in the storage device 149. In this case, "only occupant B is at home" is updated to "only occupants B and C are at home". (S68).

When the occupant C attempts to use one of the common home electric appliances (e.g., illumination apparatus), the home electric appliance outputs the operation start permission request signal (M10), and the control unit 125 of the power instruction apparatus 9 determines whether to permit the request. This determination corresponds to Step S69 in FIG. 60. To be more detailed, the requested power excess determination device 93 determines the power excess amount. When allowance is available with respect to the total power usage, the control unit 125 immediately transmits the operation start permission instruction signal to the common home electric appliance (M11). In this case, the upper power limit is set to 300 W, which is the rated maximum power of the illumination apparatus. In response, the home electric appliance (illumination apparatus) transmits the illumination information indicating that the power consumption is 250 W, to the control unit 125 of the power instruction apparatus 9 (M12). The control unit 125 of the power instruction apparatus 9 updates the total power consumption of the common home electric appliances to 300 W (illumination 250 W+illumination 250 W), by adding the power consumption of the illumination apparatus (250 W) to that of the illumination apparatus (50 W) (S70).

The occupant C then attempts to use the induction heating cooker 2 registered in advance as the exclusive electric appliance of the occupant B. As described with reference to FIG. 25 to FIG. 27, when the occupant C first touches the operation button 11A of the main power switch 11, thereby turning on the power supply, normally the controller 32 activates the display unit, e.g., the central display unit 16, and at the same time, the induction heating cooker 2 transmits the operation permission request to the power instruction apparatus 9 (M13).

Then, the control unit 125 of the power instruction apparatus 9 determines whether to permit the operation permission request. This determination corresponds to Step S71 in FIG. 60. At Step S71, because the induction heating cooker 2 is one of the exclusive electric appliances, the control unit 125 looks up the memory data stored in advance to check the usage right of the occupant B and the occupant C who are at home, and when it is confirmed that the occupant B has the right to use the appliance, the requested power excess determination device 93 determines the power excess amount (S72) as done at Step S69. When predetermined allowance (e.g., 1,000 W) or more is available with respect to the total power usage, the control unit 125 transmits the operation start permission instruction signal to the exclusive electric appliance (in this case, induction heating cooker 2) with indication that the upper power limit is 1,000 W, which corresponds to the allowance (M14). In this case, the maximum power consumption allocated to the occupant B is 3,000 W as described above, and therefore the upper limit of power usage is 3,000 W. In this example, it is known that allowance of 2,500 W is available with respect to the total power usage, and therefore the control unit 125 outputs the operation permission signal to the induction heating cooker 2, with an upper limit of 2,500 W.

When the occupant B (or occupant C supervised by occupant B) actually starts using the induction heating cooker 2 with the power of 2,000 W taking into account the cooking mode and the amount of food to be heated, the information indicating the power of 2,000 W is transmitted to the power instruction apparatus 9 (M15), to be used by the requested power excess determination device 93 for subsequent determination. When the occupant B stops using the induction heating cooker 2, the induction heating cooker 2 transmits the notification signal indicating that the operation has finished to the power instruction apparatus 9. At this point, the control unit 125 updates the power usage information of the exclusive electric appliance of the occupant B (0 W to 2,000 W), and inputs this information to the storage device 149 (S73). In the case where the heating power is decreased part way through (e.g., to 1,000 W), the information to this effect is immediately transmitted to the power instruction apparatus 9, to be used by the requested power excess determination device 93 for subsequent determination.

Figure 61:
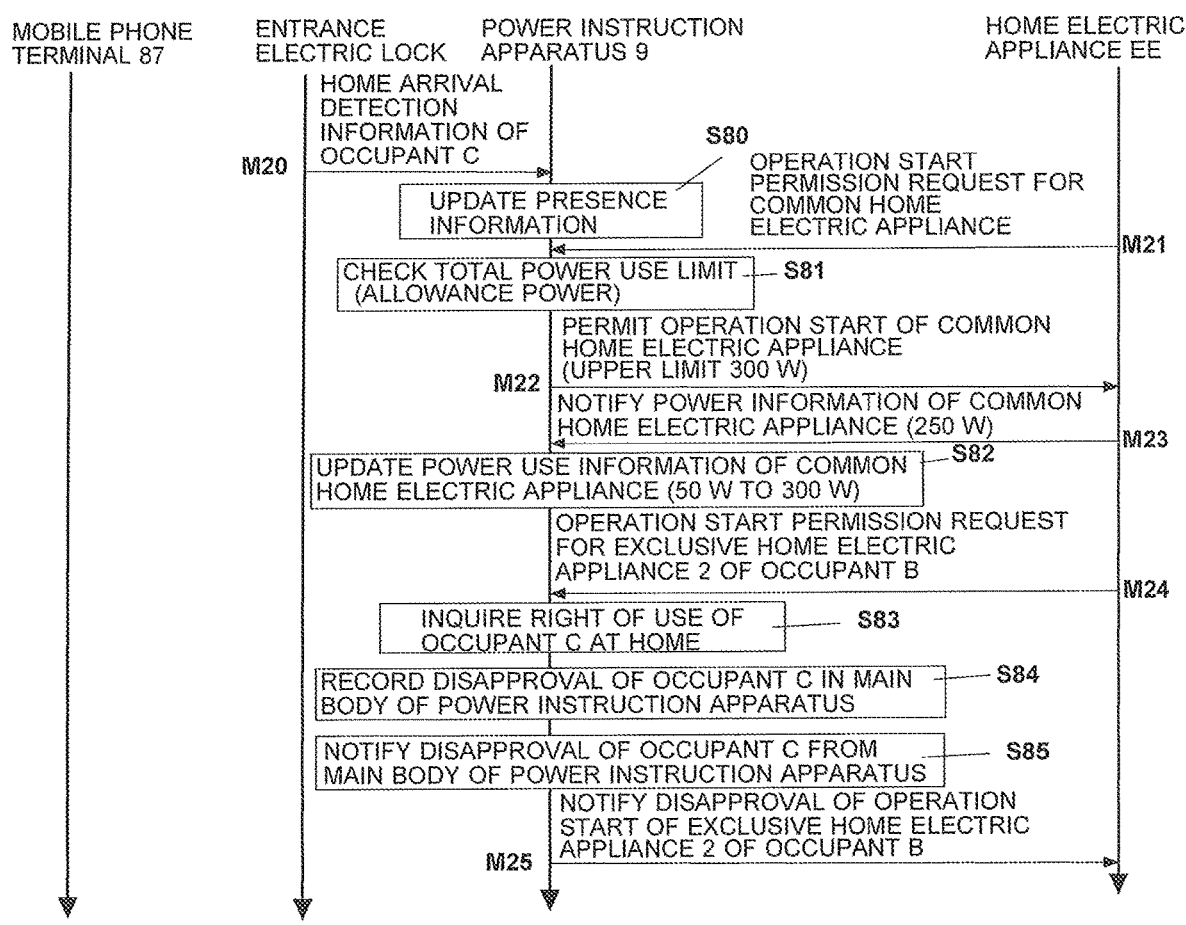
FIG. 61 is an explanatory diagram for illustrating the controlling operation performed by the power instruction apparatus according to Embodiment 1 of the present invention, triggered by the occupant coming home.
Figure 62:
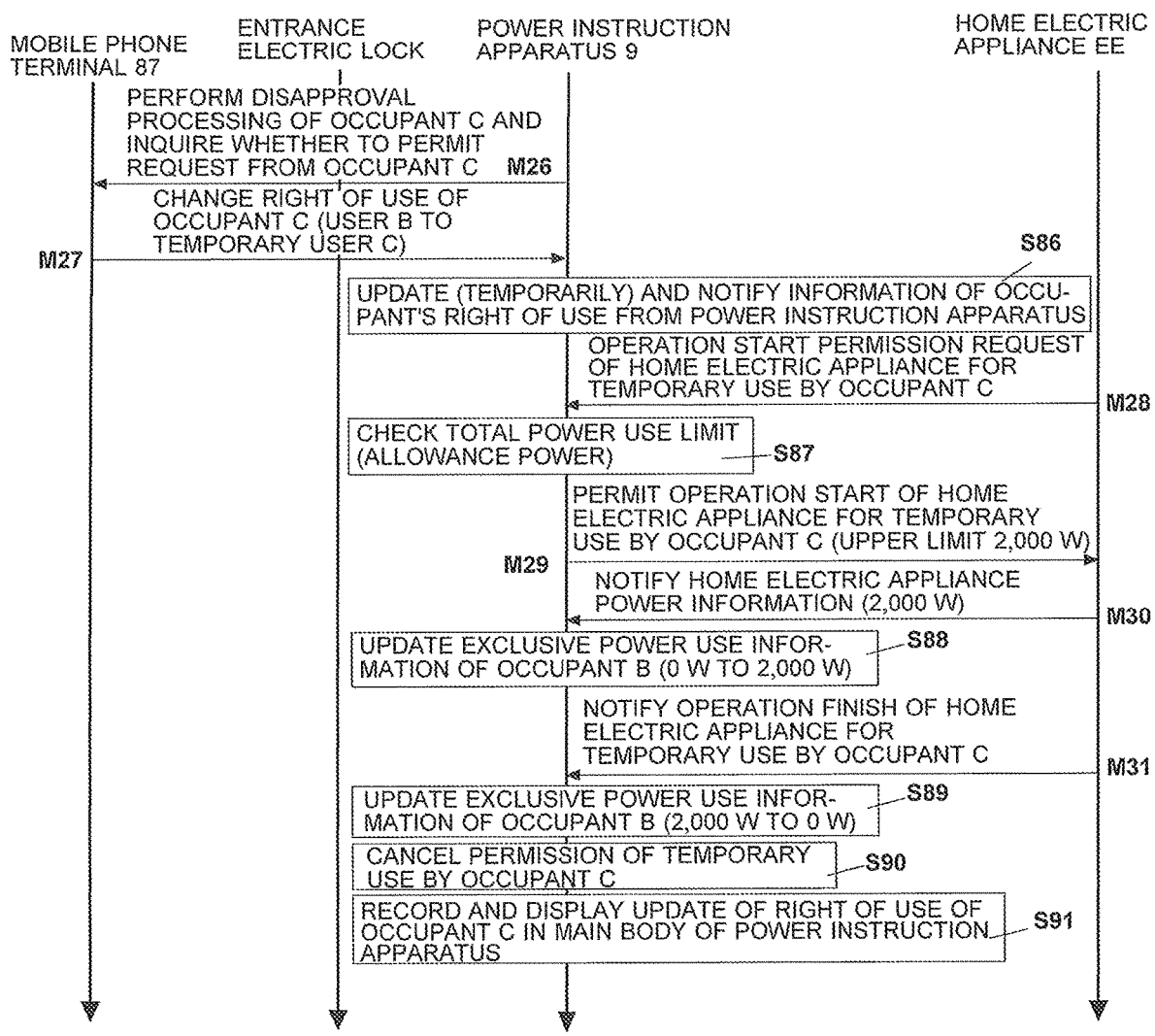
FIG. 62 is an explanatory diagram for illustrating the controlling operation performed by the power instruction apparatus according to Embodiment 1 of the present invention, triggered by the occupant coming home.

Referring now to FIG. 61 and FIG. 62, description is given regarding the case where the occupant C (child) has come home while the occupant B is away. Although reference symbols M20 to M31 are utilized in FIG. 61 and FIG. 62, it is to be noted that the reference symbol M20 is not continuous from the series of steps denoted by M1 to M15.

When the occupant C (child) unlocks the electronic lock of the entrance (inputs the password or biological information authentication), the signal representing the personal authentication determination result is input to the presence detection unit 10 as in the case of the occupant B. The presence detection unit 10 transmits the home arrival signal of the occupant C to the control unit 125 (M20), to thereby update the presence information in the storage device 149 (in this case, "all are absent" is updated to "only occupant C is at home") (S80).

In the case where the living space is dark, the control unit 125 turns on the light located outside and inside of the entrance, out of the common home electric appliances designated in advance, to facilitate the occupant C safely walking into the room. Here, although the environment detection unit 202 may detect whether the living space is dark, the control unit 125 may automatically instruct to turn on the light depending on the home arrival time. In this example, it is assumed that the occupant C has come home in the daytime, and hence no illumination apparatus is turned on. The description given hereunder represents the case where the common illumination apparatus is turned on first and the power consumption thereof is 200 W.

Next, the occupant C goes to the kitchen and uses, for example, the thermos pot (not shown) which is one of the common home electric appliances. When the occupant C operates the operation unit of the thermos pot or connects the power cord, the thermos pot first transmits an operation start permission request signal (M21), and the control unit 125 of the power instruction apparatus 9 determines whether to permit the request (S81). At this step (S81), the requested power excess determination device 93 determines the power excess amount. When allowance is available with respect to the total power usage, the control unit 125 transmits the operation start permission instruction signal to the common home electric appliance (M22). In this case, the upper power limit is set to 1,000 W. In response, the home electric appliance (thermos pot) transmits the operation start information indicating that the maximum power value at that time is 850 W, to the control unit 125 of the power instruction apparatus 9 (M23). The control unit 125 of the power instruction apparatus 9 updates the power consumption of the common home electric appliances to 1,050 W, by adding the power consumption of the thermos pot to that of the illumination apparatus (250 W) (S82).

The occupant C then attempts to use, while using the thermos pot, the induction heating cooker 2, which is the exclusive electric appliance of the occupant B, in the kitchen. When the occupant C touches the operation button 11A of the main power switch 11, thereby turning on the power supply, normally the controller 32 activates the display unit, e.g., the central display unit 16, and at the same time, the induction heating cooker 2 transmits the operation permission request to the power instruction apparatus 9 (M24).

Then, the control unit 125 of the power instruction apparatus 9 determines whether to permit the request. This determination corresponds to Step S83 in FIG. 61. At this step (S83), because the induction heating cooker 2 is one of the exclusive electric appliances, the control unit 125 looks up the memory data stored in advance to check the usage right of the occupant C who is at home, and proceeds to the next step S84 upon confirming that the occupant B who is away has the right to use the appliance, where the control unit 125 inputs to the storage device 149 the fact that the use permission request of the occupant C has been disapproved (S84), and transmits the operation start "disapproval" instruction signal to the exclusive electric appliance (in this case, induction heating cooker 2) (S85). Upon reception of this signal, the induction heating cooker 2 displays the reason of the disapproval on the display screen 129. The display may be an error code; however, it is preferable to display a brief message so that the user (in this case, occupant C) can easily understand. Naturally, a voice message may be output by the voice synthesizer 38.

When the control unit 125 of the power instruction apparatus 9 displays the reason of the disapproval on the display screen 129 of the induction heating cooker 2 as notification of the disapproval (M25) following the transmission of the operation start "disapproval" signal (S85), guidance is output urging to perform, in the case where use permission request has to be made to the occupant B, a specific operation on the induction heating cooker 2, for example, pressing one or a plurality of specific input keys or buttons. When the control unit 125 of the power instruction apparatus 9 detects that such operation has been made, or immediately after or at the same time as the transmission of "disapproval" (S85), the control unit 125 notifies the occupant B who is away to the fact that the use disapproval has been output, and asks whether the occupant B accepts the use permission request from the occupant C (M26).

Such an inquiry is transmitted from the input-output unit 124B of the power instruction apparatus 9 to the outdoor wide area communication network (communication network) 98 through the router 99A, and then reaches the mobile phone terminal 87 of the occupant B. In the case where the occupant B responds that the exclusive user may be temporarily changed to the occupant C after viewing the inquiry message transmitted from the power instruction apparatus 9 (M27), the record of the exclusive user in the storage device 149 is temporarily rewritten and such a message that the occupant C has been granted the right to use the appliance is displayed on the display screen 100A of the use limit setting device 96, on the part of the power instruction apparatus 9 (S86).

When the occupant C, who has been waiting for the permission signal of the right to use, again requests the permission to use the induction heating cooker 2 (M28), the control unit 125 of the power instruction apparatus 9 determines whether to permit the request (S87). At this step (S87), the requested power excess determination device 93 determines the power excess amount. When allowance (e.g., 2,500 W) is available with respect to the total power usage, the control unit 125 transmits the operation start permission instruction signal to the induction heating cooker 2. In this case, however, the upper power limit of the occupant C is 2,000 W (total power of electric appliances used at a time is 2,000 W or less), and therefore the control unit 125 of the power instruction apparatus 9 does not allow the occupant C to utilize the allowance power (2,500 W), and transmits to the induction heating cooker 2 the fact that the "upper limit" is 2,000 W, which is the maximum power usage allocated to the occupant C (M29).

When the occupant C actually starts using the induction heating cooker 2 with power consumption of 2,000 W, the information indicating the power of 2,000 W is transmitted to the power instruction apparatus 9 (M30), to be used by the requested power excess determination device 93 for subsequent determination. In addition, the power usage information of the electric appliance exclusive to the occupant B who is still away is updated from 0 W to 2,000 W (S88). Although the occupant B has not come home yet, 2,000 W is counted as power usage of the occupant B because the occupant B permitted the use.

When the occupant C finishes the cooking and stops using the induction heating cooker 2, the induction heating cooker 2 transmits the notification signal indicating that the operation has finished to the power instruction apparatus 9 (M31). At this point, the control unit 125 updates the power usage information of the exclusive electric appliance of the occupant B (2,000 W to 0 W), and inputs this information to the storage device 149 (S89). The control unit 125 automatically rewrites the exclusive user of the induction heating cooker 2, which is one of the exclusive electric appliances, to the occupant B (S90), and inputs such a change to the storage device 149 (S91).

Figure 64:
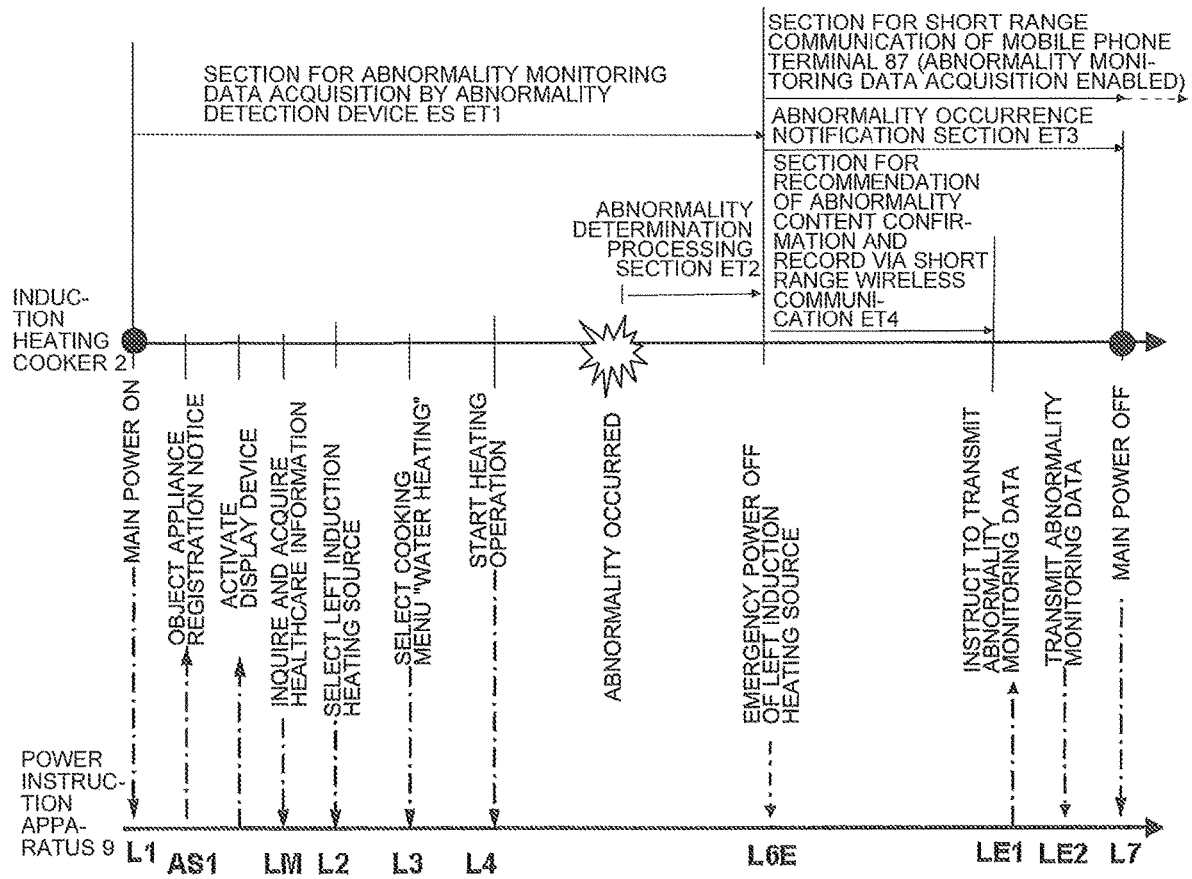
FIG. 64 is an explanatory diagram for illustrating a relationship between an abnormality monitoring data acquisition section and a heating process of the induction heating cooker in the power instruction apparatus of the present invention.
Figure 65:
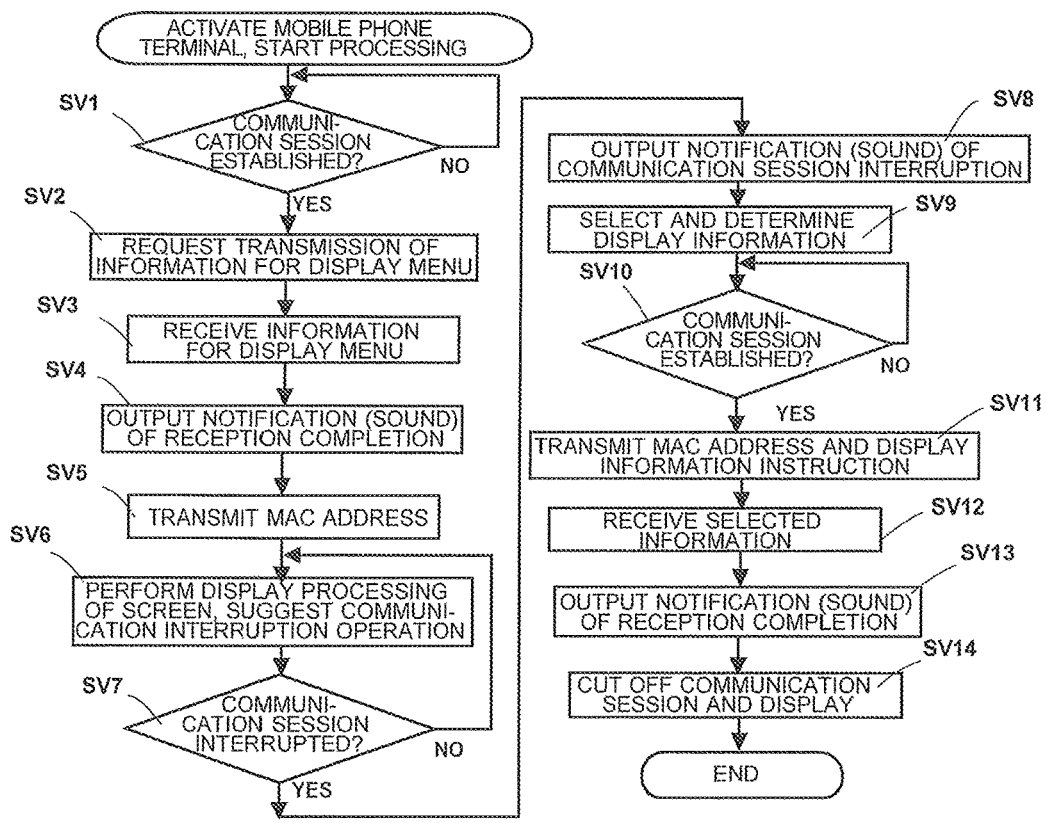
FIG. 65 is a flowchart for illustrating an operation process of acquiring abnormality monitoring data by the mobile phone terminal in the power control system according to Embodiment 1 of the present invention.

Next, description is given of the "acquisition and recording of the abnormality monitoring data of the home electric appliance", which is one of the features of Embodiment 1. FIG. 64 is an explanatory diagram for illustrating the operation of the induction heating cooker 2, which is a typical example of the home electric appliance EE. FIG. 64 is an illustration of the relationship among the operation information from the induction heating cooker 2, the heating process, and the abnormality monitoring data. FIG. 65 is a flowchart for illustrating the operation of acquiring abnormality monitoring data and identification data from the induction heating cooker 2 by the mobile phone terminal 87. The basic operation program (information processing program) illustrated in this flowchart is stored in the storage unit 186 inside the mobile phone terminal 87.

In the following description, it is assumed that, in the induction heating cooker 2, only the first heater 2L performs the heat cooking, and the second heater 2R or other heating sources do not perform heat cooking.

When the first heater 2L performs induction heating, as described with reference to the flowcharts of FIG. 53 to FIG. 55, the user first closes the main power switch 11 (sets the main power switch 11 to the ON state). When the inverter circuit 33L is actually driven to start the induction heating operation, the operation information signal L4 is transmitted to the power instruction apparatus 9.

After that, when any abnormality occurs (e.g., the temperature of the top plate 14 or the central display unit 16 increases to be abnormally high), the controller 32 determines the first state as the preliminary abnormal state and then as the abnormal state depending on the temperature. In other words, a section ET2 from the abnormality occurrence is required for the controller 32 to determine whether or not the abnormality has occurred. When the controller 32 determines the state as the abnormal state, the controller 32 outputs the instruction of immediately bringing the induction heating operation to emergency stop to the inverter circuit 33L. Further, the operation information signal L6E indicating the emergency stop of the induction heating source is transmitted to the power instruction apparatus 9. The operation information signal L6E is transmitted in the same way as the signals L1 to L4.

The "emergency stop" in Embodiment 1 refers to cut-off of the power supply to the heating drive sources such as the inverter circuit 33L, and does not refer to the stop of the function of the controller 32 itself bearing the core function of issuing control instructions. At the time point at which the power supply to the heating drive sources such as the inverter circuit 33L and the grill heater driver circuit 34 is cut off, the respective parts of the induction heating cooker 2 may already have a high temperature, and hence the cooling fan that is cooling the internal space of the main body casing 2C during the heat cooking operation is automatically stopped after a delay of a predetermined time from the time point at which the power supply to the heating drive sources such as the inverter circuit 33L and the grill heater driver circuit 34 is cut off. In other words, the main body casing 2C and the top plate 14 are cooled for several minutes or about 10 minutes so that the temperature thereof is decreased down to a predetermined temperature. Such temperature is detected by the above-mentioned temperature detection circuit 150.

Immediately after the induction heating cooker 2 outputs the instruction of bringing the induction heating operation to the emergency stop, the abnormality detection unit ES conserves the monitoring data as it is, which has been continuously acquired in the past ("abnormality monitoring data acquisition section ET1" illustrated in FIG. 63). The term "continuously" used herein does not mean completely continuous. The volume (data amount) of the abnormality monitoring data may be reduced as much as possible, and in order to secure the storage capacity of the storage device 32R to be sufficiently larger than the abnormality monitoring data, the acquisition timing of the abnormality monitoring data relating to, for example, temperature may be set to about 5- or 10-second intervals. However, when the heat cooking is performed with a large heating power (e.g., 3 kW), the heating object N is rapidly heated, and hence the monitoring accuracy and the safety level can be improved by shortening the monitoring intervals.

For example, immediately after any one of the two induction heating units (induction heating coil 2LC or 2RC), which has been supplied with power until abnormality occurrence, is brought into emergency stop, the display memory 35A temporarily stores the information representing the abnormality type determined by the controller 32 and the information identifying the estimated cause so that the abnormality occurrence can be displayed on the central display unit 16 or other units. Then, upon the instruction from the controller 32, the display unit driver circuit 35 causes the central display unit 16 to display the information representing the abnormality type and the estimated cause. The text (text data) of such guidance is displayed by retrieving and extracting a fixed phrase that the controller 32 displays from among phrases stored in advance in the display memory 35A, based on the correspondence table (data table) defining the correspondence relationship between the abnormality type and the estimated cause. In addition, when the information communication terminal device, e.g., the mobile phone terminal 87 having the short range communication (NFC) function is brought close to the NFC input-output unit 401, the display unit driver circuit 35 displays the fact that information of the detailed abnormality content and the way to manage the abnormality can be obtained. The correspondence table (data table) for displaying the fixed phase is also stored in advance in the display memory 35A.

The two NFC input-output units 401L and 401R to be subsequently described are each illuminated from below by the light emitting diode element (LED) 323 (see FIG. 27), and the LED 323 cooperates with the operation of the display unit driver circuit 35 through the controller 32. Therefore, in synchronization with the display on the mobile phone terminal 87 or other devices having the short range communication (NFC) function that the information of the detailed abnormality content and the way to manage the abnormality can be obtained, the display unit driver circuit 35 turns on the LED 323 at a predetermined timing. The specific timing to turn on the LED 323 is the first time point of the "abnormality occurrence notification section ET3" illustrated in FIG. 63. The timing to turn off the LED 323 is the end of the abnormality occurrence notification section ET3, that is, the time point at which the main power is turned off, but the LED may be automatically turned off after an elapse of a certain time period from the turn-on.

Referring next to FIG. 64, description is given of the operation of the mobile phone terminal 87 for acquiring the abnormality monitoring data from the induction heating cooker 2. FIG. 64 is an illustration of the processing process of the mobile phone terminal 87. The control program for executing this process is stored in advance in the central processing unit (CPU) 185.

In FIG. 64, reference symbol "SV" denotes the step of the processing. Description is given assuming a case where, in the induction heating cooker 2, abnormality has occurred in the middle of performing heat cooking with the first heater 2L alone, and hence the user sees the display content displayed on the central display unit 16 to confirm the details of the abnormality. The display content refers to, for example, such an explanatory text as "Abnormality is detected, and hence emergency stop has been made. Detailed information is available by bringing a mobile phone with an NFC function close to the NFC display unit".

First, the activated mobile phone terminal 87 is brought close to the NFC input-output unit 401L of the induction heating cooker 2. Then, the mobile phone terminal 87 starts the processing by activating the application software unit 188 stored in the storage unit 186. In SV1, the communication establishment unit 191 of the mobile phone terminal 87 monitors the establishment of the NFC communication session between the mobile phone terminal 87 and the induction heating cooker 2. The NFC communication is short range wireless communication utilizing the radio waves of the band of 13.56 MHz. When the user brings the mobile phone terminal 87 close to the NFC input-output unit 401L of the upper surface operation unit 26 of the induction heating cooker 2 so that the mobile phone terminal 87 approaches the induction heating cooker 2 (e.g., up to 5 cm away), the communication establishment unit 191 establishes the NFC communication session.

When the NFC communication session is established, the communication establishment unit 191 determines YES in SV1, and the operation proceeds to SV2. In SV2, the transmission processing unit 190 uses the NFC communication session established in SV1 to transmit, to the induction heating cooker 2, the information for requesting the provision of the abnormality monitoring data and the identification information of the induction heating cooker 2 (SV2). This request information is temporarily stored in the NFC storage unit 320 illustrated in FIG. 27.

Figure 66:
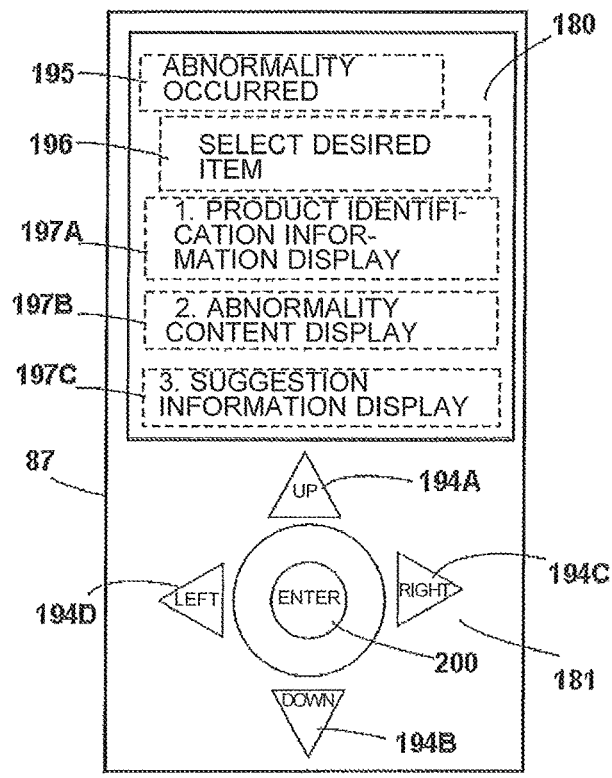
FIG. 66 is a front view of the mobile phone terminal illustrated in FIG. 65.

Subsequently, in SV3, the mobile phone terminal 87 uses the NFC communication session established in SV1 to receive, from the induction heating cooker 2, the information for displaying on the display unit 180 of the mobile phone terminal 87 an exclusive display screen for selecting the information that the user wishes to display. This information is referred to as "information for display menu" in FIG. 64. The "display menu" used herein refers to at least the following three information groups as illustrated in FIG. 66.

(1) Identification information (product identification information)

(2) Abnormality content information (detailed information explaining the abnormality content)

(3) Suggestion information (information explaining how to correctly use the product or how to manage the abnormality at the time of abnormality)

When the information for display menu is received, the reception processing unit 189 confirms the received content, and in SV4, the control unit 184 causes the mobile phone terminal 87 to output a sound. With this, the user is notified of the end of the reception (in this case, the reception of the information for display menu). Immediately after this, the mobile phone terminal 87 uses the NFC communication session established in SV1 to transmit a MAC address to the induction heating cooker 2. The reception of the MAC address by the induction heating cooker 2 enables the induction heating cooker 2 to identify the communication device in the subsequent communication in order to maintain continuity and relevance.

The user recognizes that the mobile phone terminal 87 can be separated from the induction heating cooker 2 by the notification at the time point of SV4. Even if this notification is not known, in Step SV6, the display unit 180 of the mobile phone terminal 87 displays the fact that the reception of the information for display menu has been completed and the mobile phone terminal 87 is required to be separated from the induction heating cooker 2 to once interrupt the communication, and hence the user is not meaninglessly confused. Such screen processing of the display unit 180 is executed by the display control unit 192.

The user separates the mobile phone terminal 87 from the induction heating cooker 2 so as to move the mobile phone terminal 87 close to the user to view the display unit 180. Thus, the user can perform the subsequent operation. When the distance between the mobile phone terminal 87 and the presence detection unit 10 is increased to be larger than the distance therebetween that allows radio communication, the NFC communication session established in S1 is interrupted (SV7). When the operation so far is defined as a first NFC communication session, the stage of SV7 can be referred to as the completion of the first NFC communication session.

When the NFC communication session is left not interrupted in SV7 unlike the case described above, the operation returns to the processing of SV6 to recommend that the user should once interrupt the NFC communication.

Next, in SV8, the control unit 184 causes the mobile phone terminal 87 to output a sound. With this, the user is notified that the NFC has been interrupted. The display control unit 192 uses the text data included in the information for display menu received in SV3 to generate a selection screen as illustrated in FIG. 66 (SV9). In other words, one of the three types of information that the user desires to display as illustrated in FIG. 65 is selected as the content that the user first confirms on the display unit 180 of the mobile phone terminal 87. There are a plurality of methods of selecting the type of the information in SV9, which are subsequently described in detail with reference to FIG. 65 and FIG. 66.

In SV9, when, for example, the "abnormality content information display" is selected, the NFC communication session is required to be established before this selection result is input to the induction heating cooker 2. In view of this, as described above, the user brings the mobile phone terminal 87 close to the NFC input-output unit 401L of the upper surface operation unit 26 of the induction heating cooker 2, and when the communication establishment unit 191 confirms the establishment of the NFC communication session, the communication establishment unit 191 determines YES in SV10 so that the operation proceeds to SV11.

After that, the mobile phone terminal 87 uses the NFC communication session established in SV11 to transmit the MAC address to the induction heating cooker 2 again. The induction heating cooker 2 receives the MAC address again to confirm the relevance with the previous communication. Simultaneously, the mobile phone terminal 87 transmits the display instruction of the "abnormality content information display" selected in SV9 to the induction heating cooker 2 (SV11).

Subsequently, in SV12, the mobile phone terminal 87 uses the NFC communication session established in SV10 to receive, from the induction heating cooker 2, information relating to the "abnormality content" that the user has specified to display. When the information relating to the abnormality content is received, the reception processing unit 189 confirms the reception content, and in SV13, the control unit 184 causes the mobile phone terminal 87 to output a sound. With this, the user is notified of the end of the reception of the specified information (in this case, the reception of the "abnormality content information").

After that, the control unit 184 causes the display unit 180 to display the disconnection of the NFC communication session, and unless the user inputs a new operation within a predetermined period of time, the NFC communication session is automatically disconnected to end the series of processing. The "abnormality content information" that the user has received is stored in the storage unit 186 of the mobile phone terminal 87, and hence the user can read out the content again and display the content on the display unit 180 at a later date. Further, the "abnormality content information" can be transmitted to, for example, a server of the sales company or the repair company of the induction heating cooker 2 via the wide area communication network with use of the communication function of the mobile phone terminal 87, or the mobile phone terminal 87 can be brought to the repair company, etc. to show the content of the abnormality monitoring data. In such a case, the identification information of the induction heating cooker 2 is also recorded, and hence accurate identification information can be transmitted to the repair company, etc.

The abnormality monitoring data includes the operation information signals L1 to L7, the object appliance registration signal AS1, the request signal (notice signal) AS2 for decreasing the total electric power of the home electric appliances, and the power reduction instruction signal AS3 described above. Therefore, the timing to measure the actual data indicating the abnormality (e.g., temperature or voltage value) is associated in terms of time with the timing to transmit the signals, e.g., the operation information signals L1 to L7, and the timing to receive the power reduction instruction signal AS3. Therefore, the cause can be easily analyzed after the abnormality occurrence.

When the mobile phone terminal 87 transmits the display instruction of the "abnormality content information display" to the induction heating cooker 2 in SV11, the display instruction is recorded once in the NFC storage unit 320 of the induction heating cooker 2. In response to the display instruction, the NFC control circuit 321 outputs an (abnormality control) data transmission command such that the abnormality monitoring data stored in the storage device 32R of the controller 32 is transmitted to the NFC control circuit 321.

Based on the data transmission command, the controller 32 of the induction heating cooker 2 that has been monitoring the data transmission command of the NFC control circuit 321 operates in response to the transmission command of the NFC control circuit 321. In other words, as described above, the mobile phone terminal 87 (information communication terminal device) sends the control data (control command referred to as data transmission command) to the NFC storage unit 320 of the induction heating cooker 2, which is an example of the home electric appliance EE, and the controller 32 (having the "host computer" function) of the induction heating cooker 2 operates for control based on the control command stored in the NFC storage unit 320.

Figure 67:
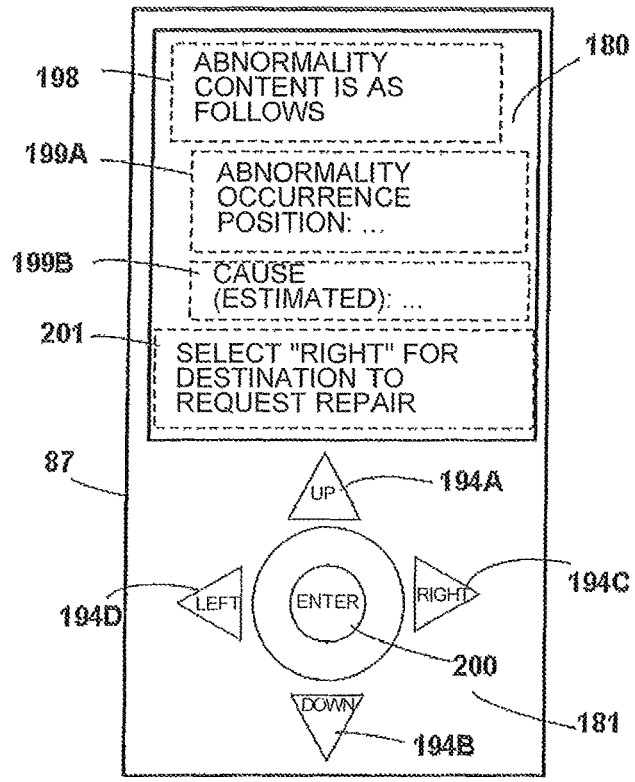
FIG. 67 is a front view of the mobile phone terminal illustrated in FIG. 65.

Next, referring to FIG. 66 and FIG. 67, description is given of the display content of the display unit 180 in a situation where the mobile phone terminal 87 acquires the abnormality monitoring data from the induction heating cooker 2. FIG. 66 is a front view of the mobile phone terminal 87, and is an illustration of the display content of the display unit 180 of the mobile phone terminal 87. The display content of the display unit 180 illustrated here is the content at the stage of Step SV9 of FIG. 65.

As illustrated in FIG. 66, the generated screen in the display unit 180 urges the user to select one of the three types of information that the user desires to display. In FIG. 66, reference symbol 195 denotes letter information indicating abnormality occurrence, reference symbol 196 denotes operation guidance information for urging the user to select the type of information to be displayed, reference symbol 197A denotes selection information indicating "product identification information display", reference symbol 197B denotes selection information indicating "abnormality content information display", and reference symbol 197C denotes selection information indicating "suggestion information display".

There are two methods of selecting, for example, the "abnormality content information display" in the display screen of FIG. 66.

First Method:

With the use of a four-direction selection key (touch type or press-button type) provided in the operation input unit 181, for example, when the selection item is to be selected sequentially downward, a downward specification selection key 194B may be pressed. When the letter information 197A is first emphatically displayed by being highlighted so that the item "product identification information display" is selected, the item "abnormality content information display" is selected through one press of the above-mentioned downward specification selection key 194B, and the letter information 197B is then emphatically displayed by being highlighted. The item "suggestion information display" displayed further below is selected through another press of the downward specification selection key 194B, and the letter information 197C is then emphatically displayed by being highlighted. Through another press of the downward specification selection key 194B, the selection returns to the first item "product identification information display", and the letter information 197A of the "product identification information display" is then emphatically displayed by being highlighted. Through pressing the downward specification selection key 194B as described above, the items are selected in a cycle. Similarly, an upward specification selection key 194A, a rightward specification selection key 194C, and a leftward specification selection key 194D are also provided in the operation input unit 181. In order to determine the selection, an enter key 200 (touch type or press-button type) provided in a central region of the operation input unit 181 may be pressed. When the enter key 200 is pressed, the processing of SV9 illustrated in FIG. 65 ends.

Second Method:

Without using the four-direction selection keys 194A to 194D provided in the operation input unit 181, the item "product identification information display" to the item "suggestion information display" can be selected through a motion of tilting leftward, rightward, or horizontally the mobile phone terminal 87 being set on a horizontal plane. As described above, the mobile phone terminal 87 incorporates the posture detection unit 183, which detects the posture (specifically, the rotational angle) when the user tilts the mobile phone terminal 87 to output the signal indicating the posture to the control unit 184. Therefore, for example, in order to obtain a state similar to that when the downward specification selection key 194B is pressed once, the mobile phone terminal 87 may be tilted so that the display unit 180 thereof is at the highest position and the downward specification selection key 1948 is at the lowest position. The enter key 200 may be pressed when the desired item is selected. When the enter key 200 is pressed, the processing of SV9 illustrated in FIG. 65 ends.

Next, FIG. 67 is described. FIG. 67 is a front view of the mobile phone terminal 87, and is an illustration of a situation where the mobile phone terminal 87 displays the abnormality monitoring data transmitted from the induction heating cooker 2. In FIG. 67, reference symbol 198 denotes letter information indicating the content of the abnormality, reference symbol 199A denotes letter information indicating the position of abnormality occurrence, and reference symbol 1998 denotes letter information indicating the cause of the abnormality. Reference symbol 201 denotes selection information for urging the user to determine whether or not to display information of the destination to request the repair or inspection of the abnormality of the product (induction heating cooker 2). When the item 201 is selected to obtain more detailed information, the rightward specification selection key 194C may be pressed once. Although not shown in FIG. 67, from when the induction heating cooker 2 is sold, the display unit 180 can display letter information including the location and the phone number for contacting the manufacturer, which is written in advance in the NFC storage unit 320 by the manufacturer.

The above-mentioned "identification information" is information unique to the induction heating cooker 2, and is important information that is required for performing correct repair and inspection. The identification information is thus desired to be recorded in the NFC storage unit 320, but the identification information may be stored in the storage device 32R of the controller 32. The identification information may also be stored in both thereof in duplicate. For example, the identification information such as the manufacturing year and month, the product (serial) number, the warranty number, etc., which are defined when the product is manufactured in the factory, may be stored in the storage device 32R, and identification information such as the selling date, the seller name, etc., which are defined when the product is sold, may be written afterward by the seller or the installer via the NFC input-output units 401L and 401R.

In Embodiment 1, the ASP server 89A can provide to the user various services relating to the home electric appliances EE such as the induction heating cooker 2 via the communication networks 98A and 98B. The database 89B of the ASP server 89A includes the user ID database for identifying the user and the application database that stores the application software for determining the control operation of the home electric appliances EE. When the mobile phone terminal 87 accesses the ASP server 89A to download (read) the control application software, not only the induction heating cooker 2 but also other home electric appliances EE can be remote controlled from remote locations outside the house (outside locations).

Further, the kitchen electric appliances such as the induction heating cooker 2 and the air-conditioning apparatus establish communication for the power reduction instruction or other instructions with respect to the main body 9A of the power instruction apparatus 9 by wireless signals, and hence the abnormality monitoring data and the identification information from the induction heating cooker 2 can be transmitted to the main body 9A of the power instruction apparatus 9 with use of the wireless communication, and can be finally transmitted to the storage device 149 in the main body 9A. With this, even when the volume of the abnormality monitoring data from the induction heating cooker 2 is large and thus there is a fear of prolonged time in the short range wireless communication (NFC) via the mobile phone terminal 87, the abnormality monitoring data can be rapidly extracted from the induction heating cooker 2.

Further, the abnormality monitoring data stored in the storage device 149 can be displayed on the LCD screen 100A of the display panel 100 through the operation from the operation input unit 117. Therefore, the user can use the display panel 100 to confirm the content of an abnormality, the estimated cause, and other suggestions even when there is no appropriate mobile phone terminal 87 or other information communication terminal devices on hand.

Similarly, the identification information may also be transmitted to the main body 9A to be stored in the storage device 149. In this manner, even if the induction heating cooker 2 was purchased several years ago and physical documents or materials such as the instruction manual and the warranty are lost, the user can confirm the content of an abnormality and the identification information when an abnormality occurs in the induction heating cooker 2. Further, even when repair or inspection is requested of the seller or the manufacturer (or the company in commission), the facts relating to the induction heating cooker 2 can be correctly transmitted, which enables quick and proper response. Thus, the user-friendliness is increased not only for the user, but also for the seller and the manufacturer.

The identification information of the home electric appliances EE such as the induction heating cooker 2 is different from the abnormality monitoring data in that the identification information does not vary, and hence the identification information is only required to be stored once in the storage device 149. Therefore, the identification information is not required to be acquired every time an abnormality occurs, but in order to reduce the hassle of finding the identification information from old records, it is desired to provide the identification information from the heating cooker when an abnormality occurs.

In the description above, specific description is given of the case of the induction heating cooker 2 as the heating cooker configured to detect an abnormality, but the present invention is also applicable to other cookers such as the rice cooker and the microwave oven, and similar effects can be obtained through such application.

Figure 68:
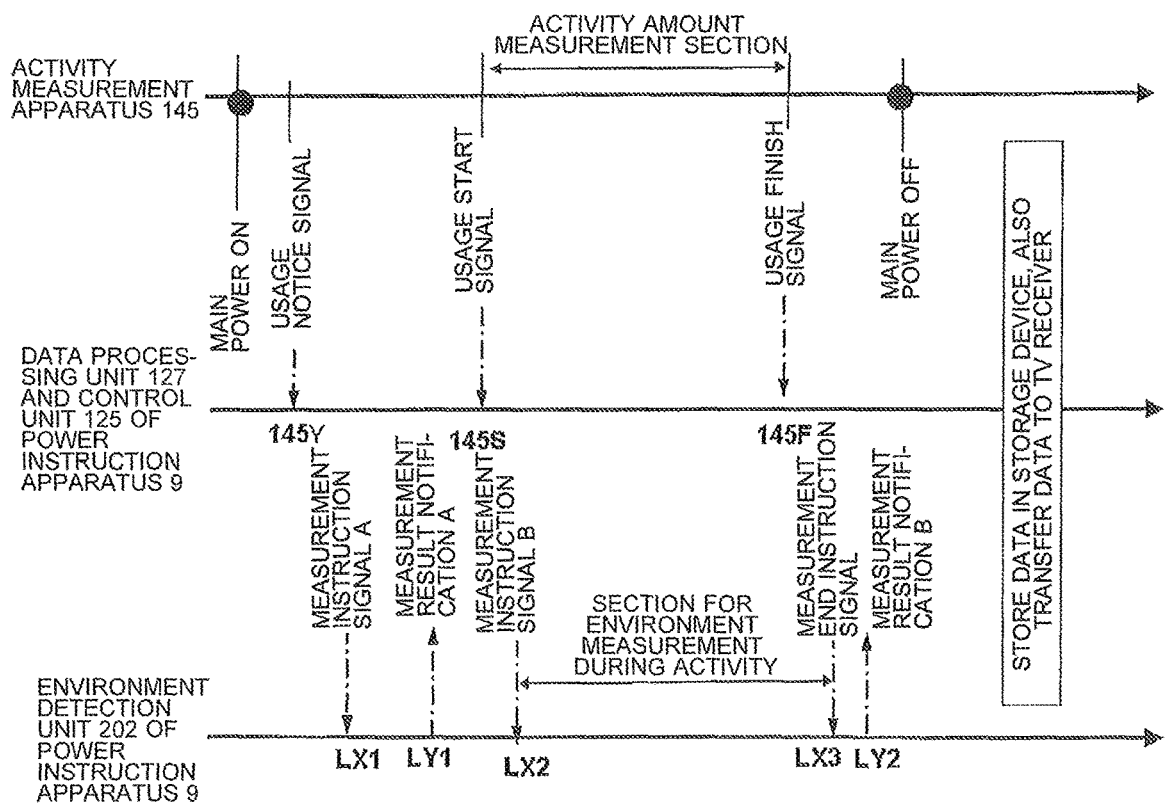
FIG. 68 is an explanatory diagram for illustrating mutual signal transmission between the power instruction apparatus and the activity measurement apparatus according to Embodiment 1 of the present invention in time series.

Referring to FIG. 68 to FIG. 72, description is now given of the power instruction apparatus corresponding to the fourth aspect of the present invention and the power control system corresponding to the fifth aspect of the present invention. FIG. 68 is an explanatory diagram for illustrating mutual signal transmission between the power instruction apparatus 9 and the activity measurement apparatus 145 in time series. Description is mainly given of the operation of the power instruction apparatus 9 acquiring the environment information of the living space HA where the activity measurement apparatus 145 is present.

Description is given based on the indoor treadmill 145A, which is an example of the activity measurement apparatus 145. When the main power of the indoor treadmill 145A is turned on and then the operation unit 145A7 thereof is operated to start preparing the exercise measurement, the control unit 145A3 of the indoor treadmill 145A transmits the predetermined usage notice signal 145Y from the transmission unit 145A4 to the healthcare processing unit 116 of the power instruction apparatus 9.

Then, the healthcare data processing unit 127 of the power instruction apparatus 9 detects the reception of the usage notice signal 145Y to transfer the reception of the usage notice signal 145Y to the control unit 125. As a result, the control unit 125 outputs a measurement instruction signal LX1 to the environment detection unit 202 so as to acquire the environment information of all of the living spaces HA that the indoor treadmill 145A could be used in (e.g., excluding the bathroom or the toilet) regardless of whether or not the living space corresponds to a location where the indoor treadmill 145A is used.

Various sensors such as the environment sensor (indoor temperature sensor) 204 and the environment sensor (indoor temperature sensor) 205 next acquire various types of information that may affect the degree of comfort for living in the house or the health during activity. Examples of the information include temperature and humidity information of the indoor air, information of the dust scattering degree (per unit volume) included in the indoor air, and pollen scattering amount information. The measurement results are transmitted from the control unit 125 of the power instruction apparatus 9 to the LCD screen 100A, the TV receiver 75, and the specific activity measurement apparatus 145 that has transmitted the usage notice signal 145Y (measurement result notification signal A in FIG. 68: LY1).

After the healthcare data processing unit 127 of the power instruction apparatus 9 receives the usage start signal 145S, the environment detection unit 202 similarly acquires the environment information from various sensors such as the environment sensor 204 and the environment sensor 205. The control unit 125 therefore outputs a measurement instruction signal LX2 to the environment detection unit 202 so as to acquire the environment information (see FIG. 68).

In this case, the control unit 125 identifies the living space where the indoor treadmill 145A is used by estimating the predetermined living space HA based on the human body detection signal from the human body detection unit 203 or the usage state of other electric appliances EE. There are various methods of estimating the living space, such as adding or incorporating a position sensor into the indoor treadmill 145A and retrieving the signal from the sensor to estimate the position, and hence detailed description thereof is omitted.

After the exercise with the indoor treadmill 145A is finished, the indoor treadmill 145A transmits the usage finish signal 145F to the healthcare data processing unit 127 of the power instruction apparatus 9. When the control unit 125 of the power instruction apparatus 9 detects the reception of the usage finish signal 145F, the control unit 125 instructs the environment detection unit 202 to end the acquisition of the environment information (measurement end instruction signal LX3). Therefore, the environment detection unit 202 collects the environment information acquired during the exercise period to transmit the information to the power instruction apparatus 9 (measurement notification signal LY2).

The environment information is also transmitted to the indoor treadmill 145A as reference information. After that, the healthcare data processing unit 127 adds the identification information including the measurement date and time and the subject to the data of the measured amount of activity, and the data is stored in the storage device 149 of the power instruction apparatus 9.

The same information is also transmitted to the TV receiver 75 to be stored in the storage device (high-capacity memory) 109 of the TV receiver 75 as well. The activity time period and the measurement time period of the environment information are preferred to completely match with each other, but the room temperature or humidity of the indoor living space does not generally change rapidly in the unit of seconds. Thus, incomplete matching does not cause a significant problem, and a deviation of about several minutes can be ignored in practical use.

In this manner, the indoor environment of the subject (occupant) at the time point of measurement of the biological data is measured, and the measurement data is recorded. When the achievement or transition of the amount of activity is analyzed at a later date, more accurate health checkup is possible in consideration of the influences of the ambient environment such as temperature and humidity.

In response to the reception of the measurement result notification signal A (measurement instruction signal LX1 of FIG. 68), the display unit of the indoor treadmill 145A, the LCD screen 100A of the display panel 100 of the power instruction apparatus 9, and the LCD screen 75D of the TV receiver 75 display the measurement results such as the temperature and humidity information of the indoor air, the information of the dust scattering degree (per unit volume) included in the indoor air, and the pollen scattering amount information. Activity suitability information is also displayed at this time.

As described above, the environment information is acquired before starting the activity for all of the living spaces HA that the indoor treadmill 145A could be used in (e.g., excluding the bathroom or the toilet) regardless of whether or not the living space corresponds to a location where the indoor treadmill 145A is used. Therefore, as illustrated in FIG. 15 and FIG. 16, before the activity measurement apparatus 145 is used, the occupant can know the living space that has a high degree of comfort and is suitable for indoor activity by the activity caution marks 480N and 480Y.

Figure 69:
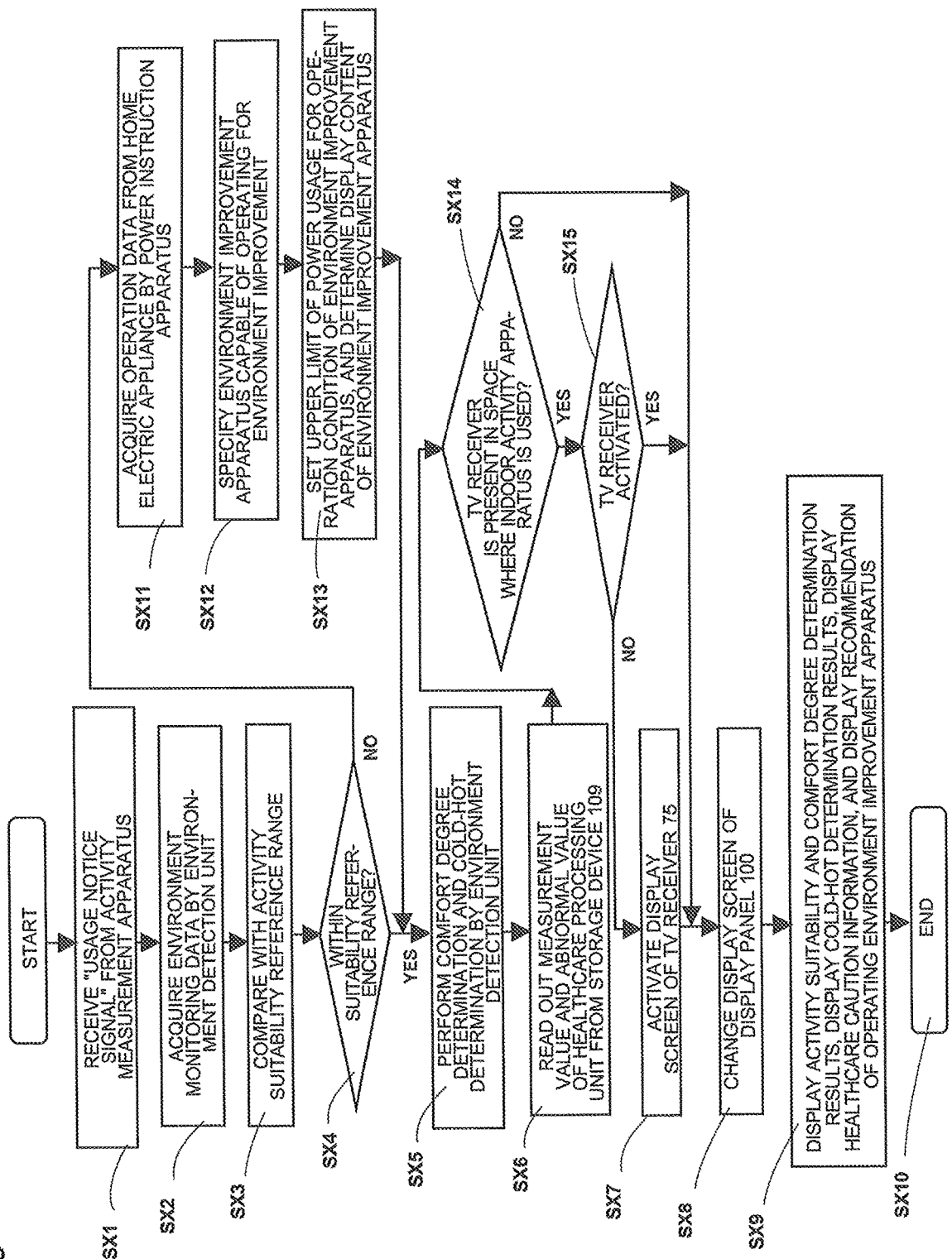
FIG. 69 is a flowchart for illustrating an activity suitability determination operation process of the power instruction apparatus according to Embodiment 1 of the present invention.
Figure 70:
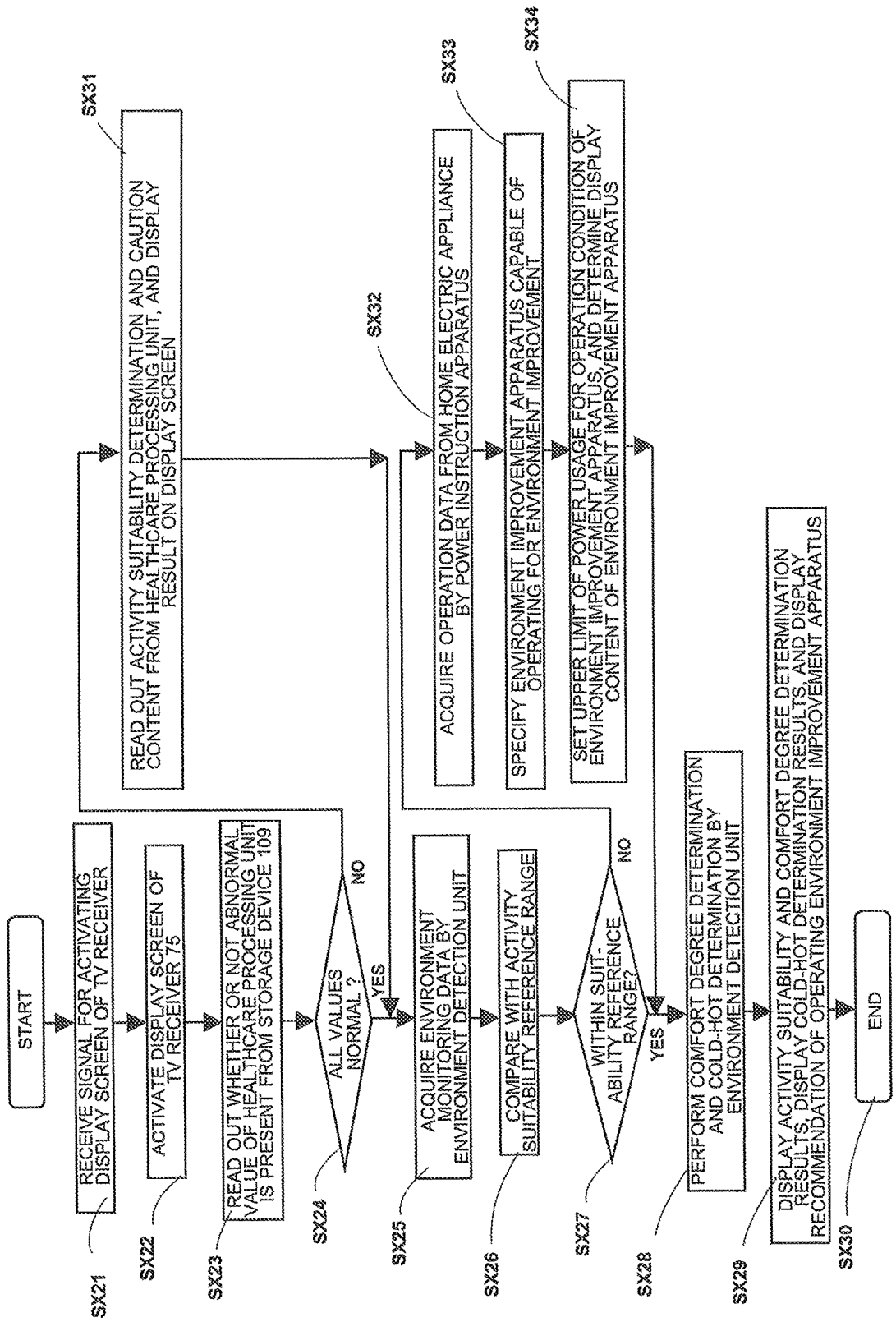
FIG. 70 is a flowchart for illustrating an activity suitability determination operation process of the power instruction apparatus according to Embodiment 1 of the present invention.
Figure 71:
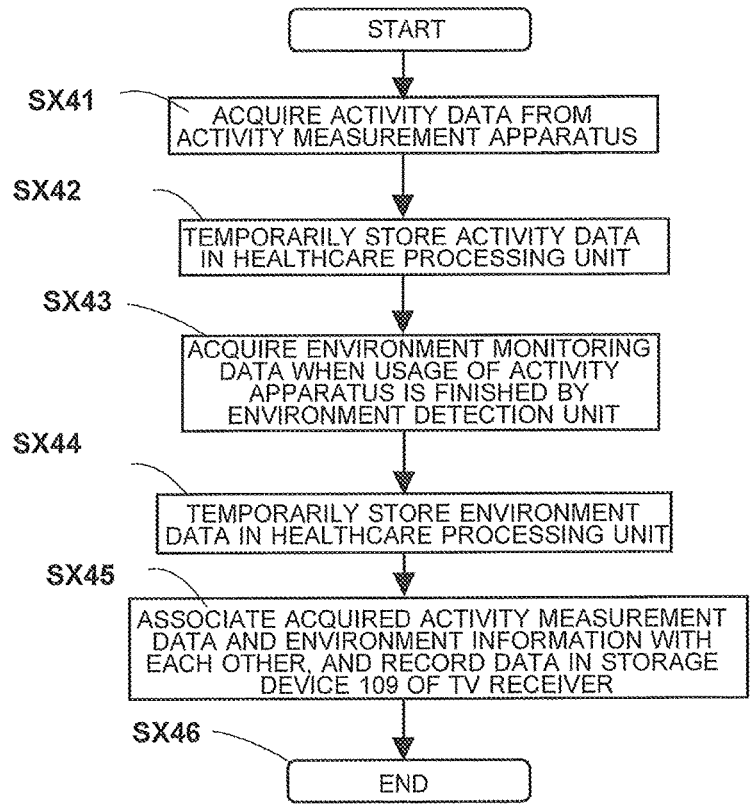
FIG. 71 is a flowchart for illustrating an operation process when the user has finished using the activity measurement apparatus of the power instruction apparatus according to Embodiment 1 of the present invention.

Referring to FIG. 69 to FIG. 71, description is now given of an activity suitability determination operation process of the power instruction apparatus according to Embodiment 1 of the present invention. FIG. 69 is a flowchart for illustrating the activity suitability determination operation process of the power instruction apparatus 9. First, the power instruction apparatus 9 receives the usage notice signal 145Y from the activity measurement apparatus 145, e.g., the indoor treadmill 145A (Step SX1). Then, the power instruction apparatus 9 acquires the environment information through the environment detection unit 202 (Step SX2).

The control unit 125 of the power instruction apparatus 9 compares the acquired environment information with a defined standard value set in advance (Step SX3), and determines whether or not the environment is suitable for indoor activity. In other words, whether the environment information falls within the suitability reference range is determined (Step SX4). When the environment is unsuitable for activity in the present environment state (e.g., the temperature and the humidity are too high), the power instruction apparatus 9 analyzes the various operation information signals L1 to L7 that have been transmitted from the various home electric appliances EE (Step SX11).

It is next determined whether or not there is a "first specific home electric appliance" ("environment improvement apparatus") SP1 that can be operated to improve the environment such as the temperature and the humidity (Step SX12). For example, when the activity measurement apparatus 145 is the indoor treadmill 145A placed in the living room, and the air-conditioning apparatus 7 (example of the environment improvement apparatus SP1) is installed in the living room, the operation conditions of the air-conditioning apparatus 7, in particular, the power upper limit and the target room temperature, are set. More preferably, it is determined to display the preferred operation conditions on the display unit of the air-conditioning apparatus 7 (including the display unit of the remote controller exclusive to the air-conditioning apparatus 7) before the activity is started in words or other methods (Step SX13). At this stage, the power instruction apparatus 9 does not output the instruction to start the operation of the air-conditioning apparatus 7.

The environment detection unit 202 next performs the "comfort degree determination" and the "cold-hot determination" in three levels as described above (Step SX5).

When there is healthcare information of the occupant using the indoor treadmill 145A measured on any of the current day or the day before in the measurement data of the healthcare instrument 410 stored in the storage device 109 of the power instruction apparatus 9, that is, in the healthcare information 412, the control unit 125 reads out the information. In this case, as described above with reference to FIG. 14, when there is caution data, the caution data is always read out (Step SX6).

Next, the control unit 125 determines whether or not the TV receiver 75 is present in the living space where the indoor treadmill 145A is used (Step SX14). When the home electric appliances EE are registered as the object of power control, the storage device 149 of the power instruction apparatus 9 stores the installation information of those home electric appliances EE, and hence whether or not the TV receiver 75 is present in each living space can be determined.

When it is determined whether or not the TV receiver 75 is present in the living space where the indoor treadmill 145A is used, it is determined whether or not the TV receiver 75 is already activated (Step SX15). On the other hand, when it is determined in the processing step (SX14) that the TV receiver 75 is not present in the living space where the indoor treadmill 145A is used, the TV receiver 75 cannot be used for notification of the environment information. Therefore, the LCD screen 100A of the display panel 100 of the power instruction apparatus 9 is changed to enable display of the activity suitability information or other information (Step SX8).

On the other hand, when it is determined that the TV receiver 75 is present in the living space where the indoor treadmill 145A is used, but the TV receiver 75 is not activated yet, the TV receiver 75 is activated (Step SX7). Then, the LCD screen 100A is set to an information visible state.

Finally, the activity suitability information and the healthcare information 412 (including the caution data) are displayed on the LCD screen 75D of the TV receiver 75 when the TV receiver 75 is present in the living space where the indoor treadmill 145A is used, or on the LCD screen 100A of the display panel 100 when the TV receiver 75 is not present in the living space. For example, when the caution data (see FIG. 14) indicates that the blood pressure is too high in the blood pressure measurement from the day before, and the body temperature is a little high on the current day, it is determined that the occupant is somewhat ill, or is in a situation where the occupant should refrain from exercising (this determination is executed by an exclusive determination program stored in the control unit 125, based on the above-mentioned various measurement values such as blood pressure and body temperature). In view of this, for example, in order to notify the occupant of a suggestion to avoid sweating through aerobic exercises by using the indoor treadmill 145A, the LCD screen 75D of the TV receiver 75 or the LCD screen 100A of the display panel 100 recommends not to activity.

When there is no problem in starting the activity, the power instruction apparatus 9 first displays the recommendation to start the operation of the air-conditioning apparatus 7. This recommendation is also displayed on the LCD screen 75D of the TV receiver 75 or the display screen 100A of the display panel 100. However, even after the display, the operation of the air-conditioning apparatus 7 cannot be started by the power instruction apparatus 9, and the operation is started only when the user operates the air-conditioning apparatus 7 by the user oneself.

When the indoor treadmill 145A includes a display unit, some kind of notification signal may be transmitted from the power instruction apparatus 9 to the indoor treadmill 145A to promote awareness similarly by the display unit. The processing of acquiring the environment information before starting the usage of the activity measurement apparatus 145 and outputting recommendations is thus finished (Step SX10).

Referring to FIG. 70, description is next given of the activity suitability determination operation of the power instruction apparatus 9 when the TV receiver 75 has been activated in the morning. FIG. 70 is a flowchart for illustrating the activity suitability determination operation process of the power instruction apparatus 9. First, the power instruction apparatus 9 activates the LCD screen 75 of the TV receiver 75 and receives a signal indicating that the TV receiver 75 is in a viewable state (Step SX21).

After that, the power instruction apparatus 9 transmits to the TV receiver 75 a signal indicating the upper power limit permitted in advance, and the system control unit 75E activates the LCD screen 75D in a range not exceeding the upper power limit (Step SX22).

When there is healthcare information measured on any of the current day or the day before in the measurement data of the healthcare instrument 410 stored in the storage device 109 of the power instruction apparatus 9, that is, in the healthcare information 412, the control unit 125 of the power instruction apparatus 9 reads out the information. In this case, as described with reference to FIG. 14, when there is caution data, the caution data is always read out (Step SX23).

The control unit 125 of the power instruction apparatus 9 determines whether or not there is caution data in the healthcare information 412 (Step SX24). When there is caution data, for example, data indicating abnormally high blood pressure or abnormally high body temperature, the operation proceeds to Step SX31.

In Step SX31, the activity suitability determination is made based on the healthcare information 412 (including the caution data), and information of the precautions based on the determination results are read out from the healthcare processing unit 116. In an actual case, the control unit 125 reads out the precautions recorded in correspondence with the state of the type (e.g., blood pressure) of the measurement data of the healthcare instrument 410, which is stored in the storage device 109 of the power instruction apparatus 9. Then, the contents to be displayed on the LCD screen 75 of the TV receiver 75 and the display screen 100A of the display panel 100 are determined among the results of the activity suitability determination and the precautions (Step SX24).

Next, in Step SX25, the control unit 125 of the power instruction apparatus 9 acquires the environment information through the environment detection unit 202 (Step SX25).

The control unit 125 of the power instruction apparatus 9 compares the acquired environment information with a defined standard value set in advance, and determines whether or not the environment is suitable for indoor activity (Step SX26). Then, in Step SX27, the activity suitability determination is made based on the environment information. For example, whether or not the environment (e.g., temperature and humidity) is suitable for aerobic exercises (e.g., exercise with the indoor treadmill 145A) is determined by determining whether or not the environment falls within the reference range set in advance by experts or others. For example, when the temperature is too high, the exhaustion level after running may be different even when the same distance is run for the same time period, and thus the activity may not be effective. That is, it is not preferred to activity under an environment with temperature and humidity that cause more fatigue than necessary. Further, when the same activity data is continuously accumulated and the activity data is analyzed or evaluated thereafter (by the occupant or by experts), the activity data may not be accurately analyzed or evaluated.

When it is determined in Step SX27 that the environment exceeds the reference range determined to be suitable for activity, that is, when the environment is unsuitable for activity (e.g., the temperature and the humidity are too high), the operation proceeds to Step SX30. In SX30, the power instruction apparatus 9 analyzes the various operation information signals L1 to L7 that have been transmitted from the various home electric appliances EE (Step SX32).

It is next determined whether or not there is a "first specific home electric appliance" ("environment improvement apparatus") SP1 that can be operated to improve the environment such as the temperature and the humidity (Step SX33). For example, when the activity measurement apparatus 145 is the indoor treadmill 145A placed in the living room, and the air-conditioning apparatus 7 (example of the environment improvement apparatus SP1) is installed in the living room, the operation conditions of the air-conditioning apparatus 7, in particular, the power upper limit and the target room temperature, are set. More preferably, it is determined to display the preferred operation conditions on the display unit of the air-conditioning apparatus 7 (including the display unit of the remote controller exclusive to the air-conditioning apparatus 7) before the activity is started in words or other methods (Step SX34). At this stage, the power instruction apparatus 9 does not output the instruction to start the operation of the air-conditioning apparatus 7.

In Step SX28, the environment detection unit 202 next performs the "comfort degree determination" and the "cold-hot determination" in three levels as described above.

The control unit 125 next automatically changes the LCD screen 75D of the TV receiver 75 (that is already activated) present in the living space where the indoor treadmill 145A is used, and causes the LCD screen 75 to display the information representing the results of the activity suitability determination, the comfort degree determination, and the cold-hot determination. Before starting the activity, the control unit 125 causes the LCD screen 75D to display words or illustrations for recommendation of operating the environment improvement apparatus SP1 (e.g., the air-conditioning apparatus 7) to adjust the air temperature or room temperature, or performing activity after the air cleanliness is improved, to thereby improve the environment for activity. The processing of acquiring the environment information before starting the usage of the activity measurement apparatus 145 and outputting recommendation when the TV receiver 75 has been activated is thus finished (Step SX30).

FIG. 71 is a flowchart for illustrating an operation process when the usage of the activity measurement apparatus 145 is finished of the power instruction apparatus 9.

The power instruction apparatus 9 acquires data of the amount of activity from the activity measurement apparatus 145 (SX41). Examples of the data include data of a running distance and a caloric value (calculated value) burned thereby.

The data of the amount of activity is temporarily stored in the healthcare processing unit 116 (SX42). Then, the environment detection unit 202 acquires the environment information of the living space HA where the activity measurement apparatus 145 is used (SX43). The environment data is also temporarily stored in the healthcare processing unit 116 (SX44).

The control unit 125 of the power instruction apparatus 9 stores and holds the data of the amount of activity acquired by the healthcare processing unit 116 from the activity measurement apparatus 145 and the environment data of the specific living space HA acquired by the environment detection unit 202 as a set in the storage device 109 (SX45). In other words, for each occupant, specific activity measurement data and measurement data of the environment state (e.g., room temperature and humidity) of the living space HA during the activity are stored as a pair in the storage device 109 in time series. The series of processing is then finished (SX46).

Referring to FIG. 72, description is now given of the operation process of the environment suitability determination when the healthcare instrument is used of the power instruction apparatus 9 according to Embodiment 1 of the present invention. FIG. 72 is an explanatory diagram for illustrating mutual signal transmission between the power instruction apparatus 9 and the healthcare instrument 410 in time series. Description is mainly given of the operation of the power instruction apparatus 9 acquiring the environment information of the living space HA where the healthcare instrument 410 is present.

Description is given of a case of the blood pressure meter 410A, which is an example of the healthcare instrument 410 described above. When the main power of the blood pressure meter 410A is turned on and then the operation unit 215 thereof is operated to start preparing for the blood pressure measurement, the control unit 217 of the blood pressure meter 410A transmits the predetermined usage notice signal 410Y from the transmission unit 314A to the healthcare processing unit 116 of the power instruction apparatus 9.

Then, the healthcare data processing unit 127 of the power instruction apparatus 9 detects the reception of the usage notice signal 410Y to transfer the reception of the usage notice signal 410Y to the control unit 125. As a result, the control unit 125 outputs a measurement instruction signal HX1 to the environment detection unit 202 so as to acquire the environment information of all of the living spaces HA that the blood pressure meter 410A could be used in (e.g., excluding the bathroom or the toilet) regardless of whether or not the living space corresponds to a location where the blood pressure meter 410A is used.

Various sensors such as the environment sensor 204 and the environment sensor 205 next acquire various types of information that may affect the degree of comfort for living in the house or the health during activity. Examples of the various types of information include temperature and humidity information of the indoor air, information of the dust scattering degree (per unit volume) included in the indoor air, and pollen scattering amount information. The measurement results are transmitted from the control unit 125 of the power instruction apparatus 9 to the LCD screen 100A, the TV receiver 75, and the specific healthcare instrument 410 that has transmitted the usage notice signal 145Y, that is, the blood pressure meter 410A (environment measurement result notification signal HY1).

After the healthcare data processing unit 127 of the power instruction apparatus 9 receives the usage start signal 410S, the environment detection unit 202 similarly acquires the environment information from various sensors such as the environment sensor 204 and the environment sensor 205. The control unit 125 therefore outputs a measurement instruction signal HX2 to the environment detection unit 202 so as to acquire the environment information.

The control unit 125 identifies the living space where the blood pressure meter 410A is used by estimating the predetermined living space HA based on the human body detection signal from the human body detection unit 203 or the usage state of other electric appliances EE. There are various methods of estimating the living space, such as adding or incorporating a position sensor into the blood pressure meter 410A and retrieving the signal from the position sensor to estimate the current position, and hence detailed description thereof is omitted.

After the blood pressure meter 410A finishes acquiring the biological data, the blood pressure meter 410A transmits the usage finish signal 410F to the healthcare data processing unit 127 of the power instruction apparatus 9. When the control unit 125 of the power instruction apparatus 9 detects the reception of the usage finish signal 410F, the control unit 125 instructs the environment detection unit 202 to end the acquisition of the environment information (the measurement end instruction signal at this time is denoted by HX3 in FIG. 72). Therefore, the environment detection unit 202 collects the environment information (room temperature, humidity, etc.) acquired during the biological data measurement to transmit the information to the power instruction apparatus 9 (environment measurement result notification signal HY2). The environment information is also transmitted to the blood pressure meter 410A as reference information. After that, the healthcare data processing unit 127 adds the identification information, including the measurement date and time and the subject, to the data of the measured blood pressure, and the data is stored in the storage device 149 of the power instruction apparatus 9. The same information is also transmitted to the TV receiver 75 to be stored in the storage device (high-capacity memory) 109 of the TV receiver 75 as well.

The biological data acquisition (blood pressure measurement) time period and the environment information measurement time period are preferred to completely match with each other, but the room temperature or humidity of the indoor living space does not generally change rapidly in the unit of seconds. Thus, incomplete matching does not cause a significant problem, and a deviation of about several minutes can be ignored in practical use.

In this manner, the indoor environment of the subject (occupant) at the time point of measurement of the blood pressure is measured, and the measurement data is recorded. When the transition of the blood pressure value is analyzed at a later date, more accurate health checkup is possible in consideration of the influences of the ambient environment such as temperature and humidity.

As described with reference to FIG. 73, when the activity measurement apparatus 145 is used, the power instruction apparatus 9 automatically outputs the measurement instruction signal to the environment detection unit 202 to acquire the environment information. Alternatively, the user can arbitrarily and manually acquire the environment information as appropriate.

Specifically, in the TV receiver 75, as described with reference to FIG. 3 and FIG. 12, when any one of the press-button operation button EV2 of the instruction switch (not shown) for environment confirmation and the operation button EV3 of the instruction switch (not shown) for environment confirmation provided on the remote controller 75R is pressed, the TV receiver 75 is activated if not already activated, the environment information acquisition instruction signal is input to the control unit 125 of the power instruction apparatus 9, the control unit 125 acquires by the environment detection unit 202 the environment information such as the temperature and the humidity of the living space HA, and the result of the acquired environment information is transmitted to the TV receiver 75. Therefore, the latest environment information can be quickly confirmed on the LCD screen 75D.

Meanwhile, in the display panel 100, as described with reference to FIG. 20, when the press-button operation button EV1 of the instruction switch (not shown) for environment confirmation is pressed, the control unit 125 outputs the environment information acquisition instruction signal to the environment detection unit 202, and the environment detection unit 202 acquires the environment information such as the temperature and the humidity of the living space HA. Therefore, the result of the acquired environment information can be quickly confirmed on the display screen 100A.

In this manner, in Embodiment 1, even when the activity measurement apparatus 145 or the healthcare instrument 410 is not used, the user can confirm as appropriate the environment state in the house, including the living space HA where the user is present. Thus, the system can be conveniently used, such as for confirmation of the dust scattering degree (air cleanliness) of a certain room after the room is cleaned, for pre-confirmation of the environment of the room for inviting a guest, and for confirmation of the environment of a room where a child or an infant is sleeping alone by a parent from a distant location.

In FIG. 7, reference symbol EV1 denotes the press-button operation button of the instruction switch (not shown) for environment confirmation, which is provided in the vicinity of the lower edge of the LCD screen 75D in the front surface of the TV receiver 75. Reference symbol EV3 denotes the operation button of the instruction switch (not shown) for environment confirmation, which is provided in the remote controller 75R of the TV receiver 75.

When any of those two operation buttons EV2 and EV3 is pressed, the TV receiver 75 is activated if not already activated, and the LCD screen 75D first displays the screen indicating various types of environment information to be subsequently described (illustrated in FIG. 15 or FIG. 16). Therefore, without displaying the portal site screen (illustrated in FIG. 11) to be subsequently described, the environment states of all of the living spaces HA in the house can be quickly confirmed in the form of a list. Detailed operations of a case where those two operation buttons EV2 and EV3 of the operation switches (not shown) for environment confirmation are operated are subsequently described.

The healthcare instrument 410 according to Embodiment 1 includes the measurement unit 214 configured to measure metabolic data of a human body (measurement data from a living body) to acquire measurement data, the memory 216 configured to temporarily store the measurement data acquired by the measurement unit, the transmission unit 314 configured to transmit the measurement data accumulated in the memory 216 to the outside, the operation unit 215 configured to control the measurement and the transmission, the instrument-side display unit 213 configured to retrieve the measurement data stored in the memory 216 and display the data, and the control unit 217 configured to process the measurement data. The transmission unit 314 transmits the measurement data so that the power instruction apparatus 9, configured to control the upper limit of the total electric power in the household by individually controlling the upper power limit of each of the plurality of electric appliances in the household, displays the measurement data on the display panel 100.

With the healthcare instrument 410, the information related to health management can also be displayed on the display panel 100 of the power instruction apparatus 9 based on the measurement data transmitted to the power instruction apparatus 9, and therefore electric energy management and health management can be performed with a single instrument.

The household power control system according to Embodiment 1 includes the power instruction apparatus 9 configured to limit the total electric power in the household by individually controlling the upper power limit of each of the plurality of electric appliances EE in the household, and the display panel 100 and the LCD screen 75D of the TV receiver 75 to be connected to the power instruction apparatus 9 via wired or wireless communication and configured to display the operation information of the power instruction apparatus 9. The power instruction apparatus 9 includes the healthcare processing unit 116 configured to process the metabolic data (healthcare information) measured by the healthcare instrument 410, and the display panel 100 is configured to switch the display between the operation information of the power instruction apparatus 9 and the metabolic data (biological data) processed by the healthcare processing unit 116, based on the operation of the user. The LCD screen 75D of the TV receiver 75 is also configured to switch the display between the measurement data (healthcare information) measured by the healthcare instrument 410 and the operation information of the power instruction apparatus 9, based on the operation of the user.

Thus, with the household power control system according to Embodiment 1, the information related to healthcare can be displayed by utilizing the information transmission system of the power instruction apparatus 9, and therefore the user is motivated to become more conscious of energy saving and health management.

The power instruction apparatus (household power instruction apparatus) 9 according to Embodiment 1 includes the use limit setting device 96 configured to receive the operation information from the plurality of home electric appliances EE in order to control the total electric power in the household by individually controlling the upper limit of the power usage of each of the plurality of electric appliances EE, and to transmit the power control signal to each of the home electric appliances EE, the healthcare processing unit 116 configured to receive the measurement data of the human body from the healthcare instrument 410, the control unit 125 configured to control the healthcare processing unit 116 and the use limit setting device 96, the environment detection unit 202 configured to collect the environment data such as indoor temperature, and the display panel 100 configured to display the power usage information, the information of the measurement data from the healthcare instrument 410, which is received by the healthcare processing unit 116, and the environment data acquired by the environment detection unit 202.

With the power instruction apparatus 9, the centralized control of the total power usage of the plurality of home electric appliances can be performed. In addition, the measurement results of the measurement data such as blood pressure received from the healthcare instruments, as well as the environment data of the living space can be displayed, and therefore the user is motivated to become more conscious of energy saving and health management, so as to make the living space more comfortable.

As is apparent from the foregoing description, the power instruction apparatus 9 according to Embodiment 1 includes the use limit setting device 96 configured to receive the operation information from the plurality of home electric appliances EE and transmit the power control signal to each of the home electric appliances EE, the healthcare processing unit 116 configured to receive the measurement data of the human body from the healthcare instrument 410, the environment detection unit 202 configured to receive the environment data measured by the environment sensor configured to measure the physical environment of the living space where the home electric appliances EE are provided, the control unit 125 configured to control the environment detection unit 202, the healthcare processing unit 116, and the use limit setting device 96, and the display panel 100 configured to display the power usage information, the environment data, and the information related to the human body measurement data.

With the power instruction apparatus 9, the electric energy management and the health management can both be performed. In addition, the environment data such as indoor temperature and the humidity can be displayed for confirmation, and therefore the environment of the living space can be confirmed on a real-time basis, which facilitates realization of a healthy life space. Further, the state of the living space where the healthcare instrument 410 is to be used can be confirmed on the display panel 100, which is the display unit of the power instruction apparatus 9, without the need to go to the living space (room), and therefore a higher level of user-friendliness can be obtained. Further, the usage environment of the home electric appliances that may affect the quality of indoor air, such as the induction heating cooker 2, the air-conditioning apparatus 7, and the air purifier (not shown) can be confirmed on the display panel 100 of the power instruction apparatus 9.

The power instruction apparatus 9 includes, for individually controlling the power usage of the first specific home electric appliance SP1 including at least one of the air-conditioning function or the air-purifying function and other electric appliances (home electric appliances EE, second specific home electric appliance SP2), the use limit setting device 96 configured to receive the operation information from the first specific home electric appliance SP1 and other home electric appliances and transmit the power control signal to the group of home electric appliances including the first specific home electric appliance SP1 and other home electric appliances, the healthcare processing unit 116 configured to receive the measurement data of the human body from the healthcare instrument 410, the environment detection unit 202 configured to receive the environment data from the environment sensor configured to measure the physical environment of the living space, the control unit 125 configured to control the environment detection unit 202, the healthcare processing unit 116, and the use limit setting device 96, and the display panel 100 serving as the display device configured to display the power usage information of the home electric appliance, the environment data, and the information related to the measurement data. The display panel 100 also serves as an input unit of the control unit 125 configured to set the upper limit of the power usage of the first specific home electric appliance SP1 and other electric appliances. Further, the display panel 100 is located in the living space (e.g., kitchen) other than the space where the first specific home electric appliance SP1 is installed (e.g., bedroom), and is configured to display, by remote control through the operation of the input unit, the operation information of the first specific home electric appliance SP1 and the environment data.

With the above-mentioned power instruction apparatus, the information related to the health management can be displayed on the same display panel 100 of the power instruction apparatus 9, and therefore the user is motivated to become more conscious of energy saving and health management. In addition, the user can confirm the environment data such as indoor temperature, humidity, and dust scattering degree displayed on the display panel 100, and therefore the environment of the living space can be confirmed on a real-time basis, which facilitates realization of a healthy life space.

Further, the state of the living space where the healthcare instrument is to be used (e.g., living room or bedroom) can be collectively confirmed on the display panel 100 of the power instruction apparatus 9 without the need to go to each living space (room), and therefore a higher level of user-friendliness can be obtained.

Still further, the start of the operation and the operating conditions of the first specific home electric appliance SP1 (air-conditioning apparatus 7 or air purifier) can be remote-controlled without the need to go to the specific living space. Therefore, in the case that one of the family members is infected with a contagious disease such as influenza, the air quality (generic term for temperature, humidity, purity, and so forth of air) of the patient's room can be improved by remote control from another room (e.g., kitchen), so as to make the patient's room more comfortable and care for the patient.

One of the plurality of home electric appliances EE is the heating cooker such as the induction heating cooker 2, which includes the display unit in which the subject having the caution data (e.g., high blood pressure and high uric acid) in the metabolic data is displayed when the main power is turned on. Accordingly, the user is urged to determine, before the cooking is started, the cooking method and the seasoning mode in consideration of the family member having the caution data, to contribute to promoting the health of the family.

The power instruction apparatus 9 is also configured to retrieve the metabolic data (measurement data) of the family and display the caution data (e.g., high blood pressure and high uric acid) and the subject on the display panel 100. Therefore, the user can recognize the points to note about the health of the family members (e.g., high blood pressure), thereby being urged to consider the cooking method and the seasoning mode, for example, reducing the use of salt.

The biological measurement data (healthcare information) measured by each of the healthcare instruments 410 may be once transferred to the mobile phone terminal 87, and then transferred to the healthcare processing unit 116. In addition, the data measured outside may be carried home in the mobile phone terminal 87, and transferred to the healthcare processing unit 116. Those are variations of data input to the healthcare processing unit 116.

The power instruction apparatus 9 according to Embodiment 1 controls the upper limit of the total electric power in the household by individually controlling the power usage of the first home electric appliances and the second home electric appliances in the household. To be more detailed, the power instruction apparatus 9 includes the environment detection unit 202 configured to receive the environment information measured by the environment sensor configured to measure the physical environment of the living space where the first and second home electric appliances are provided, the control unit 125 configured to receive the information of the scheduled home arrival time (including predicted home arrival time) from the occupant and process the information from the environment detection unit 202 and the information of the home arrival time, and the display panel 100 configured to display the power usage information and the environment information from the environment detection unit 202. The first home electric appliance (e.g., rice cooker 3) is configured to accept the reservation of the operation start time set by a direct input of the operation finish time made by the occupant. The control unit 125 outputs to the first home electric appliance, in the case where the scheduled home arrival time indicated in the communication information received from the occupant is earlier than the operation finish time (reserved finish time A) of the first home electric appliance (e.g., rice cooker 3) for which the operation finish time is reserved, the instruction to advance the operation finish time of the first home electric appliance to a time (reserved finish time B) advanced by a predetermined time from the scheduled home arrival time, provided that the condition specified in the control unit 125 is satisfied.

With the configuration according to Embodiment 1, the environment-related information can be displayed in addition to the power information, and therefore the user is motivated to become more conscious of energy saving and environment. In addition, the user can confirm the environment data such as indoor temperature, humidity, and dust scattering degree by viewing the display, and therefore the environment of the living space can be confirmed on a real-time basis, which facilitates realization of a healthy life space. Further, the state of the living space can be confirmed on the display panel 100 of the power instruction apparatus 9 without the need to go to the living space (room), and therefore a higher level of user-friendliness can be obtained.

In addition, the operation finish time of the first home electric appliance (e.g., rice cooker 3) reserved by inputting the operation finish time can be changed by the communication information from the occupant indicating the scheduled home arrival time, so that the operation can be started and finished before the occupant comes home. Further, the usage environment of the first home electric appliance can be confirmed on the display panel 100 of the power instruction apparatus 9.

Further, the operation finish time (reserved finish time A) of the first home electric appliance is restricted from being changed by remote operation, unless the condition specified in the control unit 125 is satisfied. Therefore, the first home electric appliance (e.g., rice cooker 3) can be prevented from being set to work with useless electric energy consumption, and be allowed to perform the operation without compromising the function and in an environment-friendly manner so as not to affect the operation of other home electric appliances.

The power instruction apparatus 9 according to Embodiment 1 includes the power instruction apparatus 9 configured to control the upper limit of the total electric power in the household by individually controlling the power usage of the first home electric appliances and the second home electric appliances in the household, the environment detection unit 202 configured to receive the environment information measured by the environment sensor configured to measure the physical environment of the living space where the first and second home electric appliances are provided, the control unit 125 configured to receive the information of the scheduled home arrival time (including predicted home arrival time) from the occupant and process the information from the environment detection unit 202 and the information of the home arrival time, and the display panel 100 configured to display the power usage information and the environment information from the environment detection unit 202. The first home electric appliance (e.g., rice cooker 3) is configured to accept the reservation of the operation start time set by a direct input of the operation finish time made by the occupant. The control unit 125 outputs to the first home electric appliance, in the case where the scheduled home arrival time indicated in the communication information received from the occupant is earlier than the operation finish time (reserved finish time A) of the first home electric appliance in which the operation finish time is reserved, the instruction to advance the operation finish time of the first home electric appliance to a time (reserved finish time B) advanced by a predetermined time from the scheduled home arrival time, provided that the environment condition specified in the control unit 125 is satisfied.

With the configuration according to Embodiment 1, the operation finish time of the first home electric appliance can be changed according to the scheduled home arrival time received from the occupant, which provides a higher level of user-friendliness.

The household power control system according to Embodiment 1 includes the circuit breaker BK configured to cut off the electric circuit when the first capacity limit is exceeded, the first home electric appliances and the second home electric appliances each being configured to receive power through the circuit breaker BK, the power instruction apparatus 9 configured to control the total power usage of the first home electric appliances and the second home electric appliances, the environment detection unit 202 configured to receive the environment information measured by the environment sensor configured to measure the physical environment of the living space where the first and second home electric appliances are provided, and the display device (TV receiver 75, display panel 100) configured to display the power information and the environment information. The power instruction apparatus 9 accepts the setting of the upper power limit made by the user, to the second capacity limit lower than the first capacity limit. The first home electric appliance (e.g., rice cooker 3) is configured to accept the reservation of the operation start time set by a direct input made by the occupant. The power instruction apparatus 9 includes the input-output unit 124B configured to receive the information of the scheduled home arrival time from outside the house through the communication network, and the control unit 125 configured to permit the first home electric appliance to start the operation when the operation start time is reached. The control unit 125 compares the scheduled home arrival time indicated in the communication information received from the occupant with the operation start time of the first home electric appliance in which the operation start time is reserved, and outputs, in the case where the time deviation between the above-mentioned times is larger than a predetermined time, the instruction to change the operation start time of the first home electric appliance so as to match the scheduled home arrival time, provided that the predetermined environmental condition, specified in the control unit 125 and based on the environment information related to the first home electric appliance, is satisfied.

With the configuration according to Embodiment 1, the environment-related information can be displayed in addition to the power information, and therefore the user is motivated to become more conscious of energy saving and environment. For example, the user can confirm the environment data such as indoor temperature, humidity, and dust scattering degree by viewing the display, and therefore the environment of the living space can be confirmed on a real-time basis, which facilitates realization of a healthy life space.

In addition, the state of the living space can be confirmed on the display panel 100 of the power instruction apparatus 9 and the LCD screen 75D of the TV receiver 75, without the need to go to the living space (room), and therefore a higher level of user-friendliness can be obtained.

Further, the operation finish time of the first home electric appliance (e.g., rice cooker) reserved by inputting the operation finish time can be changed by the communication information from the occupant indicating the scheduled home arrival time, so that the operation can be started and finished before the occupant comes home. Further, the usage environment of the first home electric appliance can be confirmed by viewing the display panel 100 of the power instruction apparatus and the LCD screen 75D of the TV receiver 75.

Still further, the operation finish time (reserved finish time A) or the operation start time (reserved start time A) of the first home electric appliance is restricted from being changed by remote operation, unless the condition specified in the control unit 125 is satisfied. Therefore, the first home electric appliance can be prevented from being set to work with useless electric energy consumption, and be allowed to perform the operation without compromising the expected performance and in an environment-friendly manner so as not to affect the operation of other home electric appliances.

Further, in the household power control system described in Embodiment 1, the kitchen electric appliances KP including the heating sources such as the induction heating cooker 2 are not directly connected to the network 98 present outside the house. Those kitchen electric appliances KP are connected to the network 98 via the power instruction apparatus 9, and hence the risk of false remote operation of the kitchen electric appliance KP from the outside via the network can be significantly reduced. That is, in general, the kitchen electric appliance KP does not include a high-performance fire wall function or information processing device, and hence many of them are insufficient in security. Recently, there are social problems of unauthorized invasion to kitchen electric appliances KP such as a refrigerator from the outside via a network, thus using the kitchen electric appliances KP as the agent of an attack on the information terminal apparatus and computers of other people. Specialized security agencies and others point out the risk that household routers and home electric appliances may be illegally controlled by the same method as using botnet malware to control computers of other people.

In contrast, in Embodiment 1, the kitchen electric appliance KP alone cannot directly communicate with the network 98, and can only transmit or receive information via the power instruction apparatus 9 or via the mobile phone terminal 87. Therefore, Embodiment 1 is also advantageous in terms of security, and can provide a living space that the occupant can live in without fear.

Summary of Embodiment 1

The power control system to which the first aspect is applied as described in Embodiment 1 includes: the power instruction apparatus 9 configured to limit total electric power in the household by individually controlling an upper power limit of each of the plurality of home electric appliances EE in the household; the display device (TV receiver 75 or display panel 100) to be connected to the power instruction apparatus 9 via wired or wireless communication and configured to display operation information of the power instruction apparatus 9; the activity measurement apparatus 145 configured to measure the amount of activity of the person in the household; and the healthcare instrument 410 configured to measure biological data of a person in the household. The power instruction apparatus 9 includes: the environment detection unit 202 configured to measure at least one of temperature and humidity of each of the plurality of living spaces HA in the household; and the healthcare processing unit 116 configured to acquire measurement data measured by the activity measurement apparatus 145 and the healthcare instrument 410. The display device (TV receiver 75 or display panel 100) is configured to switch the display between the environment information acquired by the environment detection unit 202 of the power instruction apparatus 9 and the measurement data measured by the activity measurement apparatus 145 or the healthcare instrument 410, based on the instruction from the user.

Thus, with the power control system according to the first aspect, the measurement information relating to health or activity of a person and the environment data of the living space can be displayed by utilizing the information transmission system of the power instruction apparatus 9. Therefore, the environment of the living space can be confirmed, and the user is motivated to become more conscious of energy saving and health management.

The activity measurement apparatus to which the second aspect is applied as described in Embodiment 1 includes: the measurement unit 145A1 configured to measure data of the amount of activity of the person (living body); the memory 145A8 configured to temporarily store the measurement data acquired by the measurement unit; the transmission unit 145A4 configured to transmit the measurement data accumulated in the memory to the power instruction apparatus 9 configured to limit total electric power in the household by individually controlling the upper power limit of each of the plurality of home electric appliances EE in the household; the operation unit 145A7 configured to output an instruction of a measurement operation and a transmission operation; the apparatus-side display unit 145A2 configured to read out and display the measurement data stored in the memory; and the control unit 145A3 configured to process the measurement data, the transmission unit 145A4 having the function of transmitting the usage notice signal 145Y to be transmitted to the power instruction apparatus 9 before start of measurement by the measurement unit 145A1.

Thus, with the activity measurement apparatus 145 to which the second aspect is applied, the information of the amount of activity can be displayed by utilizing the power instruction apparatus 9 configured to display the power usage information, and the usage notice signal 145Y can be transmitted to the power instruction apparatus 9 before measurement of the amount of activity. In addition, the activity measurement apparatus 145 can be used for a system capable of acquiring the environment information in a timely manner by the power instruction apparatus 9 so that the user can perform an activity with comfort.

The healthcare instrument 410 to which the third aspect is applied as described in Embodiment 1 includes: the measurement unit 214 configured to measure measurement data of the person (living body); the memory 216 configured to temporarily store the measurement data acquired by the measurement unit; the transmission unit 314A configured to transmit the measurement data accumulated in the memory 216 to the power instruction apparatus 9 configured to limit total electric power in the household by individually controlling the upper power limit of each of the plurality of home electric appliances EE in the household; the operation unit 215 configured to output an instruction of a measurement operation and a transmission operation; the apparatus-side display unit 213 configured to read out and display the measurement data stored in the memory 216; and the control unit 217 configured to process the measurement data, the transmission unit 314 having the function of transmitting the usage notice signal 410Y to be transmitted to the power instruction apparatus 9 before start of measurement by the measurement unit 214.

Thus, with the healthcare instrument 410 to which the third aspect is applied, the information relating to health management can be displayed by utilizing the power instruction apparatus 9 configured to display the power usage information, and the usage notice signal 410Y can be transmitted to the power instruction apparatus 9 before measurement of the human body. In addition, the healthcare instrument 410 can be used for a system capable of acquiring the environment information in a timely manner by the power instruction apparatus 9 so that the biological data can be acquired in a comfortable environment.

The power instruction apparatus 9 to which the fourth aspect is applied as described in Embodiment 1 is configured to limit total electric power in the household by individually controlling power usage of each of the plurality of home electric appliances EE in the household. The power instruction apparatus 9 includes: the environment detection unit 202 configured to measure at least one of temperature and humidity of each of the plurality of living spaces HA in the household, to thereby generate environment information; the power use limit setting device 96 configured to receive operation information from each of the plurality of home electric appliances EE to transmit the power control signal to each of the plurality of home electric appliances EE; the healthcare processing unit 116 configured to receive measurement data from the activity measurement apparatus 145 configured to measure the amount of activity of the person; the control unit 125 configured to control the healthcare processing unit 116 and the power use limit setting device 96; and the display panel 100 configured to display, collectively or individually, information of the power usage, data of the amount of activity of a person received by the healthcare processing unit 116, and the environment information of the living space HA in which the activity measurement apparatus 145 is present.

Thus, with the power instruction apparatus 9 according to Embodiment 1 to which the fourth aspect is applied, the centralized control of the total electric power in the household can be performed by individually controlling the power usage of each of the plurality of electric appliances EE in the household. In addition, the measurement results of the measurement data received from the activity measurement apparatus 145 can also be displayed, and therefore the user is motivated to become more conscious of energy saving and health management through activity.

The power control system to which the fifth aspect is applied as described in Embodiment 1 includes the power instruction apparatus 9 configured to control the total electric power in the household by individually controlling the upper power limit of each of the plurality of electric appliances EE in the household, the activity measurement apparatus 145 configured to be connected, wirelessly or by wired communication, to the power instruction apparatus 9 to measure the amount of activity of the person in the household, and the TV receiver 75 configured to receive broadcast waves from outside of the household. The power instruction apparatus 9 includes the environment detection unit 202 configured to measure at least one of temperature and humidity for each of the plurality of living spaces HA in the household, the healthcare processing unit 116 configured to acquire the measurement data measured by the activity measurement apparatus 145, and the display panel 100 configured to display the power information of the home electric appliances EE. The TV receiver 75 can display the environment information acquired by the environment detection unit 202 of the power instruction apparatus 9 and the measurement data measured by the activity measurement apparatus 145 based on the instruction from the user. When the power instruction apparatus 9 detects that the usage of the activity measurement apparatus 145 is started, the power instruction apparatus 9 causes the LCD screen 75D of the TV receiver 75 to display the determination result information representing whether or not the environment of the living space HA where the activity measurement apparatus 145 is present is suitable for activity.

Thus, with the power control system according to Embodiment 1 to which the fifth aspect is applied, before the usage of the activity measurement apparatus 145 is started, the LCD screen 75D of the TV receiver 75 installed in the living space HA where the activity measurement apparatus 145 is present can inform the user whether or not the environment of the living space HA is suitable for activity. Therefore, the activity can be started in a comfortable environment.

Although the case where one circuit breaker BK is installed in one household is described in Embodiment 1, a main circuit breaker that controls the total power of the whole house and a plurality of secondary circuit breakers may be provided, such that, for example, a first secondary circuit breaker controls the power to the air-conditioning apparatus 7, a second secondary circuit breaker controls the power to the washing-drying machine, and a third secondary circuit breaker controls the power to the cooking electric heaters in the kitchen (such as the rice cooker 3). In this case, the main circuit breaker BK collectively cuts off the power supply to the plurality of secondary circuit breakers. Even when the power supply system is branched into a plurality of lines, Embodiment 1 is similarly applicable. In this case, further, the power instruction apparatus 9 may detect the current supplied to the system of each of the branched lines, and monitor the current so as to prevent the current from exceeding the rated capacity of each secondary circuit breaker.

In Embodiment 1, the vibration sensor 241 configured to detect the vibration upon occurrence of an earthquake is mounted inside the built-in type induction heating cooker 2. This is because the built-in type induction heating cooker 2 is horizontally fixed in the kitchen furniture such as the kitchen sink, and is barely influenced by floor vibration generated when a family member runs nearby, which is advantageous for accurately detecting the vibration of an earthquake. Alternatively, the vibration sensor 241 may be mounted inside the main body 9A of the power instruction apparatus 9 fixed to the wall surface of the kitchen, instead of inside the built-in type induction heating cooker 2. In the case where the house has two stories, the vibration sensor 241 may be mounted at two positions, for example, in the furniture in a room on the second floor and in the induction heating cooker 2 in the kitchen on the first floor.

In the description of Embodiment 1, various input units are employed, for example, the switches (input units) such as the on/off button 81c to be pressed for input, touch-type input keys that utilize static capacitance change such as the first selection unit 128A, and the selection marks, frames, and arrows that appear on the display screen to be selected (designated) by the operation on the remote controller 75R, such as the special icons 412 and 417. Those input units may be combined as desired, and also input units of other types such as a voice input method may be adopted, so that the home electric appliance analyzes the voice output by the user and automatically recognizes the content of the instruction, thus making the input valid.

In the description of Embodiment 1, the power instruction apparatus 9 includes the use limit setting device 96 installed as an independent unit mounted in the main body 9A of the power instruction apparatus 9, however a different configuration may be adopted. For example, the software for executing the basic operation of the use limit setting device 96 may be incorporated in the semiconductor storage device mounted on the same circuit mount board on which the software for other components is provided. In addition, a part of the storage device 149 may be constituted of an information server located in a distant place outside the living space, to thereby achieve a system in which the information server and the power instruction apparatus 9 exchange information via the communication network. Such an information server outside the living space may be utilized, for example, for recording and storing message content to be described subsequently in Embodiment 3.

Further, the basic screen configuration for electric energy management on the LCD screen 75D of the TV receiver 75 and the basic screen configuration for display of electric energy management information and healthcare information on the display panel 100 of the power instruction apparatus 9 may have the same design. In this case, even when there are differences in input methods such as between an icon and a touch input key (switch), the user is prevented from being confused when viewing the information, operating the screen, or inputting instructions. In other words, it is just like using a single familiar or favorite screen.

As described in Embodiment 1, the communication establishment unit 191 of the mobile phone terminal 87 monitors establishment of the NFC communication session between the mobile phone terminal 87 and the induction heating cooker 2. Therefore, even during a period in which the main power of the induction heating cooker 2 is turned off, or a period in which the heat cooking is finished or suspended, when the user brings the mobile phone terminal 87 close to the NFC input-output unit 401L of the induction heating cooker 2, the NFC communication session can be established at any time. In other words, before using the induction heating cooker 2, the identification information for identifying the induction heating cooker 2 or the data of a previous abnormality can be read out for display. In order to realize this, even in an emergency case where an abnormality occurs in the induction heating cooker 2, or even in an ordinary case where the user finishes and stops the usage, the abnormality monitoring information recorded in the storage device 32R is desired to be stored in the induction heating cooker 2 for a predetermined number of times or a predetermined number of days unless a particular operation is made.

There is also a method of automatically transferring (e.g., at the time of abnormality occurrence) the abnormality monitoring data of at least the previous-time usage amount or the previous-day usage amount from the storage device 32R to the NFC storage unit 320. With this, before power is supplied to the induction heating source, the identification information and the abnormality monitoring data can be provided to the information communication terminal device, e.g., the mobile phone terminal 87 that has established a predetermined short range wireless communication state with the short range wireless communication unit 401. Thus, the user-friendliness is further improved.

Further, in Embodiment 1, the "power reduction instruction signal" AS2 output from the power instruction apparatus 9 is a signal output from the power instruction apparatus 9 for urging the user to quickly decrease the power. Description has been made that, when the total electric power is not decreased within a predetermined time period from the output of this signal, the "power reduction instruction signal" AS3 is output for forcibly decreasing the power, but those two signals may not be different signals. In other words, the signals may be the same as long as the home electric appliance EE to be controlled in terms of power can determine whether the signal is for power reduction or for power reduction instruction. Therefore, for example, when the home electric appliance EE receives the power reduction request signal AS2 and then receives the power reduction instruction signal AS3 again within the predetermined time period, it may be determined that the power of the home electric appliance is forcibly decreased by the latter signal.

In order to reliably transmit and receive signals between the power instruction apparatus 9 and the home electric appliance EE to reliably output operation instructions and notifications, for example, the power reduction request signal AS2 and the power reduction instruction signal AS3 may each be transmitted a plurality of times within a short period of time of several seconds to 1 second or less, and the reception side may receive the signal a plurality of times within 1 second. Even in this case, the reception side may perform internal processing of determining the signals as a single signal. With this, even when the communication state instantaneously deteriorates, a reliable control operation can be expected.

Further, in Embodiment 1, every time an operation such as main power input, heat cooking start, etc. changes, the induction heating cooker 2 whose power consumption is controlled by the power instruction apparatus 9 transmits the operation information signals L1 to L7 as described with reference to FIG. 52. Through reception of those signals, the power instruction apparatus 9 recognizes the power input of the induction heating cooker 2, selection of the cooking menu, and the progress of the cooking process. In addition thereto, the power instruction apparatus 9 may output a signal for inquiring about the operation status at predetermined time intervals. For example, the power instruction apparatus 9 may output to the power usage control device 8A instructions for obtaining information of the request power, the cooking status, etc., at intervals of several seconds to 30 seconds.

In Embodiment 1, although the mobile phone terminal 87 is unable to perform a direct remote operation of the home electric appliance EE from outside, the mobile phone terminal 87 may be allowed to operate a home electric appliance EE other than the TV receiver 75, inside the house. The mobile phone terminal 87 may be brought close to (or in contact with) the input-output unit of the home electric appliance EE, for transmission or reception of information and command signals via short range wireless communication (NFC).

Further, in Embodiment 1, the power usage control device 8A of the induction heating cooker 2, which receives various instruction signals from the power instruction apparatus 9, is supplied with power from the exclusive power supply (built-in battery) BT2 different from the power supply circuit 31 connected to the main power switch 11, as described with reference to FIG. 27. Therefore, the signal transmission and reception can be performed with the controller 32 after the main power switch 11 of the induction heating cooker 2 is turned off. Thus, not only when an abnormality occurs, but also when the heating operation is brought to emergency stop due to an abnormality occurrence and thus the main power switch 11 is turned off, some kind of operation information signal indicating whether or not the induction heating cooker 2 is in operation can be output in response to the request from the power instruction apparatus 9. However, without providing the exclusive power supply BT2 as described above, the main power switch 11 may be opened so that the power supply to the power usage control device 8A is also simultaneously cut off. In this configuration, when the power instruction apparatus 9 outputs the signal for inquiring about the operation status to the power usage control device 8A, the power usage control device 8A cannot output any response signal. In view of this, the power instruction apparatus 9 determines that the induction heating cooker 2 is stopped. In other words, the power instruction apparatus 9 may detect the stopping state of the induction heating cooker 2 from a distant location based on the fact that no response signal is detected.

Further, in Embodiment 1, the ASP server 89A functions as a control unit installed by the seller or the repairer of the home electric appliance EE or the provider of the information service, and serves to provide various types of services relating to the home electric appliance EE through the communication networks 98A and 98B. The ASP server 89A may include a database that may provide application software for providing useful information for the healthcare instrument 410 and the activity measurement apparatus 145 and for determining the controlling operation for the healthcare instrument 410 and the activity measurement apparatus 145.

Embodiment 2

Figure 73:
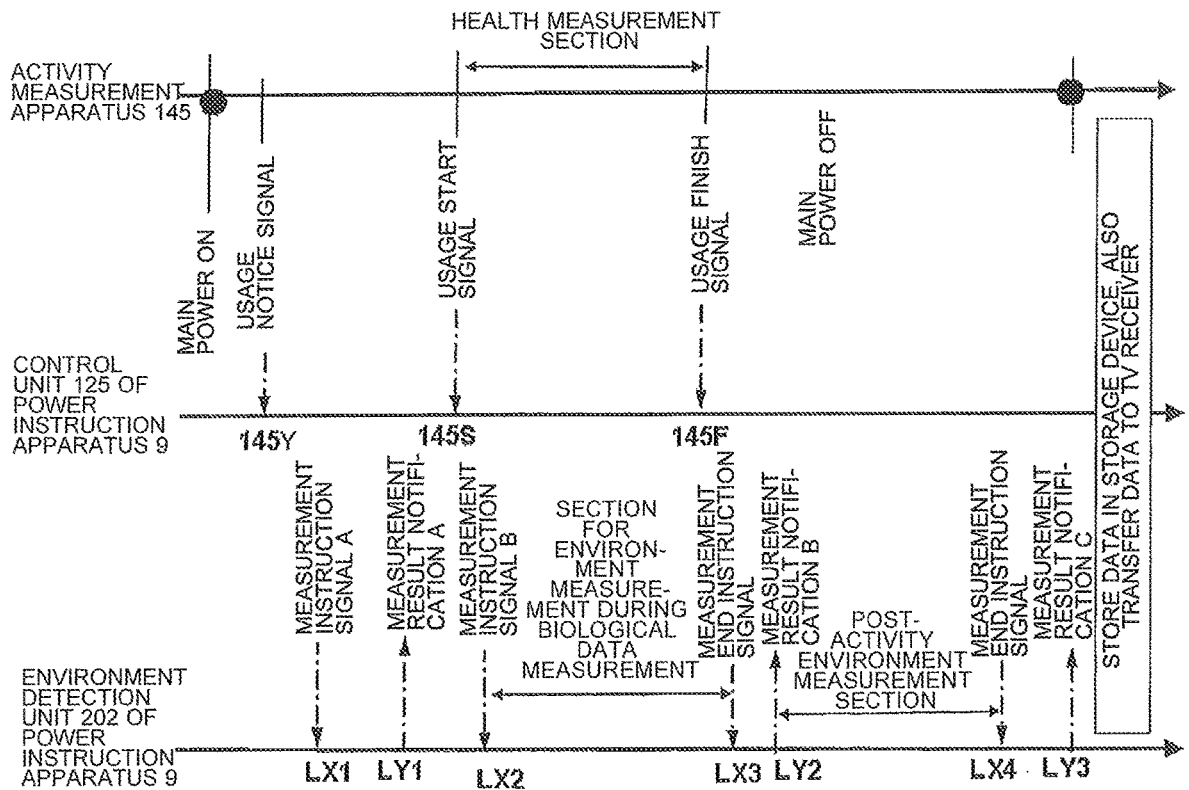
FIG. 73 is an explanatory diagram for illustrating mutual signal transmission between a power instruction apparatus and a healthcare instrument according to Embodiment 2 of the present invention in time series.

FIG. 73 is an explanatory diagram for illustrating mutual signal transmission between the power instruction apparatus 9 and the activity measurement apparatus 145 according to Embodiment 2 of the present invention in time series. The components same as or corresponding to those of Embodiment 1 are given the same reference symbols, and description thereof is omitted herein.

In Embodiment 2, when the exercise with the indoor treadmill 145A is finished, the indoor treadmill 145A transmits the usage finish signal 145F to the healthcare data processing unit 127 of the power instruction apparatus 9. When the control unit 125 of the power instruction apparatus 9 detects the reception of the usage finish signal 145F, the control unit 125 instructs the environment detection unit 202 to end the acquisition of the environment information (measurement end instruction signal LX3). Therefore, the environment detection unit 202 collects the environment information acquired during the period of exercise, and transmits the information to the power instruction apparatus 9 (measurement notification signal LY2).

The environment information acquired during the period of exercise is also transmitted to the indoor treadmill 145A as reference information. This operation is the same as Embodiment 1 so far, but Embodiment 2 has a feature in that the environment information is measured thereafter again. In other words, the environment detection unit 202 continuously acquires the environment information until a measurement end instruction signal LX4 is output. Specifically, the time at which the measurement notification signal LY2 is output is set as a start point, and, for example, the temperature, the humidity, and the dust scattering degree are measured for 30 minutes therefrom. Then, the identification information including measurement date and time is added to the measurement data of the 30 minutes (in FIG. 73, the time period indicated as "post-activity measurement section"), and the resultant is stored in the storage device 149 of the power instruction apparatus 9. Therefore, the measurement data can be read out by the TV receiver 75 at a later date to confirm the environment data during the post-activity measurement section even when the main power of the activity measurement apparatus 145 has been already turned off at the time point of a measurement result notification signal C (LY3) and thus the activity measurement apparatus 145 cannot display the measurement result.

In this manner, it is understood that the environment of the specific living space changes due to the indoor activity, and hence before the activity is started the next time, such environment information can be referred to for performing the activity in a comfortable environment. For example, immediately after the user performs hard activity indoors, the indoor dust scattering degree greatly increases. When there is a fear of adverse effects on other members of the family with breathing problems, etc., there is an advantage in that the user can make an effort so as not to significantly degrade the degree of comfort of the living space after the activity is finished, such as starting the operation of the air purifier during the activity (or in advance).

Embodiment 3

Figure 74:
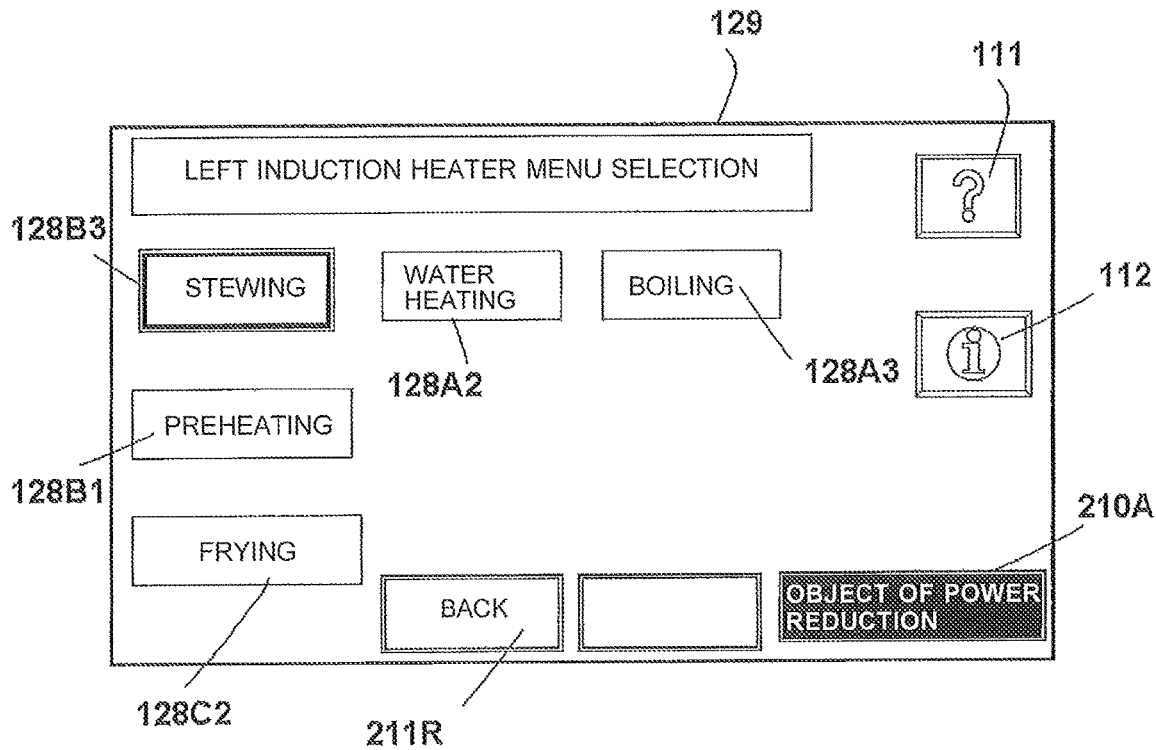
FIG. 74 is a plan view for illustrating a part of a display unit and an operation unit of an induction heating cooker according to Embodiment 3 of the present invention.
Figure 75:
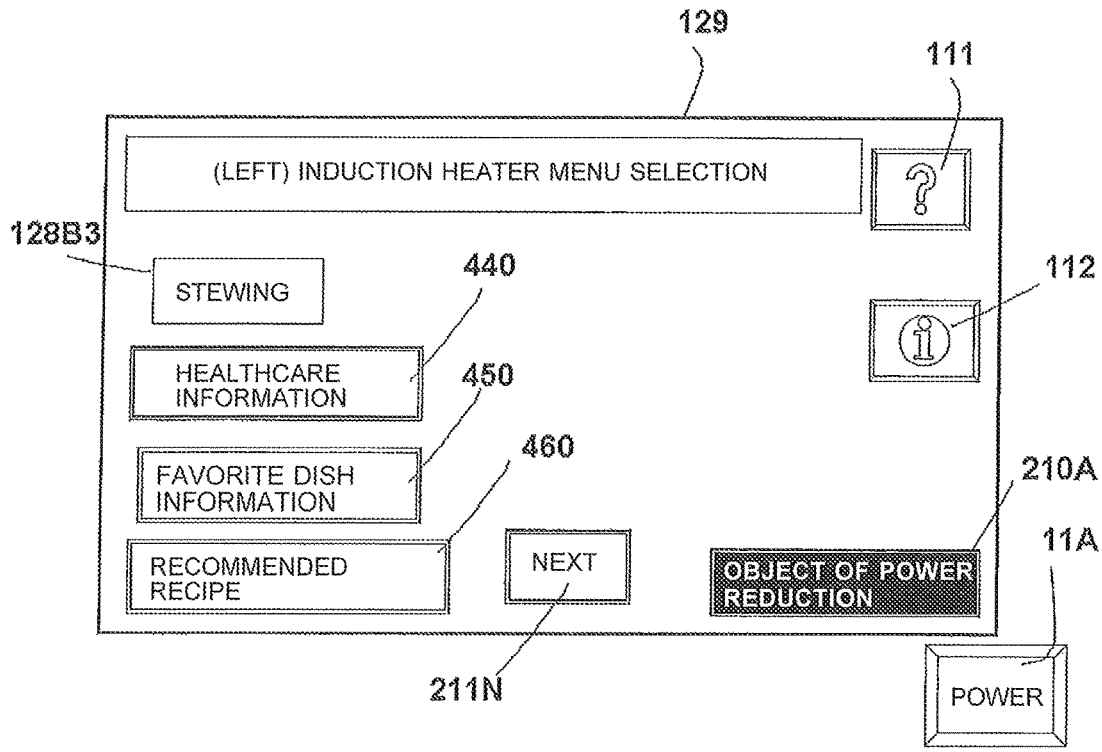
FIG. 75 is a plan view for illustrating a part of the display unit and the operation unit of the induction heating cooker illustrated in FIG. 74.
Figure 76:
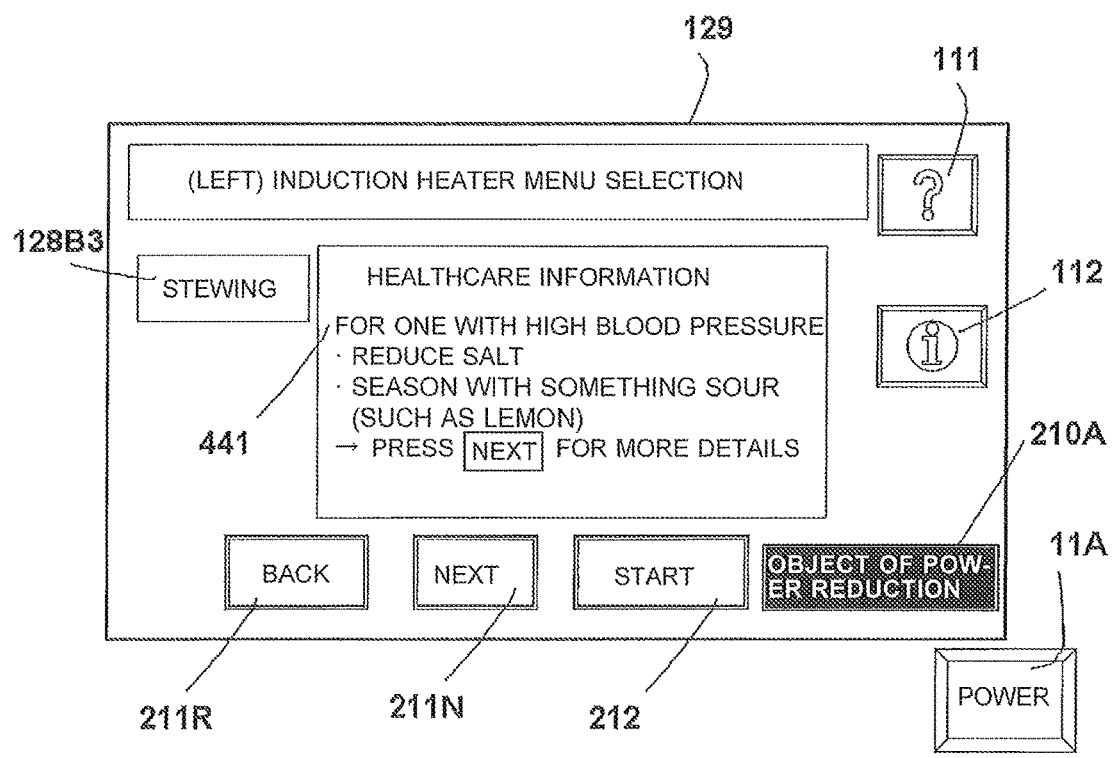
FIG. 76 is a plan view for illustrating a part of the display unit and the operation unit of the induction heating cooker illustrated in FIG. 74.
Figure 77:
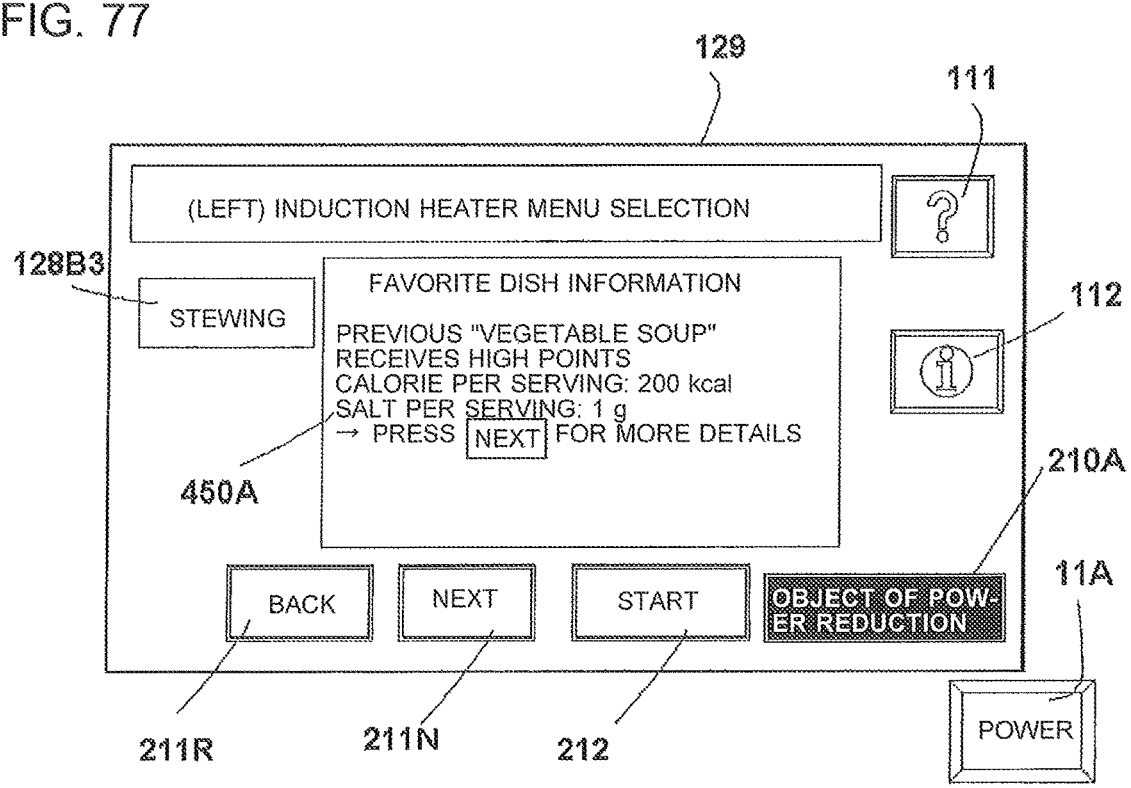
FIG. 77 is a plan view for illustrating a part of the display unit and the operation unit of the induction heating cooker illustrated in FIG. 74.
Figure 78:
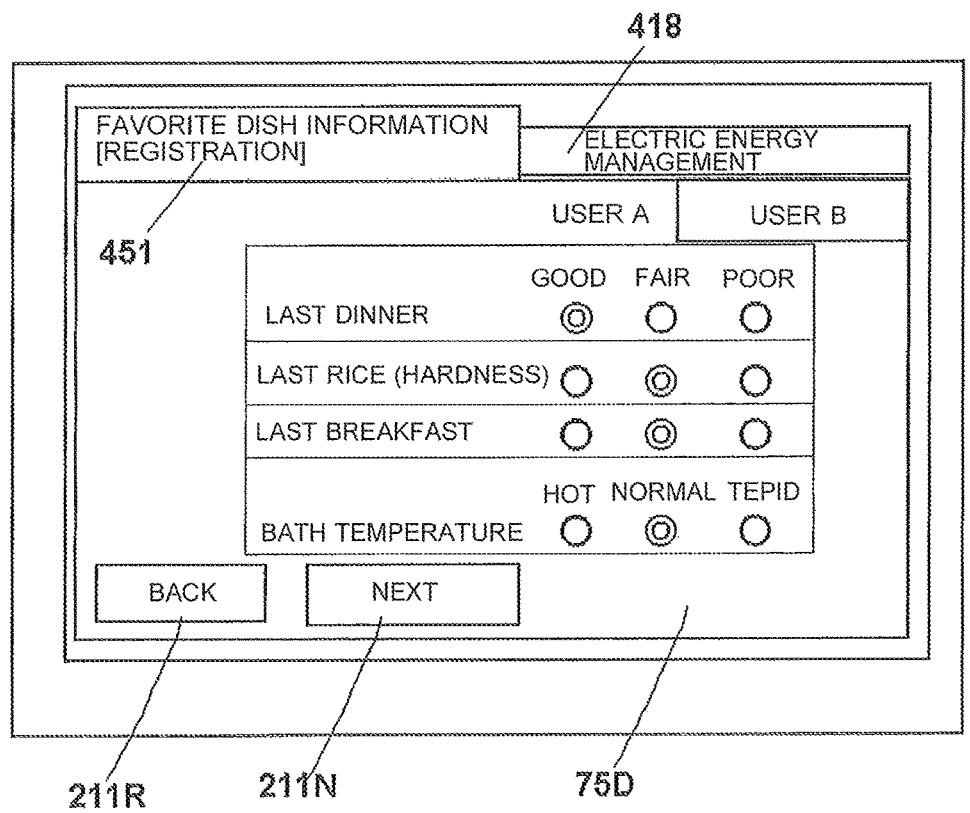
FIG. 78 is a front view for illustrating a display panel of a power instruction apparatus according to Embodiment 3 of the present invention.
Figure 79:
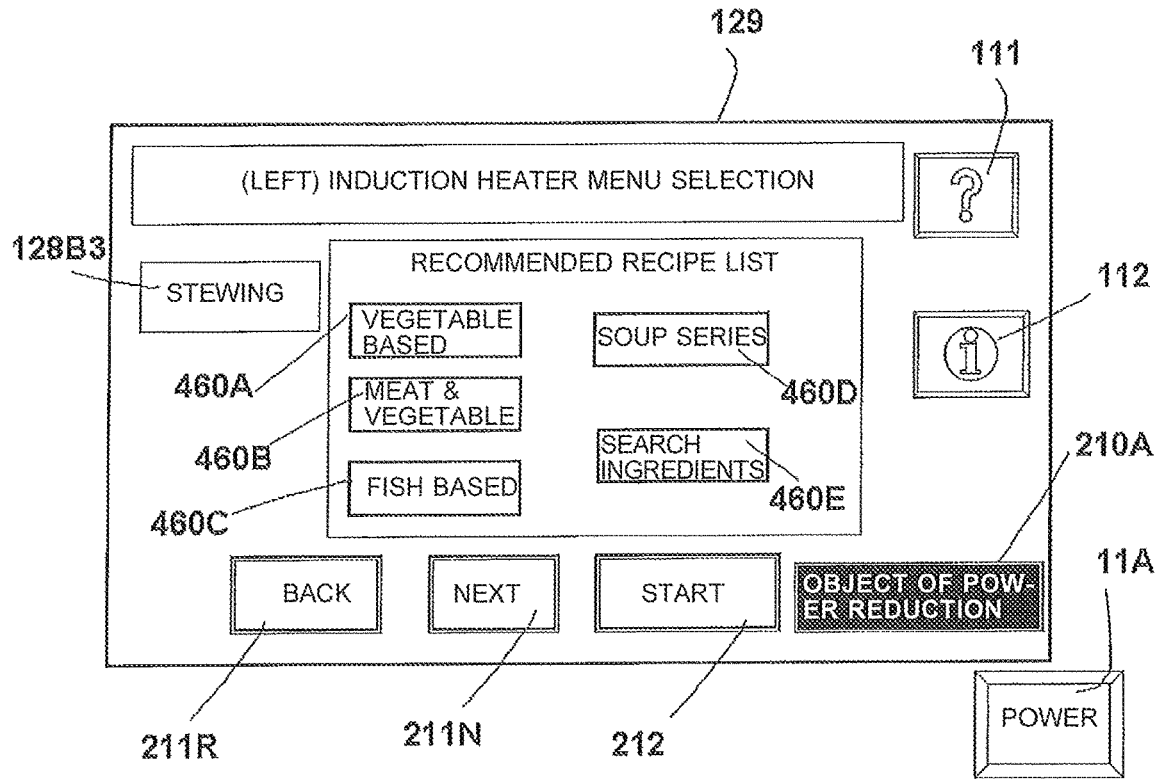
FIG. 79 is a plan view for illustrating a part of the display unit and the operation unit of the induction heating cooker illustrated in FIG. 74.
Figure 80:
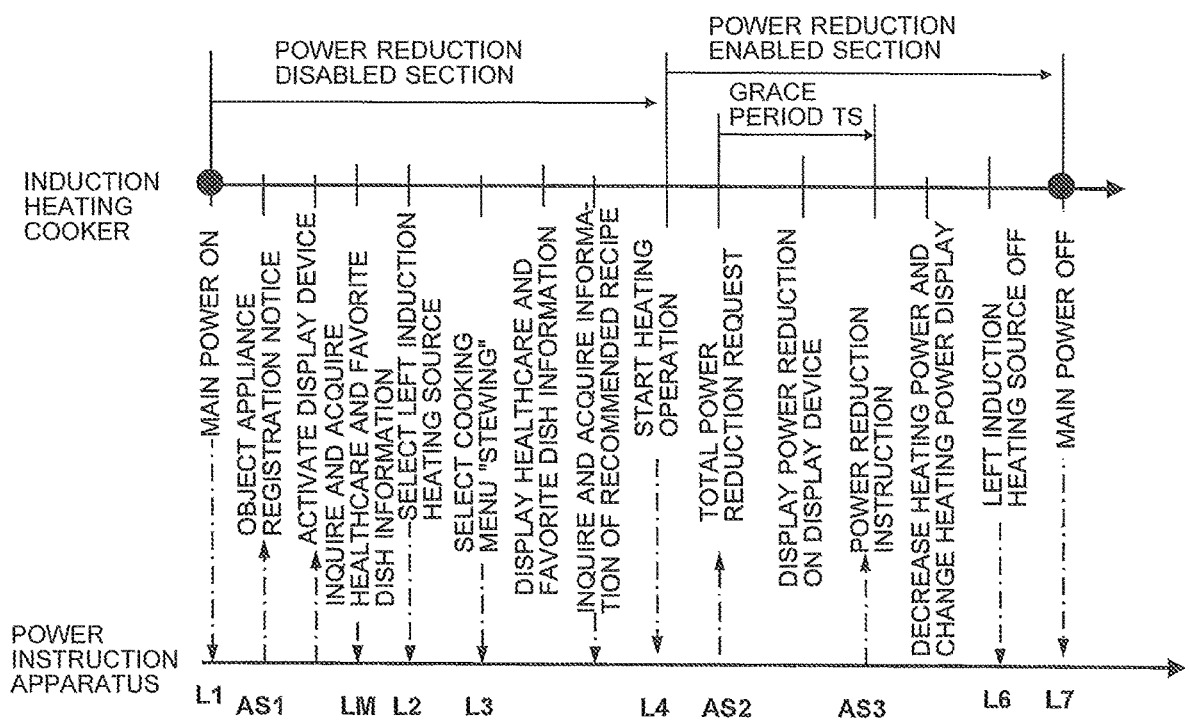
FIG. 80 is an explanatory diagram for illustrating the relationship between the operation information from the induction heating cooker and the heating process in time series.

FIG. 74 to FIG. 80 are illustrations of the power control system according to Embodiment 3 of the present invention, and the home electric appliance whose upper power limit is controlled by the power control system. FIG. 74 is a plan view for illustrating a part of the display unit and the operation unit of the induction heating cooker among the home electric appliances. FIG. 75 is a plan view for similarly illustrating a part of the display device and the operation unit. FIG. 76 is a plan view for similarly illustrating a part of the display device and the operation unit. FIG. 77 is a plan view for similarly illustrating a part of the display device and the operation unit. FIG. 78 is a front view for illustrating the display panel of the power instruction apparatus. FIG. 79 is a plan view for illustrating a part of the display unit and the operation unit of the induction heating cooker. FIG. 80 is an explanatory diagram for illustrating the relationship between the operation information from the induction heating cooker and the heating process in time series. In FIG. 74 to FIG. 80, the same components as those of Embodiment 1 are given the same reference symbols. In addition, the home electric appliances EE including the induction heating cooker 2, the rice cooker 3, the microwave oven 5, the dish washer-dryer 6, and the air-conditioning apparatus 7, the activity measurement apparatus 145, and the healthcare instrument 410 are the same as those of Embodiment 1. However, the power instruction apparatus 9 is different in that "favorite dish information", which is personal evaluation information of the meal menu and information of room temperature and bath temperature, can be recorded with respect to each of the occupants.

In FIG. 74, reference symbol 129 denotes, as described with reference to Embodiment 1, the display screen such as an LCD screen, provided in the display unit of the induction heating cooker 2 under the control of the power instruction apparatus 9. Like in Embodiment 1, the induction heating cooker 2 includes a pair of induction heaters with induction heating sources aligned in the left-right direction. When the heater 2L (not shown) on the left is selected first, the key 128A3 for selecting boil cooking, the key 12B83 for selecting stewing cooking, and so forth are displayed in a list as illustrated in FIG. 74, on the display screen 129 constituted of, for example, the LCD screen.

FIG. 74 represents the display that appears immediately after the key 12B83 for selecting stewing cooking is touched. The stewing cooking is not a priority cooking menu, and hence the first information sign 210A of "object of power reduction", indicating that the power usage may be limited during the heat cooking operation in the case that the power reduction instruction is received from the power instruction apparatus 9, is displayed in the lower right corner in the display screen 129.

When the key 12B83 for selecting stewing cooking is touched first on the screen displayed as in FIG. 74, the display content of the display screen 129 largely changes as illustrated in FIG. 75. In FIG. 75, reference symbol 440 denotes a healthcare information selection key, reference symbol 450 denotes a favorite dish information selection key, and reference symbol 460 denotes a recommended recipe selection key. Those three keys 440, 450, and 460 are also touch-type input keys like the keys 128A2, 128A3, 128B1, and 12B83 for selecting the cooking menu, and are displayed in the shape of a rectangular frame in which the titles are displayed in letters, when the input through those keys is valid. The term "recipe" herein refers to information describing a cooking method, which may also include ingredient names, amounts of use, photos of the food in process or finished, and incidental information such as salt content of the food and calorie consumption.

When the healthcare information selection key 440 is touched on the screen displayed as in FIG. 75, the display content of the display screen 129 largely changes as illustrated in FIG. 76. In FIG. 76, reference symbol 441 denotes a healthcare information display region. When any of the health-related data (e.g., blood pressure) of any family member measured by the healthcare instrument 410 is deviated from the normal range, that is, when there is a "caution data", a message to this effect is displayed in the display region 441. More specifically, words such as "A family member has high blood pressure" are displayed.

Although the blood pressure data stored in the storage device 149 of the power instruction apparatus 9 is tagged with the identification code for identifying the subject and therefore the information indicating a specific individual can also be displayed, it is herein assumed that all family members eat the same meal, and not that a special meal is cooked for a specific member. Accordingly, the personal identification information is not displayed in the example illustrated in FIG. 76.

When the favorite dish information selection key 450 is touched on the screen displayed as in FIG. 75, the display content of the display screen 129 largely changes as illustrated in FIG. 77. In FIG. 77, reference symbol 450A denotes a favorite dish information display region for displaying information of personal preference, impressions after the meal, impressions and thoughts in the living space, and so forth that the family input to the display panel 100 of the power instruction apparatus 9.

FIG. 78 is an illustration of the display screen of the display panel 100 serving as the operation unit of the use limit setting device 96 of the power instruction apparatus 9, in which the icon 451 for favorite dish information registration is displayed in the same way as the icon 418 for switching to the screen exclusive to the electric energy management and the icon 211N for proceeding to the next display screen.

FIG. 78 is an illustration of the screen for "favorite dish information registration" displayed when the icon 451 is selected. As illustrated in FIG. 78, impressions about recent meals at home, thoughts about the rice cooking mode (hardness of rice), preference of hot water temperature in the bath tub, for example higher or cooler than 40 degrees Celsius, can be input as favorite dish information. In FIG. 78, the impression of the meal eaten last evening is indicated as "good".

FIG. 79 is an illustration of the display screen 129 that appears when the recommended recipe selection key 460 is touched on the screen displayed as in FIG. 75. As illustrated in FIG. 79, the words "recommended recipe list" are displayed in the central region of the display screen 129, and recipe selection keys 460A, 460B, and 460C classifying the ingredients into three categories are displayed under the words.

Specifically, the key 460A for selecting vegetable-based recipes, the key 460B for selecting combination recipes of meat and vegetables, and the key 460C for selecting fish-based recipes are displayed. In addition, a key 460D for selecting soup recipes, and a selection key 460E for finding recipes by ingredients are also displayed at the same time. In the case of high blood pressure as described above, for example, excessive salt intake is one of the primary causes. There are two measures for improvement, that is, adopting recipes that use less salt and finding recipes that promote salt excretion.

The induction heating cooker 2 is configured to propose the two measures for improvement. Thus, the recipes tailored to the two types of measures are stored in advance in the display memory 35A (see FIG. 28) of the induction heating cooker 2. When the selection key 460E for finding recipes by ingredients is selected with the intention of promoting salt excretion from the body for example, several recipes that use, for example, lotus root are displayed on the display screen 129 of the induction heating cooker. However, a sufficient number of detailed recipes such as those that sequentially describe the ingredients and the cooking process with images may be unable to be stored in advance in the display memory 35A, because of the limitation of the memory capacity. In this example, therefore, when the user presses a key to further search for recipes (not shown) after pressing the recommended recipe selection key 460, the induction heating cooker 2 accesses the storage device 109 in the TV receiver 75 and a cooking recipe database provided by the external organization 78A, and downloads the recipes from outside. In this relation, it is preferable to add an index or keyword to the data recorded in the TV receiver 75 such as cooking programs and dietary supplement promotion programs viewed on the TV receiver 75, when storing such programs in the storage device 109, because the searching of the program can be quickly performed. In addition, the capacity for each session of downloading may be automatically limited, for example, to content (images and characters) of 1 MB or less.

When the key 211N for selecting the next screen is pressed in the healthcare information screen of FIG. 76 based on the message "Press "next" for more details" illustrated therein, two types of recommended recipes for reducing the salt intake and promoting the salt excretion tailored to those who have high blood pressure are displayed, out of "recommended recipes" as illustrated in FIG. 79.

Likewise, when any of the subjects has a high body fat rate, remedies for reducing energy intake by approximately 200 to 250 kcal per day in ordinary daily life, in order to lose 1 kg of fat each month, are suggested on the screen of FIG. 76, because it is preferable to improve the menu in addition to performing some activity in order to reduce body fat without stress. Further, recommended recipes (ingredients and cooking process for one person), the calorie value of the recipe, and actual use amount of salt are displayed.

FIG. 80 is an explanatory diagram for illustrating in chronological order how the home electric appliance EE, e.g., the induction heating cooker 2 recognizes whether the home electric appliance EE is the object of power control of the power instruction apparatus 9. FIG. 80 represents the case of the induction heating cooker 2. In FIG. 80, reference symbols L1 to L7 each denote the operation information signal transmitted from the induction heating cooker 2 to the power instruction apparatus 9, as in Embodiment 1.

Referring to FIG. 80, when the cooking menu of "stewing" is selected, the induction heating cooker 2 outputs the operation information signal L3 that is the menu selection information signal, after which three keys of the healthcare information selection key 440, the favorite dish information selection key 450, and the recommended recipe selection key 460 are displayed at the same time on the display screen 129 of the induction heating cooker 2, as illustrated in FIG. 75. When the recommended recipe selection key 460 is touched, the instruction signal is transmitted to the power instruction apparatus 9, and in return the induction heating cooker 2 acquires the recipe information from the power instruction apparatus 9.

The induction heating operation may be started upon touching one of the three keys of the healthcare information selection key 440, the favorite dish information selection key 450, and the recommended recipe selection key 460. For example, when the start key 212 is touched after the healthcare information is displayed as illustrated in FIG. 76, the induction heating operation is immediately started.

Regarding the transmission of the inquiry signal LM from the induction heating cooker 2 to the power instruction apparatus 9 for acquiring the healthcare information as illustrated in FIG. 80, the induction heating cooker 2 has extracted the caution data out of the measurement data for a "predetermined data collection period" (e.g., 7 days for high blood pressure) before the date of the inquiry. In the case where no caution data has been extracted during such a period, the healthcare information is determined as "unavailable", and the healthcare information selection key 440 is left undisplayed, or a message of "no data" is displayed instead. However, the healthcare information includes categories that have to be improved over an extended period (e.g., body fat rate), and hence the collection period is prolonged (e.g., 1 month) depending on the category of the healthcare information. In the case of high blood pressure also, the "predetermined data collection period" can be prolonged to 1 month if desired.

When the healthcare information selection key 440 is used at the step of selecting the cooking menu, the caution data is extracted only from the "predetermined data collection period" as above, however when the existing data display command key 425 illustrated in FIG. 20 is used, all the measurement data accumulated in the past (including data other than the caution data) can be displayed.

The screen illustrated in FIG. 78 includes pages for the respective evaluators, and when the occupant selects their own page with an evaluator selection icon 452 and inputs the evaluation, the input result is immediately stored in the storage device 109 of the power instruction apparatus 9, similarly to the measurement data (metabolic data, activity data, etc.) of the healthcare processing unit 116. When the amount of accumulated data increases, data more than one month old may be automatically transferred to the high-capacity memory of the TV receiver 75, or may be automatically deleted (erased).

The power control system and the home electric appliances are configured as described above, and therefore provide the same advantageous effects as those provided by Embodiment 1. In addition, the favorite dish information of the family members is centralized in the power instruction apparatus 9, so that the information can be retrieved on the display panel 100 of the power instruction apparatus 9, the induction heating cooker 2, or the rice cooker 3 whenever necessary, to utilize the information as reference for cooking.

Further, when there is caution data in the biological data acquired by the healthcare instrument 410, the caution data can be displayed on the display screen 129 of the induction heating cooker 2 in the healthcare information display region 441 (see FIG. 76). Therefore, when the user starts the operation of the induction heating cooker 2, the user can perform heat cooking in consideration of the occupant (family member) with the caution data. When a display part similar to the healthcare information display region 441 is also provided in a cooker other than the induction heating cooker 2 or other home electric appliances EE, the home electric appliance can be operated in consideration of the occupant (family member) with the caution data.

Embodiment 4

Figure 81:
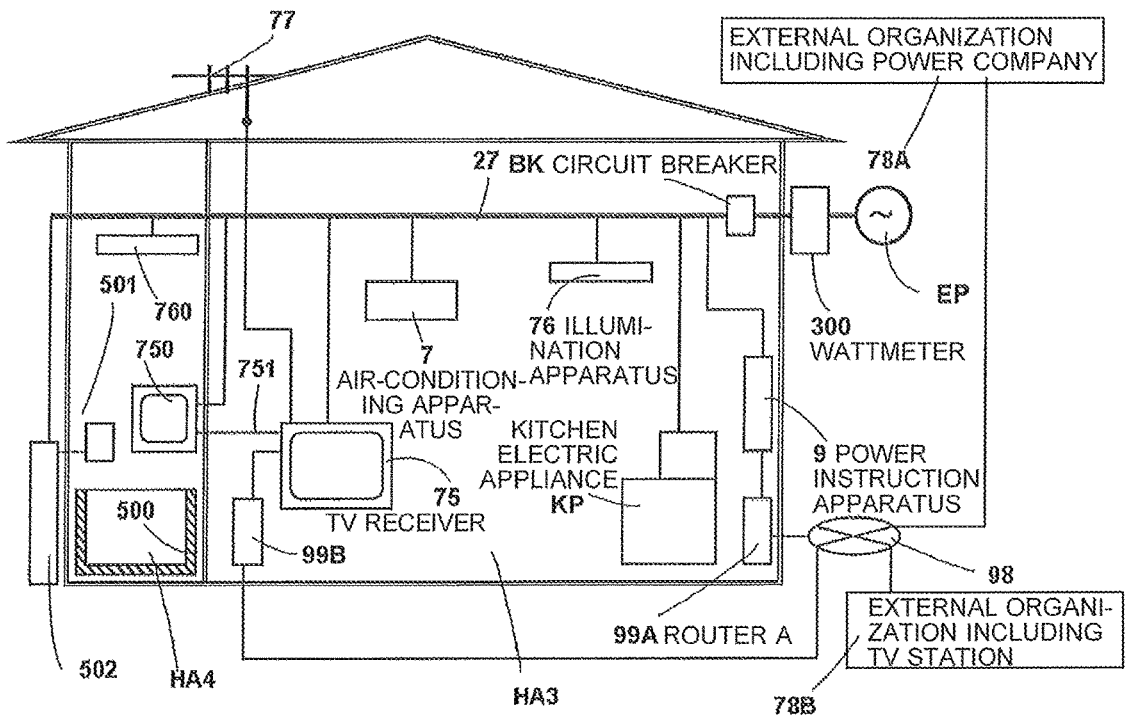
FIG. 81 is a diagram for illustrating a general configuration of a power control system for home electric appliances according to Embodiment 4 of the present invention.
Figure 82:
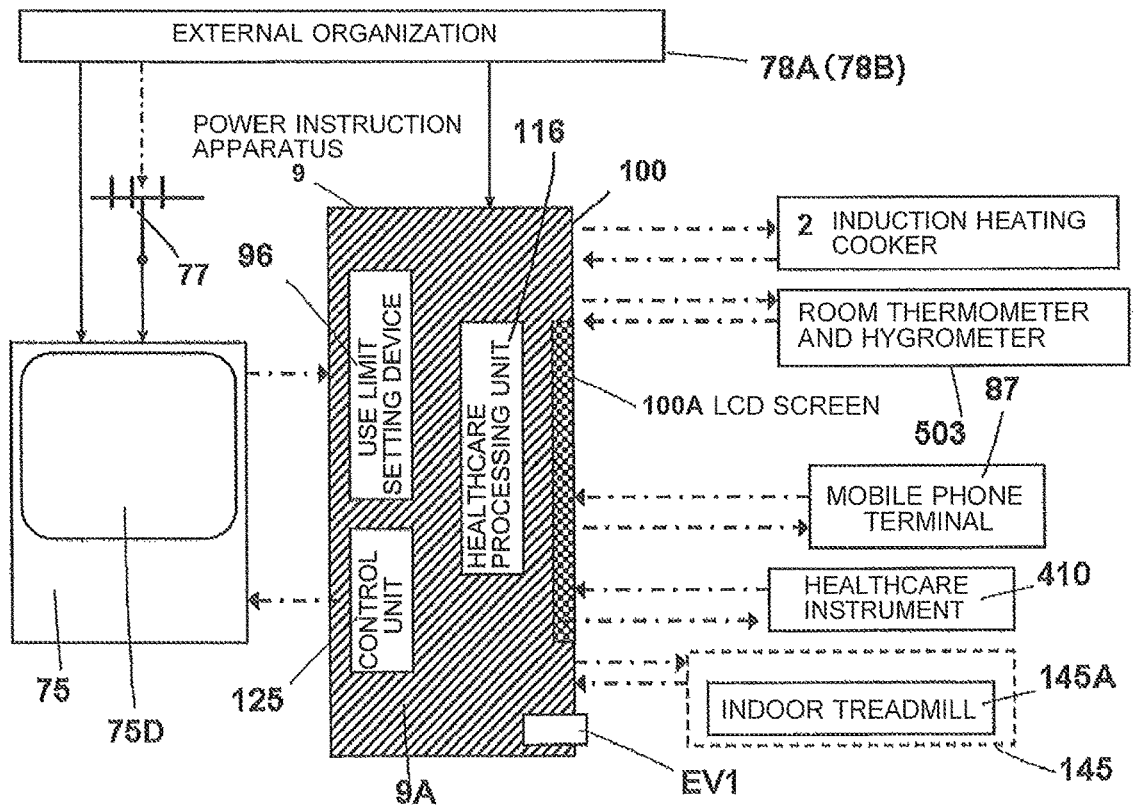
FIG. 82 is a block diagram for illustrating, partially in a vertical cross section, a configuration of a main part of the power instruction apparatus illustrated in FIG. 81.
Figure 83:
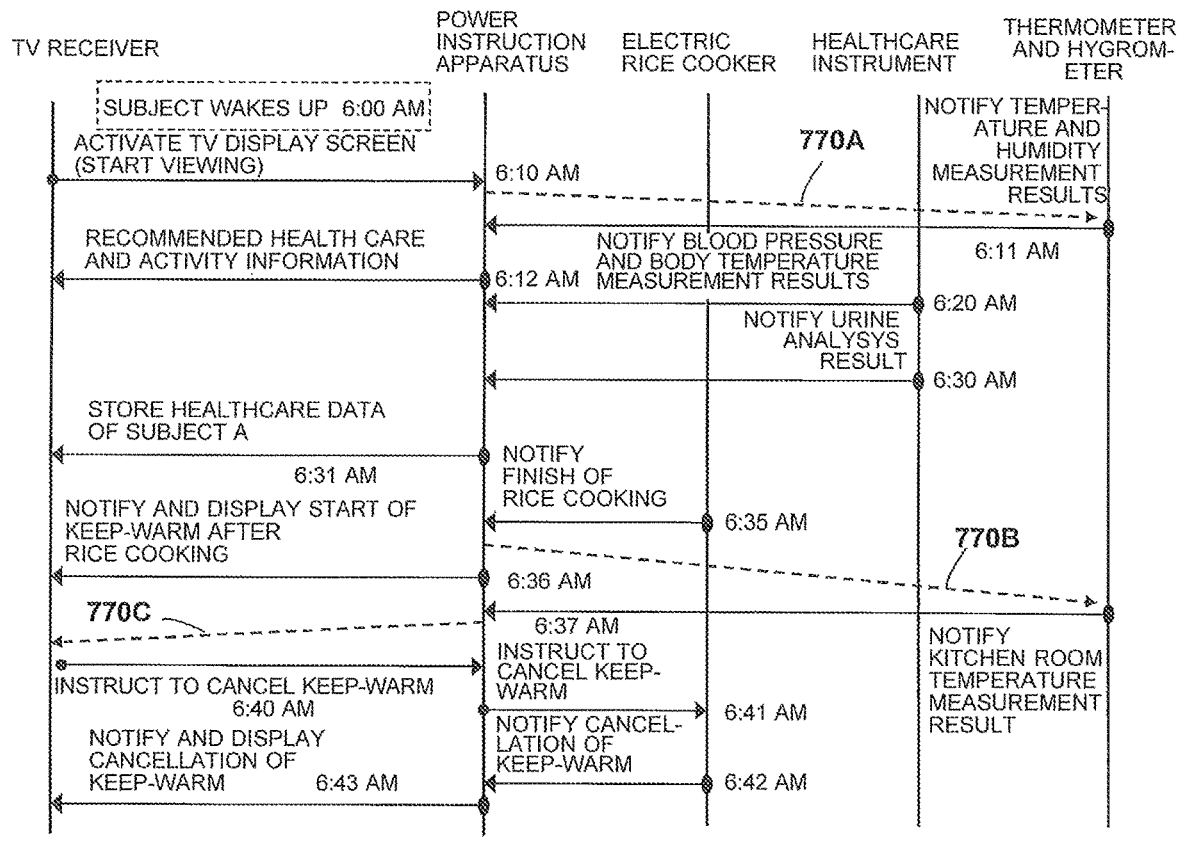
FIG. 83 is an explanatory diagram for illustrating signal transmission between the power instruction apparatus illustrated in FIG. 81 and a healthcare instrument in time series.

FIG. 81 is a schematic diagram for illustrating general configurations of a power control system for home electric appliances and a health management system according to Embodiment 4 of the present invention. FIG. 82 is a block diagram for illustrating, partially in a vertical cross section, a configuration of a main part of the power instruction apparatus according to Embodiment 4 of the present invention, and FIG. 83 is an explanatory diagram for illustrating signal transmission between the respective main parts of the power control system for home electric appliances and the health management system in time series. In the drawings, the components same as or corresponding to those of Embodiment 1 are given the same reference symbols.

In FIG. 81, reference symbol HA3 denotes a living space in a house. Reference symbol HA4 also denotes a living space, actually a bathroom. Reference symbol 500 denotes a bath tub installed in the bathroom, to which hot water is supplied from an electric hot water system 502 installed outside. Reference symbol 501 denotes a remote controller for the hot water system mounted to an inner sidewall of the bathroom HA3, to be operated by the user to start the hot water supply or set the temperature of the hot water.

The remote controller 501 for the hot water system is electrically connected to the electric hot water system 502, which is connected to the power supply line (main circuit) 27 to receive the power supply.

Reference symbol 750 denotes a TV receiver for a bathroom placed inside the bathroom HA3 and connected to the power supply line 27, and is connected to the (main) TV receiver 75 placed in the living room via a specified signal cable 751. The signal cable is used to transmit broadcast signals and the signals from the power instruction apparatus 9, however the transmission and reception of signals may be performed utilizing the power supply line as a power line carrier, or by wireless infrared communication, instead of the wired connection with a specialized cable. Reference symbol 760 denotes the illumination apparatus for the bathroom.

The bathroom TV receiver 750 according to Embodiment 4 is provided primarily for receiving pictures, sounds, and information in the bathroom, and is configured, though not provided with all of the functions of the TV receiver 75 in the living room, to receive and display the same broadcast content as the TV receiver 75 and all types of information transmitted from the power instruction apparatus 9. However, the bathroom TV receiver 750 does not include a high-capacity memory like that of the TV receiver 75. The storage unit of the bathroom TV receiver 750 is only capable of storing a short movie, and the metabolic data acquired by the healthcare instrument 410 is not accumulated. Further, when the TV receiver 75 receives the emergency earthquake information from the external organization 78B or through the power instruction apparatus 9, or when an earthquake detection device (though not shown, mounted in the power instruction apparatus 9 and the kitchen electric appliance KP) detects seismic vibration, the bathroom TV receiver 750 is turned on at the same time as the TV receiver 75, and the related information is displayed on the display screen.

As illustrated in FIG. 82, the main body 9A of the power instruction apparatus 9 includes the healthcare processing unit 116 configured to set the power usage of the electric appliances EE including the kitchen electric appliance KP, the control unit 125 constituted of electronic circuits, primarily a microcomputer, and the healthcare processing unit 116 operated under the control of the control unit 125. The LCD screen 100A having a screen size of 10 to 15 inches is mounted to the front surface of the main body 9A.

The main body 9A of the power instruction apparatus 9 is formed into a box shape having a certain thickness in FIG. 82, but the main body 9A actually has a flat plate shape having a thickness of approximately 2 to 3 cm and a weight of approximately 2 kg. Accordingly, although the main body 9A is usually hooked on the kitchen wall, the main body 9A can be placed on a kitchen table or moved to another room as necessary. The power instruction apparatus 9 includes the power cord (not shown) connectable to the power supply line 27, however the main body 9A includes therein a high-performance storage battery (not shown), so as to work without the power supply line 27. When the power supply through the power cord is disconnected, the power source is immediately switched to the storage battery automatically. The communication between the healthcare processing unit 116 and each of the electric appliances EE in the household is performed via infrared ray or wireless communication.

In addition, the main body 9A of the power instruction apparatus 9 is connected via a device, e.g., a router (not shown) to the external organization 78A having an exclusive server for providing various types of information and content through the Internet. The power instruction apparatus 9 is set so as to enable, when information is transmitted from the external organization 78A, immediate confirmation of the content of the information. The healthcare processing unit 116 in the main body 9A of the power instruction apparatus 9 includes the information reception unit 137 configured to receive the information output from the healthcare instruments 410, for example, the blood pressure meter 410A, as described in Embodiment 1. The reception unit 137 is configured to receive the information acquired by the mobile phone terminal 87, the activity information and calorie consumption information acquired by the activity measurement apparatus (e.g., indoor treadmill 145A), and so forth.

Reference symbol 503 denotes composite measurement devices each including a thermometer and a hygrometer, located at least at four positions in total, specifically, on the inner wall of the kitchen space, in the living room where the TV receiver 75 is placed, on the inner wall of the bedroom where the TV receiver 75 is placed, and inside the bathroom. The composite measurement devices 503 are thus installed at locations separated from each other, and each includes a transmission unit and a reception unit so as to individually perform infrared or wireless communication with the main body 9A of the power instruction apparatus 9. Every time the composite measurement device receives a measurement instruction signal from the power instruction apparatus 9, the composite measurement device transmits the measured temperature and humidity to the power instruction apparatus 9.

The environment detection unit 202 automatically transmits the measurement result of the temperature and the humidity at intervals of a certain time (e.g., 5 minutes) to the power instruction apparatus 9. The composite measurement devices 503 are each given a different identification code based on their location, and the identification code is added as a header to the temperature and humidity measurement data when the composite measurement devices 503 transmits the temperature and humidity data, and therefore the power instruction apparatus 9 can identify which location or living space the measurement data corresponds to.

FIG. 83 is an explanatory diagram for illustrating mutual signal transmission between main constituent parts of the power instruction apparatus of the home electric appliance and the healthcare instrument in time series. The home electric appliance EE whose upper power limit is individually controlled by the power instruction apparatus 9 is exemplified by the TV receiver 75 and the rice cooker 3. Here, it is assumed that the timer of the rice cooker 3 is set the night before in the kitchen so as to finish the rice cooking at 6:35 a.m. the next morning.

Referring to FIG. 83, the operation of the power instruction apparatus 9 and the healthcare instrument 410 starting from the wake-up time is described. One person first gets up at 6:00 a.m. and presses the designated switch of the TV receiver 75 provided in the living room to watch a TV program. At this point, the activation signal of the LCD screen 75D of the TV receiver is immediately transmitted from the TV receiver 75 to the power instruction apparatus 9 (time: 6:10 AM). The power instruction apparatus 9 outputs the measurement instruction signal, as indicated by a broken-line arrow 770A in FIG. 83, to the composite measurement device 503 (thermometer and hygrometer) in the living room where the TV receiver 75 is located, and requests acquisition of the latest environment information. The composite measurement device 503 transmits the measurement result of the temperature and humidity to the power instruction apparatus 9 (time: 6:11 AM).

The power instruction apparatus 9 then recommends the occupant to measure the blood pressure with the healthcare instrument 410 within 30 minutes after waking up, unless the data of temperature and humidity in the living room where the TV receiver 75 is located is not at an uncomfortable level to the occupant. The determination of whether or not the occupant feels discomfort with the temperature and humidity (hereinafter referred to as "discomfort degree determination") is similar to the "comfort degree determination" performed by the environment detection unit 202 in Embodiment 1. In the same temperature and humidity, when the environment is determined as "discomfort" in the discomfort degree determination, the environment is not determined as comfort in the comfort degree determination (in other words, the two determination results do not conflict with each other). In Embodiment 4, the discomfort degree determination is executed by exclusive software incorporated in the control unit 125 of the power instruction apparatus 9.

After the two types of environment measurement, that is, temperature and humidity, the power instruction apparatus 9 recommends performing light exercise such as radio calisthenics or relaxing exercise. The power instruction apparatus 9 further recommends using the activity measurement apparatus 145 in the living space that is not determined as "discomfort".

Such recommendation (suggestion for action) of calisthenics and exercise for improving health by using the activity measurement apparatus 145 is displayed on the screen of the TV receiver 75 in words and images, and is also output with voice messages for notification to the viewer. When the TV receivers 75 are located in the living room and the bedroom on the second floor, and when the occupant who has woken up turns on the TV receiver 75 in the bedroom, the TV receiver 75 in the living room is not activated. Thus, the display screen 75 of the TV receiver 75 in the bedroom on the second floor acquires and determines the environment information as described above, and also displays the recommendation of calisthenics and exercise in a specific comfortable living space (time: 6:12 AM).

When the occupant measures the blood pressure thereafter, the blood pressure meter 410A automatically transmits the blood pressure measurement data (example of biological data) to the healthcare processing unit 116 of the power instruction apparatus 9, after the measurement (time: 6:20 AM). In the case where the occupant goes to the lavatory and measures the urine components with the urine analyzer, the urine analyzer 410G automatically and immediately transmits the urine analysis result data to the healthcare processing unit 116 of the power instruction apparatus 9, after the measurement.

The healthcare processing unit 116 of the power instruction apparatus 9 immediately transmits the blood pressure data and the urine analysis data to the TV receiver 75 which has already been activated. Thus, when the occupant turns on the TV receiver in the bedroom on the second floor upon waking up, the TV receiver 75 on the second floor automatically displays the healthcare data. Here, it is also possible to activate the TV receiver 75 in the living room on the first floor instead of that on the second floor to view the healthcare data. As above, the healthcare data of the subject A who is now awake is temporarily stored in the healthcare processing unit 116 of the power instruction apparatus 9, and then recorded and accumulated in the storage device 109 of the TV receiver 75 in the living room (time: 6:31 AM).

When the rice cooker 3 transmits the information indicating that the rice cooking has finished and the keep-warm phase is entered to the power instruction apparatus 9 at 6:35, the power instruction apparatus 9 outputs the instruction to report the latest measurement result of the indoor temperature and humidity to the composite measurement device 503 in the kitchen where the rice cooker 3 is located, as indicated by a broken-line arrow 770B in FIG. 83.

The composite measurement device 503 transmits the indoor temperature and humidity in the kitchen to the power instruction apparatus 9. The TV receiver 75 outputs the instruction to stop the keep-warm operation to the power instruction apparatus 9, in the case where it is determined that the keep-warm operation is unnecessary, after the reception of the notice from the power instruction apparatus 9 indicating that the rice cooking has finished and the keep-warm phase is entered, and the reception of the temperature and humidity information indicated by an arrow 770C (time: 6:40 AM). The power instruction apparatus 9 then instructs the rice cooker 3 to stop the keep-warm operation (6:41 AM). Thereafter, the rice cooker 3 notifies the power instruction apparatus 9 that the keep-warm operation has been stopped, and the power instruction apparatus 9 sends a notification to the effect that the keep-warm operation has been stopped, to the TV receiver 75 which output the instruction to stop the keep-warm operation. Accordingly, by viewing the TV receiver 75, it is understood that the rice cooking has been finished but the keep-warm operation is not being performed, from the words or illustration displayed on the display screen 75D.

Here, although the energy-saving effect of the rice cooker 3 is improved when the keep-warm operation is stopped, the freshly cooked rice may emit an offensive odor with the lapse of time. However, when the room temperature around the rice cooker 3 is sufficiently low (e.g., winter time), the keep-warm operation may be skipped. Accordingly, the power instruction apparatus 9 compares the room temperature with criteria that permit the keep-warm phase to be skipped specified in the rice cooker 3, and outputs the instruction to stop the keep-warm operation to the rice cooker 3 in the case where the rice cooker 3 is in the environment that satisfies the criteria. Thus, when the keep-warm operation is stopped from a remote place through the TV receiver 75 and the power instruction apparatus 9, unlike the case where the user actually goes to the place where the rice cooker 3 is located and stops the keep-warm operation, the power instruction apparatus 9 looks up the situations that restrict the use of the rice cooker 3 and the criteria specified therein, and outputs the instruction to stop the keep-warm operation only when the situation is on the safe side, so as not to provoke an erroneous operation by the user.

The rice cooker 3 is configured so as to automatically enter the keep-warm phase upon finishing the rice cooking operation. Therefore, when one of the occupants stops the keep-warm operation through the TV receiver 75, the remaining occupants (family members) are unaware of such operation, and also the occupant who stopped the keep-warm operation may forget having done so, and hence trouble may be later incurred (e.g., an occupant may misunderstand that the rice cooker 3 is broken) when it is known after a considerable period of time after the completion of the rice cooking that the keep-warm operation has been stopped. Accordingly, the notice that the keep-warm operation has been stopped is displayed on the TV receiver 75, so that all the occupants may be made aware of the operation. In addition, also in the TV receivers 75 other than the one to which the instruction about the keep-warm operation has been input, the fact that the keep-warm operation has been stopped is displayed on the screen of the electric energy management of the home electric appliances EE, and the same information is also displayed on the display screen 100A of the power instruction apparatus 9, so that the occupant can be made aware that the keep-warm operation has been stopped. As a matter of course, the user can visually confirm immediately that the keep-warm operation has been stopped by viewing the LCD unit 49, or whether the keep warm switch 55 is lit up, on the rice cooker 3.

With the configuration according to Embodiment 4, for example, in the case where the external organization 78B outputs the Earthquake Early Warning, or when the house itself shakes because of the earthquake while the occupant is taking a bath, the occupant can immediately notice the occurrence on the bathroom TV receiver 750, and hence is exempted from falling into a panic owing to the sudden unexpected occurrence of an earthquake and getting hurt trying to escaping from the bathroom in haste. With the bathroom TV receiver 750, the occupant can also confirm the healthcare data in a relaxed state inside the bathroom, and register their favorite dish information. Here, even when an occupant located outside the bathroom presses the emergency cut-off button 119A to disconnect the power supply all at once, the illumination apparatus 760 in the bathroom is kept on.

Further, the temperature of the hot water for bathing can be confirmed and set to a preferred temperature with the remote controller 501 for the hot water system, so as to realize a comfortable bathing temperature. In the case where the bathroom TV receiver 750 is configured to display the special icon 414 of "emergency power cut-off" and the special icon 415 of "emergency earthquake and tidal wave news received" like the screen of the TV receiver 75 of Embodiment 1, the power supply to a predetermined type of electric appliances in the household can be disconnected by selecting the icon 414 of "emergency power cut-off" without the need to go to the place where the main body 9A of the power instruction apparatus 9 is located, and also the occupants can start evacuating the house in preparation for the tidal wave. Thus, a higher level of safety can be achieved.

Also in Embodiment 4, the activity measurement apparatus 145 outputs the usage notice signal 145Y. The healthcare instrument 410 also outputs the usage notice signal 410Y. When the user tries to first use the activity measurement apparatus 145 or the healthcare instrument 410 before activating the TV receiver 75, immediately before that, the power instruction apparatus 9 acquires the latest environment information of the living space where the activity measurement apparatus 145 or the healthcare instrument 410 is placed. Therefore, also in Embodiment 4, the temperature and humidity, the cleanliness, etc., of the air of the living space where the activity measurement apparatus 145 is used for aerobic exercises or other activities can be checked in advance.

Further, in Embodiment 4, when the usage notice signal 145Y of the activity measurement apparatus 145 or the usage notice signal 410Y of the healthcare instrument 410 is output, the power instruction apparatus 9 acquires the environment information of the living space as described above. The control unit 125 has an operation program set so that the result of the "discomfort degree determination" executed based on the acquired environment data is not only displayed on the TV receiver 75 and the display panel 100 but also transmitted to the mobile phone terminal 87 via wireless communication at the same time or substantially at the same time. Therefore, there is also an advantage in that the occupant can confirm the living space having the environment suitable for measurement of the amount of activity without activating the TV receiver 75.

Embodiment 5

Figure 84:
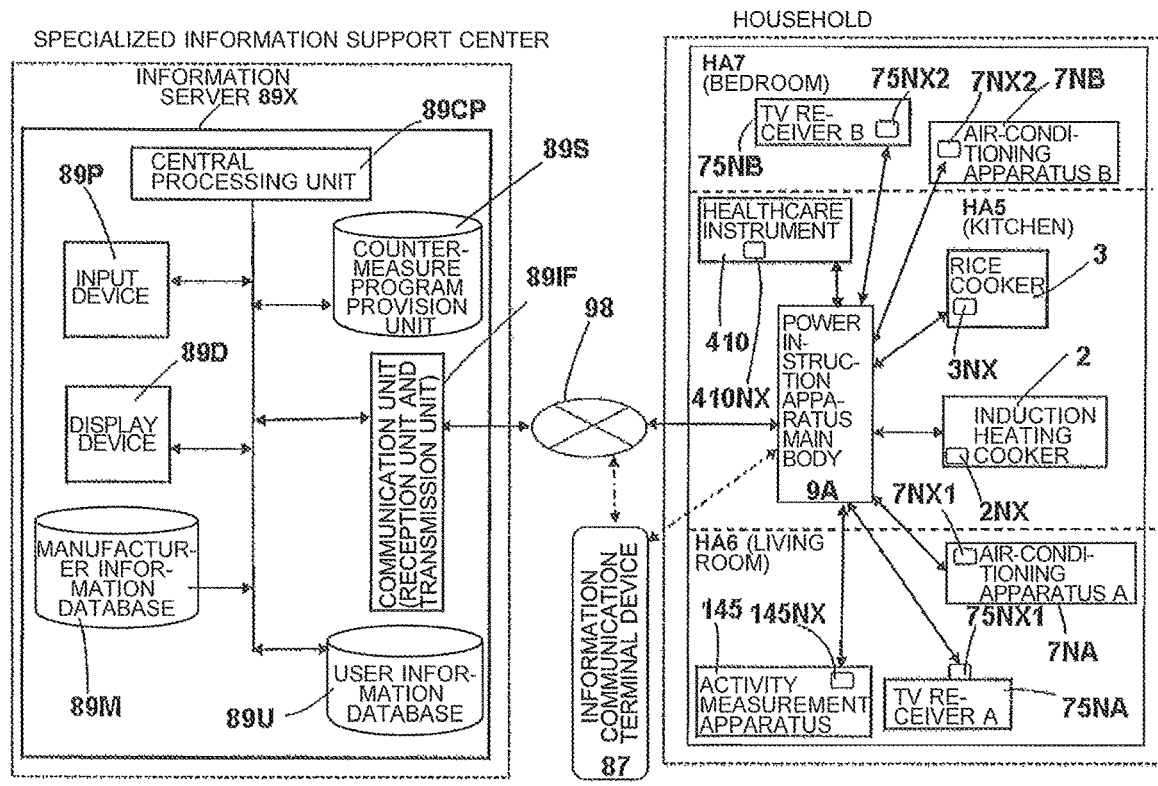
FIG. 84 is a block diagram for illustrating a general configuration of a power control system and an information server according to Embodiment 5 of the present invention.

FIG. 84 is a flowchart for illustrating the operation process of an at-home abnormality monitoring mode of the power control system and the abnormality determination processing of the home electric appliance operation server according to Embodiment 5 of the present invention. In FIG. 84, the same components as those of Embodiment 1 are given the same reference symbols. Further, all of the induction heating cooker 2, the rice cooker 3, the microwave oven 5, the dish washer-dryer 6, and the air-conditioning apparatus 7 have basically the same structure as those in Embodiment 1, but differ from those in Embodiment 1 in that a wireless communication unit capable of directly transmitting information to or receiving information from the control unit 125 of the power instruction apparatus 9 is individually provided.

Further, the healthcare processing unit 116, the environment detection unit 202, the human body detection unit 203, the healthcare instrument 410, and the activity measurement apparatus 145 are the same as those of Embodiment 1. In Embodiment 1, the information server ISV is exclusive to the home electric appliance EE, but an information server 89X in Embodiment 5 is not exclusive to the home electric appliance EE, and has a function of providing information contributing also to the user of the activity measurement apparatus 145 and the healthcare instrument 410. Further, the information server 89X is made up of a web server.

In FIG. 84, reference symbol 2NX denotes a wireless communication unit, which is a wireless communication device capable of directly transmitting information to or receiving information from the control unit 125 of the power instruction apparatus 9 in the induction heating cooker 2, and reference symbol 3NX denotes a wireless communication unit, which is a wireless communication device capable of directly transmitting information to or receiving information from the control unit 125 of the power instruction apparatus 9 in the rice cooker 3.

There are two air-conditioning apparatus 7. A first air-conditioning apparatus 7A installed in the living room includes a wireless communication unit 7X1, which is a wireless communication device capable of directly transmitting information to or receiving information from the control unit 125 of the power instruction apparatus 9. The other air-conditioning apparatus 7B is called a second air-conditioning apparatus, which is installed in the bedroom and includes a wireless communication unit 7X2, which is a wireless communication device capable of directly transmitting information to or receiving information from the control unit 125 of the power instruction apparatus 9.

There are two TV receivers 75. A first TV receiver 75NA installed in the living room includes a wireless communication unit 75NX1, which is a wireless communication device capable of directly transmitting information to or receiving information from the control unit 125 of the power instruction apparatus 9. The other TV receiver is called a second TV receiver 75NB, which is installed in the bedroom and includes a wireless communication unit 75NX2, which is a wireless communication device capable of directly transmitting information to or receiving information from the control unit 125 of the power instruction apparatus 9.

In Embodiment 5, as illustrated in FIG. 64, when the controller 32 determines that an abnormality has occurred in the induction heating cooker 2, the controller 32 immediately brings the induction heating operation to emergency stop, and transmits the operation information signal L6E indicating the emergency stop of the heating source to the power instruction apparatus 9. After that, the abnormality detection unit ES transmits to the power instruction apparatus 9 the monitoring data successively acquired in the past ("abnormality monitoring data acquisition section ET1" illustrated in FIG. 64).

The abnormality monitoring data transmitted from the abnormality detection unit ES includes the above-mentioned operation information signals L1 to L7, the object appliance registration signal AS1, the request signal (notice signal) AS2 for decreasing the total electric power of the home electric appliance, and the power reduction instruction signal AS3. Therefore, the abnormality monitoring data includes data of the timing to measure the data (e.g., temperature and voltage value) actually representing the abnormality, and data of, for example, the timing to transmit the operation information signals L1 to L7 and the timing to receive the power reduction instruction signal AS3.

The power control system according to Embodiment 5 of the present invention has a feature in that the information server 89X of a specialized information support center is provided as the external organization 78A connected to the power instruction apparatus 9 such that mutual communication is possible.

The one household in Embodiment 5 is divided into three living spaces in FIG. 84. The first living space corresponds to a kitchen HA5 in which the rice cooker 3, the induction heating cooker 2, the healthcare instrument 410, and the main body 9A of the power instruction apparatus 9 are installed.

The second living space corresponds to a living room HA6 in which the first TV receiver 75NA and the air-conditioning apparatus 7NA are installed. The third living space corresponds to a bedroom HA7 in which the TV receiver 75NB and the air-conditioning apparatus 7NB are installed. Other plurality of living spaces HA and home electric appliances are present, but illustration thereof is omitted in FIG. 84 for simplifying the description.

The information server 89X of the specialized information support center and the home electric appliances EE of the household are connected to each other with use of the communication network 98. The home electric appliance EE transmits its operation state to the information server 89X via the power instruction apparatus 9 with use of signals such as the operation information signals L1 to L7.

The information transmitted from the information server 89X of the specialized information support center to the power instruction apparatus 9 (hereinafter referred to as "assistance information") includes useful information (for the user) relating to how to handle or restore the home electric appliance EE when the home electric appliance EE is out of order or after the home electric appliance EE is subjected to automatic emergency stop (including instructions and explanations of the special operation method for restoring the home electric appliance EE), and useful information (for the user) relating to the analysis result of the cause of the failure of the home electric appliance EE, recurrence prevention, and request for repair or inspection.

The network 98 is an arbitrary communication network capable of performing bidirectional communication. The communication network may be, for example, the Internet, a wired communication network, or a satellite communication network. Further, different communication networks may be used between the transmission path from the household to the information server 89X (referred to as "upload path"), and the reverse transmission path from the information server 89X to the household (referred to as "download path"). The mobile phone terminal 87 illustrated in FIG. 84 is an example of a high-function mobile phone terminal, and the mobile phone terminal 87 may be used for any one of the above-mentioned "upload path" and "download path". For example, the home electric appliance EE may transmit a signal representing its operation state to the power instruction apparatus 9. In order for the power instruction apparatus 9 to represent the operation state of the home electric appliance EE, the power instruction apparatus 9 may convert the signal into a signal suitable for high-speed communication and transmit the obtained signal to the mobile phone terminal 87. Then, the mobile phone terminal 87 may notify the information server 89X of the operation state of the home electric appliance EE via the network 98.

The information server 89X includes a central processing unit 89CP serving as a host computer of the specialized information support center. The information server 89X further includes an input device 89P, a display device 89D, a communication unit 89IF, a manufacturer information database (technical information database) 89M, a user information database 89U, and a countermeasure program provision unit 89S configured to store application software for the home electric appliances EE.

The central processing unit 89CP performs processing such as updating the user information database 89U or creating special information as subsequently described. The input device 89P is configured to receive input operation by a specialized engineer of the specialized information support center or other people in charge. Through operation of the input device 89P, instructions such as construction and update of the user information database 89U or the manufacturer information database 89M to be subsequently described can be given.

The "manufacturer" herein refers to the designer, the manufacturer, and the seller of the above-mentioned home electric appliances EE. The "manufacturer" further includes the designer, the manufacturer, and the seller of the healthcare instrument 410 and the activity measurement apparatus 145. As necessary, the "manufacturer" further includes a specialized sports agency or a consultant providing an exercise training program for effectively performing exercise with use of the activity measurement apparatus 145.

The display device 89D causes the display screen to display various types of data in accordance with the control of the central processing unit 89CP. The communication unit 89IF corresponds to a reception unit and a transmission unit serving as an interface with respect to the communication network 98.

In the manufacturer information database 89M, the technical information of the home electric appliances EE is accumulated in advance for each type or model number. Further, the technical information of the healthcare instrument 410 and the activity measurement apparatus 145 is further accumulated in advance for each type or model number. When the home electric appliances EE have changes in details of the specification depending on the manufacturing number, the specification change depending on the manufacturing number is also accumulated.

The "technical information" herein includes various types of data such as rated usage conditions of the home electric appliances EE (e.g., rated usage power, electrical conditions such as voltage, and environment conditions such as an allowance range of the indoor temperature for use), specifications, main specifications, main apparatuses, optional components, optional functions, transition of the operation state, the display content in each operation state, processing to be performed in each operation state, restriction conditions for safe and appropriate usage, and usage precautions. The technical information of the manufacturer information database is provided from the above-mentioned manufacturer, and partially includes unique know-how of the manufacturer, for example, lifetime experiment data or weather-resistant data obtained when the home electric appliance EE is manufactured.

In the user information database 89U, the user information of the home electric appliance EE is accumulated. The user information herein refers to information obtained by converting the operation state of the home electric appliance EE received from the home electric appliance EE into an arbitrary form useful for creating provision information in the specialized information support center. The user information includes, for example, list information of the home electric appliances EE owned by each household, the living space in which the home electric appliance EE is used and its floor area, the volume of the living space, and past notification history from the user. The user information database 89U is updated as needed to reflect the operation state received from the home electric appliance EE, and is constructed as a database that can be searched by the input device 89P and the central processing unit 89CP. In the user information database 89U, the user information of the healthcare instrument 410 and the activity measurement apparatus 145 is also accumulated in advance for each type or model number. The user information further includes information of the upper limit of the total electric power of one household set to the circuit breaker BK, and, among the pieces of information stored in the storage device 149 of the power instruction apparatus 9, information of the second capacity limit set by the occupant to limit the power consumption of the various home electric appliances EE as the power control-related information.

For each user of the home electric appliance EE, a specific identifier (hereinafter referred to as "user ID", having the same aim as the "user-specific information" described in Embodiment 1) is allocated in advance. The user ID is recorded in the home electric appliance at an appropriate timing such as when the home electric appliance EE is sold or when the installation work is completed. For example, in the case of the built-in type induction heating cooker 2, when the installation work into the kitchen furniture is completed, the user ID is recorded in the storage device 32R of the controller 32 by the contractor or the manufacturer. Specific identifiers are allocated in advance also for the healthcare instrument 410 and the activity measurement apparatus 145, respectively, similarly to the user ID of the home electric appliance EE so that the user can identify those devices. Those identifiers are recorded into the devices when the devices are manufactured.

Further, for each home electric appliance EE, a specific identifier (hereinafter referred to as "home electric appliance ID", having the same aim as the "device-specific information" described in Embodiment 1) is allocated in advance. The home electric appliance ID is recorded in the home electric appliance EE when the home electric appliance EE is manufactured. For example, in the case of the induction heating cooker 2, when the installation work into the kitchen furniture is completed, the home electric appliance ID is recorded in the storage device 32R of the controller 32 by the contractor or the manufacturer. Also, for each healthcare instrument 410, a specific identifier (hereinafter referred to as "healthcare instrument ID") is allocated in advance. The healthcare instrument ID is recorded in the healthcare instrument 410 when the healthcare instrument 410 is manufactured. Similarly, also for each activity measurement apparatus 145, a specific identifier (hereinafter referred to as "activity apparatus ID") is allocated in advance. The activity apparatus ID is recorded in the activity measurement apparatus 145 when the activity measurement apparatus 145 is manufactured.

Each home electric appliance EE transmits, at a predetermined timing, the operation information signals L1 to L7 representing the operation state of each home electric appliance EE to the power instruction apparatus 9. Upon reception of the operation information signals L1 to L7, the power instruction apparatus 9 may sequentially transmit the operation information signals L1 to L7 to the information server 89X via the network 98.

Each home electric appliance EE may transmit the operation information signals representing the operation state at an arbitrary timing and frequency. For example, each home electric appliance EE may transmit the operation information signals regularly at a frequency of about once every 15 seconds or 30 seconds while the power is supplied. However, when a situation that seems to be abnormal occurs in the home electric appliance EE, the home electric appliance EE immediately performs the abnormality determination processing. For example, in the induction heating cooker 2, when the controller 32 determines whether or not the abnormality has occurred and determines that the abnormality has occurred, the controller 32 transmits the operation information signal L6E representing the emergency stop of the induction heating source to the power instruction apparatus 9. The abnormality determination processing includes a state in which, during the heat cooking operation, the user presses an operation key entirely unrelated to the continuation or end of the heat cooking operation many times, and a state in which the user simultaneously presses the operation keys or the operation buttons for contradictory instructions of the operation start and the operation stop. The controller 32 identifies those states as an example of improper operation, and transmits a special operation state signal L8 different from the above-mentioned operation information signals L1 to L7 to the power instruction apparatus 9. In the case of the operation state signal L8, the emergency stop of the induction heating source is not performed. The operation is not stopped also in the case of other home electric appliances such as the rice cooker 3 and the air-conditioning apparatus 7.

When the operation information signal L6E representing the emergency stop of the induction heating source is transmitted to the power instruction apparatus 9, the power instruction apparatus 9 outputs an instruction signal LE1 requesting the provision of the abnormality monitoring data to the home electric appliance (in this case, the induction heating cooker 2). Then, the induction heating cooker 2 transmits the monitoring data successively acquired in the "abnormality monitoring data acquisition section ET1" to the power instruction apparatus 9 (data transmission signal LE2). At this time, the induction heating cooker 2 simultaneously transmits various types of instruction information received from the power instruction apparatus 9. In other words, the induction heating cooker 2 also transmits the "power limitation information of the home electric appliance" to the power instruction apparatus 9. With this, the information server 89X can more accurately analyze the external influence in the induction heating cooker 2.

Then, the operation information signal representing that the main power is turned off is transmitted to the power instruction apparatus 9. Upon reception of each of the signals L6E, LE1, LE2, and L7, the power instruction apparatus 9 may transmit the received content of each of the signals directly to the information server 89X, but in Embodiment 5, the power instruction apparatus 9 collectively transmits the fact that the signals of the whole process have been received from the first reception of the operation information signal L1 to the reception of the signal L7 in time series. At this time, the signals L6E, LE1, LE2, and L7 are also transmitted. Therefore, the induction heating cooker 2 employs a method of temporarily storing and accumulating the operation information signals in a predetermined area of the storage device 149, and then collectively transmitting the operation information signals at once to the information server 89X.

When the operation information signal L6E representing the emergency stop of the induction heating source is not transmitted to the power instruction apparatus 9, the signals LE1 and LE2 are not output thereafter. Therefore, the information server 89X is set to not transmit any signal, to thereby reduce the information processing load of the network 98 and the information server 89X. In other words, in the series of heat cooking in which the operation information signal L7 representing that the main power is turned off normally without the occurrence of the abnormality is received, the power instruction apparatus 9 does not transmit any operation information signal or environment information. However, as subsequently described, when the induction heating cooker 2 identifies a state where the user is pressing the operation key entirely unrelated to the continuation or end of the heat cooking operation many times, upon identification of such a state, the induction heating cooker may transmit the special operation state signal L8 to the power instruction apparatus 9, and then the special operation state signal L8 may be directly transmitted to the information server 89X. In such a case, during the induction heat cooking or before the cooking starts, the information server 89X provides the correct operation method, for example, a procedure of a method of setting the heating power or setting the reservation time, as an example of the assistance information.

The operation information (including the abnormality monitoring data of the induction heating cooker 2) transmitted from the power instruction apparatus 9 is transmitted from the communication unit 89IF to the central processing unit 89CP as the abnormal operation information of the induction heating cooker 2. The central processing unit 89CP automatically performs specialized investigation and analysis of the abnormality operation of the induction heating cooker 2 and creates the assistance information based on the received operation information of the induction heating cooker 2, the technical information relating to the induction heating cooker 2 accumulated in the manufacturer information database 89M, and the user information accumulated in the user information database 89U.

For example, in the current case of the emergency stop of the induction heating cooker 2, the central processing unit 89CP may create the assistance information representing that, for example, the bottom surface of the metal pot being the heating object to be used is deformed, thereby losing the initial flat bottom surface state, and thus the bottom surface is excessively raised from the upper surface of the top plate 14, which is estimated as a situation where the heating power from the induction heating coil 2LC is not transmitted sufficiently, or that the top plate 14 is still in a high-temperature state even after the emergency stop, and hence is required to be prevented from being touched for at least 10 minutes.

As described above, it is assumed that the manufacturer assistance information includes processing to be performed when an abnormality occurs in the home electric appliance EE, and the user information includes list information of the home electric appliances EE owned in each household. In this case, the central processing unit 89CP that has received the usage state information first retrieves the user information database 89U with use of the user ID and the home electric appliance ID as retrieval keys, and then confirms that the home electric appliance EE is installed in the household.

Next, the central processing unit 89CP retrieves the manufacturer information database 89M with use of the home electric appliance ID and the device operation state as retrieval keys, and then determines the processing to be performed in this state. Examples of the processing to be performed in this state include processing of restoring the home electric appliance EE to a predetermined normal state, and processing of calling a person in charge of the operation of the information server 89X.

The central processing unit 89CP can create the assistance information for the user of the home electric appliance EE by such database retrieving processing. Further, the central processing unit 89CP can create the assistance information with use of an artificial intelligence method.

After that, in order to transmit the created assistance information to the induction heating cooker 2 having the problem, the communication unit 89IF transmits the assistance information to the power instruction apparatus 9 via the communication network 98. The transmitted assistance information is recorded in the storage device 149 of the power instruction apparatus 9, and is also transmitted to the induction heating cooker 2 in the household. In the induction heating cooker 2, the controller 32 receives the assistance information via the power usage control device 8A or other appropriate reception units.

The power instruction apparatus 9 does not transmit the operation information signal L6E to the information server 89X at the stage at which the power instruction apparatus 9 receives the operation information signal L6E from the induction heating cooker 2, and hence the assistance information from the information server 89X does not arrive before the main power of the induction heating cooker 2 is turned off. However, when the operation information signal L6E is transmitted to the information server 89X as it is upon reception to request rapid assistance information provision, the assistance information is available before the main power is turned off. In such a case, the display unit (central display unit) 16 of the induction heating cooker 2 still maintaining the display function can display the assistance information. Further, the voice synthesizer 38 can audibly notify the user of the content of the assistance information.

Meanwhile, the central processing unit 89CP uses the operation information (including the abnormality monitoring data of the induction heating cooker 2) transmitted from the power instruction apparatus 9 to update the user information database 89U. Further, the received operation information is classified and arranged to update the user information database 89U based thereon. For example, the central processing unit 89CP calculates the abnormal heat cooking state that tends to occur in the induction heating cooker 2 based on material determination information of the metal pot used when the induction heating cooker 2 is in the abnormal state or based on information of the executed heating power (input voltage or input power), and accumulates the results as the user information in the user information database 89U. The user information database 89U is updated as needed based on the received operation information, and the assistance information is obtained with use of the user information database 89U. In this manner, better assistance information can be provided.

While the user information accumulated in the user information database 89U is insufficient, in particular, while classified and typical information obtained in other home electric appliances (in the case of the induction heating cooker 2 of the new model described above, the induction heating cooker of the old model, or of a conventional model) is mainly accumulated at the initial stage, the central processing unit 89CP mainly refers to the technical information accumulated in the manufacturer information database 89M to create the assistance information. In this case, the specialized information support center may cause the display device 89D to display the received abnormal operation information of the home electric appliance EE, and the engineer or the person in charge of the operation described above may use the input device 89P to provide the defined assistance information or correct the assistance information as appropriate. The user information database 89U collects abnormal operation information of a large number of home electric appliances EE of a large number of households along with the elapse of time, and hence the database is gradually constructed to include user information sufficient for creating the assistance information.

In the description above, the home electric appliance EE provides the operation information (including the abnormality monitoring data of the induction heating cooker 2) to the information server 89X, but when the operation information is transmitted via the power instruction apparatus 9, the installation location of the home electric appliance, that is, the environment information of the living space in which the home electric appliance is present is also transmitted as a set (in a pair). Therefore, when the central processing unit 89CP analyzes the cause of the abnormal operation, more correct analysis is possible. For this purpose, in the user information database 89U, the environment during use and the abnormality occurrence state are classified for each home electric appliance (for each home electric appliance ID).

Further, in the description above, neither the power instruction apparatus 9 nor the home electric appliance EE transmits the type or the content of the assistance information desired by the user to the information server 89X, but the type or the content of the assistance information desired by the user may be transmitted thereto. For example, when the user requests the "returning method or return operation method" such that the emergency stop state can be immediately cancelled to start a normal operation, the assistance information therefor can be provided. In this case, transmission from the home electric appliance EE or the power instruction apparatus 9 requires input of the type or the content of the assistance with a certain code, etc., but the home electric appliance EE or the power instruction apparatus 9 may be set to automatically transmit this code as well. A simultaneous usage analysis of the electric appliances EE may be added as an example of the assistance information. For example, through experience of a case where, during use of the induction heating cooker 2, the power reduction instruction signal AS3 is received from the power instruction apparatus 9 many times to reduce the power, the information server 89X outputs notification as the assistance information that a power shortage state has occurred due to the usage state of other home electric appliances EE in this case. For example, as one of the types of assistance information, the user is notified of the power shortage state caused by, during the use of the induction heating cooker 2, simultaneous use of the electric heating appliance (e.g., electric stove) being one of the "registered appliances" by another occupant in a living space other than the kitchen. Further, the information server 89X provides suggestions of the method of using the induction heating cooker 2, such as there is not a significant influence on cooking even if the heating power setting of the induction heating cooker 2 is decreased by 1 stage. Still further, suggestions may be given such as, instead of using a different electric appliance EE (electric heating appliance in the example above), the air-conditioning apparatus 7 (with a humidification function) may be used for smaller power consumption, which is also desired for improving environment (humidity shortage) of the living space. In other words, assistance information can be obtained not only for the correct usage method or failure support of only one home electric appliance EE, but also for the usage method of other electric appliances EE. Also regarding the environment of the space where the home electric appliance EE is installed, the environment data such as the temperature and the humidity measured by the environment detection unit 202 is transmitted to the information server 89X, and hence highly-reliable assistance information matching with the household living space and the usage state of the electric appliance EE can be obtained.

Further, as described above, in the induction heating cooker 2, the controller 32 identifies the state in which, during the heat cooking operation, the user presses the operation key entirely unrelated to the continuation or end of the heat cooking operation many times, or the state in which the user simultaneously presses the operation keys or the operation buttons for contradictory instructions of the operation start and the operation stop as an example of improper usage, and transmits the special operation state signal L8 different from the above-mentioned operation information signals L1 to L7 to the power instruction apparatus 9. Therefore, in the case of this operation state signal L8, the induction heating source is not brought to the emergency stop, but, assuming that the user is not familiar with using the induction heating cooker 2 yet, the information server 89X may provide, to the induction heating cooker 2, the suggestion information indicating how to use the induction heating cooker 2 before starting cooking as part of the assistance information provision. When the operation state signal L8 is output, the operation state signal L8 may be stored in the storage device 149 of the power instruction apparatus 9 or the controller 32 (storage device 32R) of the induction heating cooker 2, and when the main power of the induction heating cooker 2 is turned on again, the incorrect operation may be pointed out or the correct operation may be displayed on the display unit (central display unit) 16.

The information server 89X includes the countermeasure program provision unit 89S storing the application software for coping with individual abnormality cases (hereinafter referred to as "countermeasure software"). Therefore, when the central processing unit 89CP analyzes the operation information (including the abnormality monitoring data of the induction heating cooker 2) transmitted from the power instruction apparatus 9, and determines that it is better to provide the countermeasure software for the control program of determining the operation of the controller 32 of the induction heating cooker 2, the central processing unit 89CP transmits the countermeasure software together with the above-mentioned assistance information from the communication unit 89IF to the power instruction apparatus 9, or transmits a URL code of a website for downloading the countermeasure software together with the above-mentioned assistance information, to thereby urge the user to take a countermeasure. The countermeasure software may rewrite the control program of the controller 32 of the induction heating cooker 2 in the following matter. The mobile phone terminal 87 receives the above-mentioned assistance information from the power instruction apparatus 9, and the mobile phone terminal 87 downloads the countermeasure software from the information server 89X in accordance with the assistance information. Then, the controller 32 reads the countermeasure software via the short range communication (NFC) input-output unit 401 of the induction heating cooker 2. The "countermeasure software" referred to herein is the same as "improved software" to be subsequently described as another embodiment.

As is apparent from the description above, according to Embodiment 5 illustrated in FIG. 84, useful information such as effective countermeasures and recurrence prevention measures for abnormality of the home electric appliance EE and the cause of the abnormality is available from the information server 89X of the specialized information support center connected outside of the household via the network 98. Therefore, this embodiment provides the effect that the user of each household can automatically fix problems of the home electric appliances EE without asking the manufacturer. Further, even when the user cannot fix the problems alone, the user can quickly obtain some useful suggestions, and hence can feel relief. On the other hand, the manufacturer can collect useful information such as information of the actual usage state or the actual failure state of the home electric appliance EE, and can quickly fix minor problems or small failures due to the usage state of the user, or give suggestions to the user. As compared to a related-art countermeasure of devoting human resources such as a "customer support center" for support of customers, there is an advantage in that the cost for support can be significantly reduced.

The description above refers to only failures and abnormality occurrence problems of the home electric appliance EE, but information for assistance can be similarly provided to the user (person subjected to measurement) for the activity measurement apparatus 145 and the healthcare instrument 410. For example, the user of the activity measurement apparatus 145 can be provided with an explanation of effective execution content of daily exercise or training, or how to correctly view the measurement data. Further, useful information such as the method of correctly using the healthcare instrument 410, how to view abnormality data when measured, and suggestions for fitness and meals for health maintenance can be provided to the user.

The environment information of the living space in which the activity measurement apparatus 145 or the healthcare instrument 410 is used is also provided to the specialized information support center to be used for creation of appropriate assistance information, and hence useful information of the indoor temperature or the room temperature can also be obtained in terms of health and degree of comfort. For example, aerobic exercise in a living space having a dust scattering degree higher than an allowable value has adverse effects on the respiratory system. Therefore, it is meaningful to give recommendations in advance to the user of the activity measurement apparatus 145, e.g., the indoor treadmill to pay attention to the environment and use the environment improvement apparatus, e.g., the air purifier. In the case of the activity measurement apparatus 145, the environment information of the living environment may be obtained during the section of environment measurement during activity illustrated in FIG. 68, or during a period including periods prior to and after the section. In the case of the healthcare instrument 410, the environment information of the living environment may be obtained during the section of environment measurement during biological data measurement illustrated in FIG. 72, or during a period including periods prior to and after the section. Desired conditions may be input to the information server 89X such as outputting a notification from the power instruction apparatus 9 when information representing a specific environment such as an environment causing heat stroke is obtained, and some kind of warning may be output from the power instruction apparatus 9 when the information server detects any dangerous environment condition.

The power instruction apparatus 9 may have a function as the information server 89X. In other words, the power instruction apparatus 9 may have a function to create the assistance information for the home electric appliance EE, the activity measurement apparatus 145, and the healthcare instrument 410 in the household.

In this case, the above-mentioned power instruction apparatus 9 uses the above-mentioned communication network 98 at a frequency of once a day, for example, to thereby download the content of the manufacturer information database 89M of the information server 89X to the storage device 149.

Similarly, the power instruction apparatus 9 uses the above-mentioned communication network 98 at a frequency of once a day to download the content of the user information database 89U of the information server 89X to the storage device 149. The information to be downloaded is only data relating to the home electric appliance EE connected to the power instruction apparatus 9 among the pieces of information accumulated in the user information database 89U and the manufacturer information database 89M. With this, the power instruction apparatus 9 may be an information provision apparatus including a database exclusive to the household.

According to Embodiment 5, the press-button 26Q of the assistance request switch 26S or the help mode key 111 described in Embodiment 1 may be pressed at any time to confirm the method of correctly operating the induction heating cooker 2 or precautions for setting the heat cooking conditions from the information server 89X of the specialized information support center connected outside of the household via the network 98.

At the first stage at which the main power switch 11 is turned on and the display screen 129 is activated, that is, at a stage at which no heating source to be used or cooking menu is selected, when any one of the help mode key 111 and the press-button 26Q of the assistance request switch 26S is touched, the guidance of the basic method of using the induction heating cooker 2 is displayed on the display screen 129. In this case, when setting is made in advance by the user, the induction heating cooker 2 requests the operation assistance information from the information server 89X to the power instruction apparatus 9 upon operation of the help mode key 111 or the press-button 26Q of the assistance request switch 26S. For example, when the induction heating cooker 2 was improperly used previously but is not damaged, for example, when the operation key for increasing the power consumption and the heating power and the operation key for inversely decreasing the heating power are simultaneously pressed, the controller 32 of the induction heating cooker 2 causes the display screen 129 to display the fact that improper operation is made when such improper history remains in the storage device 32R of the controller 32 of the induction heating cooker 2. In addition, even when the improper history does not remain in the storage device 32R of the controller 32 of the induction heating cooker 2 (including the case where the user sets not to keep the operation history), the information server 89X points out the improper operation as described above. Here, when other households have experienced a case of causing some kind of trouble by performing similar operations, the information server 89X also represents such a case to provide information for drawing attention so as not to perform the improper operation. Therefore, the user of each household is expected to behave so as to automatically avoid occurrence of troubles in the induction heating cooker 2 without asking the manufacturer every time.

According to Embodiment 5, when the help mode key 121 (see FIG. 45) described in detail in Embodiment 1 is pressed, the information that assists the user's operation in that situation is displayed, and a correct operation method is audibly announced through a voice guide device (not shown) separately provided. Similarly, every time the information key 133 (see FIG. 45) is operated, caution for when the operation of power limitation, etc., is input and the latest useful information (assistance information) accumulated in the manufacturer information database 89M as a mistake that frequently occurs in a large number of households are provided from the information server 89X as needed. Therefore, the occupant of each household (user of the power instruction apparatus 9) can be expected to effectively and correctly use the power instruction apparatus 9 without asking the manufacturer every time.

When the power instruction apparatus 9 receives the operation information signals L1 to L7 and the abnormality monitoring data from the home electric appliance EE, the power instruction apparatus 9 refers to the database accumulated in the storage device 149, and creates the assistance information for the home electric appliance EE by a method similar to that of the information server 89X. The power instruction apparatus 9 then transmits such assistance information to the related home electric appliance EE. The assistance information may represent, other than the way to manage the abnormality depending on the individual situation of abnormality occurrence, a computerized instruction manual that comes with the home electric appliance. The assistance information may also be used in the activity measurement apparatus 145 and the healthcare instrument 410. The home electric appliance EE, the activity measurement apparatus 145, and the healthcare instrument 410 have the home electric appliance ID, the activity apparatus ID, and the healthcare instrument ID, respectively, and hence the cumulative usage time and cumulative usage period (number of days or years) calculated from the usage start timing of each device can be identified based on the user information database. With use of those IDs, the information server 89X may provide, to the user, information on the (legal or optional) periodic maintenance check or replacement service of important functional components of the home electric appliance EE, the healthcare instrument 410, and the activity measurement apparatus 145. The power instruction apparatus 9 can also receive such information to store the information in the storage device 149 and display the information on the display screen 100A. Thus, this embodiment has an advantage in that the home electric appliance EE, the healthcare instrument 410, and the activity measurement apparatus 145 can be used safely for a long period of time.

As is apparent from the description above, Embodiment 5 proposes a first assistance information provision system for the home electric appliance. That is, the first assistance information provision system is an assistance information provision system configured to connect the induction heating cooker 2, which is an example of the home electric appliance EE, and the information server 89X to each other by the communication network 98 via the power instruction apparatus 9 configured to control the total electric power of the home electric appliance EE. The induction heating cooker 2 includes the first communication unit 2NX configured to communicate with the power instruction apparatus 9, the input unit to which the user inputs the operation conditions, and the controller 32 configured to perform the control operation unique to the device. The power instruction apparatus 9 includes the input-output unit (second communication unit) 124B configured to communicate with the information server 89X, and the environment detection unit 202 configured to acquire the environment information of the installation space of the home electric appliance EE. The information server 89X includes the communication unit 89IF configured to communicate with the power instruction apparatus 9, the manufacturer information database 89M configured to accumulate the manufacturer technical information of the induction heating cooker 2, and the user information database 89U configured to accumulate the user information of the induction heating cooker 2. The information server 89X is configured to, when the communication unit 89IF receives the abnormality occurrence signal of the induction heating cooker 2 and the environment information from the power instruction apparatus 9, identify the user of the induction heating cooker 2 based on the user information, create the assistance information representing the usage method corresponding to the abnormal state of the induction heating cooker 2 based on the operation state of the induction heating cooker 2 and the manufacturer information database 89M, and transmit, with the communication unit 89IF, the assistance information to the user identified based on the user information. The power instruction apparatus 9 further includes the display device (TV receiver 75 or display panel 100) configured to display the operation information of the induction heating cooker 2 and the environment information.

As is apparent from the description above, Embodiment 5 further proposes a second assistance information provision system for the home electric appliance. That is, the second assistance information provision system is an assistance information provision system configured to connect the home electric appliance EE and the information server 89X to each other by the communication network 98 via the mobile phone terminal 87 configured to read the operation information of the home electric appliance EE. The induction heating cooker 2, which is an example of the home electric appliance EE, includes the first communication unit 2NX configured to communicate with the mobile phone terminal 87, the input unit to which the user inputs the operation conditions, the controller 32 configured to perform the control operation unique to the device, and the environment detection unit 202 configured to acquire the environment information of the installation space of the induction heating cooker 2. The mobile phone terminal 87 includes the wireless input-output unit (sixth communication unit) 182 configured to communicate with the information server 89X, the storage device 187 configured to temporarily store the environment information acquired from the environment detection unit 202, and the display unit 180. The information server 89X includes the communication unit 89IF configured to communicate with the mobile phone terminal 87, the manufacturer information database 89M configured to accumulate the manufacturer technical information of the induction heating cooker 2, and the user information database 89U configured to accumulate the user information of the induction heating cooker 2. The information server 89X is configured to, when the communication unit 89IF receives the abnormality occurrence information of the induction heating cooker 2 and the environment information from the mobile phone terminal 87, identify the user of the induction heating cooker 2 based on the user information, create the assistance information representing the usage method corresponding to the abnormal state of the induction heating cooker 2 based on the operation state of the induction heating cooker 2 and the manufacturer information database 89M, and transmit, with the communication unit 89IF, the assistance information to the user identified based on the user information. The mobile phone terminal 87 is configured to receive the assistance information transmitted from the information server 89X, and display the received content on the display unit 180.

As is apparent from the description above, Embodiment 5 further proposes a third assistance information provision system for the home electric appliance. That is, the third assistance information provision system is an assistance information provision system configured to connect the home electric appliance EE and the information server 89X to each other by the communication network 98 via the mobile phone terminal 87 configured to read the operation information of the home electric appliance EE. The induction heating cooker 2, which is an example of the home electric appliance EE, includes the first communication unit 2NX configured to communicate with the mobile phone terminal 87, the input unit to which the user inputs the operation conditions, the controller 32 configured to perform the control operation unique to the device, the apparatus-side short range communication unit 182A configured to read the control program for the controller 32 from the mobile phone terminal 87, and the environment detection unit 202 configured to acquire the environment information of the installation space of the induction heating cooker 2. The mobile phone terminal 87 includes the wireless input-output unit 182 configured to communicate with the information server 89X, the storage device 187 configured to temporarily store the environment information acquired from the environment detection unit 202, and the display unit 180. The information server 89X includes the communication unit 89IF configured to communicate with the mobile phone terminal 87, the manufacturer information database 89M configured to accumulate the manufacturer technical information of the induction heating cooker 2, the user information database 89U configured to accumulate the user information of the induction heating cooker 2, and the countermeasure program provision unit 89S configured to store the application software of the induction heating cooker 2. The information server 89X is configured to, when the communication unit 89IF receives the abnormality occurrence information of the induction heating cooker 2 and the environment information from the mobile phone terminal 87, identify the user of the induction heating cooker 2 based on the user information, create the assistance information representing the usage method corresponding to the abnormal state of the induction heating cooker 2 based on the operation state of the induction heating cooker 2 and the manufacturer information database 89M, read out the countermeasure program corresponding to the abnormal state of the induction heating cooker 2 from the countermeasure program provision unit 89S, and transmit, with the communication unit 89IF, the assistance information and the notification of provision of the countermeasure program to the user identified based on the user information. The mobile phone terminal 87 is configured to, when receiving the assistance information transmitted from the information server 89X, display the assistance information on the display unit 180. Then, the mobile phone terminal 87 can acquire the countermeasure software from the information server 89X via the wireless input-output unit 182 in accordance with the received content.

In Embodiment 1, detailed description of the abnormality monitoring data of the induction heating cooker 2 is omitted, but the abnormality monitoring data is not limited to a case of setting a certain level (e.g., voltage value) for determination as abnormal and recording the exceeded value and the time point (time) when the certain level is exceeded. Further, the time for one instance of induction heat cooking is about 30 minutes to 40 minutes at the longest, but when the controller 32 acquires and accumulates the abnormality monitoring data in detail (short and frequent measurement timing) over the whole induction heat cooking period, the information amount accordingly increases, which increases the time for transmission to the mobile phone terminal 87 via the short range wireless communication (NFC). In addition, there is a fear of exceeding the information storage capacity of the mobile phone terminal 87. In view of this, the level (e.g., voltage value) for determination as abnormal may not be set to a certain value, and, for example, a certain range may be set therefor. A method of ignoring the variation in the range and making determination as abnormal only when deviating from the range may be adopted for improvement of reducing the storage amount of the abnormality monitoring data.

Further, the abnormality of the home electric appliance includes not only a case where an abnormal current or voltage is generated in the electric circuit, but also a case where, for example, the home electric appliance EE (induction heating cooker 2, etc.) cannot correctly receive the instruction of reduction in total electric power from the power instruction apparatus 9 to the electric appliance. In other words, the determination of abnormality is made even when, although the power instruction apparatus 9 transmits a predetermined instruction signal, the home electric appliance EE does not output a response signal therefor (the operation information signals L1 to L7 illustrated in FIG. 64 are examples) within a predetermined time period. In other words, the determination of abnormality is made even when, for example, although the induction heating cooker 2 receives a predetermined instruction signal from the power instruction apparatus 9, the controller 32 of the induction heating cooker 2 itself detects that a predetermined response signal is not output within a predetermined time period (e.g., several seconds) from the time point of reception. The abnormal situation of no response signal can also be detected by the control unit 125 of the power instruction apparatus 9, and hence the control unit 125 displays the abnormality via the display panel 100, or outputs a notification signal to the TV receiver 75 for some kind of notification.

In Embodiment 1 of the present invention, it is described that the "identification information" of the home electric appliance EE may include information that can be used for inspection based on the "System for Safety Inspection of Products for Long-Term Use" in the "Consumer Products Safety Act". The induction heating cooker 2, for example, has a function of displaying the current date and the correct time in the unit of seconds. For example, the induction heating cooker 2 may constantly calculate the number of elapsed days from when the main power is first turned on, and the controller 32 may cause the central display unit 16 or other units to display the number of elapsed years or months from the usage start date at an appropriate timing. For example, the period from the usage start may be displayed every day at the first time of starting usage, or at intervals of once a month or once a year. As a matter of course, such information of usage period (number of years, etc.) is also useful for the inspector or the repairer when the abnormality occurs, and hence the abnormality monitoring data may be transmitted from the NFC input-output unit 401 to the mobile phone terminal 87, or the induction heating cooker 2 may directly transmit the abnormality monitoring data to the power instruction apparatus 9 via wireless communication. When the abnormality monitoring data is transmitted to the power instruction apparatus 9, the information such as the usage period (number of years) may be stored in the storage device 149 for a long period of time, and the control unit 125 may update and record the information when new information arrives from the induction heating cooker 2.

The following configuration is conceivable as another embodiment. The ASP server 89A of the external organization 78A stores, in addition to the control application database for the induction heating cooker 2, revised (updated) control application software for specific induction heating cookers 2 so as to reduce or suppress the occurrence of an abnormality depending on the specific model types or manufacturing numbers (this software is hereinafter referred to as "improved software"). Further, the controller 32 of the induction heating cooker 2 has a function of rewriting a part of the built-in control program when a specific signal arrives from the outside.

Meanwhile, the storage device 149 of the power instruction apparatus 9 stores in time series the "environment information" of the respective living spaces in which the various home electric appliances EE (including the induction heating cooker 2) registered as objects of power control are installed. For example, three types of information, that is, the room temperature, the humidity, and the dust scattering level of the living space, which are assumed to adversely affect at least the normal operation of the home electric appliance EE, are recorded for 10 days to be automatically stored and held in the storage device 149. Further, the information of the date and time of power supply start and power supply stop of the home electric appliances EE (including the induction heating cooker 2) registered as the object of power control is also automatically stored for 10 days in the unit of seconds.

With the above-mentioned configuration, when the abnormality monitoring data is transmitted from the induction heating cooker 2 to the power instruction apparatus 9 via wireless communication on a certain day, the data is temporarily stored in the storage device 149. Further, the abnormality monitoring data read into the power instruction apparatus 9 via the NFC input-output unit 401 of the induction heating cooker 2 via the mobile phone terminal 87 is similarly temporarily stored in the storage device 149.

In view of this, the control unit 125 of the power instruction apparatus 9 executes data processing of arranging in time series the environment information stored in the storage device 149 and the abnormality monitoring data every time the control unit 125 receives the abnormality monitoring data from the outside, and stores the results in the storage device 149. In view of this, the abnormality monitoring data associated with the environment information can be read out by the mobile phone terminal 87 and transmitted to the ASP server 89A via the wide area communication network, to thereby request abnormality analysis in detail. Further, the mobile phone terminal 87 can download the "improved software" recommended by the ASP, and the controller 32 of the induction heating cooker 2 can read the improved software via the NFC input-output unit 401, to thereby execute a countermeasure for preventing occurrence of the abnormality. The abnormality monitoring data associated with the environment information, which is stored in the storage device 149 of the power instruction apparatus 9, may be transmitted to the external organization 78A such as the ASP server 89A from the power instruction apparatus 9 itself via the router 99A.

With such a configuration, when the external organization 78A such as the manufacturer or the specialized repair agency analyzes the abnormality monitoring data of the induction heating cooker 2, an external cause of the occurrence of the abnormality monitoring data of the induction heating cooker 2 can be analyzed, and thus more correct abnormality content analysis or countermeasures can be executed. For example, when the induction heating cooker 2 detects an abnormally high temperature and automatically stops due to operation under a state where the kitchen in which the induction heating cooker 2 is installed exceeds a predetermined upper limit temperature (e.g., 45 degrees Celsius) for some reason, it can be assumed that the abnormality is caused by the external environment. The control unit 125 of the power instruction apparatus 9 stores data of operation or stop of the electric appliance EE together with the environment information for a certain period (e.g., 10 days as described above). Therefore, a read-out instruction may be output to the control unit 125 of the power instruction apparatus 9 so as to compare such data of operation or stop of the electric appliance EE. Such data may be displayed on the display panel 100 or the TV receiver 75.

In Embodiments 1 to 5, only one type of failure of the home electric appliance is described, but the failure may include one caused when the internal electric circuit of the home electric appliance itself is actually inappropriate. In this case, the failures may be classified into a plurality of types in accordance with their danger and severity with respect to the user or the home electric appliance. For example, two types of failures, that is, an "emergency situation" and a "warning situation" may be defined. In this case, the operation of the induction heating cooker 2 is as follows. Those operations may be widely applied to other heating apparatus such as the rice cooker 3 or other home electric appliances EE such as the air-conditioning apparatus 7.

(1) "Emergency situation": The induction heating cooker 2 is liable to be damaged and has high degree of danger, and hence the operation is immediately stopped. For example, this situation corresponds to a case where, when oil cooking is performed with high heating power, the cooking oil temperature in the heating object (pot, etc.) estimated from the detected temperature of the bottom surface of the heating object increases abnormally quickly, and there is a risk of fire in that situation (the main cause resides in that the user accidentally starts to use the induction heating cooker 2 with an amount of oil smaller than a defined amount required for usage).

(2) "Warning situation": This situation has a risk of adversely affecting the function, life, etc., of the electric circuit or the display unit when the situation is not changed for a long period of time. For example, this situation corresponds to a case where the temperature of the top plate 14 of the induction heating cooker 2 is abnormally high. This case occurs when, for example, something is placed on the intake port 20, to inhibit ventilation.

When the failures are classified into those two types, in the case of the "emergency situation", the controller 32 determines that the induction heating cooker 2 is damaged in view of giving priority to safety even when the circuit or the structure of the induction heating cooker 2 itself is not the cause of the situation, and thus the heating operation is brought to emergency stop. Further, in the case of the "warning situation", for example, the central display unit 16 displays a warning or the voice notification unit 39 audibly outputs a warning, but the heating operation is not brought to the emergency stop, and the heating operation is stopped only when the temperature increase further continues. Even when the user starts cooking with a correct usage method, and the pot is determined as appropriate, there is a possibility that the bottom surface of the pot may deform in the process of long-term use to cause an abnormal heating state. Therefore, the controller 32 has a function of forcibly decreasing the induction heating power when the cooking oil temperature in the heating object increases abnormally quickly, to thereby prevent excessive temperature increase. Therefore, the abnormal rise of the cooking oil temperature as described above is not necessarily defined as an "emergency situation".

In Embodiments 1 to 5, there is no description of the specific indexes of the degree of comfort. In Embodiment 1, it is only described that default values in a range of comfort (three stages) are set to 26 degrees Celsius for temperature and below 50% for humidity as the initial setting. In general, it is difficult to express a comfortable environment with absolute numeral values. For example, the American Society of Heating, Refrigerating and Air-Conditioning Engineers (ASHRAE, 1996) defines the degree of comfort as "the state of mind which expresses satisfaction with the thermal environment". In other words, the degree of comfort means the environment condition that may cause a feeling of discomfort if the environment becomes hotter or colder than the current temperature. Therefore, the impression to the occupant does not always correspond to the sense felt from the environment, and the impression changes even depending on the feeling, the experience, and the physical condition of the occupant.

In view of this, description is given of what state is generally defined as a "comfortable indoor environment (climate)". The International Energy Agency (IEA) defines the indoor (room) state as follows.

(1) Indoor temperature: around 20 degrees Celsius in winter, and around 28 degrees Celsius in summer.

(2) Horizontal temperature in room: uniform.

(3) Vertical temperature difference in room: 3 degrees Celsius to 4 degrees Celsius or less.

In Japan, the setting temperature of an air-conditioning apparatus in rooms inside a household or offices is recommended to be 28 degrees Celsius for cooling in summer and 20 degrees Celsius for heating in winter in view of energy saving, but it is generally said that the room temperature that people actually feel comfortable is around 25 degrees Celsius.

Therefore, when the present invention is embodied, the determination of the degree of comfort may change depending on various preconditions such as the region in which the house is present, the age and sex of the occupant, etc. It is thus more preferred that the occupant can adjust, for example, the "temperature" of the degree of comfort as appropriate. Further, the power instruction apparatus 9 may incorporate an atomic clock so that the temperature is automatically changed depending on the season. Specifically, at the stage at which the occupant feels comfortable, the TV receiver 75, the power instruction apparatus 9, or the information communication terminal device, e.g., the mobile phone terminal 87 may input a signal for identifying the time point when the occupant feels comfortable to the power instruction apparatus 9, and the power instruction apparatus 9 may use the environment information (such as the temperature and the humidity) upon reception of the input for basic data for subsequent determination of the degree of comfort. By accumulating such information relating to the degree of comfort of the occupant, the power instruction apparatus 9 can determine the degree of comfort so as to be closer to the recognition and the feeling of the occupant.

According to the definition of the "comfortable indoor environment" by the International Energy Agency (IEA) described above, in view of the conditions that the horizontal temperature of the room is uniform and the vertical temperature difference in the room is 3 degrees Celsius to 4 degrees Celsius or less, when a plurality of adjacent rooms are horizontally and continuously present in the house, the degree of comfort may be degraded even when the rooms have a large difference in indoor temperature therebetween. The large difference may also apply stress (also referred to as "heat shock") to an occupant with less physical strength and elderly occupants. For example, in FIG. 16 of Embodiment 1, there are four living spaces, that is, the living room, the kitchen, the bedroom, and the bathroom in one house, and the temperature difference between the bedroom (31 degrees Celsius) and the living room (26 degrees Celsius) is 5 degrees Celsius. When such a temperature difference is a predetermined value or more, it is preferred that the TV receiver 75 or the power instruction apparatus 9 output or display some cautions or notifications. Particularly in cold areas in winter, for example, the living room or the kitchen where the occupants gather tends to have a high temperature (e.g., 28 degrees Celsius) through use of the air-conditioning apparatus 7 or heating appliances. When the occupant exits from the living room or the kitchen to go to the bathroom to take a bath, there is a risk of heat shock. Therefore, it is conceivable to devise control such as to slightly increase the temperature of the bathroom or a space just before the bathroom (lavatory) by the power instruction apparatus 9 before taking a bath (by transmitting a bath notice signal to the control unit 125 via the TV receiver 75 or through direct operation of the input operation unit of the display panel 100 of the power instruction apparatus 9).

In Embodiment 1, description is given of outputting the suggestion information 489. The suggestion information including suggestions relating to whether or not the home electric appliance, in particular, the first specific home electric appliance SP1 can be operated or relating to the operating condition of the appliance are displayed in words in accordance with the current situation of the living space. Therefore, an effect that the environment of the living space can be more appropriately controlled is expected (see FIG. 17). The basic data of the suggestions is stored in the storage device 149 used as the storage unit of the healthcare processing unit 116. The same data is also stored in the storage device (high-capacity memory) 109 of the TV receiver 75. In view of this, when the activity measurement apparatus 145 or the healthcare instrument 410 is intended to be used, the suggestion information may include the environment suitability information as a reference for the activity with the activity measurement apparatus, or when the healthcare instrument 410 is intended to be used, the suggestion information may include the environment information (e.g., room temperature) that is required to be noted.

Further, in Embodiment 1, description is given of the operation in which the environment detection unit 202 transmits a signal of "level 1 warning" to the control unit 125 when the temperature reaches 29 degrees Celsius and the humidity reaches 70%, and transmits a signal of "level 2 warning" to the control unit 125 when the room temperature becomes 30 degrees Celsius or higher and the humidity exceeds 75%. When the activity measurement apparatus 145 or the healthcare instrument 410 is intended to be used, the TV receiver 75 and the display panel 100 may output a warning representing that, at the temperature and the humidity that cause output of the level 1 warning or the level 2 warning, training or activity for measurement of the amount of activity may be prevented, and the biological data acquisition such as body temperature measurement or blood pressure measurement for health management may also be prevented. Further, it is more preferred to employ a configuration in which the healthcare processing unit 116 transmits a predetermined display instruction signal to the activity measurement apparatus 145 or the healthcare instrument 410 so that the display information of the display unit in the activity measurement apparatus 145 or the healthcare instrument 410 (the display unit 213 in the blood pressure meter 410A, or the display unit 145A2 in the indoor treadmill 145A) includes such a warning.

It is generally said that the blood pressure is preferred to be measured at the same time every day, but the measurement may be forgotten in daily life. Therefore, the blood pressure is preferred to be measured at predetermined specific times in the time period in the morning a short time after getting up, the time period of lunch, and the time period in the early evening or dinner. In view of this, it is preferred that, with use of the clock function incorporated in the power instruction apparatus 9, the TV receiver 75 urge the user to measure the blood pressure at 7:00 in the morning, 13:00 in the daytime, and 20:00 in the evening. Alternatively, the timer clock function incorporated in the TV receiver 75 for recording may be used to automatically activate the TV receiver 75 when the predetermined time arrives in the same manner as above. However, electric energy is wastefully used unless the TV receiver 75 is activated when the human body detection unit 203 detects that the occupant is present. Therefore, it is desired that the TV receiver 75 be automatically activated as described above when the presence detection unit 10 described in Embodiment 1 detects that the occupant is present.

When the TV receiver 75 is automatically activated, the LCD screen 75D displays a message urging the user to measure their blood pressure with the blood pressure meter 410A. When the LCD screen 75D displays a message to recommend measurement of the blood pressure, in a case where the environment detection unit 202 obtains the environment information that is not preferred for usage start of the activity measurement apparatus 145 or measurement start of other healthcare instruments 410, it is more preferred that the LCD screen 75D simultaneously display the environment information. In this manner, a habit of regularly measuring the blood pressure and then using the activity measurement apparatus 145 for activity can be achieved through cooperation between the power instruction apparatus 9 and the TV receiver 75.

In Embodiment 1, the instruction switches (not shown) for environment confirmation are operated with use of the press-button operation buttons EV1, EV2, and EV3 that are directly operated by the occupant, but the instruction switches may be electrostatic touch input keys, or the instruction switches may be provided in the form of icons displayed in the LCD screen 75D of the TV receiver 75 or the display panel 100. In Embodiment 1, a mechanical press-button type is adopted so that input operation can be made even when the TV receiver 75 is not activated.

In Embodiment 1, the activity measurement apparatus 145 is used by the occupant inside the household forming the living space HA, but the activity measurement apparatus 145 may be used outside the household, that is, outdoors. The power instruction apparatus 9 or the TV receiver 75 may store the sum of the amount of outdoor activity and the amount of indoor activity. Similarly, the healthcare instrument 410 may be used not only indoors, but also outdoors.

It is to be understood that Embodiments disclosed above are merely examples in all aspects and in no way intended to limit the present invention. The substantial scope of the present invention is defined by the appended claims and not by Embodiments, and modifications made within the scope and spirit equivalent to those of the claims are duly included in the present invention.

INDUSTRIAL APPLICABILITY

The power control system according to the present invention is not only applicable to private households, but broadly applicable to stores and small-scale plants where commercial-use electric appliances are installed.

REFERENCE SIGNS LIST

AS1 object appliance registration signal
AS2 power reduction request signal
AS3 power reduction instruction signal
BK circuit breaker
EE home electric appliance
EP AC 200 V power source (commercial power source)
ES abnormality detection unit
FL floor surface
H1 preheating phase
H2 rice cooking phase
H2A high heat phase (time period for priority cooking menu)
H2B low heat phase
H3 steaming phase
H4 keep-warm phase
HA living space
KC refrigerant circuit
KP kitchen electric appliance
T1 target temperature
T2 second temperature
T3 third temperature
SL ceiling
SW wall
SP1 first specific electric appliance (air-conditioning apparatus etc.)
SP2 second specific electric appliance (rice cooker, microwave oven etc.)
1 system kitchen (kitchen furniture)
1A casing
2 induction heating cooker
2A main body
2C main body casing
2L first heater
2R second heater
2LC induction heating coil
2RC induction heating coil
3 rice cooker (electric rice cooker)
4 grill cooker
5 microwave oven
6 dish washer-dryer
7 air-conditioning apparatus
8A to 8E power usage control device (power usage control unit)
9 power instruction apparatus
9A main body
9C recess
10 presence detection unit
11 main power switch
11A main power switch operation button
12L power control dial
12R power control dial
13 operation panel
14 top plate
15 metal frame
16 display unit (central display unit)
17L left display panel
17R right display panel
18L left display unit
18R right display unit
19 electronic lock (entrance electronic lock)
20 intake port
21 exhaust port
22 grill chamber
23 receiving tray
24 gridiron
25 cooking object
26 upper surface operation unit
26Q press-button
26S assistance request switch
27 power supply line (main line, main circuit, power supply path)
28 grill lid
28A handle
30 controller
30 power supply line
31 power supply circuit
32 controller
32R storage device
33L inverter circuit
33R inverter circuit driver circuit
34H electric heater (sheath heater)
35 display unit driver circuit
36A menu selection display section
36B display section
37 catalyst heater
38 voice synthesizer
39 speaker
40 inner pot
41 rice cooker main body casing
42 lid
43 operation unit
44 rice cooking start button
45 heating device (heating unit)
46 inner lid
47 steam port
48 steam duct
49 LCD unit
50 steam processor
51 tank lid
52 steam inlet
53 steam outlet
54A sixth information sign
54C seventh information sign
56 power saving switch
57 presence management menu selection key 58A display screen selection key
58B display screen selection key
58C message setting selection key
59A family name column
59B presence status display column
59C scheduled home arrival time display column
59D reserved appliance display column
59E exclusive appliance display column
59F power usage display column
60 control device (controller)
61 power source unit
62 control unit
63 temperature sensor
64 operation device clock device
66 water level sensor
67 bottom plate
68 water temperature sensor
69A message registration instruction key
69B message replay instruction key
69C personal display section/occupant selection key
69D display section
69E sound pickup unit
69F number input key (ten key)
69G cancel key
69H enter key
69L date selection key
69M date selection key
69N date selection key
69K input command key
69T time display section
70 door
70A door knob
71 operation unit
72 power source switch
73 start button
74 heating time setting dial
75 TV receiver (display device)
75A ROM
75B RAM
75C image processing unit 75D LCD screen
75E system control unit
75G power supply unit
75J input-output functional device
75K input-output functional device
75L input-output functional device
75M input-output functional device
75N external network communication device
75R remote controller
75S power FET
76 illumination apparatus
77 outdoor antenna
78A external organization
78B external organization
78C communication service provider
79 facility
80 base station
81 left heater operation unit
81a frying button
81b 3 kW button
81c on/off button
82 right heater operation unit
82a frying button
82b 3 kW button
82c on/off button
83a grill menu button
83b start/stop button
83c left arrow button
83d right arrow button
83e time-down button
83f time-up button
84 start/stop button LED
85 arrow button LED
86 time button LED
87 mobile phone terminal
88 relay server
89A ASP server
89CP central processing unit
89D display device
89IF communication unit
89M manufacturer information database
89U user information database
89P input device
89S countermeasure program provision unit
89X information server
90 boil over detection device
91 required power adder
92 comparator
93 requested power excess determination device
94 power usage reduction rate determination device
95 priority order setting device
95A semiconductor memory
96 use limit setting device
96A semiconductor memory
97 communication unit
98 wide area communication network (communication network)
99A router A
99B router B
100 display panel (display device)
100A LCD screen
101 maximum allowable power display section
102 current power consumption display section
103 power allowance display section
104 power reduction request notification section
105 current time display section
106 display and setting key for power use limit setting device
96
106A to 106D selection key
107 use status display section
107A,
107B name display section
108 use display section
109 storage device (high-capacity memory)
110 information key
111 help mode key
112 information key
113E estimated finish time information sign
113S use start time information sign
114,
115 mark
116 healthcare processing unit
117 operation input unit
118 confirmation button
119 emergency cut-off button
120 key
121 help mode key
122 third heater
123 electric heating device
124A,
124B input-output unit
124C input-output unit
125 control unit
126 operation unit 127 data processing unit
128A first selection unit
128B second selection unit
128C third selection unit
128N1L selection key of left induction heating unit
128N1R selection key of right induction heating unit
129 display screen
130 top plate
131 casing
132L left operation unit
132M central operation unit
132R right operation unit
133 information key
135 current detection unit
136 input-output unit
137 information reception unit
138 memory (ROM)
139 memory (RAM)
145 activity measurement apparatus
145A indoor treadmill
145A8 memory
145B running calorie meter
145Y usage notice signal
146 electric vacuum cleaner
147 clock circuit
148A projection
148B recess
149 storage device
150 temperature detection circuit
152 space
153 space
158 press-button key (operation unit)
159 absence setting key
167 front door
167C handle
179 operation unit
180 display unit
180A display screen
181 operation unit
182 wireless input-output unit
182A apparatus-side near-field communication unit
182B NFC wireless input-output unit
183 posture detection unit
184 control unit
185 central processing unit (CPU)
186 storage unit
187 ROM/RAM unit
188 application software unit
189 reception processing unit
190 transmission processing unit
191 communication establishment unit
192 display control unit
193 selection determination unit
194 notification unit
194A to 194D selection key
195 letter information
196 operation guidance information
197A to 197C selection information
198, 199A, 199B letter information
200 enter key
201 selection information
202 environment detection unit
203 human body detection unit
204, 205 environment sensor (indoor temperature sensor)
206 environment sensor (outdoor temperature sensor)
207, 208 human body sensor
210 display unit
210A first information sign
210B second information sign
210C third information sign
210D fourth information sign
211N, 211R input key
212 start key
213 display unit
214 measurement unit
215 operation unit
216 memory
217 control unit
218H electricity rate classification information
218L electricity rate classification information
218M electricity rate classification information
219 mark
224 indoor temperature detection device
225 indoor control unit
226 power source unit
227 operation unit
228 display unit
230, 231 time shift key
240 clock circuit
241 vibration sensor
250, 251 time-setting key
253 rice-cooking finish time indicator
254 time indicator
300 wattmeter
301 power line
302 current clamp
312 electric vacuum cleaner
320 NFC storage unit
321 NFC control circuit
322 antenna
323 light emitting diode element (LED)
401 near-field communication (NFC) input-output unit
401L near-field communication (NFC) input-output unit
401R near-field communication (NFC) input-output unit
410 healthcare instrument
410A blood pressure meter
410B electrocardiograph 410C heart rate meter
410D clinical thermometer
410E weight scale
410F body fat scale
410G urine analyzer
410Y usage notice signal
411 icon
412 to 415 special icon
417 icon (for selecting healthcare information)
418 icon (for electric energy management)
419 icon (for living environment information)
420 information key
421 help mode key
424 wireless input-output unit
425 icon
426 icon (input key)
427 wireless input-output unit
430 caution information light/display instruction switch
440 healthcare information selection key
441 healthcare information display region
450 favorite dish information selection key
451 favorite dish information display region
460 favorite recipe selection key
460A to 460E recipe selection key
470 to 473 display region
474 temperature/humidity information sign
475 comfort mark
476 caution mark 477 cold-hot information sign
478 absence mark
479 operation information sign for first specific electric appliance
480 activity caution mark
481 icon
482 operation information sign for second specific electric appliance
483 change information sign
484 unsuitable environment information sign
485 pollen scattering amount information sign
486 ventilation fan operation information sign
487 operation intensity information sign
488 blank section
489 suggestion section
490 to 492 icon
500 advise region
501 remote controller for hot water supply
502 electric hot water system
503 composite measurement device
750 TV receiver
751 signal cable
760 illumination apparatus

The invention claimed is:

1. A power control system, comprising:
a power instruction apparatus configured to limit total electric power in a household by individually controlling an upper power limit of each of a plurality of home electric appliances in the household;
a display device configured to display operation information of the power instruction apparatus; and
an activity measurement apparatus configured to measure an amount of activity of a user in the household,
the display device and the activity measurement apparatus being each communicably connected to the power instruction apparatus via wired or wireless communication, wherein the activity measurement apparatus is configured to transmit a usage notice signal to the power instruction apparatus before measurement of the amount of activity of the user,
the power instruction apparatus including an environment detection unit configured to acquire environment information of at least one of measured temperature and measured humidity of each of a plurality of living spaces in the household,
the display device being configured to display information indicating a difference between the total electric power in the household and a total power usage by the plurality of home electric appliances in the household, the environment information acquired by the environment detection unit of the power instruction apparatus and the measurement data measured by the activity measurement apparatus, in response to an instruction from a user.

2. The power control system of claim 1, wherein, when the power instruction apparatus detects that usage of the activity measurement apparatus is to be started, the power instruction apparatus causes the display device to display determination result information representing whether or not an environment of a living space in which the activity measurement apparatus is present is suitable for activity.

3. The power control system of claim 2,
wherein, when the power instruction apparatus determines that the environment of the living space in which the activity measurement apparatus is present is unsuitable for activity, the power instruction apparatus determines whether or not an environment improvement apparatus that can be operated is installed in the living space in which the activity measurement apparatus is present, and
wherein, when the environment improvement apparatus that can be operated is determined to be installed in the living space in which the activity measurement apparatus is present, the power instruction apparatus sets an operation condition of the environment improvement apparatus to improve the living space in which the activity measurement apparatus is present to be an environment suitable for activity and causes the display device to display a message urging an operation of the environment improvement apparatus.

4. The power control system of claim 1, further comprising a healthcare instrument communicably connected to the power instruction apparatus via wired or wireless communication, the healthcare instrument being configured to measure biological data of a user in the household,
wherein the display device is configured to display the biological data measured by the activity measurement apparatus, in response to an instruction from a user.

5. The power control system of claim 4,
wherein the healthcare instrument being a blood pressure measuring device communicably connected to the power instruction apparatus via wired or wireless communication,
wherein the display device is automatically activated at a predetermined time in a day, and
wherein, when the display device is automatically activated at the predetermined time, the display device displays a message for urging a user to measure blood pressure with the blood pressure measuring device.

6. The power control system of claim 4,
wherein one of the plurality of home electric appliances is a heating cooker,
wherein the power instruction apparatus includes a storage device configured to store the biological data measured by the healthcare instrument and caution data indicating that the biological data has an abnormal value, and
wherein, when the biological data associated with the caution data stored in the power instruction apparatus includes data serving as a reference to a cooking method or cooking content of the heating cooker, the display device displays the data serving as the reference.

7. The power control system of claim 4,
wherein one of the plurality of home electric appliances is a heating cooker having a display unit,
wherein the power instruction apparatus includes a storage device configured to store the biological data measured by the healthcare instrument and caution data indicating that the biological data has an abnormal value, and
wherein, when the biological data associated with the caution data stored in the power instruction apparatus includes data serving as a reference to a cooking method or cooking content of the heating cooker, the data serving as the reference is displayed on the display unit on the heating cooker.

8. The power control system of claim 1, further comprising a TV receiver configured to receive broadcast waves from outside of the household,
wherein the TV receiver is configured to display information displayed on the display device, in response to an instruction from a user.

9. The power control system of claim 1, wherein the power instruction apparatus further includes an operation unit of an instruction switch for environment confirmation, the instruction switch being arbitrarily operated by a user to output an instruction for acquiring the environment information from the environment detection unit.

10. The power control system of claim 1, wherein the display device further includes an operation unit of an instruction switch for environment confirmation, the instruction switch being arbitrarily operated by a user to output an instruction for acquiring the environment information from the environment detection unit.

11. The power control system of claim 1,
wherein at least one of the plurality of home electric appliances further includes a vibration sensor configured to detect an earthquake,
wherein, when the vibration sensor detects a seismic intensity equal to or higher than a predetermined level, the vibration sensor transmits a vibration detection signal to the power instruction apparatus, and
wherein, when the power instruction apparatus receives the vibration detection signal and at least one of the plurality of home electric appliances is using a heating unit, the power instruction apparatus cuts off power supply to the heating unit.

12. The power control system of claim 1,
wherein the power instruction apparatus further includes a main body installed in the household in a fixed state,
wherein the main body includes a vibration sensor configured to detect an earthquake, and
wherein, when the vibration sensor detects a seismic intensity equal to or higher than a predetermined level and at least one of the plurality of home electric appliances is using a heating unit, the power instruction apparatus cuts off power supply to the heating unit.

13. A power control system, comprising:
a power instruction apparatus configured to limit total electric power in a household by individually controlling an upper power limit of each of a plurality of home electric appliances in the household;
a display device configured to display operation information of the power instruction apparatus;
an activity measurement apparatus configured to measure an amount of activity of a user; and
a healthcare instrument configured to measure biological data of a user,
the display device, the activity measurement apparatus, and the healthcare instrument being each communicably connected to the power instruction apparatus via wired or wireless communication, wherein the activity measurement apparatus and the healthcare instrument is each configured to transmit a usage notice signal to the power instruction apparatus before measurement of the amount of activity of the user or measurement of the biological data of the user, respectively,
the display device being configured to display information indicating a difference between the total electric power in the household and a total power usage by the plurality of home electric appliances in the household, the measurement data measured by the activity measurement apparatus and the biological data measured by the healthcare instrument, in response to an instruction from a user.

14. An activity measurement apparatus, comprising:
a measurement unit configured to measure data of an amount of activity of a user;
a memory configured to temporarily store the measurement data acquired by the measurement unit;
a transmission unit configured to:
transmit, before measurement of the amount of activity of the user, a usage notice signal to a power instruction apparatus; and
transmit the measurement data stored in the memory to the power instruction apparatus configured to:
limit total electric power in a household by individually controlling an upper power limit of each of a plurality of home electric appliances in the household; and
display information indicating a difference between the total electric power in the household and a total power usage by the plurality of home electric appliances in the household;
an operation unit configured to output an instruction of a measurement operation of the measurement unit and a transmission operation; and
a control unit configured to process the measurement data.

15. A healthcare instrument, comprising:
a measurement unit configured to measure biological data;
a memory configured to temporarily store the measurement data acquired by the measurement unit;
a transmission unit configured to:
transmit, before the measurement of the biological data, a usage notice signal to a power instruction apparatus; and
transmit the measurement data stored in the memory to the power instruction apparatus configured to:
limit total electric power in a household by individually controlling an upper power limit of each of a plurality of home electric appliances in the household; and
display information indicating a difference between the total electric power in the household and a total power usage by the plurality of home electric appliances in the household;
an operation unit configured to output an instruction of a measurement operation of the measurement unit and a transmission operation; and
a control unit configured to process the measurement data.

16. A power instruction apparatus configured to limit total electric power in a household by individually controlling power usage of each of a plurality of home electric appliances in the household, the power instruction apparatus comprising:
an environment detection unit configured to measure at least one of temperature and humidity of each of a plurality of living spaces in the household to generate environment information;
a power use limit setting device configured to receive operation information from each of the plurality of home electric appliances to transmit a power control signal to each of the plurality of home electric appliances;
a healthcare processing unit configured to receive measurement data from an activity measurement apparatus configured to measure an amount of activity of a user and receive, before measurement of the amount of activity of the user, a usage notice signal from the activity measurement apparatus;
a control unit configured to control the healthcare processing unit and the power use limit setting device; and
a display device configured to display, collectively or individually, information indicating a difference between the total electric power in the household and a total power usage by the plurality of home electric appliances in the household, data of the amount of activity received by the healthcare processing unit, and the environment information of a living space in which the activity measurement apparatus is present.

17. The power instruction apparatus of claim 16,
wherein one of the plurality of home electric appliances is a heating cooker,
wherein the power instruction apparatus further comprises a storage device configured to store biological data measured by a healthcare instrument configured to measure the biological data of a user in the household and caution data indicating that the biological data has an abnormal value, and
wherein, when the caution data includes cooking reference data serving as a reference to a cooking method or cooking content of the heating cooker, the display device displays the cooking reference data.

18. The power instruction apparatus of claim 16, further comprising an operation unit of an instruction switch for environment confirmation, the instruction switch being arbitrarily operated by a user to output, to the control unit, an instruction for acquiring the environment information from the environment detection unit.

19. The power instruction apparatus of claim 16, wherein the display device further includes an operation unit of an instruction switch for environment confirmation, the instruction switch being arbitrarily operated by a user to output, to the control unit, an instruction for acquiring the environment information from the environment detection unit.

20. The power instruction apparatus of claim 16,
wherein at least one of the plurality of home electric appliances includes a vibration sensor configured to detect an earthquake, and
wherein, when the control unit receives a vibration detection signal from the at least one of the plurality of home electric appliances including the vibration sensor and at least one of the plurality of home electric appliances is using a heating unit, the control unit outputs, to the at least one of the plurality of home electric appliances using the heating unit, an instruction for performing an operation to cut off power supply to the heating unit.

21. The power instruction apparatus of claim 16,
wherein one of the plurality of home electric appliances is a heating cooker having a display unit,
wherein the power instruction apparatus further comprises a storage device configured to store biological data measured by a healthcare instrument configured to measure the biological data of a user in the household and caution data indicating that the biological data has an abnormal value, and
wherein, when the biological data associated with the caution data includes data serving as a reference to a cooking method or cooking content of the heating cooker, the data serving as the reference is displayed on the display unit on the heating cooker.

22. A power instruction apparatus configured to limit total electric power in a household by individually controlling power usage of each of a plurality of home electric appliances in the household, the power instruction apparatus comprising:
a healthcare processing unit configured to:
receive measurement data from an activity measurement apparatus configured to measure an amount of activity of a user and receive, before measurement of the amount of activity of the user, a usage notice signal from the activity measurement apparatus; and
receive measurement data from a healthcare instrument configured to measure biological data of a user and receive, before measurement of the biological data of the user, a usage notice signal from the activity measurement apparatus; and
a display device communicably connected to the power instruction apparatus via wired or wireless communication and configured to display, collectively or individually, information indicating a difference between the total electric power in the household and a total power usage by the plurality of home electric appliances in the household, data of the amount of activity received by the healthcare processing unit, and the biological data of the user received by the healthcare processing unit.

* * * * *